US012612410B2

(12) United States Patent
Hoyt et al.

(10) Patent No.: US 12,612,410 B2
(45) Date of Patent: Apr. 28, 2026

(54) MULTI-CYCLIC IRAK AND FLT3 INHIBITING COMPOUNDS AND USES THEREOF

(71) Applicants: CHILDREN'S HOSPITAL MEDICAL CENTER, Cincinnati, OH (US); THE UNITED STATES OF AMERICA, AS REPRESENTED BY THE SECRETARY, DEPT. OF HEALTH AND HUMAN SERVICES, Bethesda, MD (US); KUROME THERAPEUTICS, INC., Cincinnati, OH (US)

(72) Inventors: Scott Bryan Hoyt, Arlington, VA (US); Craig Joseph Thomas, Gaithersburg, MD (US); Daniel T. Starczynowski, Cincinnati, OH (US); Jan Susan Rosenbaum, Cincinnati, OH (US); Gabriel Gracia Maldonado, Aguadilla, PR (US)

(73) Assignees: CHILDREN'S HOSPITAL MEDICAL CENTER, Cincinnati, OH (US); The United States of America, as Represented by the Secretary, Dept. of Health and Human Services, Bethesda, MD (US); KUROME THERAPEUTICS, INC., Watertown, MA (US)

( * ) Notice: Subject to any disclaimer, the term of this patent is extended or adjusted under 35 U.S.C. 154(b) by 271 days.

(21) Appl. No.: 18/258,586

(22) PCT Filed: Dec. 23, 2021

(86) PCT No.: PCT/US2021/065037

§ 371 (c)(1),
(2) Date: Jun. 21, 2023

(87) PCT Pub. No.: WO2022/140647

PCT Pub. Date: Jun. 30, 2022

(65) Prior Publication Data

US 2024/0294530 A1 Sep. 5, 2024

Related U.S. Application Data

(60) Provisional application No. 63/129,895, filed on Dec. 23, 2020.

(51) Int. Cl.

| | |
|---|---|
| *C07D 487/04* | (2006.01) |
| *A61K 31/496* | (2006.01) |
| *A61K 31/4985* | (2006.01) |
| *A61K 31/541* | (2006.01) |
| *A61K 31/635* | (2006.01) |
| *A61P 35/02* | (2006.01) |
| *C07D 519/00* | (2006.01) |

(52) U.S. Cl.

CPC .......... *C07D 487/04* (2013.01); *A61K 31/496* (2013.01); *A61K 31/4985* (2013.01); *A61K 31/541* (2013.01); *A61K 31/635* (2013.01); *A61P 35/02* (2018.01); *C07D 519/00* (2013.01)

(58) Field of Classification Search

CPC ...... C07D 487/04; A61P 35/02; A61K 31/496
See application file for complete search history.

(56) References Cited

U.S. PATENT DOCUMENTS

| | | | | |
|---|---|---|---|---|
| 7,709,468 | B2 | 5/2010 | Calderwood et al. | |
| 8,673,905 | B2 * | 3/2014 | Luk ........................ | A61P 35/02 514/249 |
| 10,584,115 | B2 | 3/2020 | Baiazitov et al. | |
| 2012/0083492 | A1 | 4/2012 | Fernandez et al. | |
| 2018/0071303 | A1 | 3/2018 | Abella et al. | |
| 2020/0199123 | A1 | 6/2020 | Starczynowski et al. | |
| 2020/0270242 | A1 | 8/2020 | Starczynowski et al. | |
| 2021/0179625 | A1 | 6/2021 | Romero et al. | |

FOREIGN PATENT DOCUMENTS

| | | | |
|---|---|---|---|
| WO | 2007028051 | A2 | 3/2007 |
| WO | 2012052745 | A1 | 4/2012 |
| WO | 2012123470 | A1 | 9/2012 |
| WO | 2014210255 | A1 | 12/2014 |
| WO | 2017223414 | A1 | 12/2017 |

(Continued)

OTHER PUBLICATIONS

Extended European Search Report issued in European Patent Application No. 21912215.7, dated Oct. 11, 2024, 10 pages.

(Continued)

*Primary Examiner* — Kamal A Saeed

(74) *Attorney, Agent, or Firm* — Morgan, Lewis & Bockius LLP

(57) ABSTRACT

Some embodiments of the disclosure include inventive compounds (e.g., compounds of Formula (I)) and compositions (e.g., pharmaceutical compositions) which inhibit IRAK and/or FLT3 and which can be used for treating, for example, certain diseases. Some embodiments include methods of using the inventive compound (e.g., in compositions or in pharmaceutical compositions) for administering and treating (e.g., diseases such as hematopoietic cancers, myelodysplastic syndromes (MDS), acute myeloid leukemia (AML), etc.), Additional embodiments provide disease treatment using combinations of the inventive IRAK and/or FLT3 inhibiting compounds with other therapies, such as cancer therapies.

20 Claims, No Drawings

(56) References Cited

FOREIGN PATENT DOCUMENTS

| | | | |
|---|---|---|---|
| WO | 2018038988 | A2 | 3/2018 |
| WO | 2019002606 | A1 | 1/2019 |

OTHER PUBLICATIONS

International Search Report and Written Opinion issued in PCT/US2023/068897, mailed Dec. 19, 2023, 11 pages.
Pubchem CID 66599118, Create date: Nov. 30, 2012 (Nov. 30, 2012), entire document.
International Search Report and Written Opinion issued in PCT/US2021/065037, mailed Mar. 22 2022, 8 pages.
Diab et al., "Dual Inhibition of Mnk2 and FLT3 for potential treatment of acute myeloid leukaemia," European Journal of Medicinal Chemistry, 2017, 139:762-772.
Barreyro et al., "Chronic immune response dysregulation in MDS pathogenesis," Blood, 2018, 132(15):1553-1560.
Genung et al., "Chapter Four Small Molecule Inhibition of Interleukin-1 Receptor-Associated Kinase 4 (IRAK4)," In Progress in Medicinal Chemistry, vol. 56, 2017, pp. 117-163.
McElroy et al., "Interleukin-1 receptor-associated kinase 4 (IRAK4) inhibitors: an updated patent review (2016-2018)," Expert Opinion on Therapeutic Patents, 2019, DOI: 10.1080/13543776.2019.1597850.
Wiese et al., "Investigational IRAK-4 inhibitors for the treatment of rheumatoid arthritis," Expert Opinion on Investigational Drugs, 2020, 29(5):475-482.
Seganish et al., "Inhibitors of interleukin-1 receptor-associated kinase 4 (IRAK4): a patent review (2012-2015)," Expert Opinion on Therapeutic Patents, 2016, 26(8):917-932.
Office Action issued in Eurasian Patent Application No. 202391815, mailed Apr. 10, 2024, 19 pages.
Office Action issued in Japanese Patent Application No. 2023-537923, mailed Jul. 29, 2025, 13 pages.
Pourbasheer et al., "Quantitative structure-activity relationship (QSAR) study of interleukin-1 receptor associated kinase 4 (IRAK-4) inhibitor activity by genetic algorithm and multiple linear regression (GA-MLR) method," Journal of Enzyme Inhibition and Medicinal Chemistry, 2010, vol. 25, No. 6, pp. 844-853.
Office Action issued in Chinese Patent Application No. 202180093913.0, dated Dec. 11, 2025, 23 pages.
Fundamental Medicine: Molecular Pharmacology, edited by Ba Denian, Heilongjiang Science and Technology Press, 1st edition, publication date: May 31, 1999, pp. 299-302 (see page 8 of Office Action, first paragraph, for a concise description of this reference).
Office Action issued in Israeli Patent Application No. 303887, dated Feb. 15, 2026, 3 pages.

* cited by examiner

MULTI-CYCLIC IRAK AND FLT3 INHIBITING COMPOUNDS AND USES THEREOF

CROSS-REFERENCE TO RELATED APPLICATIONS

The present application is a U.S. National Stage Patent Application of International Application No. PCT/US2021/065037, filed Dec. 23, 2021, which claims priority to U.S. Provisional Application No. 63/129,895, filed Dec. 23, 2020, each of which is incorporated herein by reference in its entirety.

GOVERNMENT RIGHTS

This invention was made in the performance of a Cooperative Research and Development Agreement with the National Institutes of Health, an Agency of the Department of Health and Human Services. The Government of the United States has certain rights in this invention.

FIELD OF THE DISCLOSURE

The present disclosure generally relates to compounds and compositions which are kinase inhibitors and the use of the same in treating diseases and disorders, including cancers.

BACKGROUND

Myelodysplastic syndromes (MDS) are malignant, potentially fatal blood diseases that arise from a defective hematopoietic stem/progenitor cell, confer a predisposition to acute myeloid leukemia (AML) (Corey et al., 2007; Nimer, 2008), and often progress to chemotherapy-resistant secondary acute myeloid leukemia (sAML). A majority of patients having MDS die of marrow failure, immune dysfunction, and/or transformation to overt leukemia.

MDS are heterogeneous diseases with few treatment options, as there is a lack of effective medicines capable of providing a durable response. Current treatment options for MDS are limited but include allogeneic HSC transplantation, demethylating agents, and immunomodulatory therapies (Ebert, 2010). While hemopoietic stem cell (HSC) transplantation can be used as a curative treatment for MDS, this option is unavailable to many older patients, who instead receive supportive care and transfusions to ameliorate disease complications. Unfortunately, MDS clones can persist in the marrow even after HSC transplantation, and the disease invariably advances (Tehranchi et al., 2010). For advanced disease or high-risk MDS, patients may also receive immunosuppressive therapy, epigenetic modifying drugs, and/or chemotherapy (Greenberg, 2010). Despite recent progress, most MDS patients exhibit treatment-related toxicities or relapse (Sekeres, 2010a). Overall, the efficacy of these treatments is variable, and generally life expectancies are only slightly improved as compared to supportive care. The complexity and heterogeneity of MDS, and the lack of human xenograft models are obstacles which are challenging for identifying and evaluating novel molecular targets for this disease.

Approximately 30% of MDS patients also develop aggressive AML due to acquisition of additional mutations in the defective hematopoietic stem/progenitor cell (HSPC) (Greenberg et al., 1997). AML is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages. Several risk factors and chromosomal abnormalities have been identified, but the specific cause is not clear. As an acute leukemia, AML progresses rapidly and is typically fatal within weeks or months if left untreated. The prognosis for AML that arises from MDS is worse as compared to other types of AML.

Several compounds are known to treat blood disorders and cancers (e.g. MDS, AML), but do so inadequately. While some known compounds, such as Quizartinib, Gilteritinib, and Crenolanib, can be used to treat AML, some of these treatments do not result in complete remission or partial remission. In some instances, for example, treatment can result in adaptive resistance or selecting mutations that are resistant to inhibitors, as with Quizartinib, in particular, where repeated administration can lead to desensitization in tumor cell suppression of proliferation (Melgar et al., 2019).

In treating MDS and/or AML, there is a need to develop therapies capable of inhibiting the adaptive resistance mechanism, to improve survival in the context of AML and MDS. There is also an unmet need in AML for drugs that increase overall survival, decrease the length of hospital stay as well as hospital readmission rates, overcome acquired resistance to other treatments, and increase the success rate for hematopoietic stem cell transplant. There is additionally a need for drugs for treating MDS which can slow the conversion rate to AML, and decrease transfusion dependence.

It is therefore necessary to develop treatments and methods of effectively treating MDS and/or AML, and/or other conditions or disorders characterized by dysregulated (e.g., hyperactive) IRAK (e.g., IRAK 1 and/or 4). Additionally, in doing so, it will be important to determine whether a patient is likely to be responsive to a particular treatment or method of treatment. Certain embodiments of the disclosure can address one or more of these issues.

SUMMARY OF THE DISCLOSURE

In one aspect, the present disclosure relates to a compound of Formula (I):

(I)

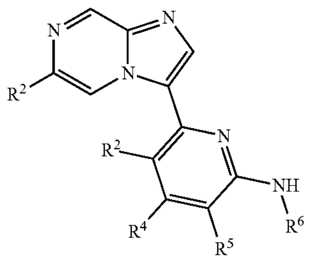

or a salt, ester, solvate, optical isomer, geometric isomer, salt of an isomer, prodrug, or derivative thereof, wherein:

$R^2$, $R^3$, $R^4$, and $R^5$ are each independently selected from H, halogen, hydroxy, oxo (=O), —CN, amino, amido, —O-aryl, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, spiro-fused cycloalkyl, heterocyclyl, aryl, heteroaryl, or fused ring heteroaryl, wherein amino, amido, —O-aryl, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more of halogen, hydroxy, oxo, methanoyl (—COH), carboxy (—$CO_2H$), nitro (—$NO_2$), —$NH_2$, —$NHCH_3$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl, wherein two adjacent optional substituents can bond or fuse to form a ring;

$R^6$ is selected from (Ia)

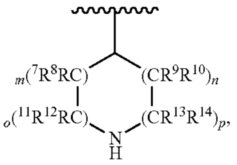

or (Ib)

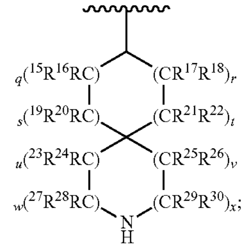

$R^7$, $R^8$, $R^9$, $R^{10}$, $R^{11}$, $R^{12}$, $R^{13}$, and $R^{14}$ are each independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are each independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl; and m, n, o, p, q, r, s, t, u, v, w, and x are each independently selected from 0, 1, 2, 3, 4, or 5; where q+r+s+t is at least 1, and where u+v+w+x is at least 1.

In one aspect, the compound of Formula (I) is a compound of Formula (IIf):

Formula (IIf)

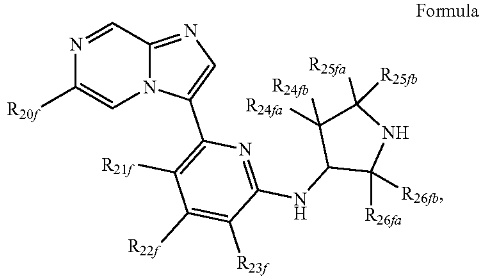

or a salt, ester, solvate, optical isomer, geometric isomer, or salt of an isomer thereof; wherein: $R_{20f}$ is selected from H, halogen, $C_1$-$C_6$ alkyl, $C_1$-$C_6$ alkoxy, $C_3$-$C_6$ cycloalkyl, —O—$(CH_2)_a$—($C_3$-$C_6$ cycloalkyl), and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocyclyl is optionally substituted with one or more substituents selected from halogen, $C_1$-$C_6$ alkyl, $C_1$-$C_6$ alkoxy, —OH, and =O wherein two adjacent optional substituents can bond or fuse to form a ring; $R_{21f}$, $R_{22f}$, and $R_{23f}$ are each independently selected from H and halogen; $R_{24fa}$, $R_{24fb}$, $R_{25fa}$, $R_{25fb}$, $R_{26fa}$, and $R_{26fb}$ are each independently selected from H, halogen, —OH, $C_1$-$C_6$ alkyl, and $C_1$-$C_6$ alkoxy, wherein $C_1$-$C_6$ alkyl and $C_1$-$C_6$ alkoxy are each optionally substituted with one or more halogen atoms; and a is selected from 0, 1, 2, 3, 4, 5, and 6. In one embodiment, one or more of $R_{24fa}$, $R_{24fb}$, $R_{25fa}$, $R_{25fb}$, $R_{26fa}$, and $R_{26fb}$ is independently selected from halogen, —OH, optionally substituted $C_1$-$C_6$ alkyl, and optionally substituted $C_1$-$C_6$ alkoxy. In one embodiment, $R_{20f}$ is H. In one embodiment, at least one of (i)-(viii) applies: (i) $R_{20f}$ is selected from t-butyl, unsubstituted $C_3$ cycloalkyl, pyrrolidinyl, —$OCH_3$, —$OCH_2CH_3$,

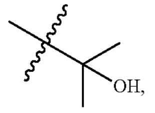

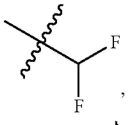

,

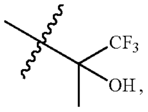

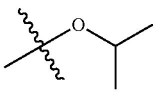

,

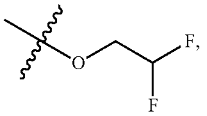

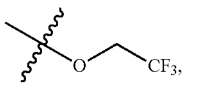

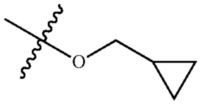

,

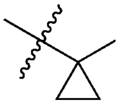

,

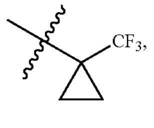

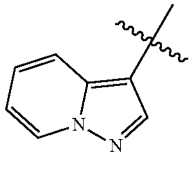

,

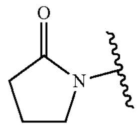

,

-continued

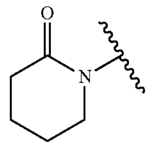, 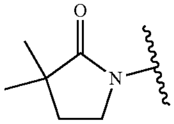, 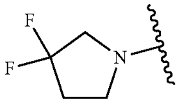,

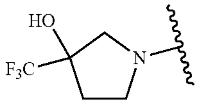, 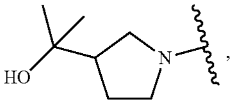,

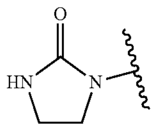, 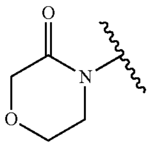, and 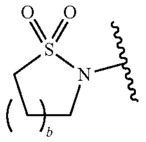

wherein b is 1 or 2; (ii) $R_{20f}$ is

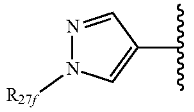

wherein $R_{27f}$ is selected from —$CH_3$,

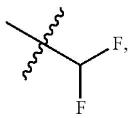 and 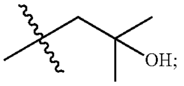

(iii) $R_{20f}$ is

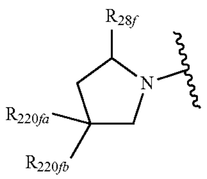

wherein $R_{28f}$ is ═O and $R_{220fa}$ and $R_{220fb}$ are each —$CH_3$ or $R_{220fa}$ and $R_{220fb}$ bond or fuse to form oxetanyl; (iv) $R_{21f}$, $R_{22f}$, and $R_{23f}$ are each H; (v) $R_{21f}$ and $R_{23f}$ are each F and $R_{22f}$ is H; (vi) $R_{21f}$ and $R_{23f}$ are each H and $R_{22f}$ is F; (vii) $R_{24fa}$, $R_{24fb}$, $R_{25fa}$, $R_{25fb}$, $R_{26fa}$, and $R_{26fb}$ are each H; (viii) $R_{25fa}$, $R_{25fb}$, $R_{26fa}$, and $R_{26fb}$ are each H and $R_{24fa}$ and/or $R_{24fb}$ are selected from F, —$CH_3$, and —$CF_3$. In one embodiment, the compound is selected from:

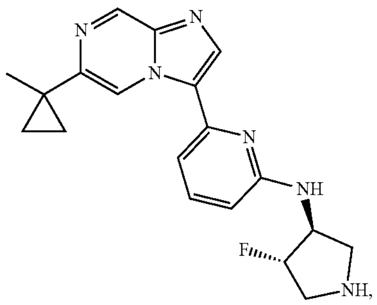

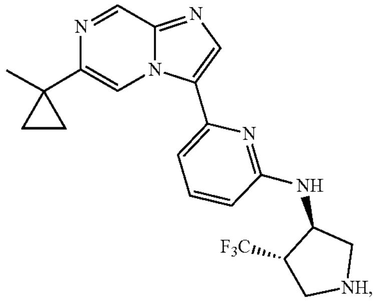

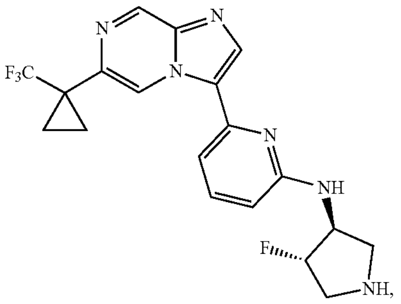

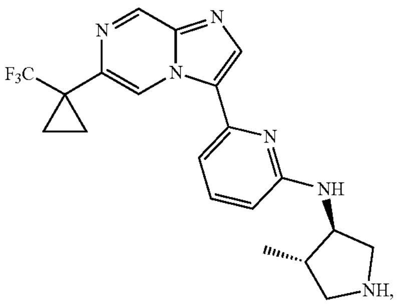

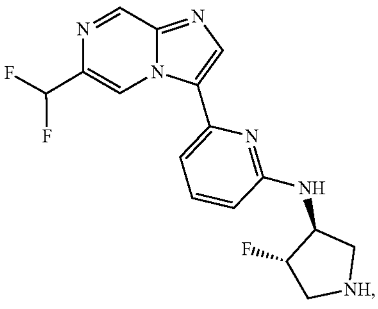

-continued
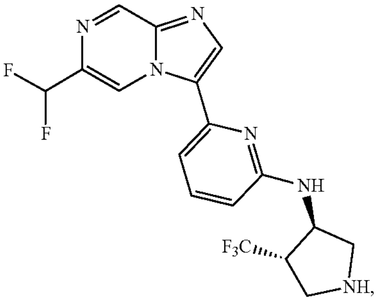
,
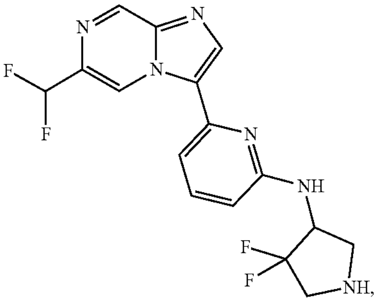
,
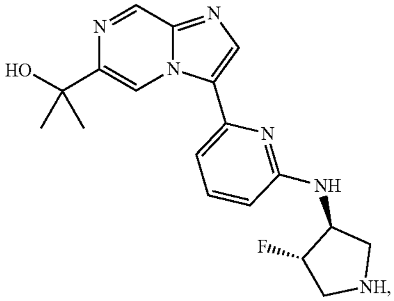
,
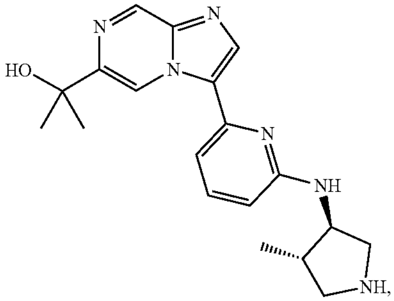
,
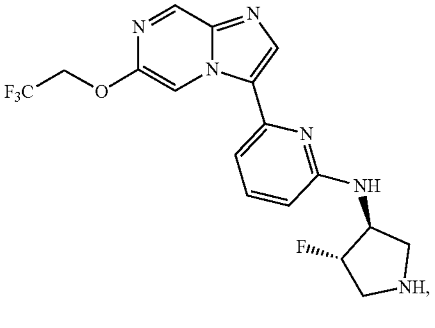
,
-continued
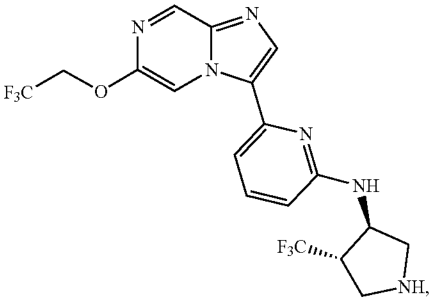
,
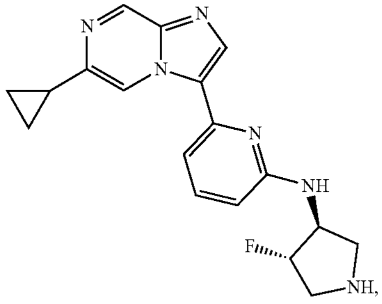
,
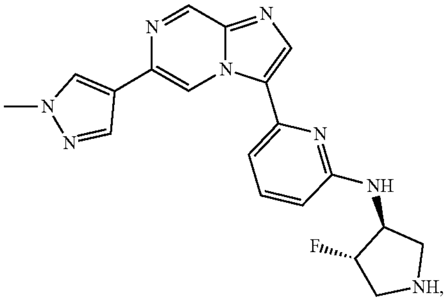
,
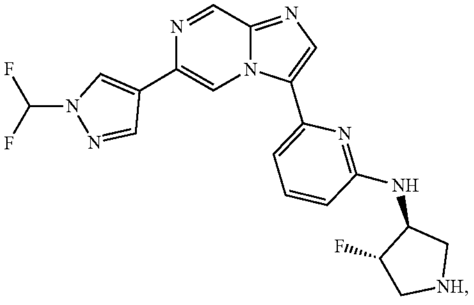
,
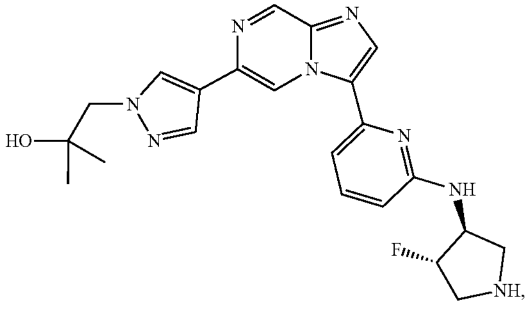
, -continued
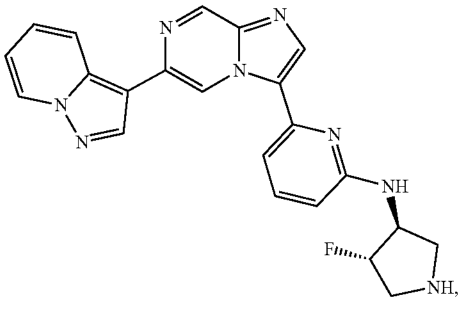
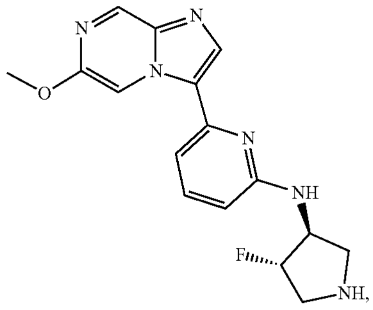
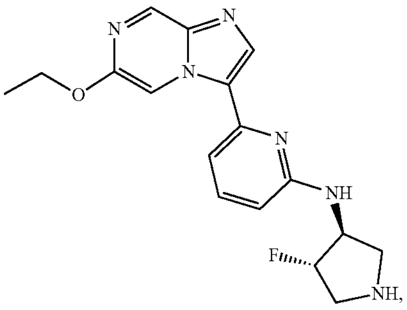
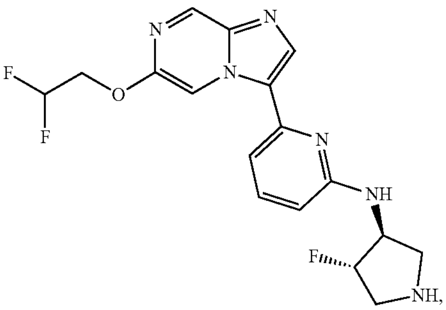
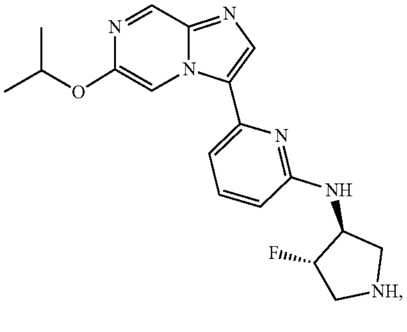
-continued
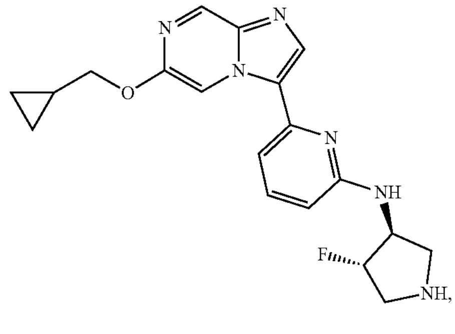
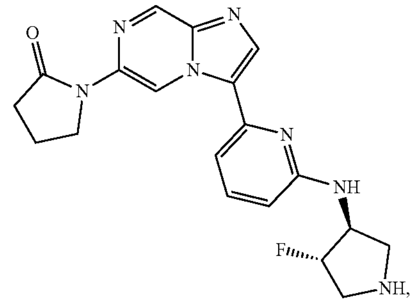
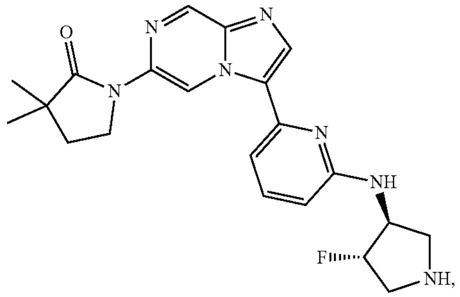
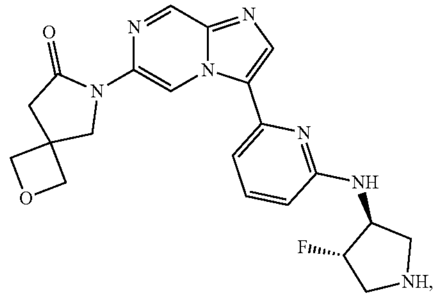
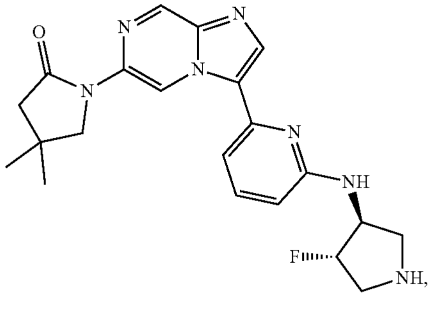

-continued
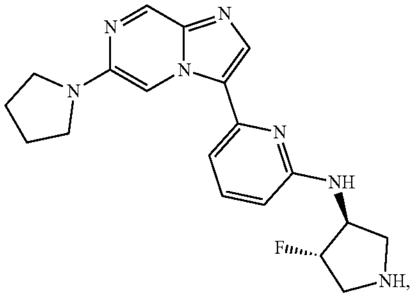 [SMILES: F[C@H]1CNC[C@@H]1Nc1cccc(-c2cnc3cnc(N4CCCC4)cn23)n1]
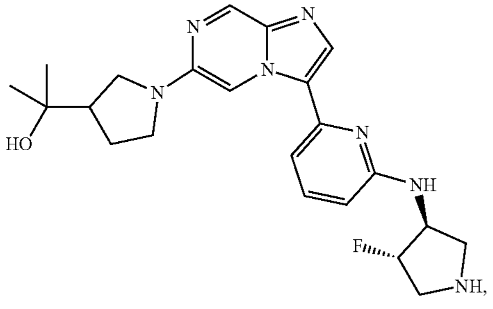
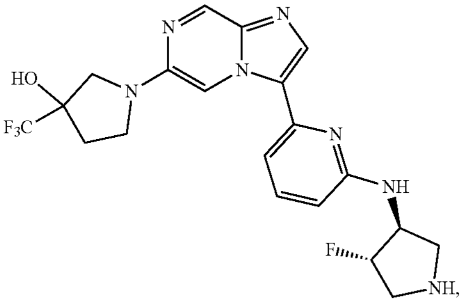
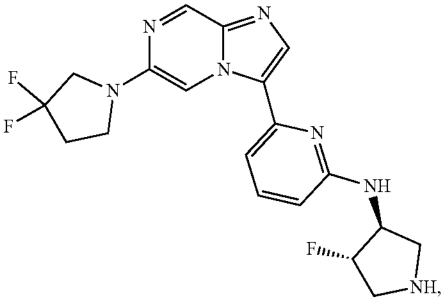
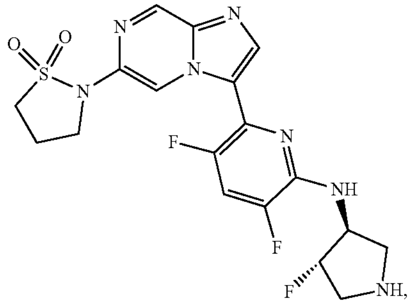
-continued
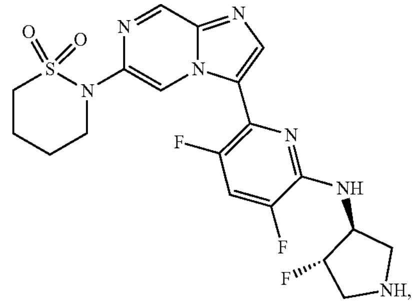
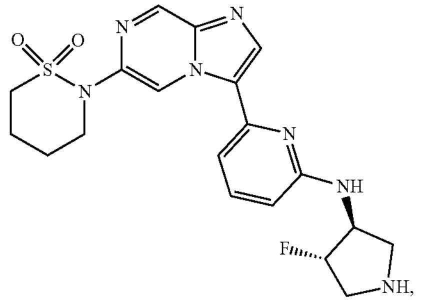
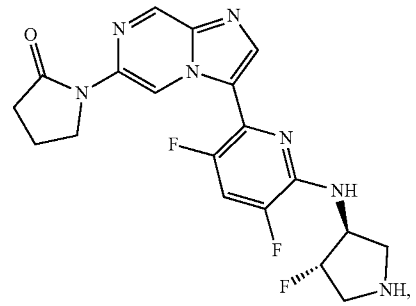
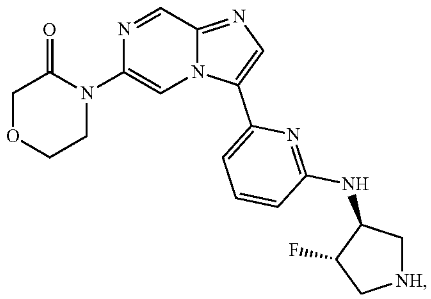
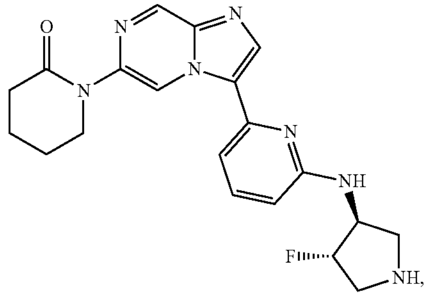

-continued
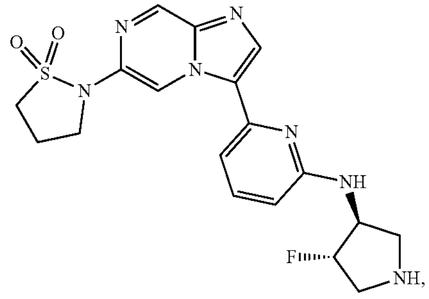
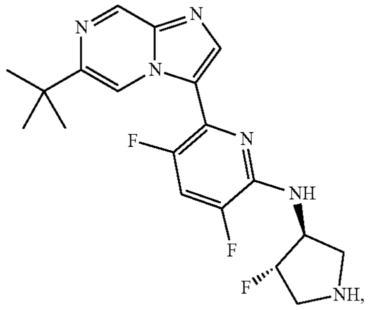
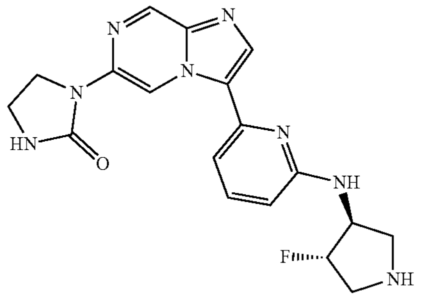
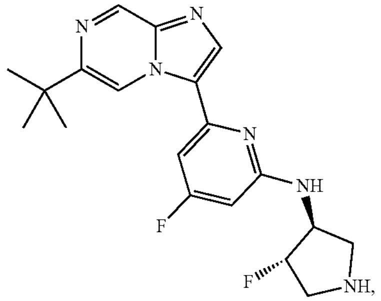
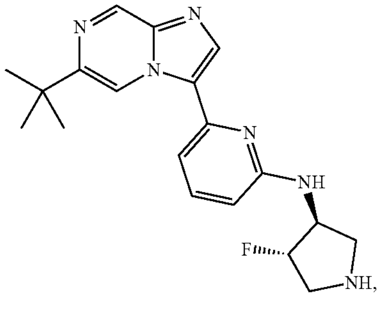
-continued
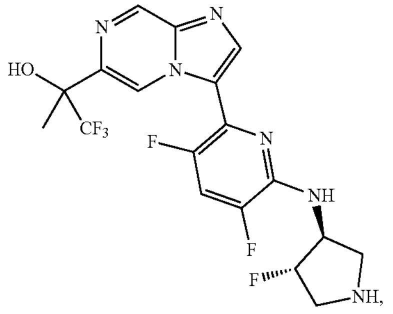
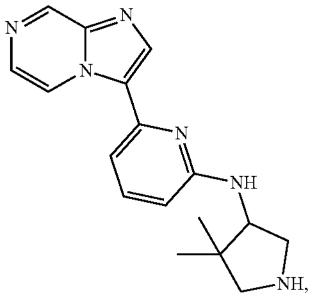
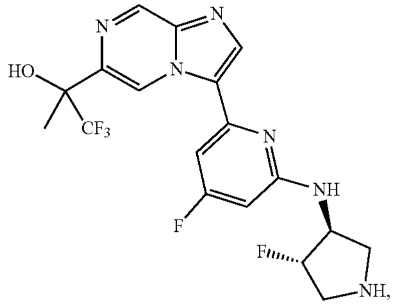
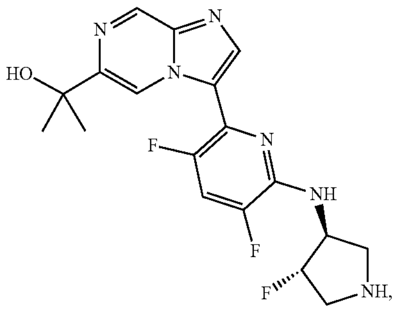
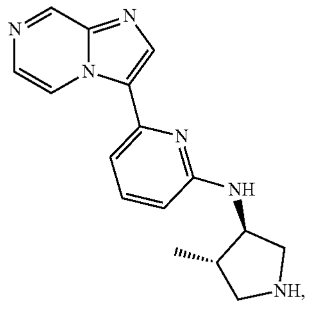

-continued
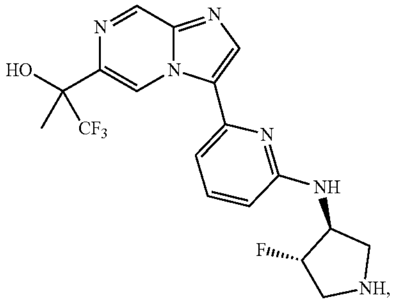
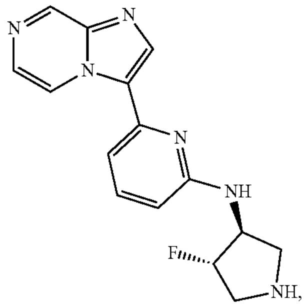
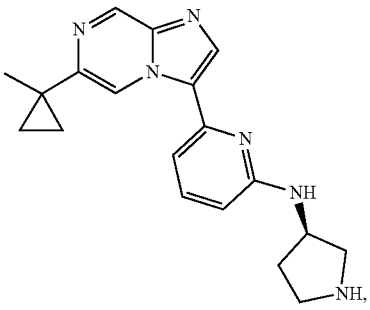
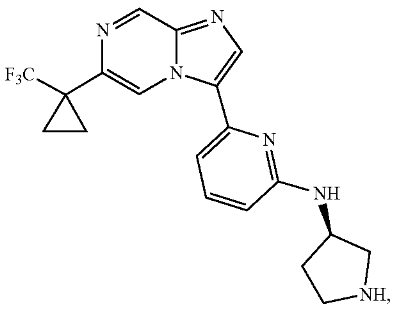
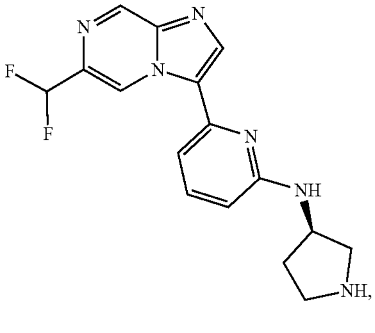
-continued
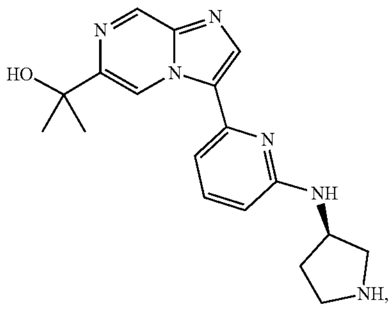
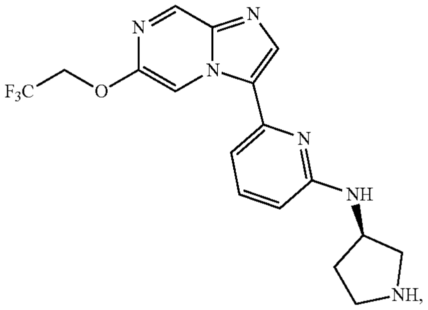
and
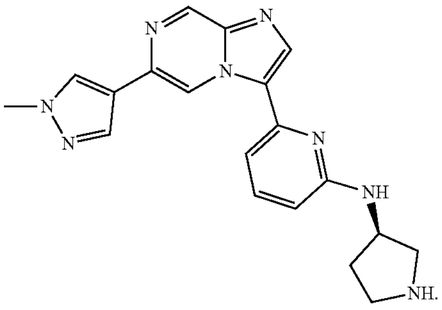
In another aspect, the compound of Formula (I) is a compound of Formula (IIg):
Formula (IIg)
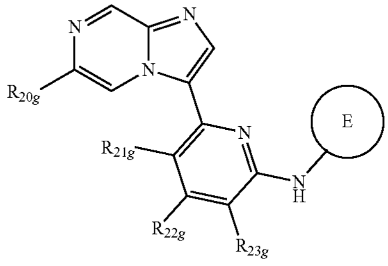
,
or a salt, ester, solvate, optical isomer, geometric isomer, or salt of an isomer thereof; wherein:
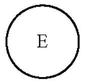

is selected from

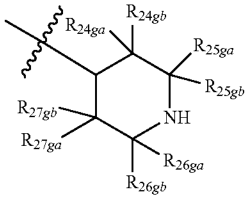

and

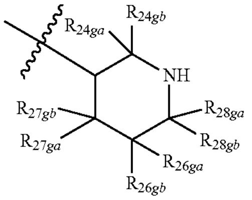

;

$R_{20g}$ is selected from H, $C_1$-$C_6$ alkyl, $C_1$-$C_6$ alkoxy, $C_3$-$C_6$ cycloalkyl, and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocycyl is optionally substituted with one or more substituents selected from halogen, $C_1$-$C_6$ alkyl, $C_3$-$C_6$-cycloalkyl, —OH, and =O; $R_{21g}$, $R_{22g}$, and $R_{23g}$ are each independently selected from H and halogen; and $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ are each independently selected from H, halogen, —OH, and $C_1$-$C_6$ alkyl. In one embodiment, one or more of $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ is independently selected from halogen, —OH, and $C_1$-$C_6$ alkyl. In one embodiment, $R_{20g}$ is H. In one embodiment, at least one of (i)-(xi) applies: (i) $R_{20g}$ is selected from t-butyl, unsubstituted $C_3$ cycloalkyl,

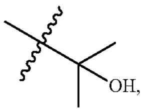

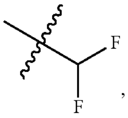

,

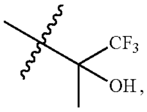

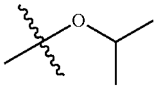

,

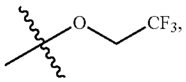

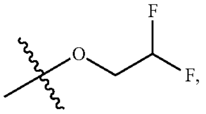

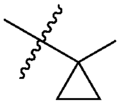

,

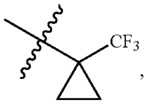

,

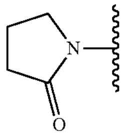

,

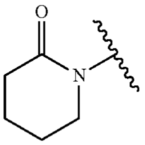

,

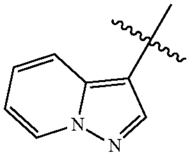

,

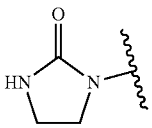

,

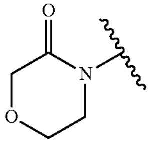

, and

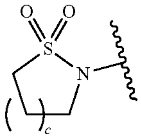

wherein c is 1 or 2; (ii) $R_{20g}$ is

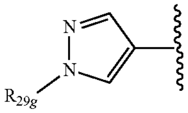

wherein $R_{29g}$ is selected from unsubstituted $C_3$ cycloalkyl, —$CH_3$,

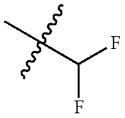

, and

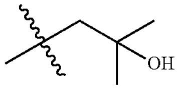

;

(iii) $R_{21g}$, $R_{22g}$, and $R_{23g}$ are each H; (iv) $R_{21g}$ and $R_{23g}$ are each F and $R_{22g}$ is H; (v) $R_{21g}$ and $R_{23g}$ are each H and $R_{22g}$ is F; (vi)

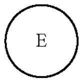

is

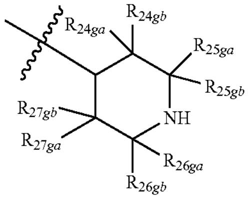

, each of $R_{24ga}$, $R_{24gb}$, $R_{25ga}$, $R_{25gb}$, $R_{26ga}$, $R_{26gb}$, $R_{27ga}$, and $R_{27gb}$ is H; (vii)

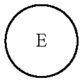

is

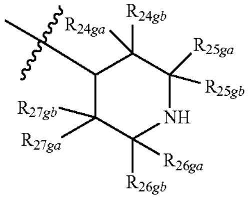

, each of $R_{24ga}$, $R_{25ga}$, $R_{25gb}$, $R_{26ga}$, $R_{26gb}$, $R_{27ga}$, and $R_{27gb}$ is H and $R_{24gb}$ is F; (viii)

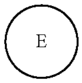

is

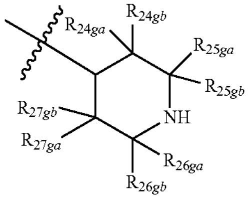

, each of $R_{24ga}$, $R_{24gb}$, $R_{25ga}$, $R_{26ga}$, $R_{26gb}$, $R_{27ga}$, and $R_{27gb}$ is H and $R_{25gb}$ is —$CH_3$; (ix)

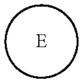

is

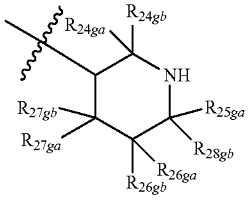

, each of $R_{24ga}$, $R_{24gb}$, $R_{26ga}$, $R_{26gb}$, $R_{27ga}$, $R_{27gb}$, $R_{28ga}$, and $R_{28gb}$ is H; (x)

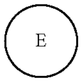 is 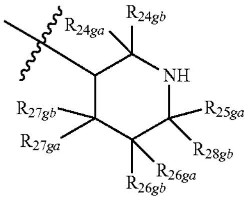,
each of $R_{24ga}$, $R_{24gb}$, $R_{26ga}$, $R_{26gb}$, $R_{28ga}$, and $R_{28gb}$ is H and $R_{27ga}$ and/or $R_{27gb}$ is F or —$CH_3$; (xi)
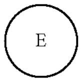 is 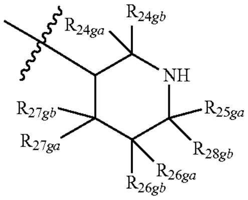,
each of $R_{24ga}$, $R_{24gb}$, $R_{27ga}$, $R_{27gb}$, $R_{26ga}$, $R_{28ga}$, and $R_{28gb}$ is H and $R_{26gb}$ is F or —$CH_3$. In one embodiment, the compound is selected from:
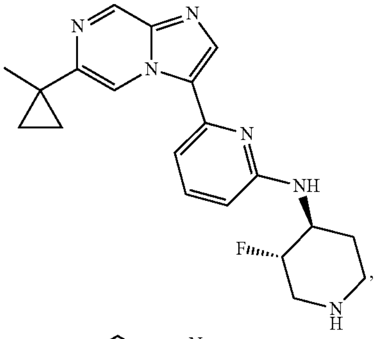
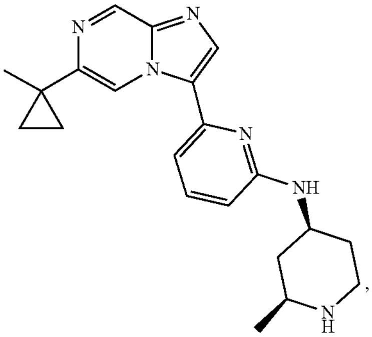
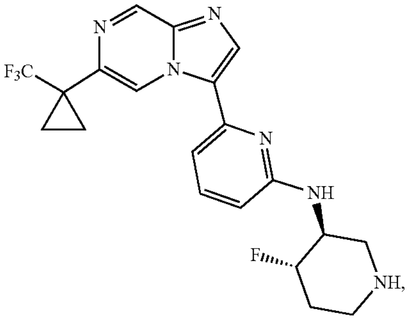
-continued
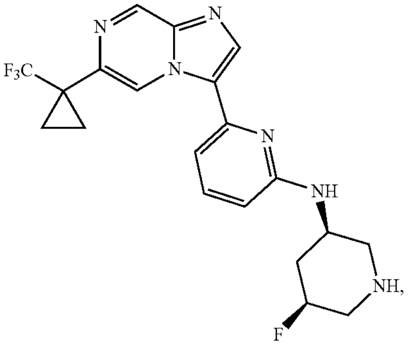
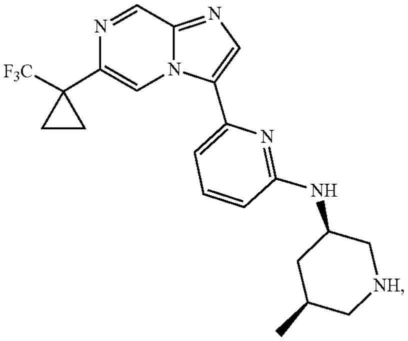
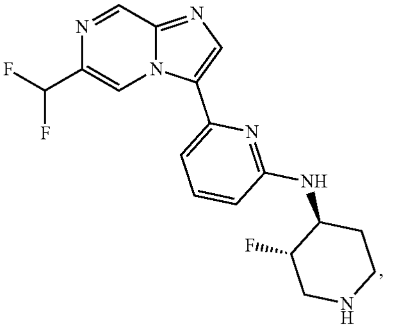
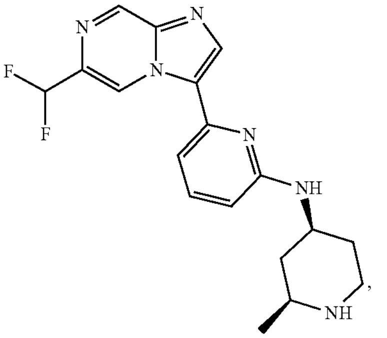
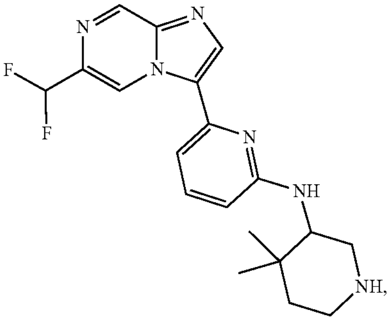

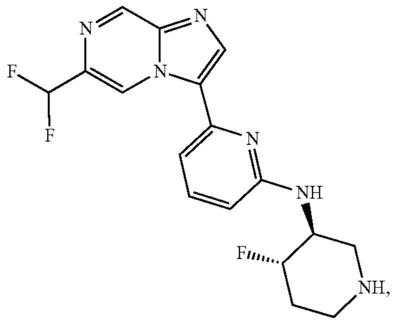
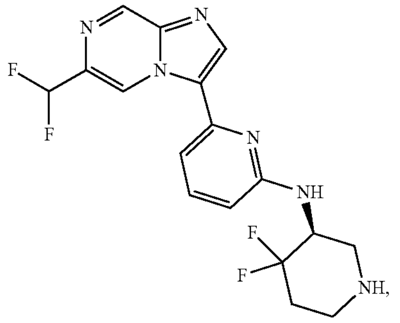
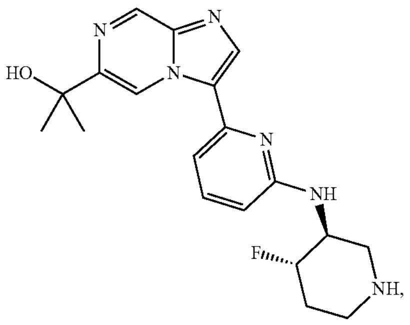
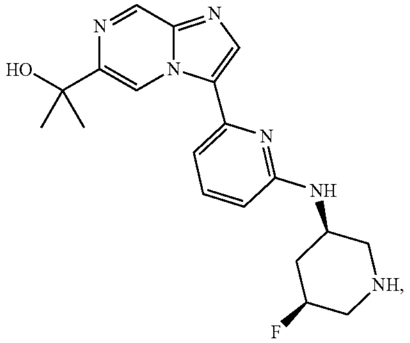
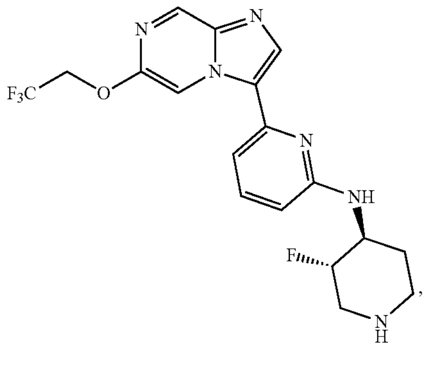
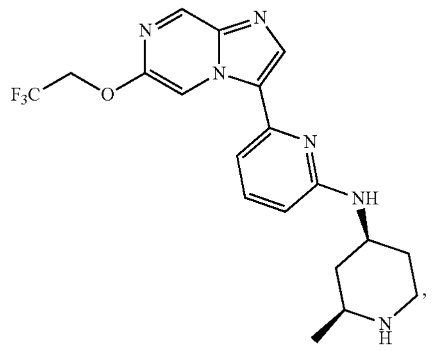
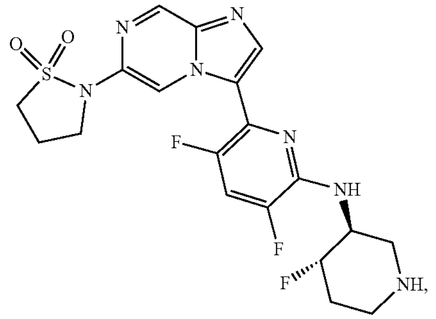
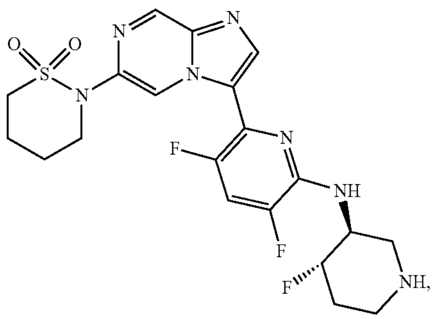
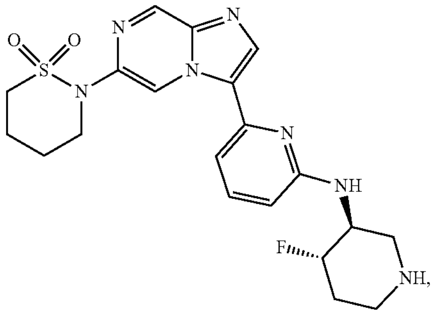
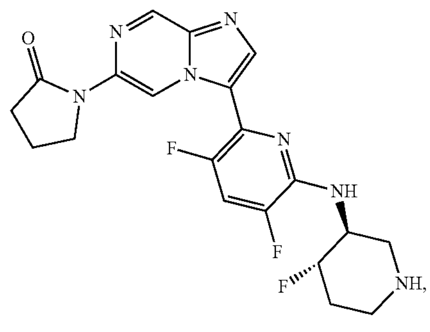

-continued
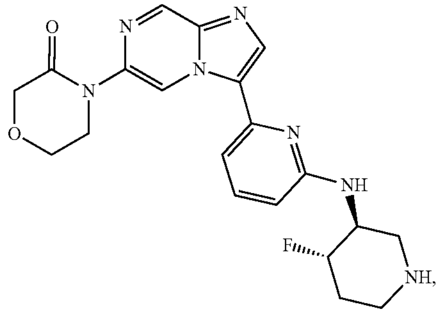
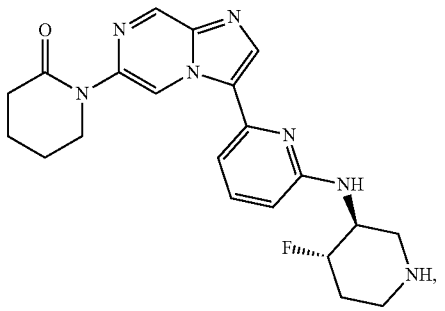
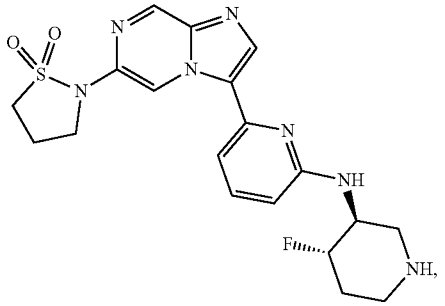
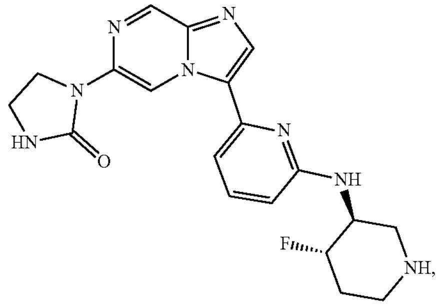
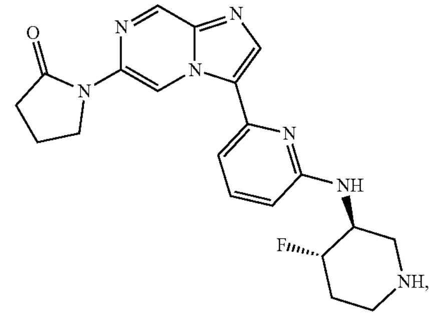
-continued
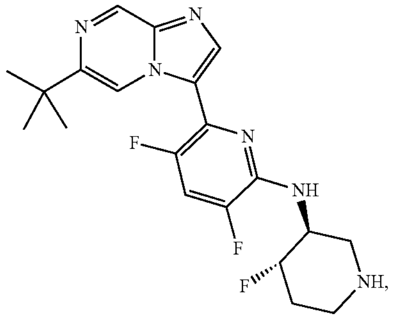
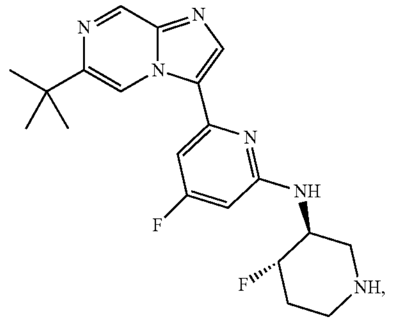
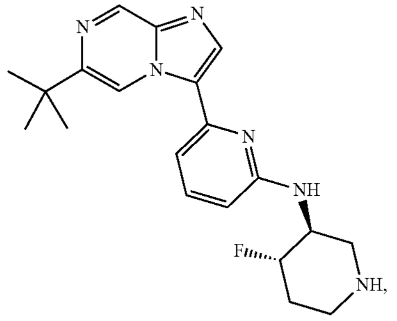
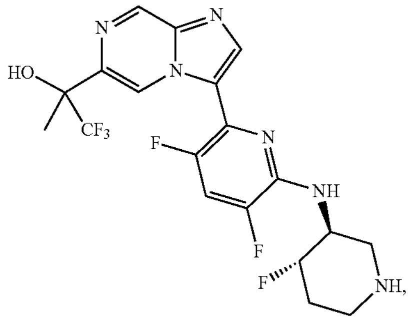
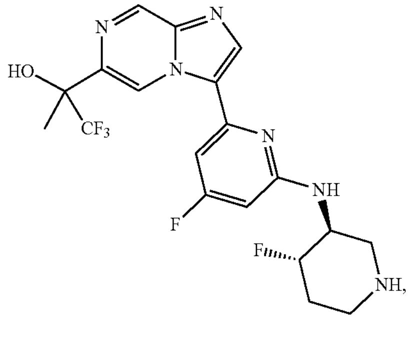

-continued
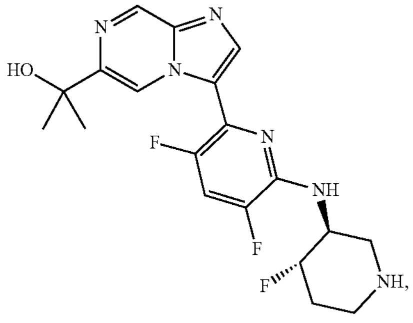
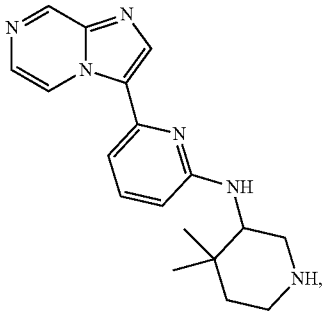
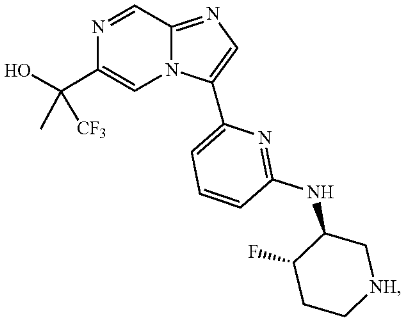
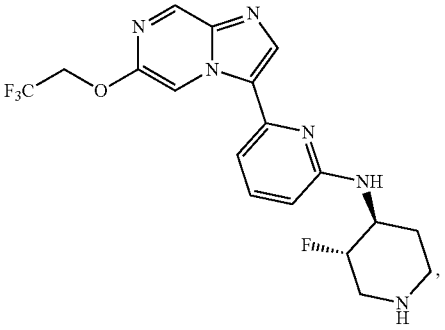
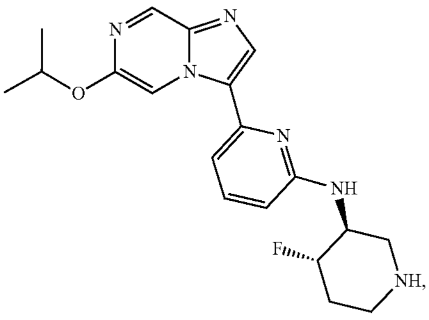
-continued
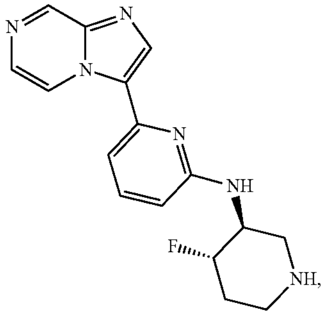
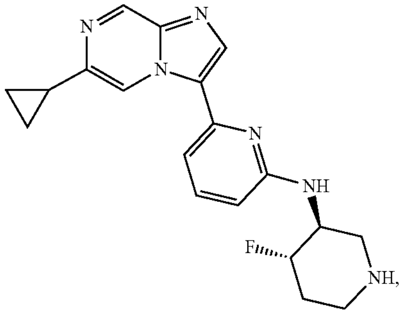
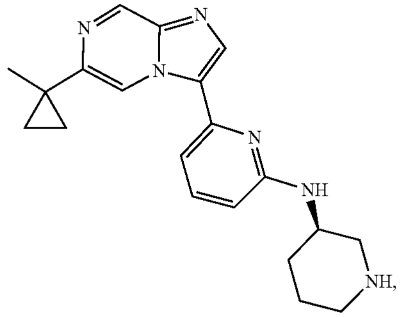
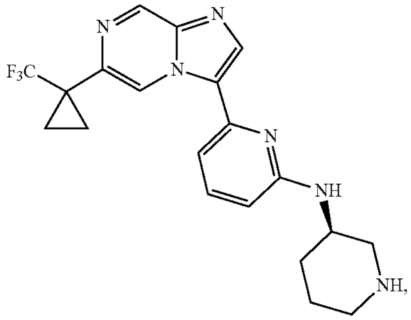
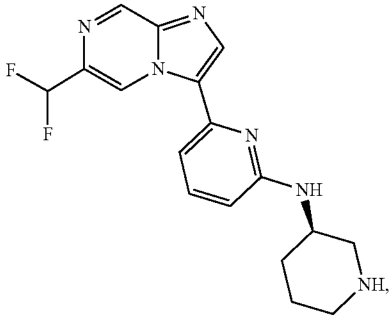

-continued
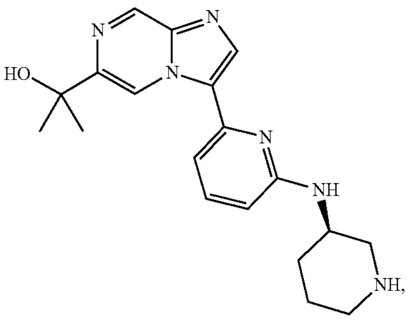
,
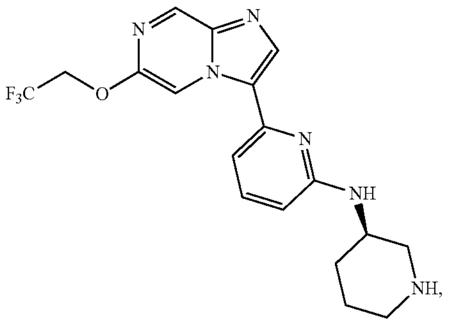
,
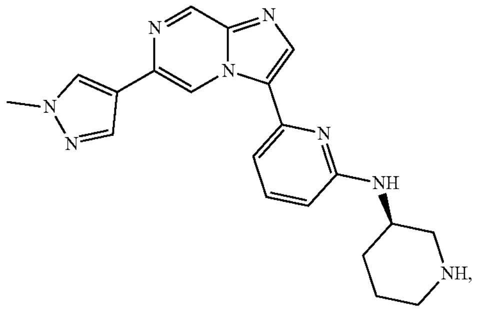
,
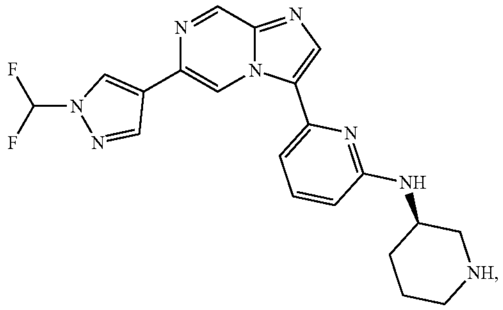
,
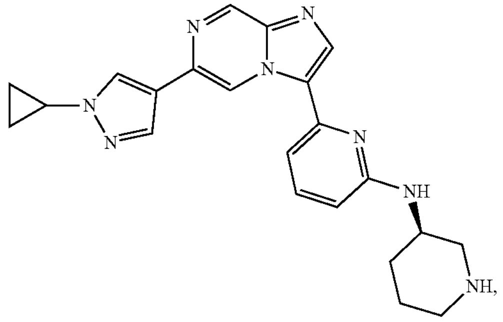
,
-continued
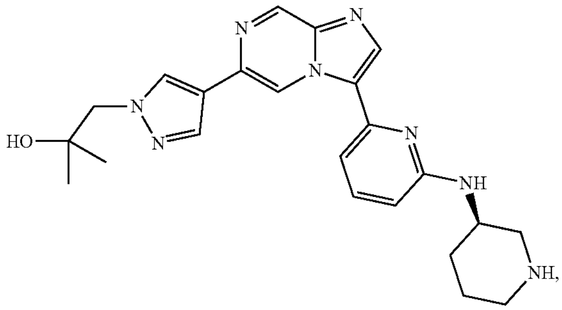
,
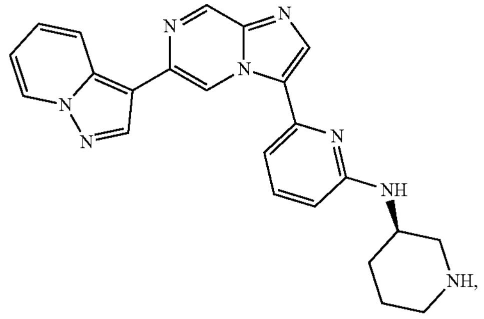
,
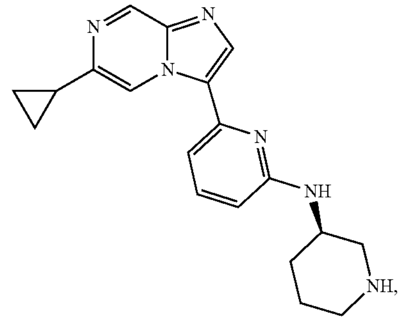
,
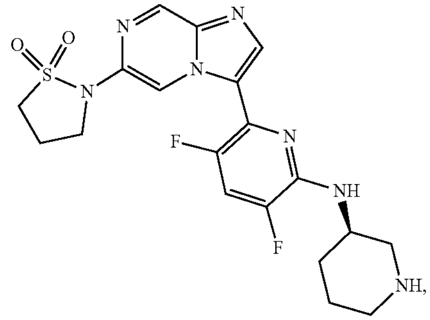
,
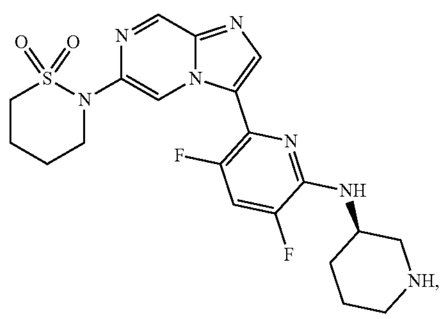
, -continued
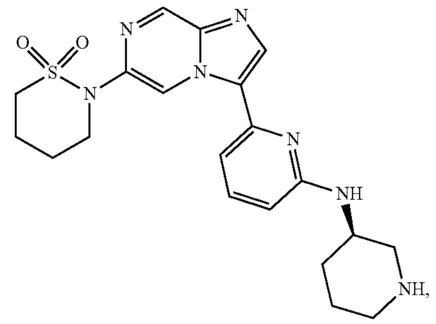
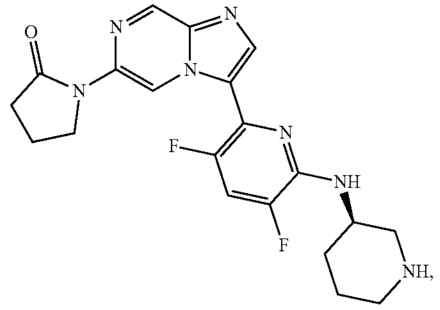
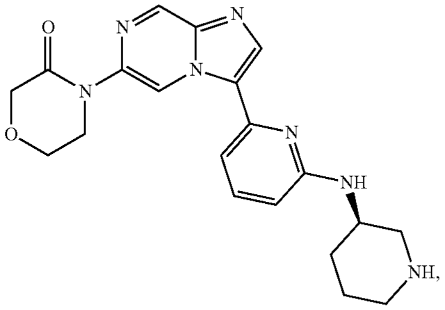
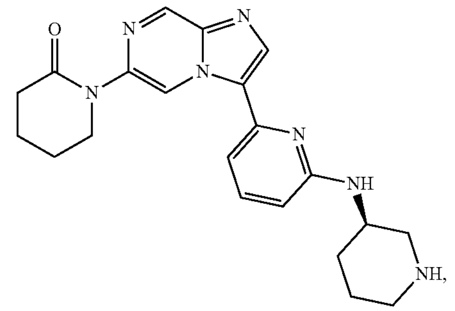
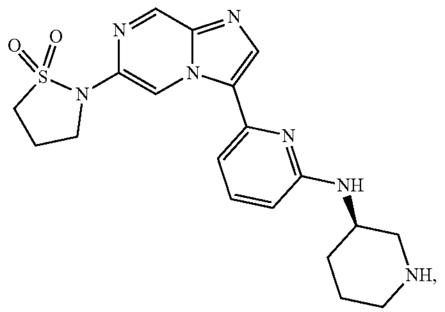
-continued
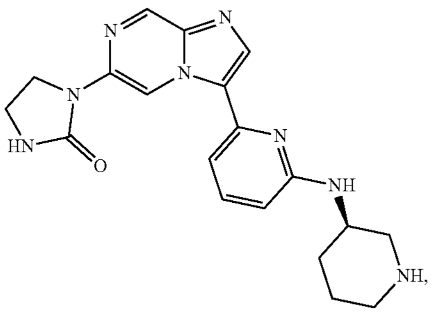
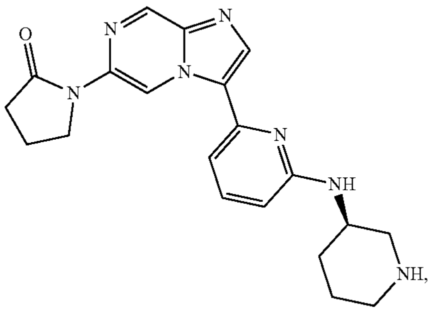
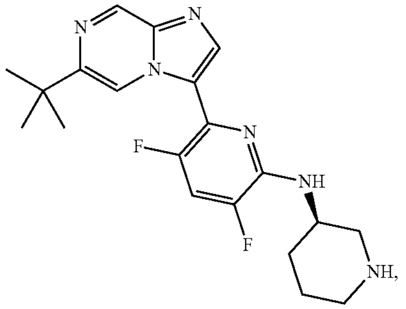
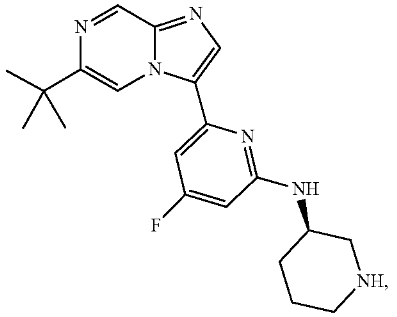
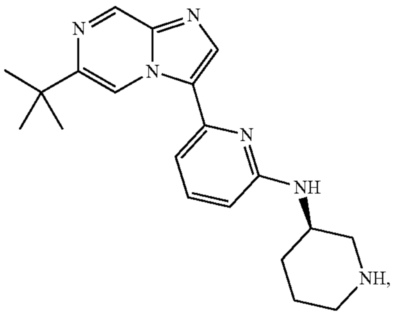

-continued
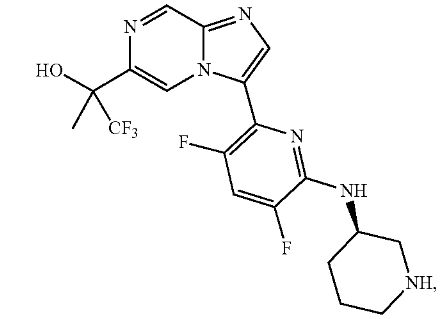
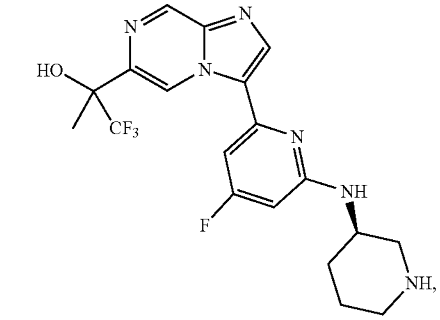
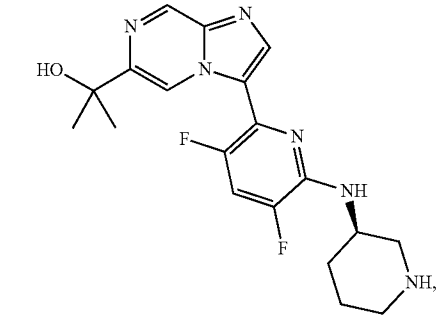
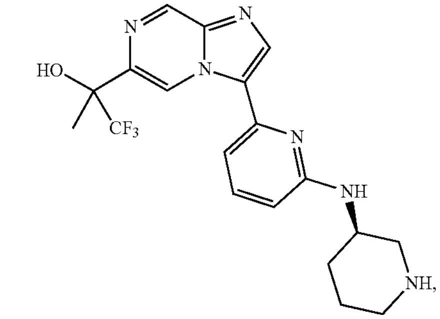
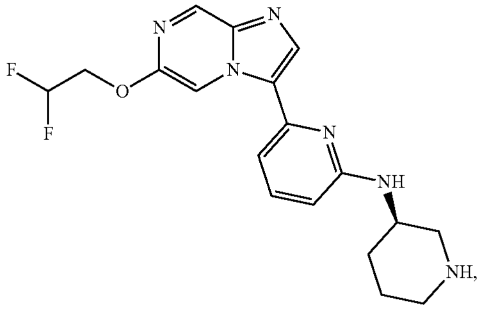
-continued
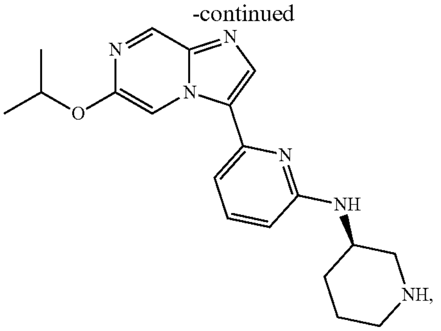
and
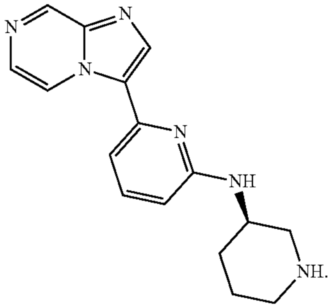
In another aspect, the compound of Formula (I) is a compound of Formula (IIh):
Formula (IIh)
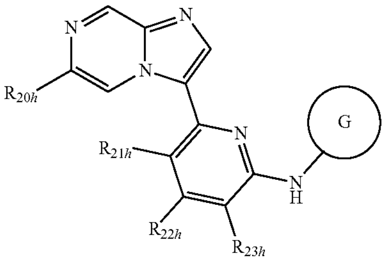
,
or a salt, ester, solvate, optical isomer, geometric isomer, or salt of an isomer thereof; wherein:
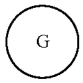
is selected from
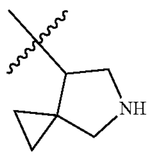
,
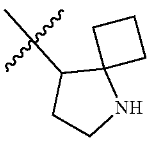
, and
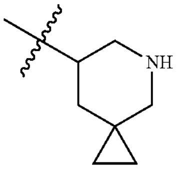
;

$R_{20h}$ is selected from H, $C_1$-$C_6$ alkyl, $C_1$-$C_6$ alkoxy, and $C_3$-$C_6$ cycloalkyl, wherein $C_1$-$C_6$ alkyl and $C_1$-$C_6$ alkoxy are each optionally substituted with one or more substituents selected from halogen and —OH, and wherein $C_3$-$C_6$ cycloalkyl is optionally substituted with one or more substituents selected from $C_1$-$C_6$ alkyl and halogen; and $R_{21h}$, $R_{22h}$, and $R_{23h}$ are each independently selected from H and halogen. In one embodiment, $R_{20h}$ is H. In one embodiment, at least one of (i)-(v) applies: (i) $R_{20h}$ is selected from

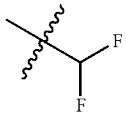 , 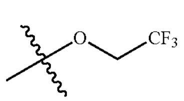 , 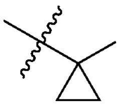 , and

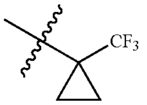 ;

(ii) $R_{21h}$, $R_{22h}$, and $R_{23h}$ are each H; (iii) $R_{21h}$ and $R_{23h}$ are each F and $R_{22h}$ is H; (iv) $R_{21h}$ and $R_{23h}$ are each H and $R_{22h}$ is F; (v)

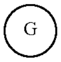 is 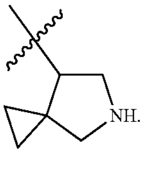

In one embodiment, compound is selected from:

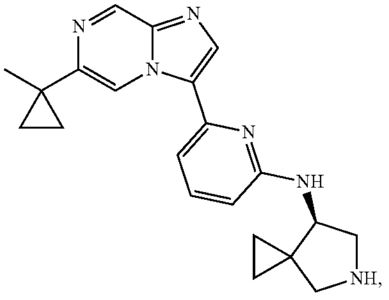

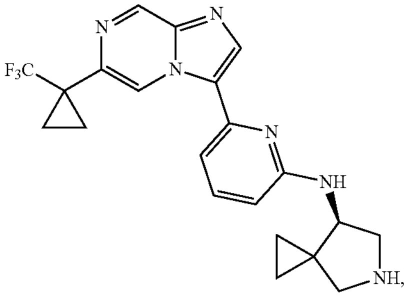

-continued

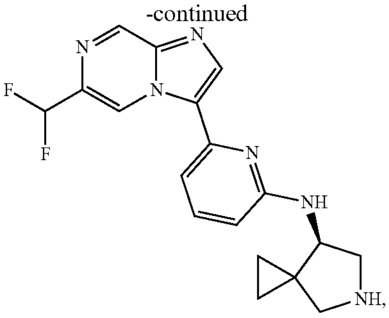

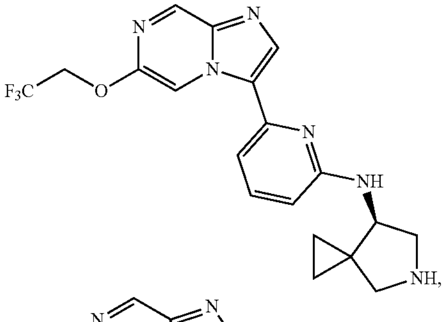 and

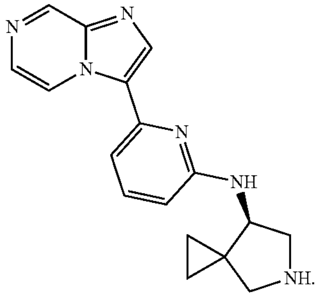

In one embodiment, the compound of Formula (I) is an inhibitor of at least one of IRAK1, IRAK4, and FLT3. In one embodiment, the compound of Formula (I) is an inhibitor of at least two of IRAK1, IRAK4, and FLT3. In one embodiment, the compound of Formula (I) is an inhibitor of IRAK1 and IRAK4. In one embodiment, the compound of Formula (I) is an inhibitor of IRAK1, IRAK4, and FLT3. In one embodiment, FLT3 is selected from WT FLT3, activated FLT3, and mutated FLT3. In one embodiment, the mutated FLT3 is D835Y mutated FLT3 or F691L mutated FLT3.

In another aspect, the present disclosure provides a composition comprising a compound of Formula (I) wherein the composition further comprises a formulary ingredient, an adjuvant, or a carrier. In one embodiment, the composition is used in combination with one or more of: a chemotherapy agent, a BCL2 inhibitor, an immune modulator, a BTK inhibitor, a DNA methyltransferase inhibitor/hypomethylating agent, an anthracycline, a histone deacetylase (HDAC) inhibitor, a purine nucleoside analogue (antimetabolite), an isocitrate dehydrogenase 1 or 2 (IDH1 and/or IDH2) inhibitor, an antibody-drug conjugate, an mAbs/immunotherapy, a Plk inhibitor, a MEK inhibitor, a CDK inhibitor, a CDK9 inhibitor, a CDK8 inhibitor, a retinoic acid receptor agonist, a TP53 activator, a CELMoD, a smoothened receptor antagonist, an ERK inhibitor including an ERK2/MAPK1 or ERK1/MAPK3 inhibitor, a PI3K inhibitor, an mTOR inhibitor, a steroid or glucocorticoid receptor modulator, an EZH2 inhibitor, a hedgehog (Hh) inhibitor, a Topoisomerase I inhibitor, a Topoisomerase II inhibitor, an aminopeptidase/Leukotriene A4 hydrolase inhibitor, a FLT3/Axl/ALK inhibitor, a FLT3/KIT/PDGFR, PKC, and/or KDR inhibitor, a Syk inhibitor, an E-selectin inhibitor, an NEDD8-activator, an MDM2 inhibitor, a PLK1 inhibitor, an Aura A inhibitor, an aurora kinase inhibitor, an EGFR inhibitor, an AuroraB/C/VEGFR1/2/3/FLT3/CSF-1R/Kit/PDGFRA/B inhibitor, an AKT 1, 2, and/or 3 inhibitor, a ABL1/2/SRC/EPHA2/LCK/YES1/KIT/PDGFRB/FYN inhibitor, a farnesyltransferase inhibitor, a BRAF/MAP2K1/MAP2K2 inhibitor, a Menin-KMT2A/MLL inhibitor, and a multikinase inhibitor. In one embodiment, the composition is used in combination with a BCL2 inhibitor. In one embodiment, the BCL2 inhibitor is venetoclax or a pharmaceutically acceptable salt thereof.

In yet another aspect, the present disclosure provides a method of treating a disease or disorder in a subject, the method comprising administering to the subject a therapeutically effective amount of a compound of Formula (I) or a composition comprising a compound of Formula (I). In one embodiment, the method comprises administering to the subject a composition comprising the therapeutically effective amount of the compound of Formula (I) and a formulary ingredient, an adjuvant, or a carrier. In one embodiment, the disease or disorder is responsive to at least one of interleukin-1 receptor-associated kinase (IRAK) inhibition and fms-like tyrosine kinase 3 (FLT3) inhibition. In one embodiment, the administration comprises parenteral administration, a mucosal administration, intravenous administration, subcutaneous administration, topical administration, intradermal administration, oral administration, sublingual administration, intranasal administration, or intramuscular administration. In one embodiment, the compound of Formula (I) is administered to the subject in an amount of from about 0.005 mg/kg subject body weight to about 1,000 mg/kg subject body weight. In one embodiment, the disease or disorder comprises a hematopoietic cancer. In one embodiment, the disease or disorder comprises myelodysplastic syndrome (MDS) and/or acute myeloid leukemia (AML). In one embodiment, the disease or disorder comprises lymphoma, leukemia, chronic lymphocytic leukemia (CLL), chronic myeloid leukemia (CML), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL with MYD88 mutation, follicular lymphoma, or marginal zone lymphoma. In one embodiment, the disease or disorder comprises at least one cancer selected from glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, or one or more inflammatory diseases or autoimmune disease characterized by overactive IRAK1 and/or IRAK4, or combinations thereof. In one embodiment, the disease or disorder comprises one or more inflammatory diseases or autoimmune disease selected from chronic inflammation, sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, or combinations thereof. In one embodiment, the disease or disorder comprises: (i) MDS, MDS with a splicing factor mutation, MDS with a mutation in isocitrate dehydrogenase 1, MDS with a mutation in isocitrate dehydrogenase 2; or (ii) AML with a splicing factor mutation, AML having enhanced IRAK4-Long expression and/or activity relative to IRAK4-Short, and/or wherein the AML is not driven by FLT3 mutations but expresses IRAK4-Long. In one embodiment, the MDS with a splicing factor mutation comprises MDS with a splicing factor mutation in U2AF1 or SF3B1 and the AML splicing factor mutation comprises AML with a splicing factor mutation in U2AF1 or SF3B1. In one embodiment, the disease or disorder comprises DLBCL, and wherein the DLBCL comprises a L265P MYD88 mutant (ABC) subtype of DLBCL or a S219C MYD88 mutant (GCB) subtype of DLBCL. In one embodiment, the method further comprises administering to the subject one or more additional therapies selected from: a chemotherapy agent, a BCL2 inhibitor, an immune modulator, a BTK inhibitor, a DNA methyltransferase inhibitor/hypomethylating agent, an anthracycline, a histone deacetylase (HDAC) inhibitor, a purine nucleoside analogue (antimetabolite), an isocitrate dehydrogenase 1 or 2 (IDH1 and/or IDH2) inhibitor, an antibody-drug conjugate, an mAbs/immunotherapy, a Plk inhibitor, a MEK inhibitor, a CDK inhibitor, a CDK9 inhibitor, a CDK8 inhibitor, a retinoic acid receptor agonist, a TP53 activator, a CELMoD, a smoothened receptor antagonist, an ERK inhibitor including an ERK2/MAPK1 or ERK1/MAPK3 inhibitor, a PI3K inhibitor, an mTOR inhibitor, a steroid or glucocorticoid receptor modulator, an EZH2 inhibitor, a hedgehog (Hh) inhibitor, a Topoisomerase I inhibitor, a Topoisomerase II inhibitor, an aminopeptidase/Leukotriene A4 hydrolase inhibitor, a FLT3/Axl/ALK inhibitor, a FLT3/KIT/PDGFR, PKC, and/or KDR inhibitor, a Syk inhibitor, an E-selectin inhibitor, an NEDD8-activator, an MDM2 inhibitor, a PLK1 inhibitor, an Aura A inhibitor, an aurora kinase inhibitor, an EGFR inhibitor, an AuroraB/C/VEGFR1/2/3/FLT3/CSF-1R/Kit/PDGFRA/B inhibitor, an AKT 1, 2, and/or 3 inhibitor, a ABL1/2/SRC/EPHA2/LCK/YES1/KIT/PDGFRB/FYN inhibitor, a farnesyltransferase inhibitor, a BRAF/MAP2K1/MAP2K2 inhibitor, a Menin-KMT2A/MLL inhibitor, and a multikinase inhibitor. In one embodiment, the additional therapy is a BCL2 inhibitor. In one embodiment, the BCL2 inhibitor is venetoclax or a pharmaceutically acceptable salt thereof. In one embodiment, the disease or disorder is a BCL2 inhibitor resistant disease or disorder. In one embodiment, the disease or disorder is a venetoclax resistant disease or disorder. In one embodiment, the disease or disorder is a FLT3 inhibitor resistant disease or disorder. In one embodiment, disease or disorder is BCL2 inhibitor resistant acute myeloid leukemia (AML). In one embodiment, the disease or disorder is venetoclax resistant acute myeloid leukemia (AML). In one embodiment, the disease or disorder is FLT3 inhibitor resistant acute myeloid leukemia (AML). In one embodiment, the disease or disorder is BCL2 inhibitor resistant refractory acute myeloid leukemia (AML). In one embodiment, the disease or disorder is venetoclax resistant refractory acute myeloid leukemia (AML). In one embodiment, the disease or disorder is FLT3 inhibitor resistant refractory acute myeloid leukemia (AML). In one embodiment, the disease or disorder is BCL2 inhibitor resistant relapsed acute myeloid leukemia (AML). In one embodiment, the disease or disorder is venetoclax resistant relapsed acute myeloid leukemia (AML). In one embodiment, the disease or disorder is FLT3 inhibitor resistant relapsed acute myeloid leukemia (AML). In one embodiment, the compound of Formula (I) or the composition comprising a compound of Formula (I) and the one or more additional therapies are administered together in one administration or composition. In one embodiment, the compound of Formula (I) or the composition comprising a compound of Formula (I) and the one or more additional therapies are administered separately in more than one administration or more than one composition. In one embodiment, the disease or disorder is alleviated by inhibiting at least one of IRAK1, IRAK4, and FLT3 in the subject. In one embodiment, the disease or disorder is alleviated by inhibiting at least two of IRAK1, IRAK4, and FLT3 in the subject. In one embodiment, the disease or disorder is alleviated by inhibiting IRAK1 and IRAK4 in the subject. In one embodiment, the disease or disorder is alleviated by inhibiting IRAK1, IRAK4, and FLT3 in the subject. In one embodiment, FLT3 is selected from WT FLT3, activated FLT3, and mutated FLT3. In one embodiment, the mutated FLT3 is D835Y mutated FLT3 or F691L mutated FLT3.

DETAILED DESCRIPTION OF THE DISCLOSURE

The following related applications are incorporated by reference herein in their entirety, and for all purposes: U.S. Patent Application No. 62/414,058, Overexpression of U2AF1 as a Genetic Predictor of Activated IRAK, filed Oct. 28, 2016; U.S. Patent Application No. 62/429,289, Overexpression of U2AF1 as a Genetic Predictor of Activated IRAK, filed Dec. 2, 2016; PCT Patent Publication No. WO 2018081738, TREATMENT OF DISEASES ASSOCIATED WITH ACTIVATED IRAK, filed Oct. 30, 2017; U.S. patent application Ser. No. 16/339,692, TREATMENT OF DISEASES ASSOCIATED WITH ACTIVATED IRAK, filed Apr. 4, 2019; U.S. Patent Application No. 61/826,211, Combination Therapy for MDS, filed May 22, 2013; PCT Patent Publication No. WO 2014190163, Combination Therapy for MDS, filed May 22, 2014; U.S. Pat. No. 9,168,257, Combination Therapy for MDS, issued Oct. 27, 2015; U.S. Pat. No. 9,504,706, Combination Therapy for MDS, issued Nov. 29, 2016; U.S. Pat. No. 9,855,273, Combination Therapy for MDS, issued Jan. 2, 2018; U.S. Pat. No. 10,487,329, Methods and Compositions for the Treatment of Head and Neck Cancer, issued Nov. 26, 2019; U.S. Patent Application No. 62/375,965, Compounds, Compositions, Methods for Treating Diseases, and Methods for Preparing Compounds, filed Aug. 17, 2016; PCT Patent Publication No. WO 2018038988, Compounds, Compositions, Methods for Treating Diseases, and Methods for Preparing Compounds, filed Aug. 16, 2017; U.S. patent application Ser. No. 16/326,571, COMPOUNDS, COMPOSITIONS, METHODS FOR TREATING DISEASES, AND METHODS FOR PREPARING COMPOUNDS, filed Feb. 19, 2019; U.S. patent application Ser. No. 16/804,518, COMPOUNDS, COMPOSITIONS, METHODS FOR TREATING DISEASES, AND METHODS FOR PREPARING COMPOUNDS, filed Feb. 28, 2020; U.S. Patent Application No. 62/812,948, COMPOUNDS, COMPOSITIONS, METHODS FOR TREATING DISEASES, AND METHODS FOR PREPARING COMPOUNDS, filed Mar. 1, 2019; U.S. Patent Application No. 63/059,815, Multi-Cyclic IRAK and FLT3 Inhibiting Compounds and Uses Thereof, filed Jul. 31, 2020; International Patent Application No. PCT/US2021/044089, Multi-Cyclic IRAK and FLT3 Inhibiting Compounds and Uses Thereof, filed Jul. 31, 2021; U.S. Patent Application No. 63/125,654, Multi-Cyclic IRAK and FLT3 Inhibiting Compounds and Uses Thereof, filed Dec. 15, 2020; and U.S. Patent Application No. 63/285,663, IRAK Inhibitors Combination Therapies, filed Dec. 3, 2021.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the disclosure include inventive compounds (e.g., compounds of Formula (I)). Other embodiments include compositions (e.g., pharmaceutical compositions) comprising the inventive compound. Still other embodiments of the disclosure include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Yet further embodiments include methods for determining whether a particular patient is likely to be responsive to such treatment with the inventive compounds and compositions.

Unless otherwise noted, terms are to be understood according to conventional usage by those of ordinary skill in the relevant art.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

As used herein, in relation to compounds of Formulae (I), (II), (III), etc., the term "attached" signifies a stable covalent bond, certain preferred points of attachment being apparent to those of ordinary skill in the art.

As used herein (unless otherwise specified), the term "alkyl" means a monovalent, straight or branched hydrocarbon chain, which can be fully saturated, mono- or polyunsaturated and can include di- and multivalent radicals, having the number of carbon atoms designated (i.e., $C_1$-$C_{10}$ means one to ten carbons). For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-heptyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Double bonds can occur in any stable point along the chain and the carbon-carbon double bonds can have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds. Further examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "alkoxy" means any of the above alkyl, alkenyl, or alkynyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

The term "alkylene," by itself or as part of another substituent, means, unless otherwise stated, a divalent radical derived from an alkyl, alkenyl, or alkynyl group, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl, one or both rings can be substituted.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms can optionally be oxidized, and the nitrogen heteroatom can optionally be quaternized. The heteroatom(s) 0, N, P, S, and Si can be placed at any interior position of the heteroalkyl group or at the position at which the alkyl group is attached to the remainder of the molecule. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two heteroatoms can be consecutive, such as, for example, $—CH_2—NH—OCH_3$.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

As used herein (unless otherwise specified), the term "halogen" or "halo" means monovalent Cl, F, Br, or I. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

As used herein (unless otherwise specified), the term "aryl" means a monovalent, monocyclic or bicyclic, 5, 6, 7, 8, 9, 10, 11, or 12 member aromatic hydrocarbon group and also means polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. Examples of aryl groups include, but are not limited to, phenyl, naphthyl, tolyl, and xylyl. For an aryl that is bicyclic, one or both rings can be substituted.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Heteroaryl groups (or rings) can contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl, one or both rings can be substituted.

An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e. g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl, —$C_{0-16}$alkylCOOR$_4$, —$C_{0-16}$ alkylCONR$_5$R$_6$ wherein $R_4$, $R_5$ and $R_6$ are independently selected from hydrogen, $C_1$-$C_{11}$alkyl, aryl$C_0$-$C_{11}$alkyl, or $R_5$ and $R_6$ are taken together with the nitrogen to which they are attached forming a cyclic system containing 3 to 8 carbon atoms with or without one $C_{1-16}$alkyl, aryl$C_0$-$C_{16}$alkyl, or $C_0$-$Cl_{16}$alkylaryl substituent. Aryl includes but is not limited to pyrazolyl and triazolyl.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The terms "cycloalkyl" and "heterocycloalkyl", also referred to as "heterocyclyl", by themselves or in combination with other terms, mean, unless otherwise stated, cyclic versions of "alkyl" and "heteroalkyl," respectively. Examples of cycloalkyl include, but are not limited to, cyclopropyl, cyclobutyl, cyclopentyl, cyclohexyl, 1-cyclohexenyl, 3-cyclohexenyl, cycloheptyl, and the like. As used herein (unless otherwise specified), the term "heterocycloalkyl" or "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Additionally, for heterocycloalkyl, a heteroatom can occupy the position at which the heterocycle is attached to the remainder of the molecule. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl,). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl, one or both rings can be substituted and the like. A "cycloalkylene" and a "heterocycloalkylene," alone or as part of another substituent, means a divalent radical derived from a cycloalkyl and heterocycloalkyl, respectively.

As used herein (unless otherwise specified), the term "hetero atom" means an atom selected from nitrogen atom, oxygen atom, or sulfur atom.

As used herein (unless otherwise specified), the terms "hydroxy" or "hydroxyl" means a monovalent —OH group.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' can have a specified number of carbons (e.g., "$C_1$-$C_4$ alkylsulfonyl").

The term "carbonyloxy" represents a carbonyl group attached through an oxygen bridge.

In the above definitions, the terms "alkyl" and "alkenyl" can be used interchangeably in so far as a stable chemical entity is formed, as would be apparent to those skilled in the art.

The term "linker" refers to attachment groups interposed between substituents. In some embodiments, the linker includes amido (—CONH—R″ or —NHCO—R″), thioamido (—CSNH—R″ or —NHCS—R″), carboxyl (—$CO_2$—R″ or —OCOR″), carbonyl (—CO—R″), urea (—NHCONH—R″), thiourea (—NHCSNH—R″), sulfonamido (—$NHSO_2$—R″ or —$SO_2$NH—R″), ether (—O—R″), sulfonyl (—$SO_2$—R″), sulfoxyl (—SO—R″), carbamoyl (—$NHCO_2$—R″ or —OCONH—R″), or amino (—NHR″) linking moieties.

Each of the above terms (e.g., "alkyl," "heteroalkyl," "aryl," and "heteroaryl", and so forth) includes both substituted and unsubstituted forms of the indicated radical. Preferred substituents for each type of radical are provided herein.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

A "substituent group," as used herein, means a non-hydrogen substituent group that may be, and preferably is, a group selected from the following moieties:

(A) —$NH_2$, —SH, —CN, —$CF_3$, —$NO_2$, halogen, hydroxy, oxo, —CN, methanoyl (—COH), carboxy (—$CO_2$H), nitro (—$NO_2$), —N($CH_3$)$_2$, ethynyl (—CCH), propynyl, sulfo (—$SO_3$H), —$CONH_2$, —$CONHCH_3$, —CON($CH_3$)$_2$, unsubstituted $C_1$-$C_7$ alkyl, unsubstituted $C_1$-$C_7$ heteroalkyl, unsubstituted $C_1$-$C_7$ perfluorinated alkyl, unsubstituted $C_1$-$C_7$ alkoxy, unsubstituted $C_1$-$C_7$ haloalkoxy, unsubstituted cycloalkyl, unsubstituted heterocycloalkyl, unsubstituted aryl, unsubstituted heteroaryl, and (B) $C_1$-$C_7$ alkyl, $C_1$-$C_7$ heteroalkyl, $C_1$-$C_7$ perfluorinated alkyl, $C_1$-$C_7$ alkoxy, $C_1$-$C_7$ haloalkoxy, cycloalkyl, heterocycloalkyl, aryl, and heteroaryl, substituted with at least one substituent selected from:

(i) —$NH_2$, —SH, —CN, —$CF_3$, —$NO_2$, halogen, hydroxy, oxo, —CN, methanoyl (—COH), carboxy (—$CO_2H$), nitro (—$NO_2$), —$N(CH_3)_2$, ethynyl (—CCH), propynyl, sulfo (—$SO_3H$), $CONH_2$, —$CONHCH_3$, —$CON(CH_3)_2$, unsubstituted $C_1$-$C_7$ alkyl, unsubstituted $C_1$-$C_7$ heteroalkyl, unsubstituted $C_1$-$C_7$ perfluorinated alkyl, unsubstituted $C_1$-$C_7$ alkoxy, unsubstituted $C_1$-$C_7$ haloalkoxy, unsubstituted cycloalkyl, unsubstituted heterocycloalkyl, unsubstituted aryl, unsubstituted heteroaryl, and (ii) $C_1$-$C_7$ alkyl, $C_1$-$C_7$ heteroalkyl, $C_1$-$C_7$ perfluorinated alkyl, $C_1$-$C_7$ alkoxy, $C_1$-$C_7$ haloalkoxy, cycloalkyl, heterocycloalkyl, aryl, and heteroaryl, substituted with at least one substituent selected from:

(a) —$NH_2$, —SH, —CN, —$CF_3$, —$NO_2$, halogen, hydroxy, oxo, —CN, methanoyl (—COH), carboxy (—$CO_2H$), nitro (—$NO_2$), —$N(CH_3)_2$, ethynyl (—CCH), propynyl, sulfo (—$SO_3H$), $CONH_2$, —$CONHCH_3$, —$CON(CH_3)_2$, unsubstituted $C_1$-$C_7$- alkyl, unsubstituted $C_1$-$C_7$ heteroalkyl, unsubstituted $C_1$-$C_7$ perfluorinated alkyl, unsubstituted $C_1$-$C_7$ alkoxy, unsubstituted $C_1$-$C_7$ haloalkoxy, unsubstituted cycloalkyl, unsubstituted heterocycloalkyl, unsubstituted aryl, unsubstituted heteroaryl, and (b) $C_1$-$C_7$ alkyl, $C_1$-$C_7$ heteroalkyl, $C_1$-$C_7$ perfluorinated alkyl, $C_1$-$C_7$ alkoxy, $C_1$-$C_7$ haloalkoxy, cycloalkyl, heterocycloalkyl, aryl, and heteroaryl, substituted with at least one substituent selected from: —$NH_2$, —SH, —CN, —$CF_3$, —$NO_2$, halogen, hydroxy, oxo, —CN, methanoyl (—COH), carboxy (—$CO_2H$), nitro (—$NO_2$), —$N(CH_3)_2$, ethynyl (—CCH), propynyl, sulfo (—$SO_3H$), $CONH_2$, —$CONHCH_3$, —$CON(CH_3)_2$, unsubstituted $C_1$-$C_7$ alkyl, unsubstituted $C_1$-$C_7$ heteroalkyl, unsubstituted $C_1$-$C_7$ perfluorinated alkyl, unsubstituted $C_1$-$C_7$ alkoxy, unsubstituted $C_1$-$C_7$ haloalkoxy, unsubstituted cycloalkyl, unsubstituted heterocycloalkyl, unsubstituted aryl, unsubstituted heteroaryl.

A "size-limited substituent" or "size-limited substituent group," as used herein, means a group, e.g., selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2-20-membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4-8-membered heterocycloalkyl.

A "lower substituent" or "lower substituent group," as used herein, means a group, e.g., selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2-8-membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5-7-membered heterocycloalkyl.

The term "about" used in the context of a numeric value indicates a range of +/−10% of the numeric value, unless expressly indicated otherwise.

Some compounds of the disclosure can have one or more chiral centers and can exist in and be isolated in optically active and racemic forms, for any of the one or more chiral centers. Some compounds can exhibit polymorphism. The compounds of the present disclosure (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing," "analyzing," and "assaying" can be used interchangeably and can include quantitative and/or qualitative determinations.

As used herein, the term "monitoring" with reference to a type of cancer refers to a method or process of determining the severity or degree of the type of cancer or stratifying the type of cancer based on risk and/or probability of mortality. In some embodiments, monitoring relates to a method or process of determining the therapeutic efficacy of a treatment being administered to a patient.

As used herein, "outcome" can refer to an outcome studied. In some embodiments, "outcome" can refer to survival/mortality over a given time horizon. For example, "outcome" can refer to survival/mortality over 1 month, 3 months, 6 months, 1 year, 5 years, or 10 years or longer. In some embodiments, an increased risk for a poor outcome indicates that a therapy has had a poor efficacy, and a reduced risk for a poor outcome indicates that a therapy has had a good efficacy.

As used herein, the term "high risk clinical trial" refers to one in which the test agent has "more than minimal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms “modulated” or “modulation,” or “regulated” or “regulation” and “differentially regulated” can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term “subject” refers to any suitable (e.g., treatable) member of the animal kingdom. In the methods, the subject is preferably a mammal. In the methods, the subject is preferably a human patient. In the methods, the subject may be a mammalian pediatric patient. In the methods, the pediatric patient is a mammalian (e.g., preferably human) patient under 18 years of age, while an adult patient is 18 or older.

As used herein, the term “treating” (and its variations, such as “treatment” “treating,” “treat,” and the like) is, unless stated otherwise, to be considered in its broadest context and refers to obtaining a desired pharmacologic and/or physiologic effect. In particular, for example, the term “treating” may not necessarily imply or require that an animal is treated until total recovery. Accordingly, “treating” includes amelioration of the symptoms, relief from the symptoms or effects associated with a condition, decrease in severity of a condition, or preventing, preventively ameliorating symptoms, or otherwise reducing the risk of developing a particular condition. In some aspects, “treating” may not require or include prevention. As used herein, reference to “treating” an animal includes but is not limited to prophylactic treatment and therapeutic treatment. The effect can be prophylactic in terms of completely or partially preventing a disease or symptom thereof and/or can be therapeutic in terms of a partial or complete cure for a disease and/or adverse effect attributable to the disease. “Treatment,” as used herein, covers any treatment of a disease in a subject, preferably in a mammal (e.g., in a human), and may include one or more of: (a) preventing the disease from occurring in a subject which may be predisposed to the disease but has not yet been diagnosed as having it; (b) inhibiting the disease, i.e., arresting its development; and (c) relieving the disease, i.e., causing regression or elimination of the disease and/or relieving one or more disease symptoms. In particular aspects of the methods, such as conditions or disorders characterized by dysregulated IRAK expression or dysregulated (e.g., hyperactive) IRAK-mediated signaling pathway(s), treatment may be or include reducing such expression or signaling. “Treatment” can also encompass delivery of an agent or administration of a therapy in order to provide for a pharmacologic effect, even in the absence of a disease or condition. Any of the compositions (e.g., pharmaceutical compositions) described herein can be used to treat a suitable subject.

“Therapeutically effective amount” means an amount effective to achieve a desired and/or beneficial effect. An effective amount can be administered in one or more administrations. In the methods, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size or blood cell count, or any other suitable measurement.

As used herein, the term “marker” or “biomarker” refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, an mRNA “isoform” is an alternative transcript for a specific mRNA or gene. This term includes pre-mRNA, immature mRNA, mature mRNA, cleaved or otherwise truncated, shortened, or aberrant mRNA, modified mRNA (e.g. containing any residue modifications, capping variants, polyadenylation variants, etc.), and the like.

“Antibody” or “antibody peptide(s)” refer to an intact antibody, or a binding fragment thereof that competes with the intact antibody for specific binding; this definition also encompasses monoclonal and polyclonal antibodies. Binding fragments are produced by recombinant DNA techniques, or by enzymatic or chemical cleavage of intact antibodies. Binding fragments include Fab, Fab', $F(ab')_2$, Fv, and single-chain antibodies. An antibody other than a “bispecific” or “bifunctional” antibody is understood to have each of its binding sites identical. An antibody, for example, substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

Embodiments of the disclosure set forth herein include inventive compounds (e.g., compounds of Formula (I), such as compounds of Formula (II) and Formula (III)). Other embodiments include compositions (e.g., pharmaceutical compositions) comprising the inventive compound. Still other embodiments of the disclosure include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer or blood disorders). Some embodiments include methods of determining whether a patient is suitable for, or likely to respond favorably to, a particular treatment. Further embodiments include methods for making the inventive compounds. Additional embodiments of the disclosure are also discussed herein.

Compounds and Compositions, Including Pharmaceutical Compositions

Some embodiments of the disclosure include compounds having a structure according to Formula (I):

(I)

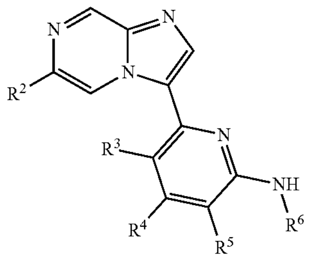

or a salt, ester, solvate, optical isomer, geometric isomer, salt of an isomer, prodrug, or derivative thereof. In some embodiments, the compound is a pharmaceutically acceptable salt, ester, solvate, optical isomer, geometric isomer, salt of an isomer, prodrug, or derivative of a compound of Formula (I). In some embodiments, the compound is not an ester, not a solvate, and not a prodrug.

In exemplary embodiments, $R^2$, $R^3$, $R^4$, and $R^5$ are independently selected from H, halogen, hydroxy, oxo, —CN, amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, spiro-fused cycloalkyl, heterocyclyl, aryl, heteroaryl, or fused ring heteroaryl, which amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_2$-$C_6$ alkoxy, cycloalkyl, spiro-fused cycloalkyl, heterocyclyl, aryl, heteroaryl, or fused ring heteroaryl is optionally substituted with one or more of halogen, hydroxy, (=O), —O, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl, wherein two adjacent optional substituents can bond or fuse to form a ring.

In some embodiments, $R^2$ can be H, halogen, hydroxy, oxo, —CN, amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, heterocyclyl, spiro-fused cycloalkyl, aryl, heteroaryl, or fused ring heteroaryl, which amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, heterocyclyl, spiro-fused cycloalkyl, heterocyclyl, aryl, heteroaryl, or fused ring heteroaryl is optionally substituted with one or more of halogen, hydroxy, oxo (=O), —O, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ heteroalkyl, $C_1$-$C_7$ haloalkyl, $C_1$-$C_7$ perfluorinated alkyl, $C_1$-$C_7$ alkoxy, $C_1$-$C_7$ haloalkoxy, cycloalkyl, heterocyclyl, spiro-fused cycloalkyl, aryl, fused ring aryl, heteroaryl, fused ring heteroaryl, or $C_1$-$C_7$ alkyl which is substituted with cycloalkyl; $R^3$, $R^4$, and $R^5$ can be H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more of halogen, hydroxy, oxo, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl, wherein two adjacent optional substituents can bond or fuse to form a ring.

$R^6$ can be (Ia)

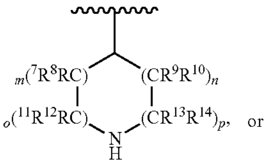

or (Ib)

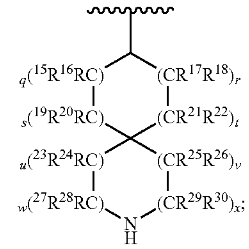

;

$R^7$, $R^8$, $R^9$, $R^{10}$, $R^{11}$, $R^{12}$, $R^{13}$, $R^{14}$ can be H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl; $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ can be H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl; and m, n, o, p, q, r, s, t, u, v, w, and x can be 0, 1, 2, 3, 4, or 5, where q+r+s+t is at least 1, and where u+v+w+x is at least 1.

In some embodiments, $R^2$ is H, halogen, hydroxy, O-aryl, amino, $C_1$-$C_7$ alkyl, $C_2$-$C_7$ alkenyl, $C_2$-$C_7$ alkynyl, $C_1$-$C_7$ alkoxy, cycloalkyl, heterocyclyl, aryl, fused ring aryl, heteroaryl, or fused ring heteroaryl, which O-aryl, amino, $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, fused ring aryl, heteroaryl, or fused ring heteroaryl is optionally substituted with one or more of halogen, hydroxy, (=O), —O, —CN, amino, cycloalkyl, spiro-fused cycloalkyl, heterocyclyl, aryl, heteroaryl, fused ring aryl, fused ring heteroaryl, pyrrolyl, piperidyl, piperazinyl, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl. In some embodiments, $R^2$ is H, halogen, hydroxy, O-aryl, amino, $C_1$-$C_7$ alkyl, $C_1$-$C_7$ alkoxy, cycloalkyl, heterocyclyl, aryl, fused ring aryl, heteroaryl, or fused ring heteroaryl which O-aryl, amino, $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, heteroaryl, or fused ring heteroaryl is optionally substituted with one or more of halogen, hydroxy, amino, cycloalkyl, spiro-fused cycloalkyl, heterocyclyl, aryl, heteroaryl, pyrrolyl, piperidyl, piperazinyl, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl. In some embodiments, $R^2$ is H, $C_1$, hydroxy, —$NHCH_3$, —$N(CH_3)_2$, —$OCH_3$, —$OCF_3$, —$OCHF_2$, —OPh, —$CF_3$, —$CHF_2$, unsubstituted $C_1$-$C_7$ alkyl, substituted amino, substituted $C_1$-$C_7$ alkyl, substituted cycloalkyl, unsubstituted cycloalkyl, unsubstituted heterocyclyl, substituted pyrazolyl, substituted fused ring heteroaryl, or unsubstituted fused ring heteroaryl. In some embodiments, $R^2$ is not H.

In some embodiments, $R^3$ is H, halogen, hydroxy, —CN, methanoyl (—COH), carboxy (—$CO_2H$), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl. In some embodiments, $R^3$ is H, halogen, hydroxy, —CN, methyl, —$CF_3$, or methoxy.

In some embodiments, $R^4$ is H, halogen, hydroxy, —CN, methanoyl (—COH), carboxy (—$CO_2H$), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl. In some embodiments, $R^4$ is H, halogen, hydroxy, —CN, methyl, —$CF_3$, or methoxy.

In some embodiments, $R^5$ is H, halogen, hydroxy, —CN, methanoyl (—COH), carboxy (—$CO_2H$), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl. In some embodiments, $R^5$ is H, halogen, hydroxy, —CN, methyl, —$CF_3$, or methoxy.

In some embodiments, $R^4$ is methyl or —$CF_3$, and at least one of $R^3$ and $R^5$ is H or halogen.

In some embodiments, there is a chiral center at the $R^6$ attachment carbon. In some embodiments, the chiral center is an R chiral center, an S chiral center, or a racemate. In certain embodiments, the chiral center can be represented by the following bonds 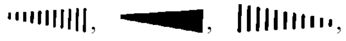 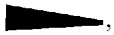, or ——. Where a chiral center is possible at other positions of the compounds according to Formula (I), as would appreciated by one skilled in the art, the straight bond shown can also be can be 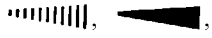 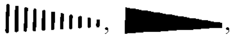, or ——.

In some embodiments, $R^6$ is (Ia)

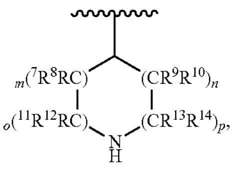

or (Ib)

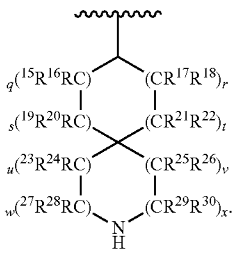

In some embodiments, $R^7$, $R^8$, $R^9$, $R^{10}$, $R^{11}$, $R^{12}$, $R^{13}$, $R^{14}$ are independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, cycloalkyl, spiro-fused cycloalkyl, heterocyclyl, aryl, heteroaryl, or fused ring heteroaryl is optionally substituted with one or more halogen, hydroxy, oxo, methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

In one embodiment, at least one of $R^7$, $R^1$, $R^9$, $R^{10}$, $R^{11}$, $R^{12}$, $R^{13}$, and $R^{14}$ is not H. In another embodiment, each of $R^7$, $R^8$, $R^9$, $R^{10}$, $R^{11}$, $R^{12}$, $R^{13}$, and $R^{14}$, if present, is H.

In some embodiments, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, cycloalkyl, spiro-fused cycloalkyl, heterocyclyl, aryl, heteroaryl, or fused ring heteroaryl is optionally substituted with one or more halogen, hydroxy, oxo, methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

In one embodiment, at least one of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ is not H. In another embodiment, each of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$, if present, is H.

In some embodiments, m, n, o, p, q, r, s, t, u, v, w, and x are independently selected from 0, 1, 2, 3, 4, or 5, where q+r+s+t is at least 1, and where u+v+w+x is at least 1.

Some embodiments of the disclosure include compounds having a structure according to Formula (I):

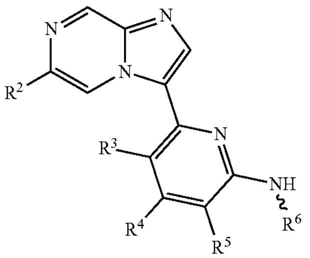

wherein the wavy bond from Y to $R^6$ (i.e., ) indicates that, in some instances, there is a chiral center at the $R^6$ attachment carbon. In some embodiments, where there is a chiral center at the $R^6$ attachment carbon, the wavy bond can indicate an R chiral center, an S chiral center, or a racemate. In certain embodiments,  can be , , , , or . Where a chiral center is possible at other positions of the compounds according to Formula (I), as would appreciated by one skilled in the art, the straight bond shown can also be can be , , 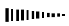, , or .

In some embodiments, $R^6$ is (Ia), giving a structure of Formula (II), as follows:

(II)

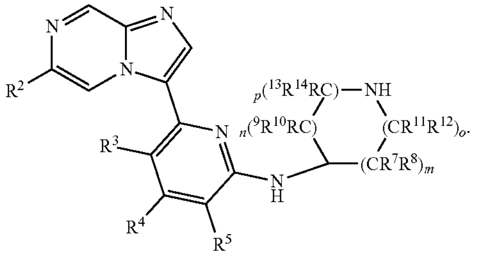

In some embodiments according to Formula (II), m is 0 or 1, n is 0 or 1, o is 0 or 1, and p is 0 or 1.

In some embodiments, $R^7$, $R^8$, $R^9$, and $R^{10}$ are H, and at least one of $R^{11}$, $R^{12}$, $R^{13}$, and $R^{14}$ is not H, and/or $R^{11}$, $R^{12}$, $R^{13}$, and $R^{14}$ are H, and at least one of $R^7$, $R^8$, $R^9$, and $R^{10}$ is not H. In particular embodiments, $R^7$, $R^8$, $R^9$, $R^{10}$, $R^{11}$, $R^{12}$, $R^{13}$, and $R^{14}$ are independently selected from H, halogen, hydroxy, oxo, methanoyl (—COH), carboxy (—$CO_2H$), $C_1$-$C_7$ alkyl, $C_1$-$C_7$ alkoxy, cycloalkyl, or spiro-fused cycloalkyl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, cycloalkyl, or spiro-fused cycloalkyl is optionally substituted with one or more halogen. In some embodiments, $R^7$, $R^1$, $R^9$, and $R^{10}$ are H, and at least one of $R^{11}$, $R^{12}$, $R^{13}$, and $R^{14}$ is halogen, hydroxy, oxo, methanoyl (—COH), carboxy (—$CO_2H$), $C_1$-$C_7$ alkyl, $C_1$-$C_7$ alkoxy, cycloalkyl, or spiro-fused cycloalkyl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, cycloalkyl, or spiro-fused cycloalkyl is optionally substituted with one or more halogen. In some embodiments, $R^{11}$, $R^{12}$, $R^{13}$, and $R_{14}$ are H, and at least one of $R^7$, $R^1$, $R^9$, and $R^{10}$ is halogen, hydroxy, oxo, methanoyl (—COH), carboxy (—$CO_2H$), $C_1$-$C_7$ alkyl, $C_1$-$C_7$ alkoxy, cycloalkyl, or spiro-fused cycloalkyl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, cycloalkyl, or spiro-fused cycloalkyl is optionally substituted with one or more halogen. In some embodiments, at least one of $R^7$, $R^1$, $R^9$, and $R^{10}$ is halogen, hydroxyl, $C_1$-$C_7$ alkyl, $C_1$-$C_7$ haloalkyl, $C_1$-$C_7$ alkoxy, cycloalkyl, or spiro-fused cycloalkyl. In some embodiments, at least one of $R^7$, $R^8$, $R^9$, and $R^{10}$ is F, hydroxyl, methyl, methoxy, —$CHF_2$, —$CF_3$, cyclopropyl, spiro-fused cyclopropyl, spiro-fused cyclobutyl, or spiro-fused cyclopentyl. In some embodiments, both of $R^7$ and $R^8$ or both of $R^9$ and $R^{10}$ are F, or both of $R^7$ and $R^8$ or both of $R^9$ and $R^{10}$ are methyl. In some embodiments, at least one of $R^{11}$, $R^{12}$, $R^{13}$, and $R^{14}$ is halogen, hydroxyl, $C_1$-$C_7$ alkyl, $C_1$-$C_7$ haloalkyl, $C_1$-$C_7$ alkoxy, cycloalkyl, or spiro-fused cycloalkyl. In some embodiments, at least one of $R^{11}$, $R^{12}$, $R^{13}$, and $R^{14}$ is F, hydroxyl, methyl, methoxy, —$CHF_2$, —$CF_3$, cyclopropyl, spiro-fused cyclopropyl, spiro-fused cyclobutyl, or spiro-fused cyclopentyl. In some embodiments, both of $R^{11}$ and $R^{12}$ or both of $R^{13}$ and $R^{14}$ are F, or wherein both of $R^{11}$ and $R^{12}$ or both of $R^{13}$ and $R^{14}$ are methyl Further to any embodiment above wherein the compound has the structure of Formula (II), the compound can have a structure according to any of (IIa)-(IIe), wherein V, W, X, Y, and Z can independently represent any of $R^7$, $R^8$, $R^9$, $R^{10}$, $R^{11}$, $R^{12}$, $R^{13}$, or $R^{14}$, and wherein at least one of V, W, X, Y, and Z is not H.

(IIa)

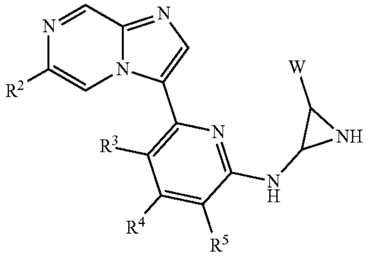

(IIb)

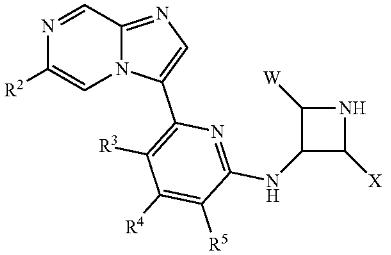

(IIc)

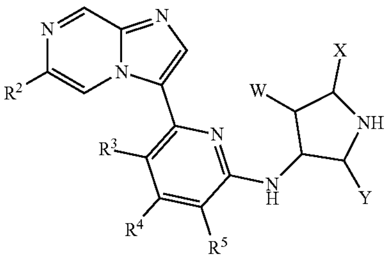

-continued (IId)

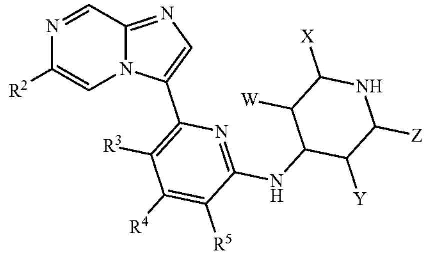

(IIe)

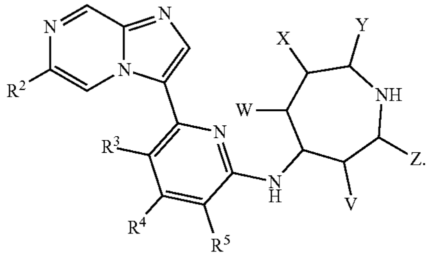

In an embodiment, the compound of Formula (II) is a compound of Formula (IIf)

Formula (IIf)

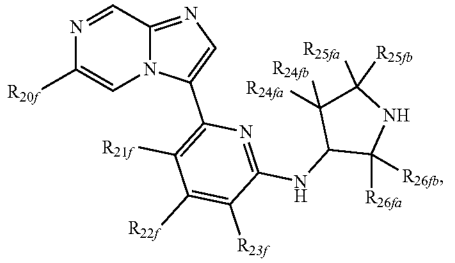

or a salt, ester, solvate, optical isomer, geometric isomer, or salt of an isomer thereof; wherein:

$R_{20f}$ is selected from H, halogen, $C_1$-$C_6$ alkyl, $C_1$-$C_6$ alkoxy, $C_3$-$C_6$ cycloalkyl, —O—$(CH_2)_a$—($C_3$-$C_6$ cycloalkyl), and $C_3$-$C_9$ heterocyclyl, wherein $C_1$-$C_6$ alkyl and $C_1$-$C_6$ alkoxy are each optionally substituted with one or more substituents selected from —OH and halogen, $C_3$-$C_6$cycloalkyl is optionally substituted with one or more substituents selected from $C_1$-$C_6$ alkyl and halogen, and $C_3$-$C_9$ heterocyclyl is optionally substituted with one or more substituents selected from halogen, $C_1$-$C_6$ alkyl, $C_1$-$C_6$ alkoxy, —OH, and ═O;

$R_{21f}$, $R_{22f}$, and $R_{23f}$ are each independently selected from H and halogen;

$R_{24fa}$, $R_{24fb}$, $R_{25fa}$, $R_{25fb}$, $R_{26fa}$, and $R_{26fb}$ are each independently selected from H, halogen, —OH, $C_1$-$C_6$ alkyl, and $C_1$-$C_6$ alkoxy, wherein $C_1$-$C_6$ alkyl and $C_1$-$C_6$ alkoxy are each optionally substituted with one or more halogen atoms; and a is selected from 0, 1, 2, 3, 4, 5, and 6.

In an embodiment, one or more of $R_{24fa}$, $R_{24fb}$, $R_{25fa}$, $R_{25fb}$, $R_{26fa}$, and $R_{26fb}$ is independently selected from halogen, —OH, optionally substituted $C_1$-$C_6$ alkyl, and optionally substituted $C_1$-$C_6$ alkoxy. In another embodiment, each of $R_{24fa}$, $R_{24fb}$, $R_{25fa}$, $R_{25fb}$, $R_{26fa}$, and $R_{26fb}$ is H.

In an embodiment, $R_{20f}$ is H. In another embodiment, $R_{20f}$ is not H. In an embodiment, $R_{20f}$ is unsubstituted $C_1$-$C_6$ alkyl. In one embodiment, $R_{20f}$ is t-butyl. In another embodiment, $R_{20f}$ is $C_1$-$C_6$ alkyl substituted with one or more —OH and/or halogen. In one embodiment, $R_{20f}$ is $C_1$-$C_6$ alkyl substituted with one or more —OH and/or F. In one embodiment, $R_{20f}$ is selected from

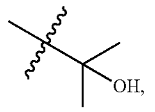

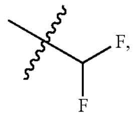

and

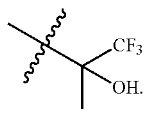

In another embodiment, $R_{20f}$ is unsubstituted $C_1$-$C_6$ alkoxy. In one embodiment, $R_{20f}$ is selected from —$OCH_3$, —$OCH_2CH_3$, and

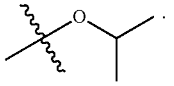 [SMILES: *OC(C)C]

In another embodiment, $R_{20f}$ is $C_1$-$C_6$ alkoxy substituted with one or more fluorine atoms. In one embodiment, $R_{20f}$ is selected from

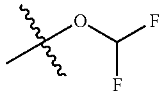

and

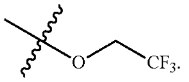

In another embodiment, $R_{20f}$ is $C_3$-$C_6$ cycloalkyl. In one embodiment, $R_{20f}$ is unsubstituted $C_3$ cycloalkyl. In one embodiment, $R_{20f}$ is $C_3$ cycloalkyl substituted with $C_1$-$C_6$ alkyl. In one embodiment, $R_{20f}$ is

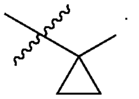 [SMILES: *C1(C)CC1]

In one embodiment, $R_{20f}$ is $C_3$ cycloalkyl substituted with one or more fluorine atoms. In one embodiment, $R_{20f}$ is

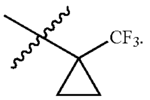 [SMILES: *C1(C(F)(F)F)CC1]

In another embodiment, $R_{20f}$ is —O—$(CH_2)_a$—($C_3$ cycloalkyl). In one embodiment, $R_{20f}$ is

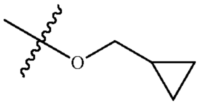

In another embodiment, $R_{20f}$ is unsubstituted $C_3$-$C_9$ heterocyclyl. In one embodiment, $R_{20f}$ is selected from pyrrolidinyl and

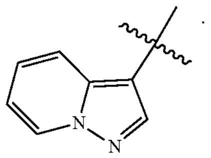 [SMILES: *c1cnn2ccccc12]

In another embodiment, $R_{20f}$ is $C_3$-$C_9$ heterocyclyl substituted with one or more substituents selected from halogen, $C_1$-$C_6$ alkyl, $C_1$-$C_6$ alkoxy, —OH, =O, and —$O^-$ wherein adjacent substituents can bond or fuse to form a ring. In one embodiment, $R_{20f}$ is

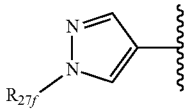

wherein $R_{20f}$ is selected from $C_1$-$C_6$ alkyl, $C_3$-$C_6$ cycloalkyl, and $C_3$-$C_9$ heterocyclyl, wherein $C_1$-$C_6$ alkyl and $C_3$-$C_6$ cycloalkyl are each optionally substituted with one or more halogen and/or —OH. In one embodiment, $R_{20f}$ is

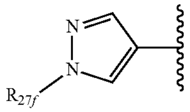

wherein $R_{27f}$ is unsubstituted $C_1$-$C_6$ alkyl. In one embodiment, $R_{20f}$ is

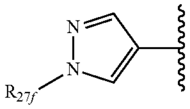

wherein $R_{27f}$ is —$CH_3$. In one embodiment, $R_{20f}$ is

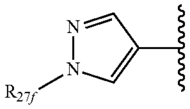

wherein $R_{27f}$ is $C_1$-$C_6$ alkyl substituted with one or more —OH and/or F. In one embodiment, $R_{20f}$ is

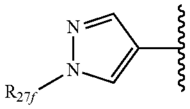

wherein $R_{27f}$ is selected from

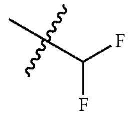

and

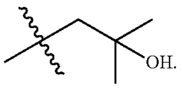

In another embodiment, $R_{20f}$ is pyrrolidinyl substituted with one or more substituents selected from halogen, $C_1$-$C_6$ alkyl, $C_1$-$C_6$ alkoxy, —OH, =O, and —$O^-$ wherein adjacent substituents can bond or fuse to form a ring. In one embodiment, $R_{20f}$ is

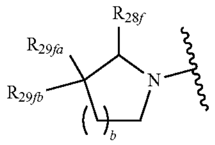

wherein $R_{28f}$ is selected from H and =O, $R_{29fa}$ and $R_{29fb}$ are each independently selected from H, $C_1$-$C_6$ alkyl, —OH, and halogen, wherein the $C_1$-$C_6$ alkyl is optionally substituted with one or more halogen, and b is 1 or 2. In one embodiment, $R_{29fa}$ and $R_{29fb}$ are each independently selected from H, —$CH_3$,

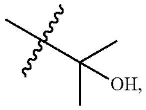 [SMILES: *C(C)(C)O]

—$CF_3$, —OH, and F. In one embodiment, $R_{20f}$ is selected from

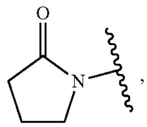
,
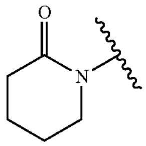
,
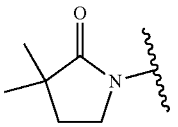
,
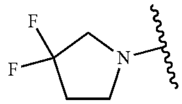
,
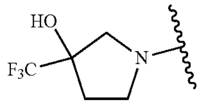
, and
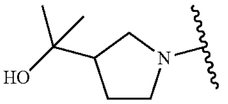

In one embodiment, $R_{20f}$ is

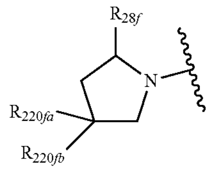

wherein $R_{28f}$ is =O and $R_{220fa}$ and $R_{220fb}$ are each independently selected from H, $C_1$-$C_6$ alkyl, and $C_1$-$C_6$ alkoxy wherein $C_1$-$C_6$ alkyl and $C_1$-$C_6$ alkoxy optionally bond or fuse to form a ring. In one embodiment, $R_{20f}$ is

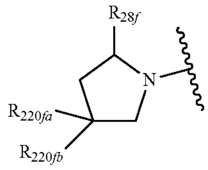

wherein $R_{28f}$ is =O and $R_{220fa}$ and $R_{220fb}$ are each —$CH_3$. In one embodiment, $R_{20f}$ is

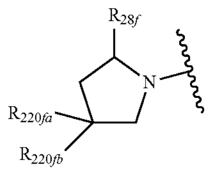

wherein $R_{28f}$ is =O and $R_{220fa}$ and $R_{220fb}$ bond or fuse to form oxetanyl. In another embodiment, $R_{20f}$ is

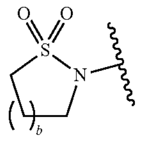

wherein b is 1 or 2. In another embodiment, $R_{20f}$ is selected from

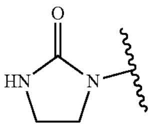

and

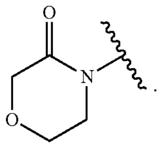

.

In an embodiment, each of $R_{21f}$, $R_{22f}$, and $R_{23f}$ is H. In an embodiment, $R_{21f}$ and $R_{23f}$ are each independently halogen and $R_{22f}$ is H. In one embodiment, $R_{21f}$ and $R_{23f}$ are each F and $R_{22f}$ is H. In an embodiment, $R_{21f}$ and $R_{23f}$ are each H and $R_{22f}$ is halogen. In one embodiment, $R_{21f}$ and $R_{23f}$ are each H and $R_{22f}$ is F.

In an embodiment, each of $R_{24fa}$, $R_{24fb}$, $R_{25fa}$, $R_{25fb}$, $R_{26fa}$, and $R_{26fb}$ is H. In an embodiment, each of $R_{25fa}$, $R_{25fb}$, $R_{26fa}$, and $R_{26fb}$ is H and $R_{24fa}$ and/or $R_{24fb}$ is halogen. In one embodiment, each of $R_{24fb}$, $R_{25fa}$, $R_{25fb}$, $R_{26fa}$, and $R_{26fb}$ is H and $R_{24fa}$ is F. In one embodiment, each of $R_{25fa}$, $R_{25fb}$, $R_{26fa}$, and $R_{26fb}$ is H and each of $R_{24fa}$ and $R_{24fb}$ is F. In an embodiment, $R_{25fa}$, $R_{25fb}$, $R_{26fa}$, and $R_{26fb}$ are each H and $R_{24fa}$ and/or $R_{24fb}$ is $C_1$-$C_6$ alkyl. In one embodiment, each of $R_{25fa}$, $R_{25fb}$, $R_{26fa}$, and $R_{26fb}$ is H and each of $R_{24fa}$ and $R_{24fb}$ is —$CH_3$. In one embodiment, each of $R_{24fb}$, $R_{25fa}$, $R_{25fb}$, $R_{26fa}$, and $R_{26fb}$ is H and $R_{24fa}$ is —$CH_3$. In an embodiment, $R_{25fa}$, $R_{25fb}$, $R_{26fa}$, and $R_{26fb}$ are each H and $R_{24fa}$ and/or $R_{24fb}$ is $C_1$-$C_6$ alkyl substituted with one or more halogen. In an embodiment, $R_{25fa}$, $R_{25fb}$, $R_{26fa}$, and $R_{26fb}$ are each H and $R_{24fa}$ and/or $R_{24fb}$ is $C_1$ alkyl substituted with one or more F. In one embodiment, $R_{24fa}$, $R_{25fa}$, $R_{25fb}$, $R_{26fa}$, and $R_{26fb}$ are each H and $R_{24fb}$ is —$CF_3$.

In an embodiment, the compound of Formula (IIf) has one or more stereocenters. In one embodiment, the compound of Formula (IIf) comprises a stereocenter where the moiety

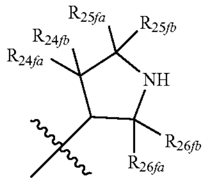

connects to the remaining portion of Formula (IIf). In one embodiment, the compound of Formula (IIf) comprises a stereocenter at one or more of $R_{24fa}$, $R_{24fb}$, $R_{25fa}$, $R_{25fb}$, $R_{26fa}$, and/or $R_{26fb}$. In one embodiment, the compound of Formula (IIf) comprises a stereocenter on $R_{20f}$.

In an embodiment, the compound of Formula (IIf) is selected from:

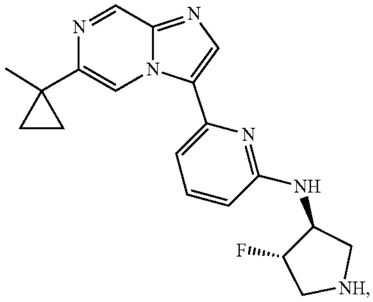

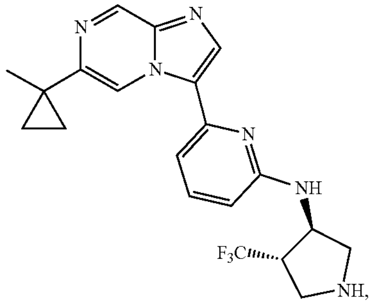

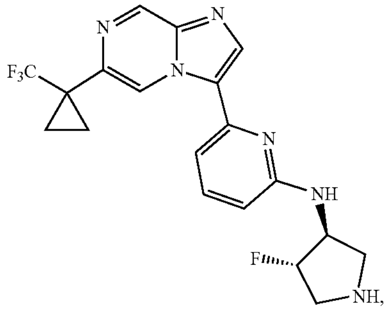

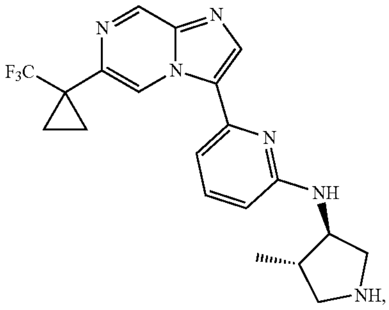

-continued
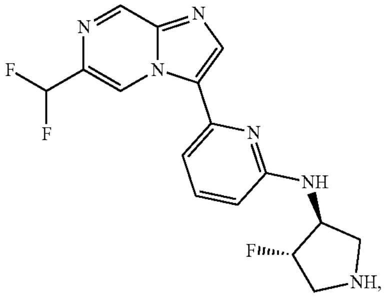
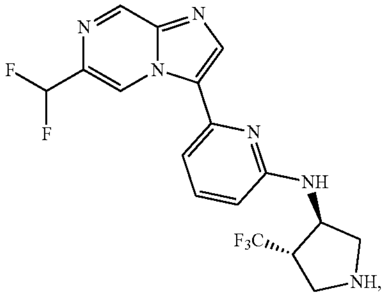
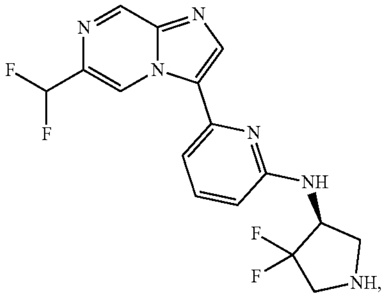
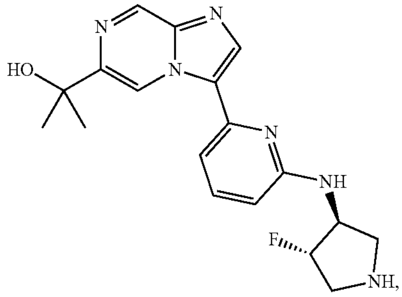
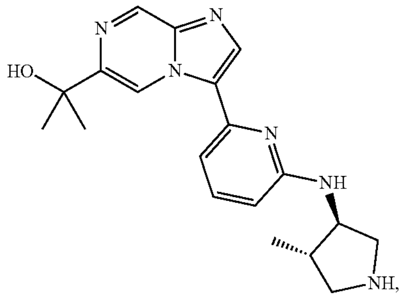
-continued
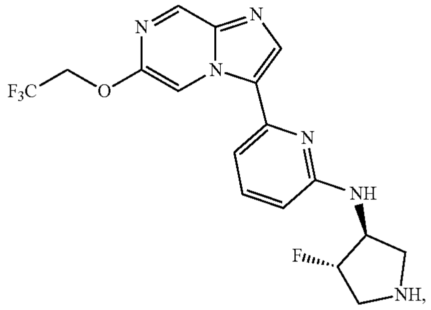
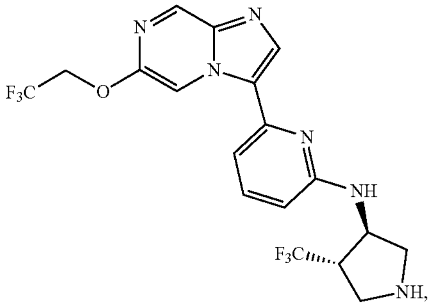
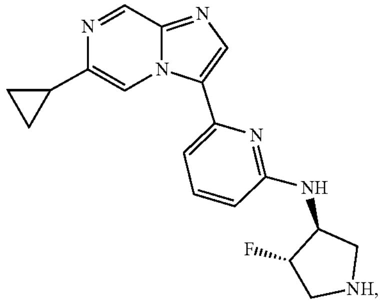
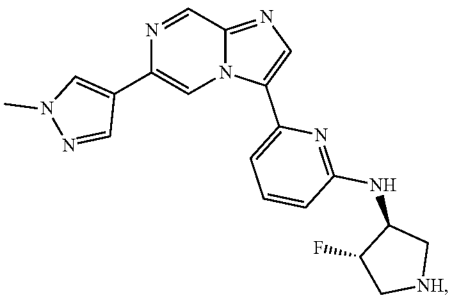
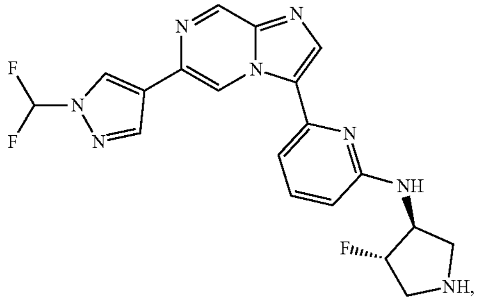

-continued
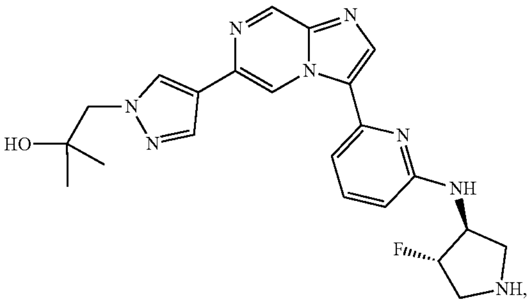
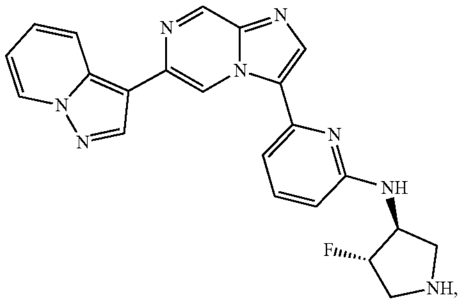
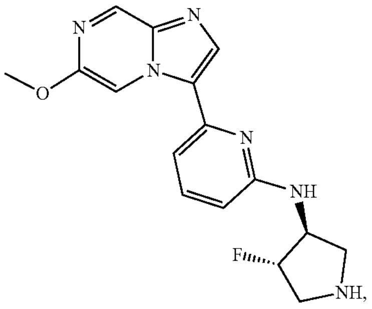
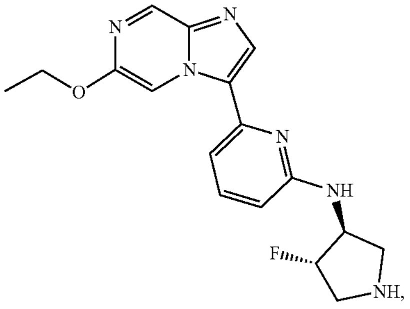
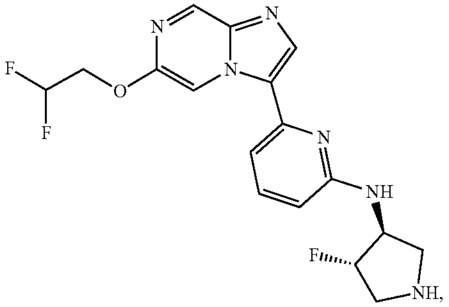
-continued
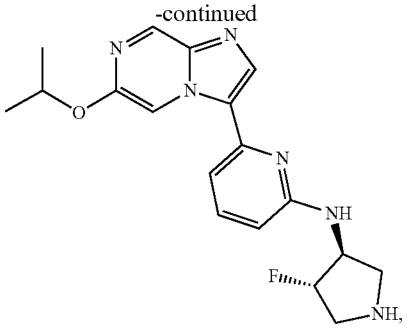
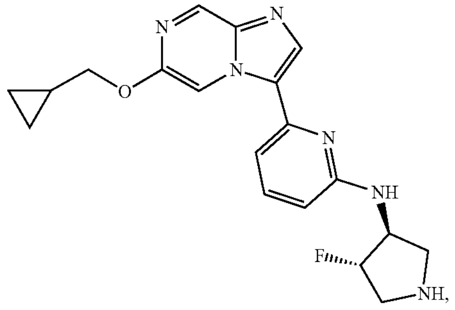
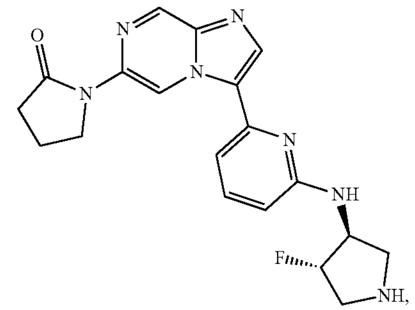
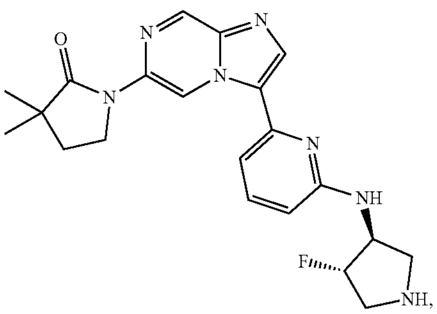
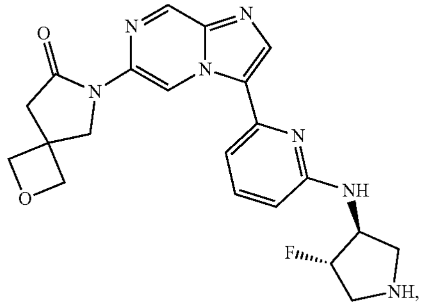

-continued
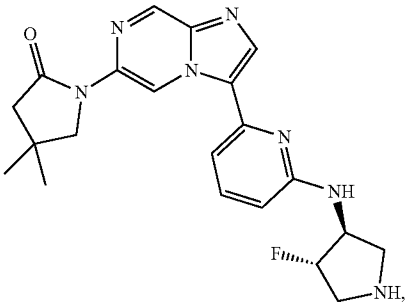
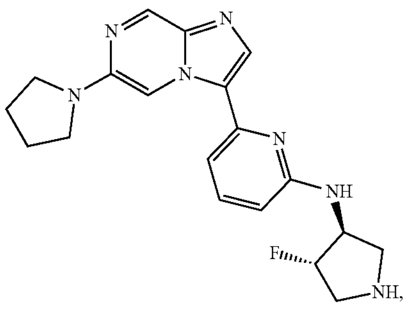
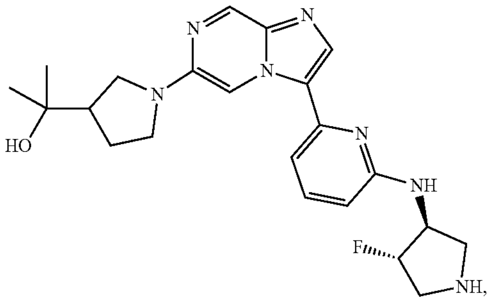
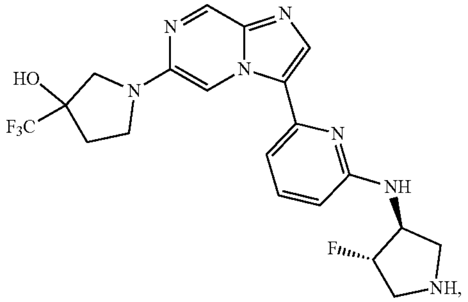
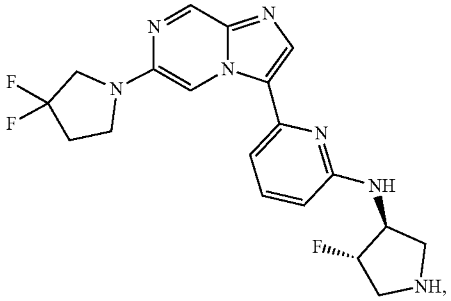
-continued
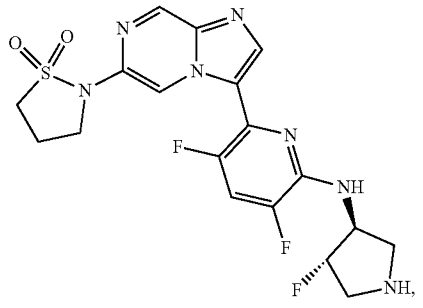
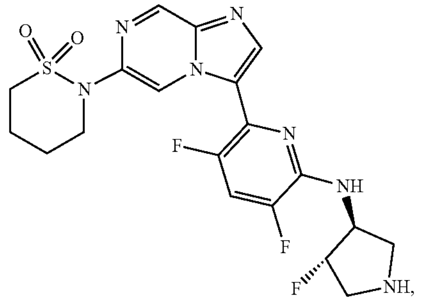
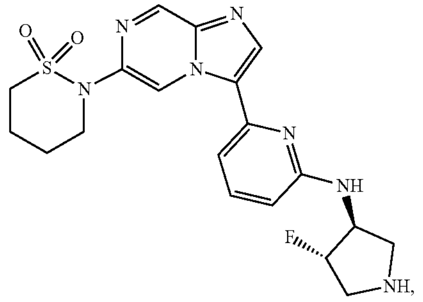
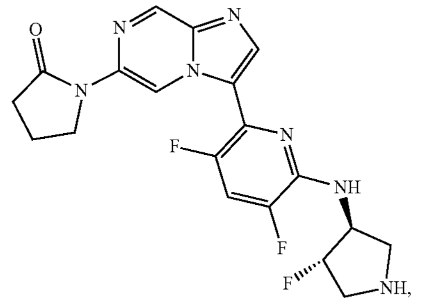
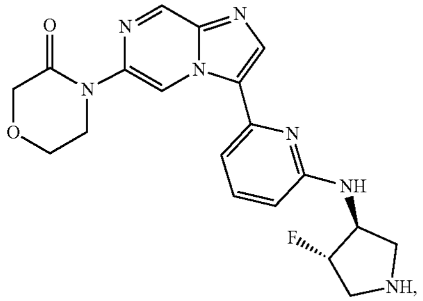

-continued
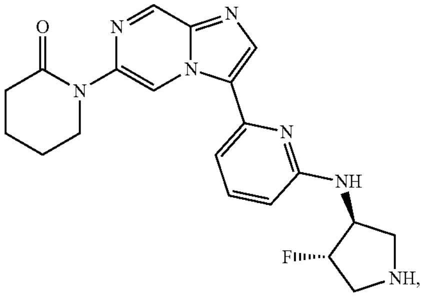
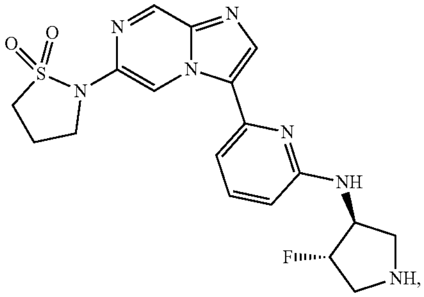
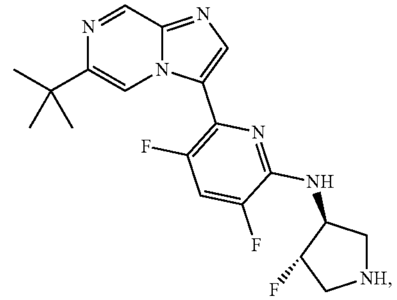
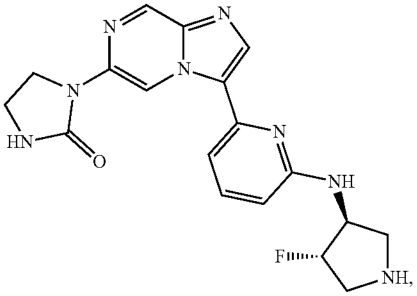
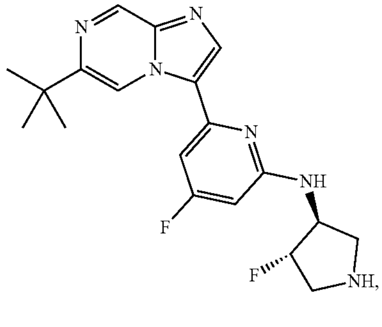
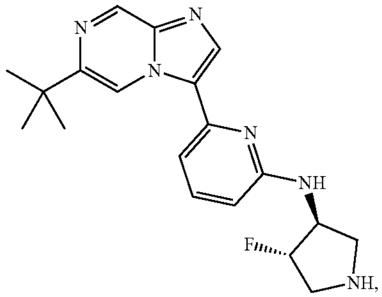
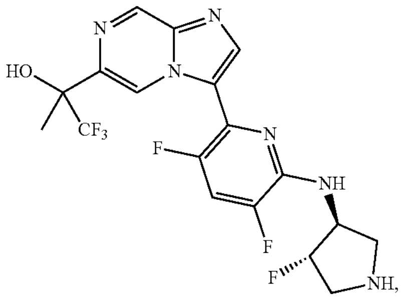
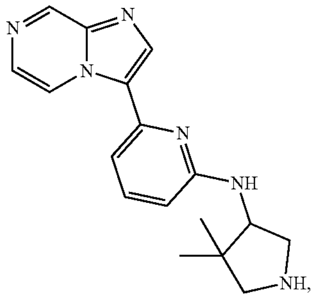
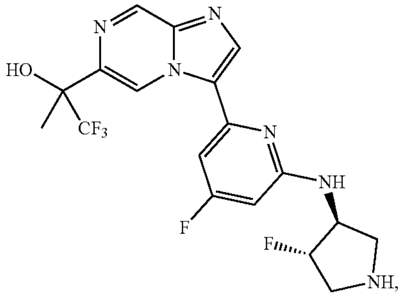
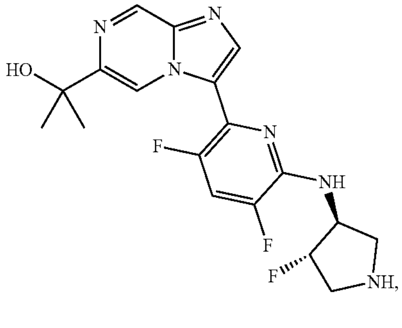

-continued
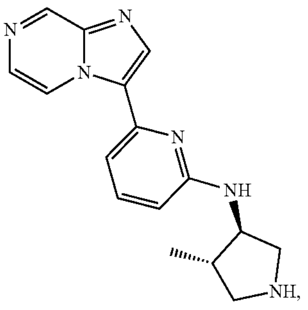
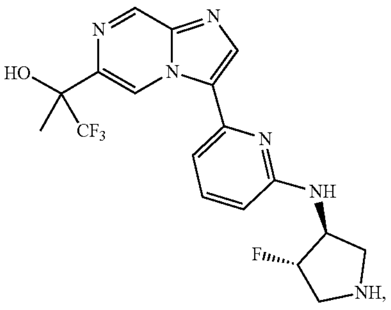
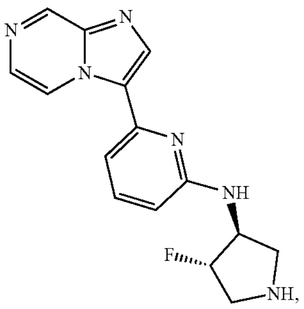
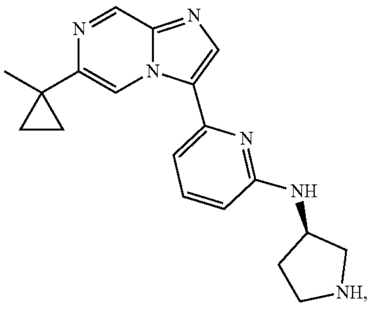
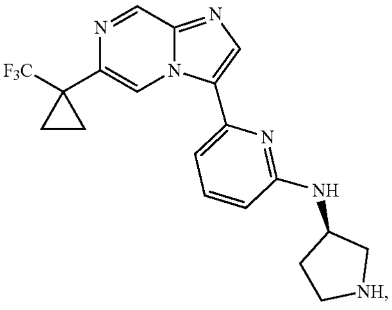
-continued
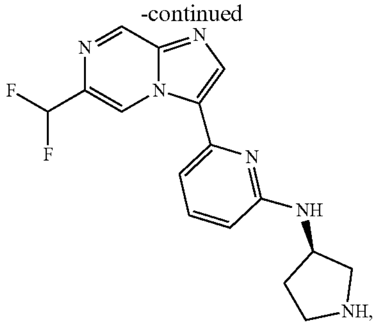
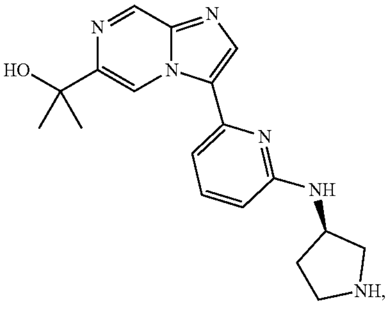
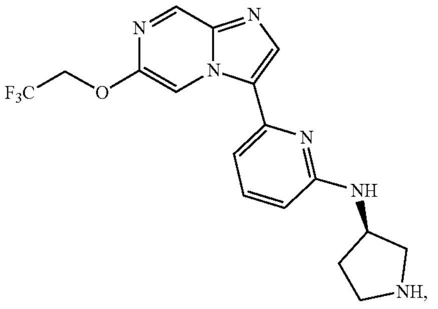
and
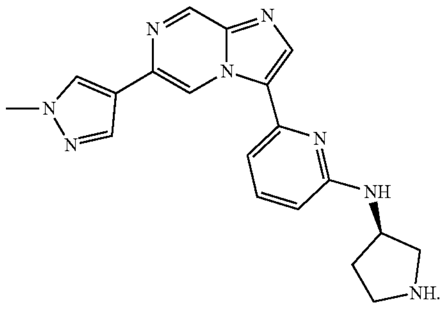
In an embodiment, the compound of Formula (II) is a compound of Formula (IIg)
Formula (IIg)
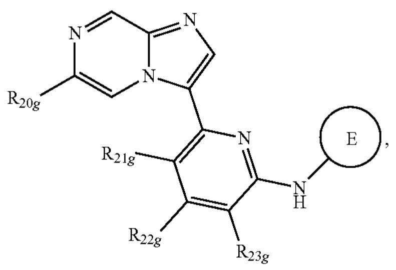
or a salt, ester, solvate, optical isomer, geometric isomer, or salt of an isomer thereof; wherein:

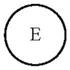

is selected from

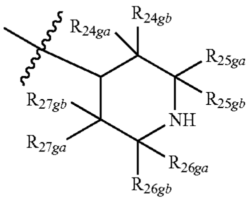

and

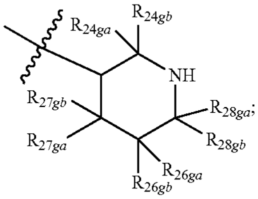

$R_{20g}$ is selected from H, $C_1$-$C_6$ alkyl, $C_1$-$C_6$ alkoxy, $C_3$-$C_6$ cycloalkyl, and $C_3$-$C_9$ heterocyclyl, wherein $C_1$-$C_6$ alkyl and $C_1$-$C_6$ alkoxy are each optionally substituted with one or more substituents selected from —OH and halogen, $C_3$-$C_6$ cycloalkyl is optionally substituted with one or more substituents selected from $C_1$-$C_6$ alkyl and halogen, and $C_3$-$C_9$ heterocycyl is optionally substituted with one or more substituents selected from halogen, $C_1$-$C_6$ alkyl, $C_3$-$C_6$-cycloalkyl, —OH, and =O;

$R_{21g}$, $R_{22g}$, and $R_{23g}$ are each independently selected from H and halogen; and $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ are each independently selected from H, halogen, —OH, or $C_1$-$C_6$ alkyl.

In an embodiment, one or more of $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ is independently selected from halogen and $C_1$-$C_6$ alkyl. In another embodiment, each of $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ is H.

In an embodiment, $R_{20g}$ is H. In another embodiment, $R_{20g}$ is unsubstituted $C_1$-$C_6$ alkyl. In one embodiment, $R_{20g}$ is t-butyl. In another embodiment, $R_{20g}$ is $C_1$-$C_6$ alkyl substituted with one or more F and/or —OH. In one embodiment, $R_{21i}$ is selected from

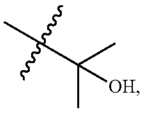

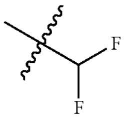

, and

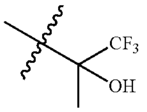

In another embodiment, $R_{20g}$ is unsubstituted $C_1$-$C_6$ alkoxy. In one embodiment, $R_{20g}$ is

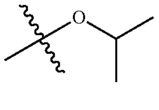

In another embodiment, $R_{20g}$ is $C_1$-$C_6$ alkoxy substituted with one or more F and/or —OH. In one embodiment, $R_{20g}$ is selected from

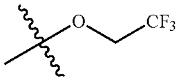

and

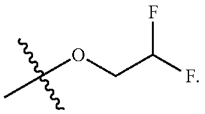

In another embodiment, $R_{20g}$ is unsubstituted $C_3$-$C_6$ cycloalkyl. In one embodiment, $R_{20g}$ is unsubstituted $C_3$ cycloalkyl. In one embodiment, $R_{20g}$ is $C_3$ cycloalkyl substituted with $C_1$-$C_6$ alkyl. In one embodiment, $R_{20g}$ is

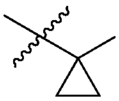

In one embodiment, $R_{20g}$ is $C_3$ cycloalkyl substituted with one or more $C_1$-$C_6$ alkyl and one or more fluorine atoms. In one embodiment, $R_{20g}$ is

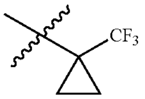

In another embodiment, $R_{20g}$ is $C_3$-$C_9$ heterocycyl substituted with one or more substituents selected from $C_1$-$C_6$ alkyl, $C_3$-$C_6$-cycloalkyl, $C_3$-$C_9$-heterocyclyl, —OH, —C=O, and halogen. In one embodiment, $R_{20g}$ is

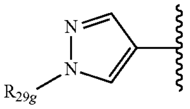

wherein $R_{29g}$ is selected from $C_1$-$C_6$ alkyl, $C_3$-$C_6$ cycloalkyl, and $C_3$-$C_9$ heterocyclyl, wherein $C_1$-$C_6$ alkyl and $C_3$-$C_6$ cycloalkyl are each optionally substituted with one or more halogen and/or —OH. In one embodiment, $R_{20g}$ is

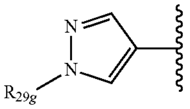

wherein $R_{29g}$ is unsubstituted $C_1$-$C_6$ alkyl. In one embodiment, $R_{20g}$ is

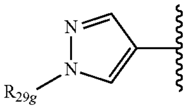

wherein $R_{29g}$ is —$CH_3$. In one embodiment, $R_{20g}$ is

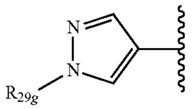

wherein $R_{29g}$ is $C_1$-$C_6$ alkyl substituted with one or more —OH and/or F. In one embodiment, $R_{20g}$ is

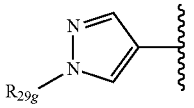

wherein $R_{29g}$ is selected from

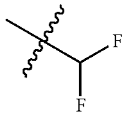

and

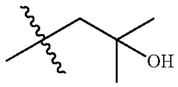

.

In one embodiment, $R_{20g}$ is

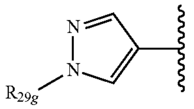

wherein $R_{29g}$ is unsubstituted $C_3$-$C_6$ cycloalkyl. In one embodiment, $R_{20g}$ is

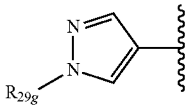

wherein $R_{29g}$ is unsubstituted $C_3$ cycloalkyl. In one embodiment, $R_{20g}$ is pyrrolidinyl monosubstituted with —C═O. In one embodiment, $R_{20g}$ is

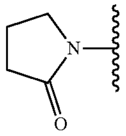

.

In another embodiment, $R_{20g}$ is piperidinyl monosubstituted with —C═O. In one embodiment, $R_{20g}$ is

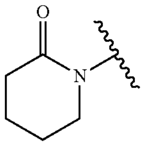

.

In another embodiment, $R_{20g}$ is

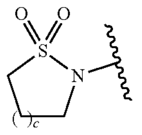

wherein c is 1 or 2. In another embodiment, $R_{20g}$ is selected from

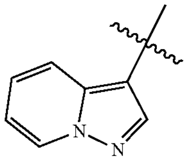

,

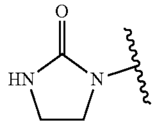

and

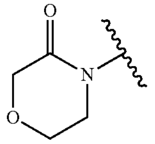

.

In an embodiment, each of $R_{21g}$, $R_{22g}$, and $R_{23g}$ is H. In an embodiment, $R_{21g}$ and $R_{23g}$ are each independently halogen and $R_{22g}$ is H. In one embodiment, $R_{21g}$ and $R_{23g}$ are each F and $R_{22g}$ is H. In an embodiment, $R_{21g}$ and $R_{23g}$ are each H and $R_{22g}$ is halogen. In one embodiment, $R_{21g}$ and $R_{23g}$ are each H and $R_{22g}$ is F.

In an embodiment,

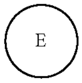

is

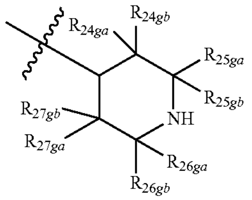

, each of $R_{24ga}$, $R_{24gb}$, $R_{25ga}$, $R_{25gb}$, $R_{26ga}$, $R_{26gb}$, $R_{27ga}$, and $R_{27gb}$ is H. In an embodiment, each of $R_{25ga}$, $R_{25gb}$, $R_{26ga}$, $R_{26gb}$, $R_{27ga}$, and $R_{27gb}$ is H and $R_{24g}$a and/or $R_{24g}$b is halogen. In one embodiment, each of $R_{24ga}$, $R_{25ga}$, $R_{25gb}$, $R_{26ga}$, $R_{26gb}$, $R_{27ga}$, and $R_{27gb}$ is H and $R_{24gb}$ is F. In an embodiment, each of $R_{24ga}$, $R_{24gb}$, $R_{26ga}$, $R_{26gb}$, $R_{27ga}$, and $R_{27gb}$ is H and $R_{25ga}$ and/or $R_{25gb}$ is unsubstituted $C_1$-$C_6$ alkyl. In one embodiment, each of $R_{24ga}$, $R_{24gb}$, $R_{25ga}$, $R_{26ga}$, $R_{26gb}$, $R_{27ga}$, and $R_{27gb}$ is H and $R_{25gb}$ is —$CH_3$.

In an embodiment,

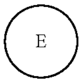

is

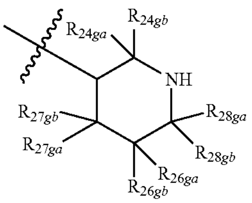

, each of $R_{24ga}$, $R_{24gb}$, $R_{26ga}$, $R_{26gb}$, $R_{27ga}$, $R_{27gb}$, $R_{28ga}$, and $R_{28gb}$ is H. In an embodiment, each of $R_{24ga}$, $R_{24gb}$, $R_{26ga}$, $R_{26gb}$, $R_{28ga}$, and $R_{28gb}$ is H and $R_{27g}$a and/or $R_{27g}$b is halogen. In one embodiment, each of $R_{24ga}$, $R_{24gb}$, $R_{26ga}$, $R_{26gb}$, $R_{28ga}$, and $R_{28gb}$ is H and each of $R_{27ga}$ and $R_{27gb}$ is F. In one embodiment, each of $R_{24ga}$, $R_{24gb}$, $R_{26ga}$, $R_{26gb}$, $R_{27ga}$, $R_{28ga}$, and $R_{28gb}$ is H and $R_{27gb}$ is F. In an embodiment, each of $R_{24ga}$, $R_{24gb}$, $R_{26ga}$, $R_{26gb}$, $R_{28ga}$, and $R_{28gb}$ is H and $R_{27ga}$ and/or $R_{27gb}$ is unsubstituted $C_1$-$C_6$ alkyl. In one embodiment, each of $R_{24ga}$, $R_{24gb}$, $R_{26ga}$, $R_{26gb}$, $R_{28ga}$, and $R_{28gb}$ is H and each of $R_{27g}$a and $R_{27g}$b is —$CH_3$. In another embodiment, each of $R_{24ga}$, $R_{24gb}$, $R_{27ga}$, $R_{27gb}$, $R_{28ga}$, and $R_{28gb}$ is H and $R_{26g}$a and/or $R_{26g}$b is halogen. In one embodiment, each of $R_{24ga}$, $R_{24gb}$, $R_{26ga}$, $R_{27ga}$, $R_{27gb}$, $R_{28ga}$, and $R_{28gb}$ is H and $R_{26gb}$ is F. In an embodiment, each of $R_{24ga}$, $R_{24gb}$, $R_{27ga}$, $R_{27gb}$, $R_{28ga}$, and $R_{28gb}$ is H and $R_{26ga}$ and/or $R_{26gb}$ is unsubstituted $C_1$-$C_6$ alkyl. In one embodiment, each of $R_{24ga}$, $R_{24gb}$, $R_{26ga}$, $R_{27ga}$, $R_{27gb}$, $R_{28ga}$, and $R_{28gb}$ is H and $R_{26gb}$ is —$CH_3$.

In an embodiment, the compound of Formula (IIg) comprises one or more stereocenters. In one embodiment, the compound of Formula (IIg) comprises a stereocenter on $R_{20g}$. In one embodiment, the compound of Formula (IIg) comprises a stereocenter where the

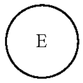

moiety connects to the remaining portion of Formula (IIg). In one embodiment, one or more of $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and/or $R_{28gb}$ comprises a stereocenter.

In an embodiment, the compound of Formula (IIg) is selected from:

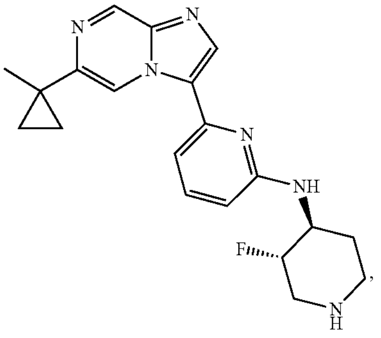

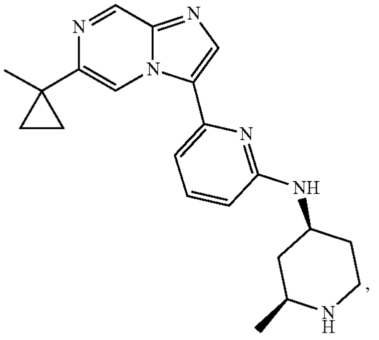

-continued

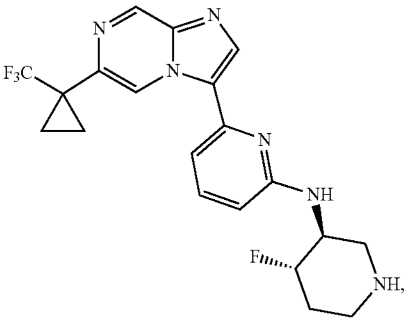

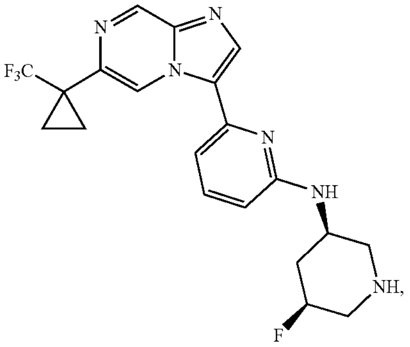

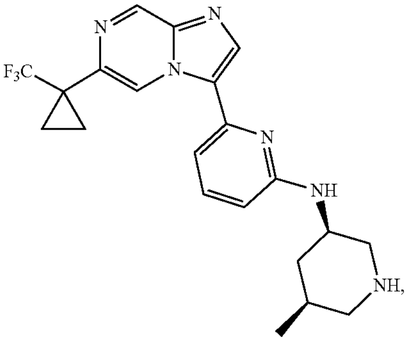

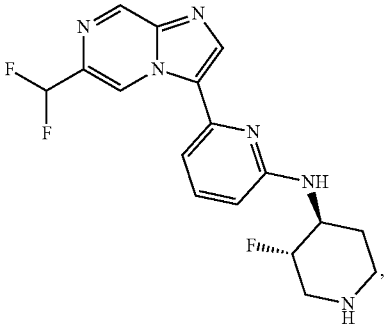

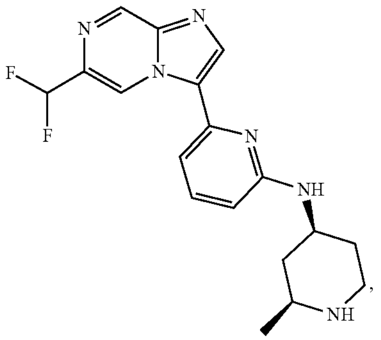

-continued
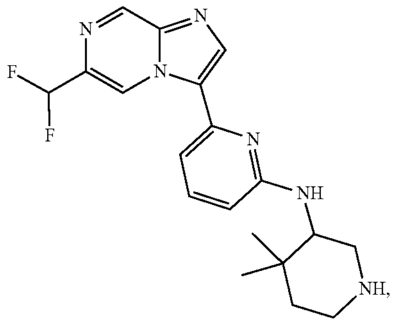
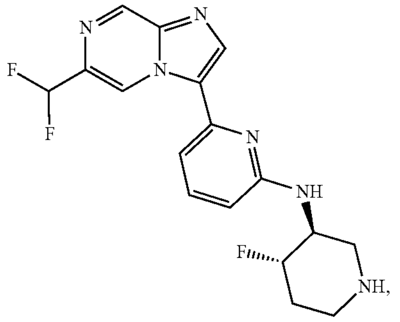
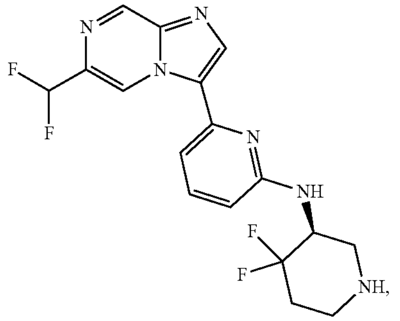
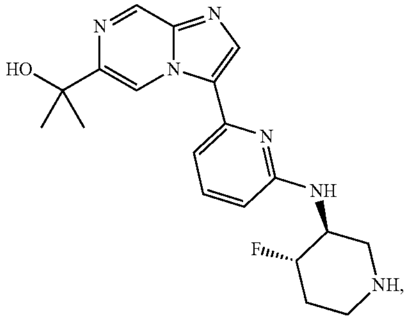
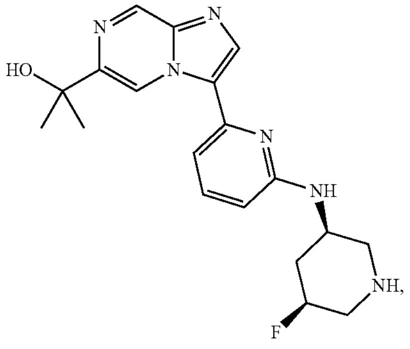
-continued
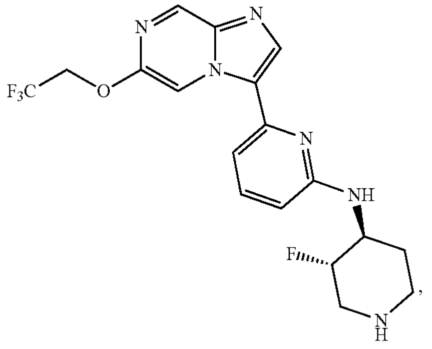
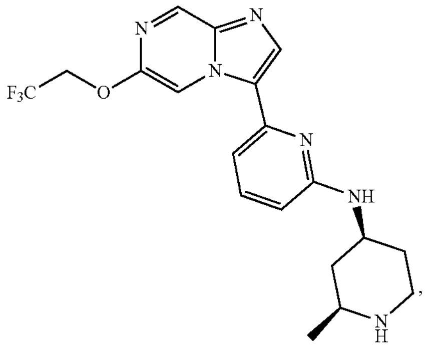
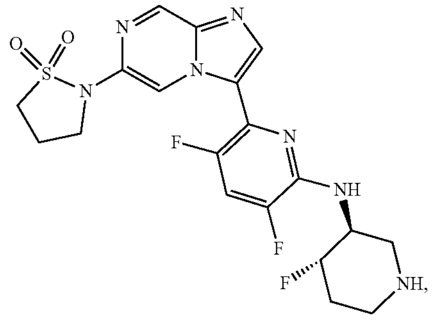
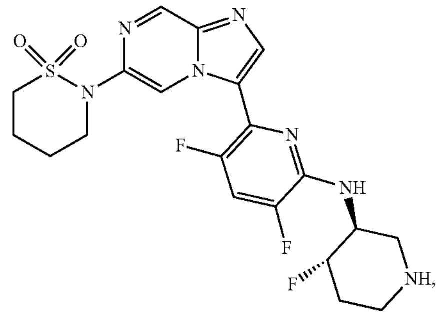
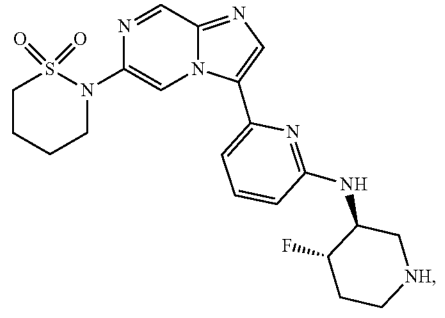

-continued
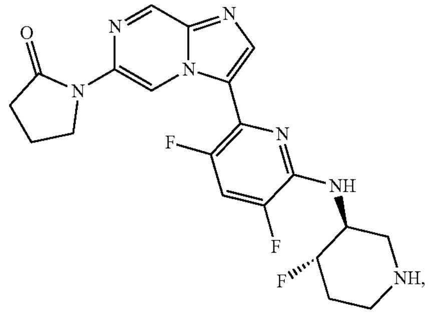
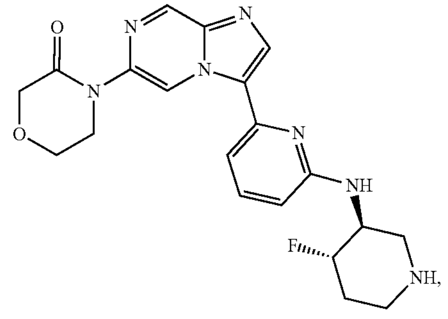
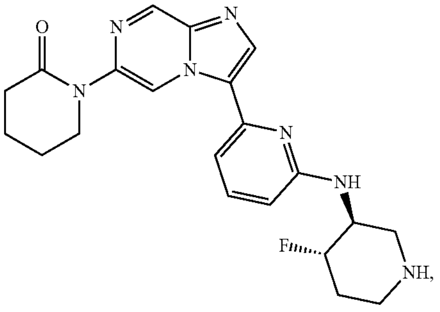
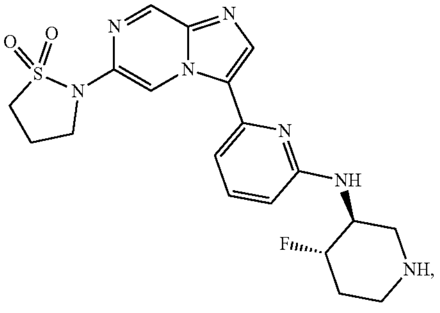
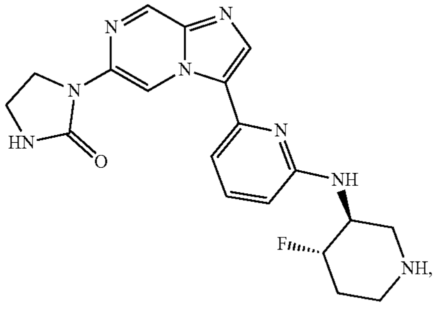
-continued
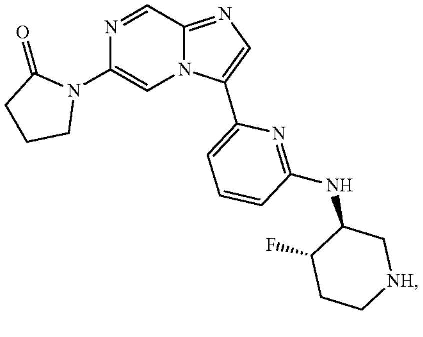
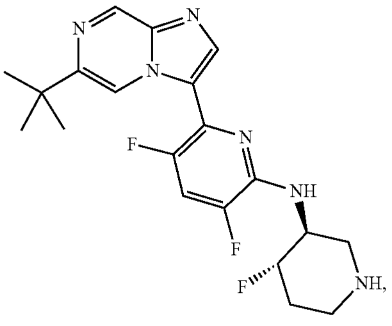
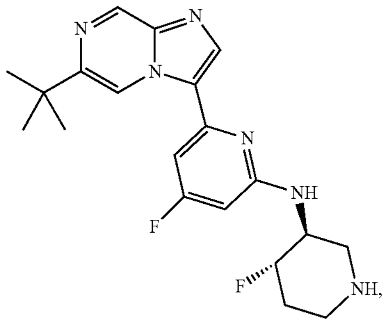
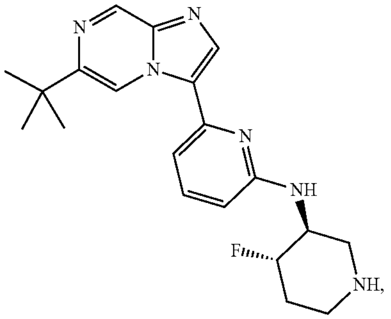
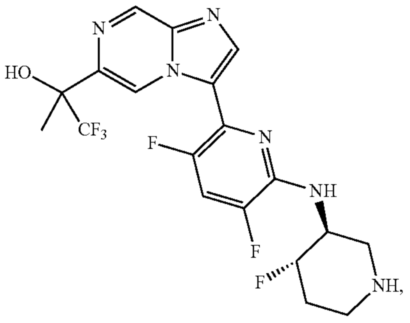

-continued
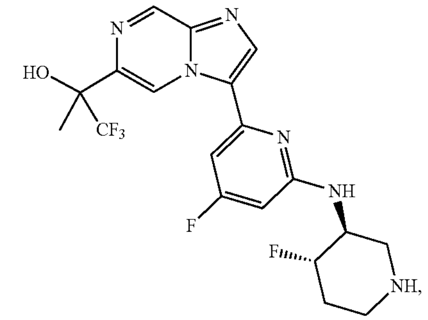
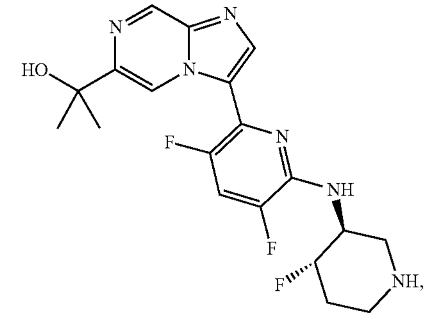
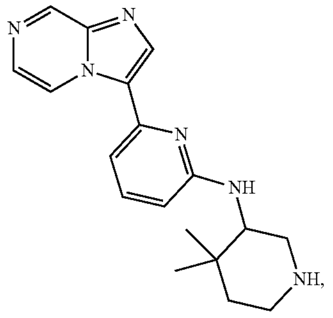
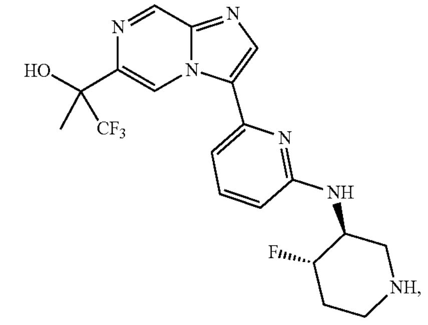
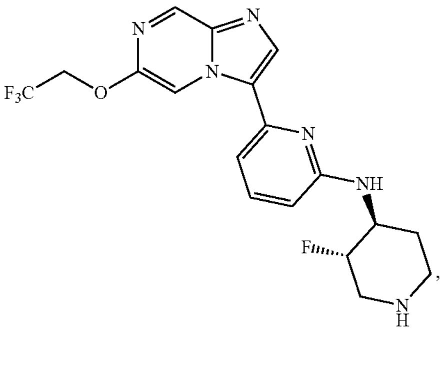
-continued
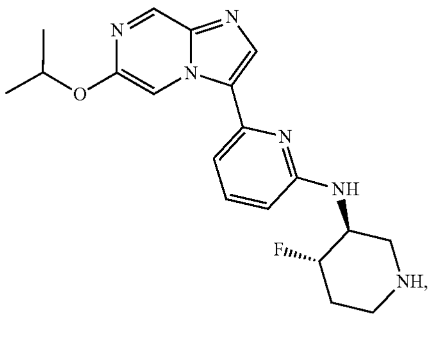
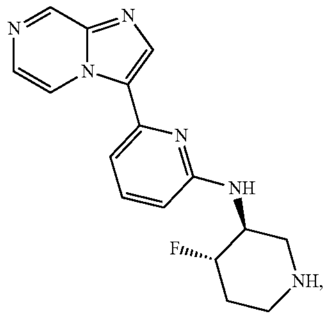
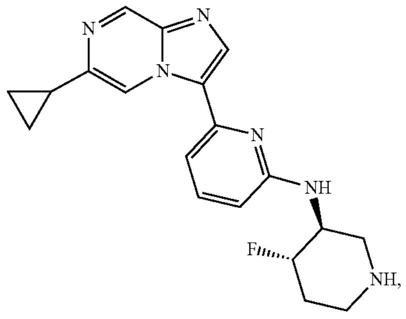
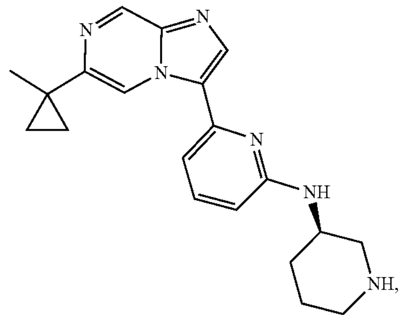
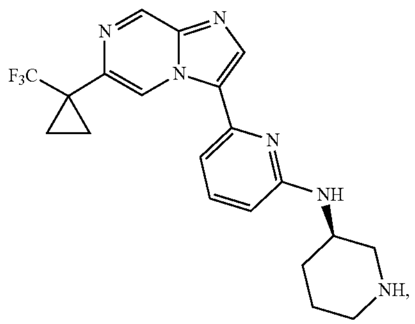

-continued
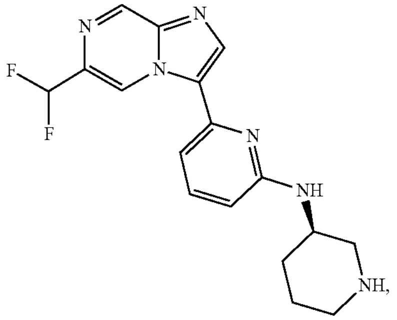
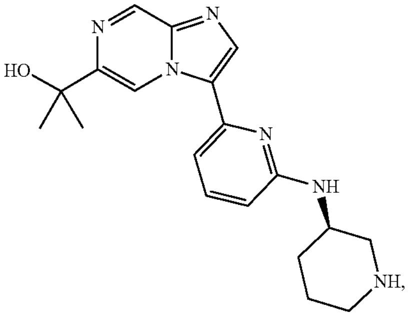
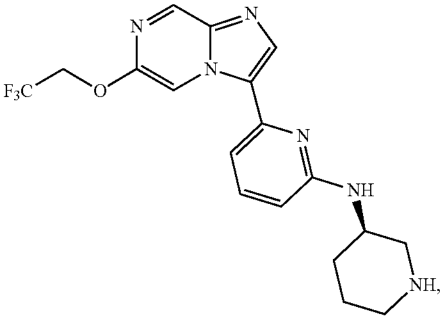
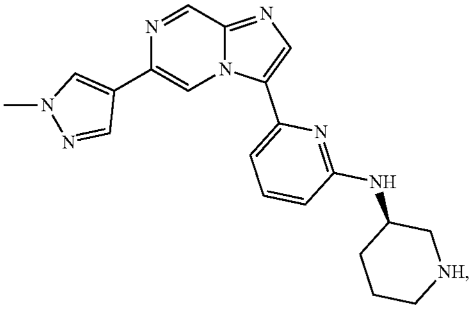
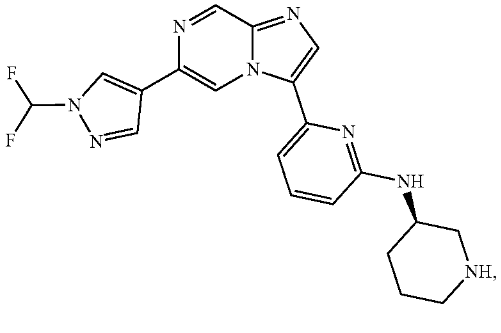
-continued
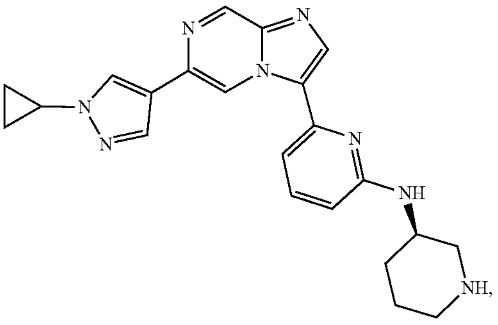
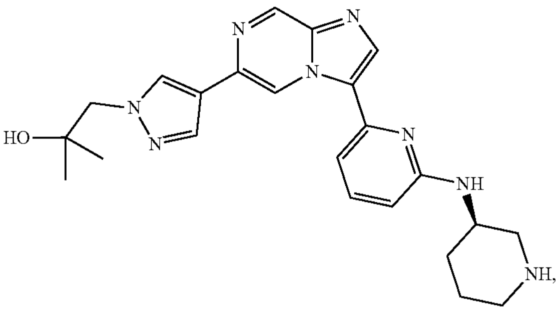
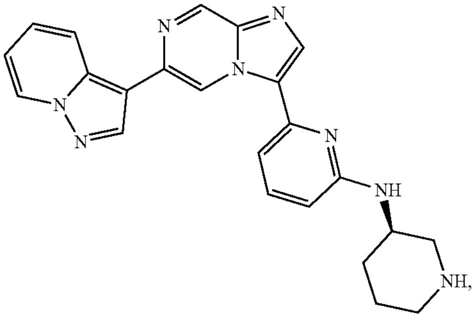
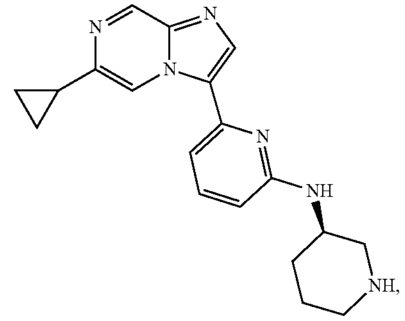
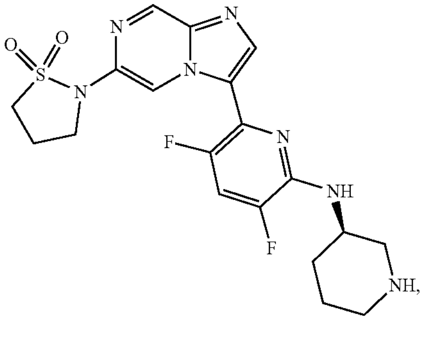

-continued
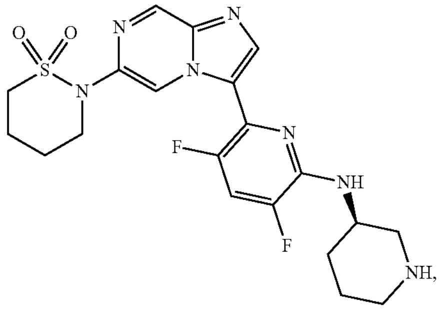
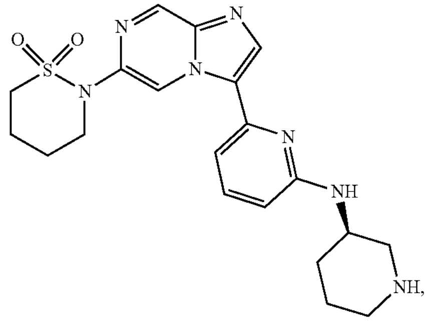
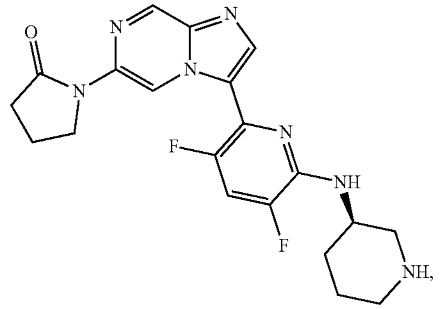
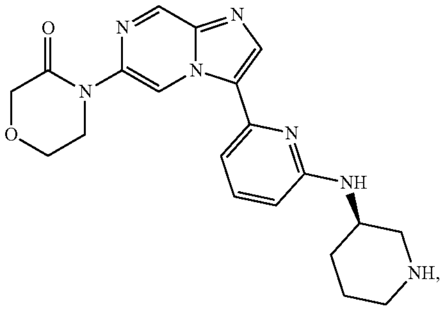
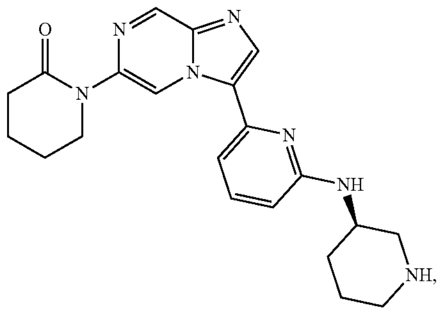
-continued
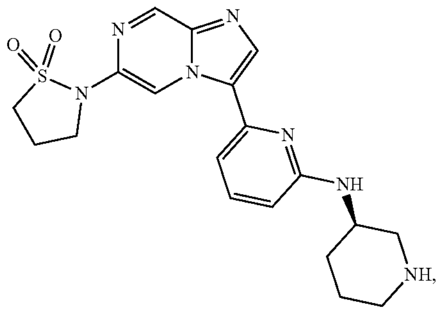
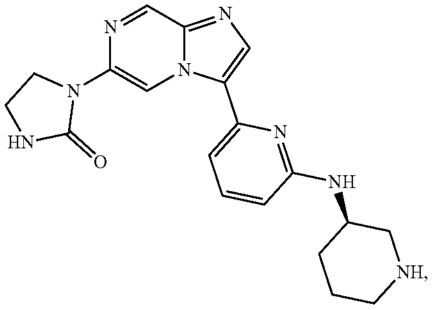
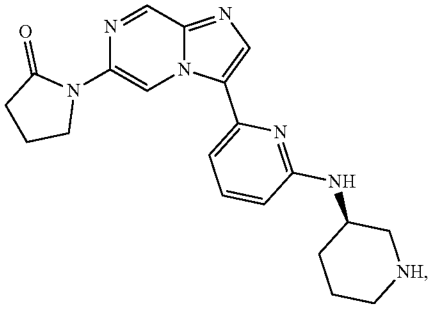
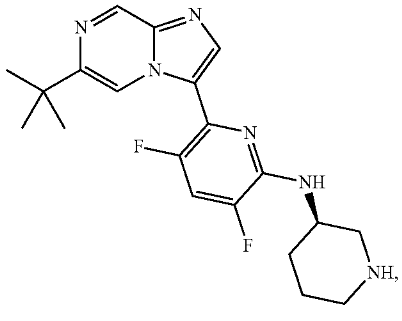
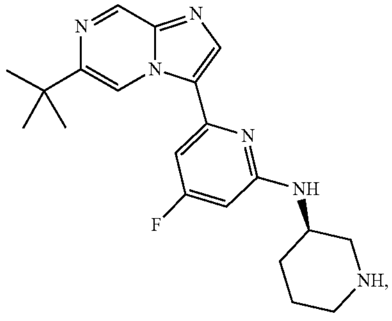

-continued
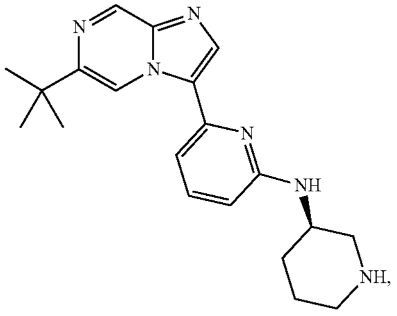
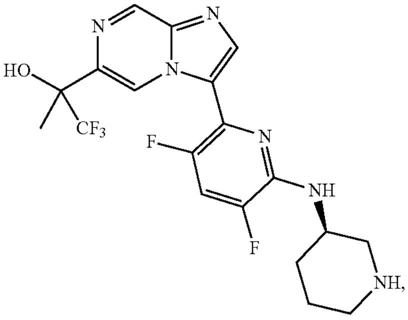
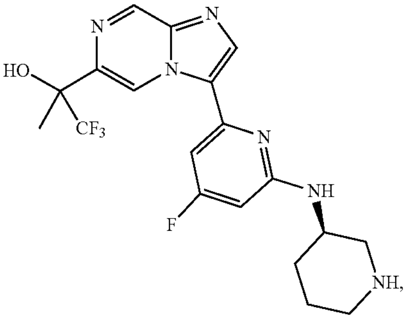
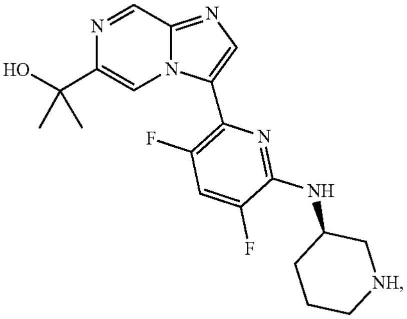
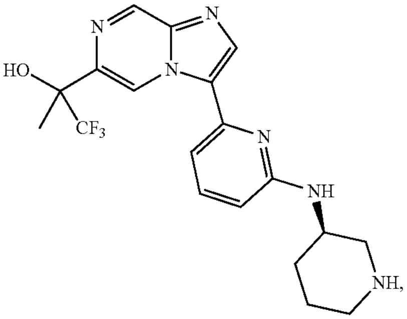
-continued
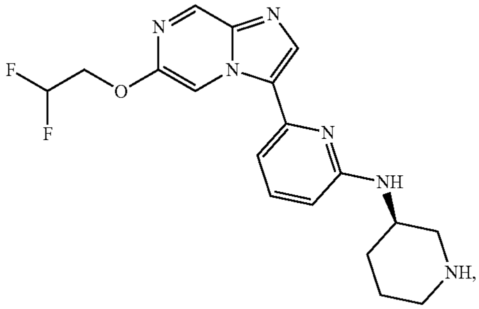
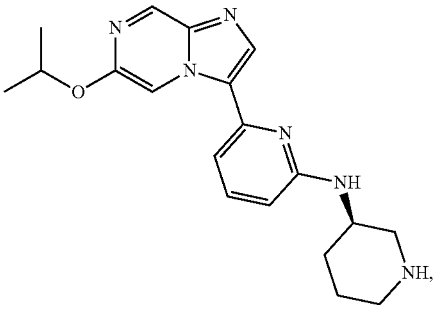
and
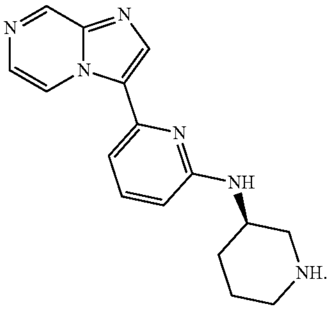
In an embodiment, the compound of Formula (II) is a compound of Formula (IIh):
Formula (IIh)
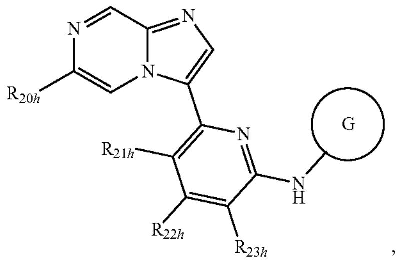
or a salt, ester, solvate, optical isomer, geometric isomer, or salt of an isomer thereof;
wherein:
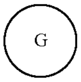

is selected from

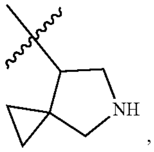
,
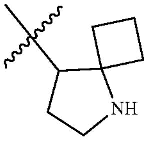
, and
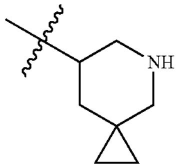
;

$R_{20h}$ is selected from H, $C_1$-$C_6$ alkyl, $C_1$-$C_6$ alkoxy, and $C_3$-$C_6$ cycloalkyl, wherein $C_1$-$C_6$ alkyl and $C_1$-$C_6$ alkoxy are each optionally substituted with one or more substituents selected from halogen and —OH, and $C_3$-$C_6$ cycloalkyl is optionally substituted with one or more substituents selected from $C_1$-$C_6$ alkyl and halogen; and $R_{21h}$, $R_{22h}$, and $R_{23h}$ are each independently selected from H and halogen.

In an embodiment, $R_{20h}$ is H. In another embodiment, $R_{20h}$ is $C_1$-$C_6$ alkyl substituted with one or more halogen. In one embodiment, $R_{20h}$ is

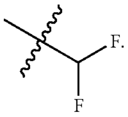 [SMILES: *C(F)F]

In another embodiment, $R_{20h}$ is $C_1$-$C_6$ alkoxy substituted with one or more halogen. In one embodiment, $R_{20h}$ is

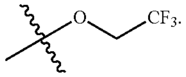

In another embodiment, $R_{20h}$ is unsubstituted $C_3$-$C_6$ cycloalkyl. In one embodiment, $R_{20h}$ is unsubstituted $C_3$ cycloalkyl. In another embodiment, $R_{20h}$ is $C_3$-$C_6$ cycloalkyl substituted with one or more $C_1$-$C_6$ alkyl. In one embodiment, $R_{20h}$ is

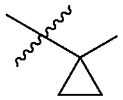

In another embodiment, $R_{20h}$ is $C_3$-$C_6$ cycloalkyl substituted with one or more $C_1$-$C_6$ alkyl and one or more fluorine atoms. In one embodiment, $R_{20h}$ is

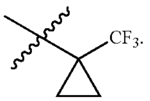 [SMILES: *C1(C(F)(F)F)CC1]

In an embodiment, $R_{21h}$, $R_{22h}$, and $R_{23h}$ are each H. In an embodiment, $R_{21h}$ and $R_{23h}$ are each independently halogen and $R_{22h}$ is H. In one embodiment, $R_{21h}$ and $R_{23h}$ are each F and $R_{22h}$ is H. In an embodiment, $R_{21h}$ and $R_{23h}$ are each H and $R_{22h}$ is halogen. In one embodiment, $R_{21h}$ and $R_{23h}$ are each H and $R_{22h}$ is F.

In an embodiment,

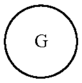
is
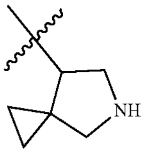
.

In an embodiment, the compound of Formula (IIh) comprises one or more stereocenters. In one embodiment, the compound of Formula (IIh) comprises a stereocenter on $R_{20h}$. In one embodiment, the compound of Formula (IIh) comprises a stereocenter where the

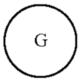

moiety connects to the remaining portion of Formula (IIh).

In an embodiment, the compound of Formula (IIh) is selected from:

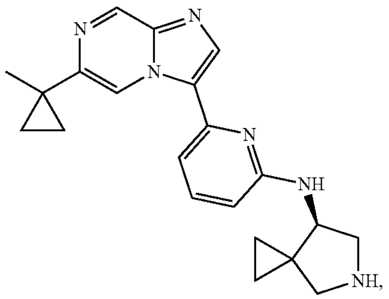

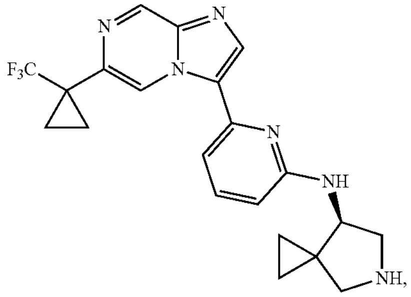

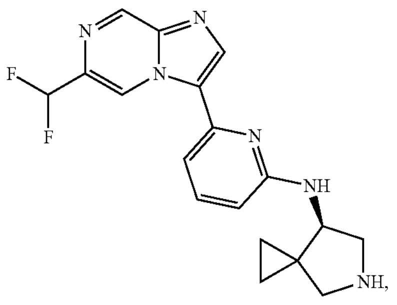

-continued

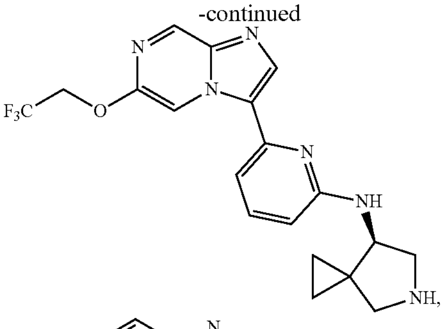

and

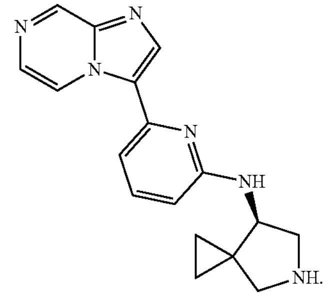

In some embodiments, $R^6$ is (Ib), giving a structure of Formula (III), as follows:

(III)

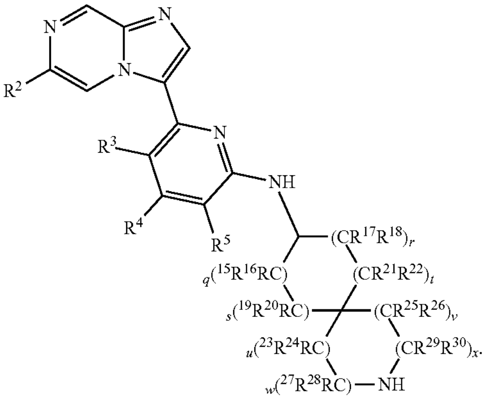

In some embodiments according to Formula (III), q, r, s, t, u, v, w, and x are independently 0, 1, or 2. In some embodiments, q is 0 or 1, r is 0 or 1, s is 0 or 1, t is 0 or 1, u is 0 or 1, v is 0 or 1, w is 0 or 1, and x is 0 or 1.

In some embodiments, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are independently selected from H, halogen, hydroxy, oxo, methanoyl (—COH), carboxy (—$CO_2H$), $C_1$-$C_7$ alkyl, $C_1$-$C_7$ alkoxy, or spiro-fused cycloalkyl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, or spiro-fused cycloalkyl is optionally substituted with one or more halogen. In some embodiments, one or more of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are H. In some embodiments, all of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are H.

Further to any embodiment above wherein the compound has the structure of Formula (III), the compound can have a structure according to any of (IIIa)-(IIIp), as follows:

(IIIa)

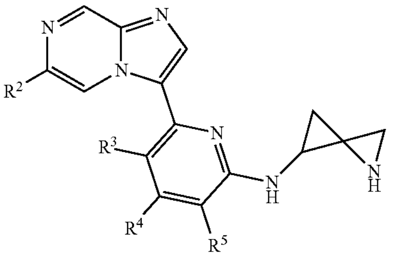

(IIIb)

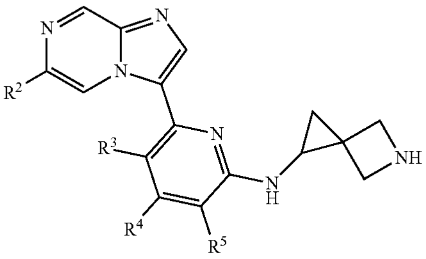

(IIIc)

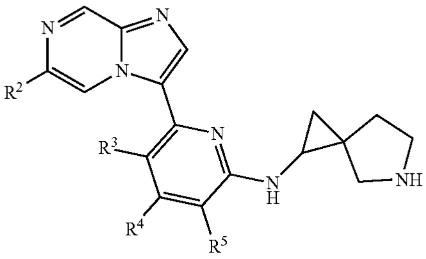

(IIId)

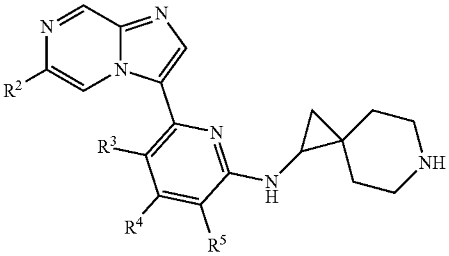

(IIIe)

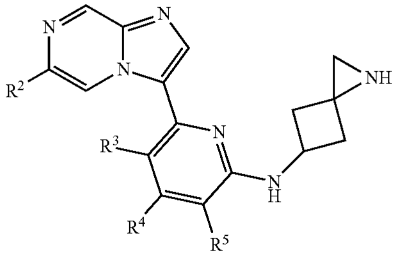

(IIIf)

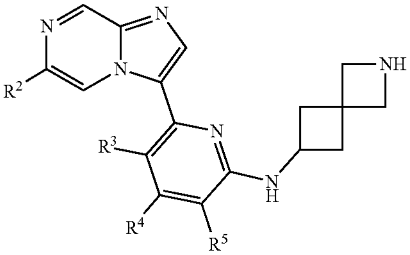

-continued (IIIg)

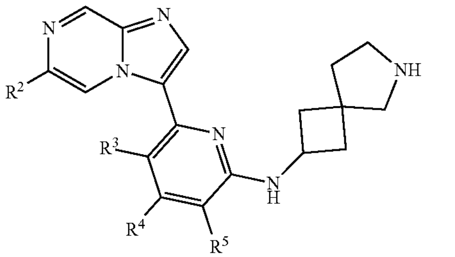

(IIIh)

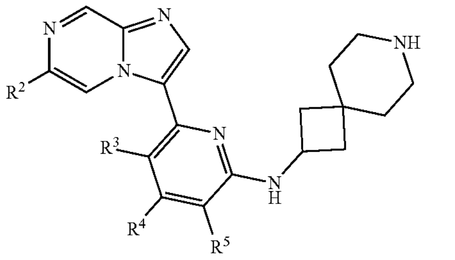

(IIIi)

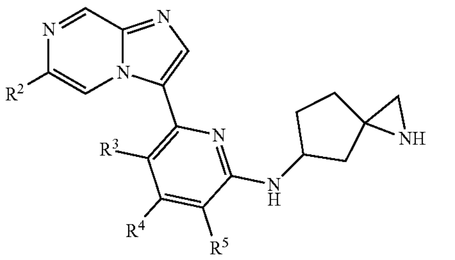

(IIIj)

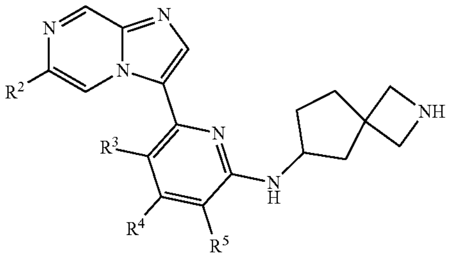

(IIIk)

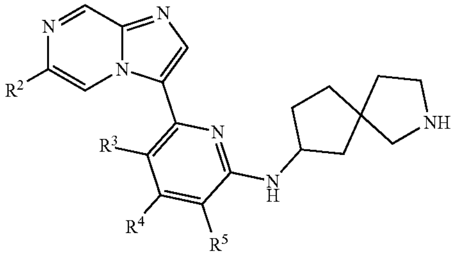

(IIIl)

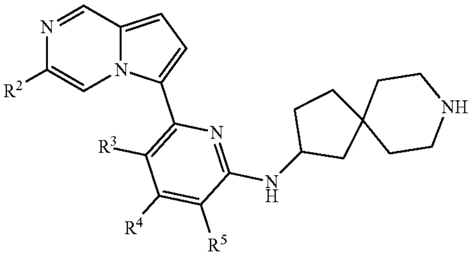

-continued (IIIm)

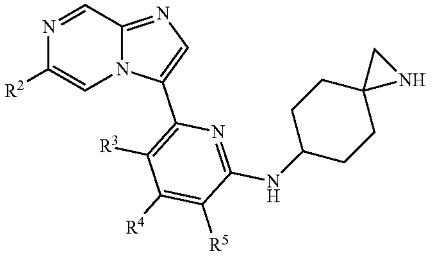

(IIIn)

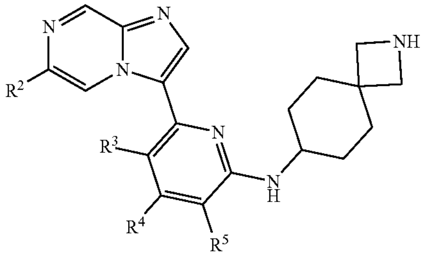

(IIIo)

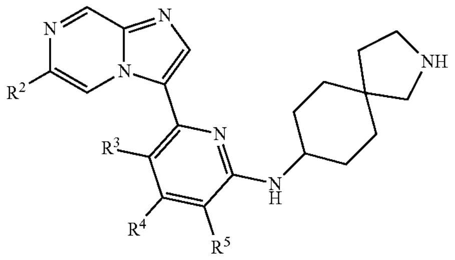

(IIIp)

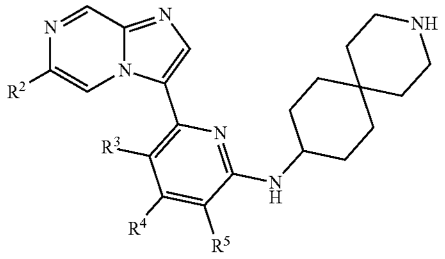

In some embodiments, the compounds of Formula (I), such as compounds of Formula (II) or Formula (III), can be any of those specified in Compounds 1-132, as listed in Tables 1-21. In some embodiments, the compound can be Compound 1, Compound 5, Compound 6, Compound 8, Compound 12, Compound 14, Compound 16, Compound 35, Compound 40, Compound 44, Compound 45, Compound 46, Compound 47, Compound 51, or Compound 55.

In some embodiments, the compounds of Formula (I), such as compounds of Formula (II) or Formula (III), can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, the compounds of the disclosure having a chiral center and can exist in and be isolated in optically active and racemic forms. In other embodiments, compounds may exhibit polymorphism. Some embodiments of the present disclosure encompass any racemic, optically active, polymorphic, or stereoisomeric form, or mixtures thereof, of a compound described herein, including isotopically-labeled and radio-labeled compounds. See e.g., Goding, 1986, Monoclonal Antibodies Principles and Practice; Academic Press, p. 104. Such isomers can be isolated by standard resolution techniques, including e.g., fractional crystallization, chiral chromatography, and the like. See e.g., Eliel, E. L. & Wilen S. H., 1993, Stereochemistry in Organic Compounds; John Wiley & Sons, New York. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In some embodiments, compounds disclosed herein have asymmetric centers and can occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein can also contain unnatural proportions of atomic isotopes at one or more of the atoms that constitute such compounds. For example, the compounds can be radiolabeled with radioactive isotopes, such as for example tritium ($^3H$), iodine-125 ($^{125}I$), or carbon-14 ($^{14}C$). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein may be provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailability in oral administration, and the like. The prodrug can also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water solubility is beneficial. Conventional procedures for the selection and preparation of suitable prodrug derivatives are described, for example, in Design of Prodrugs, (ed. H. Bundgaard, Elsevier, 1985), which is hereby incorporated herein by reference for the limited purpose describing procedures and preparation of suitable prodrug derivatives.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present disclosure can exist in multiple crystalline or amorphous forms. In general, all physical forms are equivalent for the compounds and methods contemplated herein and are intended to be within the scope disclosed herein.

In certain embodiments, one or more compounds of the disclosure (e.g., Formula (I)) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the disclosure (e.g., Formula (I)) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Methods for Preparing Compounds of Formula (I)

Some embodiments of the present disclosure include methods for the preparation of compounds of Formula (I). In certain embodiments, a compound of Formula (I) can be prepared comprising one or more of the steps set forth in Examples 1-24 herein. The synthetic routes shown and described in Examples 1-24 can, for example, be used to prepare Compounds 1-132, as set forth in Tables 1-21, and structurally related compounds.

Pharmaceutical Compositions and Formulations

Some embodiments of the present disclosure include compositions comprising one or more compounds of the disclosure (e.g., Formula (I)). In certain embodiments, the composition is a pharmaceutical composition, such as compositions that are suitable for administration to animals (e.g., mammals, primates, monkeys, humans, canine, feline, porcine, mice, rabbits, rats, etc.). In some embodiments, there is provided a pharmaceutical composition comprising a compound disclosed herein and a pharmaceutically acceptable excipient. The compound can be a compound of any of Formulae (I)—(III) as disclosed herein, a compound as set forth in Tables 1-21, or a pharmaceutically acceptable salt, ester, solvate, optical isomer, geometric isomer, salt of an isomer, prodrug, or derivative thereof. In some embodiments, the compound is set forth in any of Tables 1-21 herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science,* 1977, 66, 1-19). Certain specific compounds disclosed herein contain both basic and acidic functionalities that allow the compounds to be converted into either base or acid addition salts.

Compounds disclosed herein can exist as salts, such as with pharmaceutically acceptable acids. Accordingly, the compounds contemplated herein include such salts. Examples of such salts include hydrochlorides, hydrobromides, sulfates, methanesulfonates, nitrates, maleates, acetates, citrates, fumarates, tartrates (e.g., (+) tartrates, (−)-tartrates, or mixtures thereof including racemic mixtures), succinates, benzoates, and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —$NHSO_3H$, —COOH and —$P(O)(OH)_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e. g., methyl, ethyl, tert-butyl, pivaloyloxymethyl, and the like, and those esters known in the art for modifying solubility or hydrolysis characteristics for use as sustained release or prodrug formulations.

In some instances, the pharmaceutical composition is non-toxic, does not cause side effects, or both. In some embodiments, there may be inherent side effects (e.g., it may harm the patient or may be toxic or harmful to some degree in some patients).

In some embodiments, one or more compounds of the disclosure (e.g., Formula (I)) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the compounds disclosed herein can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that can also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. This suspension can be formulated according to known methods using those suitable dispersing or wetting agents and suspending agents that have been mentioned above. The sterile injectable preparation can also a sterile injectable solution or suspension in a non toxic parenterally-acceptable diluent or solvent, for example, as a solution in 1,3-butanediol. Among the acceptable vehicles, carriers, and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCIENCES (17th Ed., Mack Pub. Co., Easton, PA) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, The Pharmacological Basis for Therapeutics (7th ed.).

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Aqueous suspensions normally contain the active materials in admixture with excipients suitable for the manufacture of aqueous suspension. Such excipients can be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which can be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate Also included are solid form preparations that are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the disclosure such as Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein can additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

There are provided various pharmaceutical compositions useful for ameliorating certain diseases and disorders. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

There are provided various pharmaceutical compositions useful for ameliorating certain diseases and disorders. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Methods of Treating and Preventing Disease

In addition to their ability to inhibit IRAK, IRAK inhibitors have been demonstrated to have selectivity for multiple kinases. In some embodiments, compounds described herein according to Formula (I), such as Compounds 1-132, as listed in Tables 1-21, exhibit have inhibitory action against one or more kinase, such as interleukin-1 receptor-associated kinase (IRAK) and FMS-like tyrosine kinase 3 (FLT3). The inhibitory action against one or more kinase, such as IRAK and FLT3, can allow for treatment and/or prevention of diseases in an animal (e.g., mammals, porcine, canine, avian (e.g., chicken), bovine, feline, primates, rodents, monkeys, rabbits, mice, rats, and humans) using a compound of the disclosure (e.g., Formula (I)) including, but not limited to hematopoietic cancers (e.g., disorders of hematopoietic stem cells in the bone marrow or disorders related to myeloid lineage), MDS, AML, myeloproliferative disease, and diseases (e.g., hematopoietic cancers) related to mutations in IRAK1, IRAK4, and/or FLT3 (e.g., mutations in the juxtamembrane region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation).

In some embodiments, the compounds of the disclosure can inhibit the activity of one or more of FLT3, mutations of FLT3 (e.g., mutations in the juxtamembrane region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation), IRAK4 (interleukin-1 receptor associated kinase 4), isoforms of IRAK4, mutations of IRAK4, IRAK1 (interleukin-1 receptor associated kinase 1), isoforms of IRAK1, and/or mutations of IRAK1. In some embodiments, the compounds of the disclosure can inhibit the activity of one or both of FLT3 and mutations of FLT3 (e.g., mutations in the juxtamembrane region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation) and optionally inhibits one or more of IRAK4, isoforms of IRAK4, mutations of IRAK4, IRAK 1, isoforms of IRAK1, or mutations of IRAK1. In some embodiments, the compounds of the disclosure can inhibit the activity of one or both of FLT3 and mutations of FLT3 (e.g., mutations in the juxtamembrane region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation) and optionally inhibits one or both of IRAK4 and IRAK1, or an isoform or mutation thereof. In some embodiments, the compounds of the disclosure can inhibit FLT3 in combination with IRAK4, IRAK1, or with IRAK4 and IRAK1.

In some embodiments, compounds exhibit inhibitory activity against IRAK and/or FLT-3 with activities≥1 μM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 nM, or even greater. In some embodiments, the compounds exhibit inhibitory activity against IRAK and/or FLT-3 with activities between 0.1 nM and 1 nM, e.g., about 0.1, 0.2, 0.3, 0.4, 0.5, 0.6, 0.7, 0.8, 0.9 or 1.0 nM. In some embodiments, compounds described herein exhibit inhibitory activity against IRAK and/or FLT-3 with activities≤0.1 μM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 1-100 nM, 0.1-1 nM, 0.1-100 nM, 0.1-200 nM, 1-200 nM, 10-200 nM, 100-200 nM, 200-500 nM, 0.1-500 nM, 1-500 nM, 10-500 nM, 500-1000 nM, 0.1-1000 nM, 1-1000 nM, 10-1000 nM, or 100-1000 nM. In some embodiments, the inhibitory activity is less than 0.1 nM, less than 1 nM, less than 10 nM, less than 100 nM, or less than 1000 nM. In some embodiments, the inhibitory activity is in the range of about 1-10 nM, 10-100 nM, 0.1-1 μM, 1-10 μM, 10-100 μM, 100-200 μM, 200-500 μM, or even 500-1000 μM. It is understood that for purposes of quantification, the terms "activity," "inhibitory activity," "biological activity," "IRAK activity," "IRAK1 activity," "IRAK4 activity," "FLT-3 activity," and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition.

In some embodiments, hematopoietic cancers that can be treated in an animal (e.g., mammals, porcine, canine, avian (e.g., chicken), bovine, feline, primates, rodents, monkeys, rabbits, mice, rats, and humans) using a compound of the disclosure (e.g., Formula (I)) include, but are not limited to hematopoietic cancers and cancers of the myeloid line of blood cells, cancers with an increased risk of occurrence due to other blood disorders, cancers with an increased risk of occurrence due to chemical exposure (e.g., anti-cancer therapies or occupational chemical exposure), cancers with an increased risk of occurrence due to ionizing radiation (e.g., anti-cancer therapies), cancers evolving from myelodysplastic syndromes, cancers evolving from myeloproliferative disease, and cancers of the B cells.

In some embodiments, hematopoietic cancers that can be treated include, but are not limited to, MDS, ANVIL, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL) (e.g. ABC DLBCL with MYD88 mutation (e.g., L265P)), follicular lymphoma, or marginal zone lymphoma, or combinations thereof.

In some embodiments, cancers characterized by dysregulated IRAK expression (IRAK1 and/or IRAK4) and/or IRAK-mediated intracellular signaling, can be treated, and include, but are not limited to, glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, and the like, and combinations thereof.

In some embodiments, compounds of the present disclosure can be used to inhibit targets in the context of additional conditions characterized by overactive IRAK1 and/or IRAK4. According to particular aspects of the disclosure, compounds of the present disclosure can be used to inhibit overactive IRAK1 and/or IRAK4 in conditions such as inflammatory diseases and autoimmune disease, wherein said inflammatory diseases and autoimmune diseases are characterized by overactive IRAK1 and/or IRAK4. In some embodiments, inflammatory and autoimmune diseases characterized by dysregulated (e.g., hyperactive) IRAK expression (IRAK1 and/or IRAK4) and/or IRAK-mediated intracellular signaling, can be treated, and include, but are not limited to, chronic inflammation (i.e., associated with viral and bacterial infection), sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, and the like, and combinations thereof.

In certain embodiments, MDS that can be treated in a subject (e.g., mammals, porcine, canine, avian (e.g., chicken), bovine, feline, primates, rodents, monkeys, rabbits, mice, rats, and humans) using a compound of the disclosure (e.g., Formula (I)) include but are not limited to NMS with a splicing factor mutation, MDS with a mutation in isocitrate dehydrogenase 1, MDS with a mutation in isocitrate dehydrogenase 2, refractory cytopenia with unilineage dysplasia (e.g., refractory anemia, refractory neutropenia, and refractory thrombocytopenia), refractory anemia with ring sideroblasts, refractory cytopenia with multilineage dysplasia (e.g., refractory cytopenia with multilineage dysplasia and ring sideroblasts and animals/humans with pathological changes not restricted to red cells such as prominent white cell precursor and platelet precursor (megakaryocyte) dysplasia), refractory anemias with excess blasts I and II, 5q-syndrome, megakaryocyte dysplasia with fibrosis, and refractory cytopenia of childhood. In some embodiments, NMS that can be treated include, but are not limited to, MDS that is inherited, MDS with an increased risk of occurrence due to an inherited predisposition, MDS with an increased risk of occurrence due to other blood disorders, NMS with an increased risk of occurrence due to chemical exposure, NMS with an increased risk of occurrence due to ionizing radiation, MDS with an increased risk of occurrence due to cancer treatment (e.g., a combination of radiation and the radiomimetic alkylating agents such as busulfan, nitrosourea, or procarbazine (with a latent period of 5 to 7 years) or DNA topoisomerase inhibitors), MDS evolving from acquired aplastic anemia following immunosuppressive treatment and Fanconi's anemia, MDS with an increased risk due to an mutation in splicing factors, MDS with an increased risk due to a mutation in isocitrate dehydrogenase 1, and MDS with an increased risk due to a mutation in isocitrate dehydrogenase 2. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. In the methods, the term "subject" may refer to both human and non-human subjects. In some instances, the subject is in need of the treatment (e.g., by showing signs of disease, e.g. MDS, AML, cancer, autoimmune disease, inflammatory condition, etc., or by having a low blood cell count).

In some embodiments, MDS that can be treated in a subject (e.g., mammals, porcine, canine, avian (e.g., chicken), bovine, feline, primates, rodents, monkeys, rabbits, mice, rats, and humans) using a compound of the disclosure (e.g., Formula (I)) include, but are not limited to MDS that can be treated by inhibiting one or more of FLT3 (e.g., using FLT3 inhibitors), mutations of FLT3 (e.g., using inhibitors of FLT3 mutants), IRAK4 (e.g., using IRAK4 inhibitors), mutations of IRAK4 (e.g., using inhibitors of IRAK4 mutants), IRAK1 (e.g., using IRAK 1 inhibitors), and/or mutations of IRAK1 (e.g., using inhibitors of IRAK1 mutant). In certain embodiments, MDS that can be treated include, but are not limited to MDS that can be treated by inhibiting IRAK4 (or its mutations), MDS that can be treated by inhibiting and IRAK1 (or its mutations), or MDS that can be treated by inhibiting IRAK4 (or its mutations) and IRAK1 (or its mutations). In some embodiments, MDS that can be treated include, but are not limited to MDS that can be treated by inhibiting FLT3 in combination with IRAK4, IRAK1, or both IRAK4 and IRAK1. In some embodiments, inhibiting FLT3 in combination with IRAK4, IRAK1, or both IRAK4 and IRAK1 provides for treating tumors with FLT3 mutations, which can be or become resistant to FLT3 inhibitors due to adaptive resistance mechanism(s), e.g., driven by IRAK. In some embodiments, MDS that can be treated is characterized by MDS having enhanced IRAK4-Long expression and/or activity relative to IRAK4-Short, and/or wherein the MDS is not driven by FLT3 mutations but expresses IRAK4-Long, based on the use of IRAK4L and the ratio of IRAK4L to IRAK4S (e.g. as described in U.S. patent application Ser. No. 16/339,692; and Smith, M. A., et al. (2019). "U2AF1 mutations induce oncogenic IRAK4 isoforms and activate innate immune pathways in myeloid malignancies." *Nat Cell Biol* 21(5): 640-650. DOI: 10.1038/s41556-019-0314-5, both incorporated by reference herein in their entirety).

In some embodiments, AML that can be treated in a subject (e.g., mammals, porcine, canine, avian (e.g., chicken), bovine, feline, primates, rodents, monkeys, rabbits, mice, rats, and humans) using a compound of the disclosure (e.g., Formula (I)) include, but are not limited to AML that is inherited, AML with an increased risk of occurrence due to an inherited predisposition, AML with one or more recurrent genetic abnormality (e.g., with inversions or translocations, such as MLLT3/MLL which is a translocation between chromosome 9 and 11 ("MLL") AML with translocation between chromosomes 8 and 21, AML with translocation or inversion in chromosome 16, AML with translocation between chromosomes 9 and 11, APL (M3) with translocation between chromosomes 15 and 17, AML with translocation between chromosomes 6 and 9, AML with translocation or inversion in chromosome 3, and the like), AML (megakaryoblastic) with a translocation between chromosomes 1 and 22, AML with myelodysplasia-related changes, AML related to previous chemotherapy or radiation (such as, for example, alkylating agent-related AML, topoisomerase II inhibitor-related AML, and the like), AML not otherwise categorized (does not fall into above categories—similar to FAB classification; such as, for example, AML minimally differentiated (M0), AML with minimal maturation (M1), AML with maturation (M2), acute myelomonocytic leukemia (M4), acute monocytic leukemia (M5), acute erythroid leukemia (M6), acute megakaryoblastic leukemia (M7), acute basophilic leukemia, acute panmyelosis with fibrosis, and the like), myeloid sarcoma (also known as granulocytic sarcoma, chloroma or extramedullary myeloblastoma), undifferentiated and biphenotypic acute leukemias (also known as mixed phenotype acute leukemias), AML with an increased risk of occurrence due to other blood disorders, AML with an increased risk of occurrence due to chemical exposure, AML with an increased risk of occurrence due to ionizing radiation, AML evolving from myelodysplastic syndromes, AML evolving from myeloproliferative disease, AML with an increased risk due to an FLT3 mutation, AML with an increased risk due to an FLT3 mutation in the juxtamembrane region of FLT3, AML with an increased risk due to an FLT3 mutation of an internal tandem duplication in the juxtamembrane region of FLT3, AML with an increased risk due to an FLT3 mutation in the kinase domain of FLT3, AML with an increased risk due to the FLT3 mutation D835Y, AML with an increased risk due to the FLT3 mutation D835V, AML with an increased risk due to the FLT3 mutation F691L, and AML with an increased risk due to the FLT3 mutation R834Q, and the like. In some embodiments, AML that can be treated include AML that by inhibiting one or more of FLT3 (e.g., using FLT3 inhibitors), mutations of FLT3 (e.g., using inhibitors of FLT3 mutants), IRAK4 (e.g., using IRAK4 inhibitors), mutations of IRAK4 (e.g., using inhibitors of IRAK4 mutants), IRAK1 (e.g., using IRAK 1 inhibitors), and/or mutations of IRAK1 (e.g., using inhibitors of IRAK1 mutant). In certain embodiments, AML that can be treated include, but are not limited to AML that can be treated by inhibiting IRAK4 (or its mutations), MDS that can be treated by inhibiting and IRAK1 (or its mutations), or AML that can be treated by inhibiting IRAK4 (or its mutations) and IRAK1 (or its mutations). In some embodiments, AML that can be treated include, but are not limited to AML that can be treated by inhibiting FLT3 in combination with IRAK4, IRAK1, or both IRAK4 and IRAK1. In some embodiments, inhibiting FLT3 in combination with IRAK4, IRAK1, or both IRAK4 and IRAK1 provides for treating tumors with FLT3 mutations which can be or become resistant to FLT3 inhibitors due to adaptive resistance mechanism(s), e.g. driven by IRAK. In some embodiments, AML that can be treated is characterized by AML having enhanced IRAK4-Long expression and/or activity relative to IRAK4-Short, and/or wherein the AML is not driven by FLT3 mutations but expresses IRAK4-Long, based on the use of IRAK4L and the ratio of IRAK4L to IRAK4S (e.g. as described in U.S. patent application Ser. No. 16/339,692; and Smith, M. A., et al. (2019). "U2AF1 mutations induce oncogenic IRAK4 isoforms and activate innate immune pathways in myeloid malignancies." *Nat Cell Biol* 21(5): 640-650. DOI: 10.1038/s41556-019-0314-5, both incorporated by reference herein in their entirety).

In some embodiments, hematopoietic cancers that can be treated in a subject (e.g., mammals, porcine, canine, avian (e.g., chicken), bovine, feline, primates, rodents, monkeys, rabbits, mice, rats, and humans) using a compound of the disclosure (e.g., Formula (I)) include, but are not limited to hematopoietic cancers (e.g. MDS, AML, DLBCL, and the like, as described previously) that can be treated by inhibiting (e.g., reducing the activity or expression of) one or more of FLT3 (e.g., using FLT3 inhibitors), mutations of FLT3 (e.g., using inhibitors of FLT3 mutants), IRAK4 (e.g., using IRAK4 inhibitors), isoforms of IRAK4, mutations of IRAK4 (e.g., using inhibitors of IRAK4 mutants), IRAK1 (e.g., using IRAK 1 inhibitors), isoforms of IRAK1, or mutations of IRAK1 (e.g., using inhibitors of IRAK1 mutants). In certain embodiments, hematopoietic cancers that can be treated include, but are not limited to cancers that can be treated by inhibiting (e.g., reducing the activity or expression of) FLT3 (or its mutations) and IRAK4 (or its mutations), hematopoietic cancers that can be treated by inhibiting (e.g., reducing the activity or expression of) FLT3 (or its mutations) and IRAK1 (or its mutations), or hematopoietic cancers that can be treated by inhibiting (e.g., reducing the activity or expression of) FLT3 (or its mutations), IRAK4 (or its isoforms or mutations), and IRAK1 (or its isoforms mutations). In some embodiments, hematopoietic cancer that can be treated include, but are not limited to hematopoietic cancer that can be treated by inhibiting FLT3 in combination with IRAK4, IRAK1, or both IRAK4 and IRAK1. In some embodiments, inhibiting FLT3 in combination with IRAK4, IRAK1, or both IRAK4 and IRAK1 provides for treating tumors with FLT3 mutations which can be or become resistant to FLT3 inhibitors due to adaptive resistance mechanism(s), e.g. driven by IRAK. In some embodiments, hematopoietic cancer that can be treated is characterized by hematopoietic cancer having enhanced IRAK4-Long expression and/or activity relative to IRAK4-Short, and/or wherein the hematopoietic cancer is not driven by FLT3 mutations but expresses IRAK4-Long, based on the use of IRAK4L and the ratio of IRAK4L to IRAK4S (e.g. as described in U.S. patent application Ser. No. 16/339,692; and Smith, M. A., et al. (2019). "U2AF1 mutations induce oncogenic IRAK4 isoforms and activate innate immune pathways in myeloid malignancies." *Nat Cell Biol* 21(5): 640-650. DOI: 10.1038/s41556-019-0314-5, both incorporated by reference herein in their entirety).

In some embodiments, cancers that can be treated include, but are not limited to, glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, and the like, and combinations thereof, that can be treated by inhibiting FLT3 in combination with IRAK4, IRAK1, or both IRAK4 and IRAK1. In some embodiments, inhibiting FLT3 in combination with IRAK4, IRAK1, or both IRAK4 and IRAK1 provides for treating tumors with FLT3 mutations which can be or become resistant to FLT3 inhibitors due to adaptive resistance mechanism(s), e.g., driven by IRAK. In some embodiments, cancer that can be treated is characterized by cancer having enhanced IRAK4-Long expression and/or activity relative to IRAK4-Short, and/or wherein the cancer is not driven by FLT3 mutations but expresses IRAK4-Long, based on the use of IRAK4L and the ratio of IRAK4L to IRAK4S (e.g. as described in U.S. patent application Ser. No. 16/339,692; and Smith, M. A., et al. (2019). "U2AF1 mutations induce oncogenic IRAK4 isoforms and activate innate immune pathways in myeloid malignancies." *Nat Cell Biol* 21(5): 640-650. DOI: 10.1038/s41556-019-0314-5, both incorporated by reference herein in their entirety).

In some embodiments, inflammatory and autoimmune diseases characterized by dysregulated (e.g., hyperactive) IRAK expression (IRAK1 and/or IRAK4) and/or IRAK-mediated intracellular signaling, that can be treated include, but are not limited to, chronic inflammation (i.e., associated with viral and bacterial infection), sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, and the like, and combinations thereof, that can be treated by inhibiting FLT3 in combination with IRAK4, IRAK1, or both IRAK4 and IRAK1. In some embodiments, inhibiting FLT3 in combination with IRAK4, IRAK1, or both IRAK4 and IRAK1 provides for treating inflammatory and autoimmune diseases with FLT3 mutations which can be or become resistant to FLT3 inhibitors due to adaptive resistance mechanism(s), e.g., driven by IRAK. In some embodiments, inflammatory and autoimmune disease that can be treated is characterized by inflammatory and autoimmune disease having enhanced IRAK4-Long expression and/or activity relative to IRAK4-Short, and/or wherein the inflammatory and autoimmune disease is not driven by FLT3 mutations but expresses IRAK4-Long, based on the use of IRAK4L and the ratio of IRAK4L to IRAK4S (e.g. as described in U.S. patent application Ser. No. 16/339,692; and Smith, M. A., et al. (2019). "U2AF1 mutations induce oncogenic IRAK4 isoforms and activate innate immune pathways in myeloid malignancies." *Nat Cell Biol* 21(5): 640-650. DOI: 10.1038/s41556-019-0314-5, both incorporated by reference herein in their entirety).

As related to treating MDS (e.g., MDS with a splicing factor mutation, MDS with a mutation in isocitrate dehydrogenase 1, or MDS with a mutation in isocitrate dehydrogenase 2), treating can include but is not limited to prophylactic treatment and therapeutic treatment. As such, treatment can include, but is not limited to: preventing NMS (e.g., MDS with a splicing factor mutation, MDS with a mutation in isocitrate dehydrogenase 1, or NMS with a mutation in isocitrate dehydrogenase 2); reducing the risk of NMS (e.g., NMS with a splicing factor mutation, NMS with a mutation in isocitrate dehydrogenase 1, or NMS with a mutation in isocitrate dehydrogenase 2); ameliorating or relieving symptoms of NMS (e.g., MDS with a splicing factor mutation, MDS with a mutation in isocitrate dehydrogenase 1, or NMS with a mutation in isocitrate dehydrogenase 2); eliciting a bodily response against MDS (e.g., NMS with a splicing factor mutation, NMS with a mutation in isocitrate dehydrogenase 1, or MDS with a mutation in isocitrate dehydrogenase 2); inhibiting the development or progression of NMS (e.g., MDS with a splicing factor mutation, MDS with a mutation in isocitrate dehydrogenase 1, or MDS with a mutation in isocitrate dehydrogenase 2); inhibiting or preventing the onset of symptoms associated with NMS (e.g., MDS with a splicing factor mutation, MDS with a mutation in isocitrate dehydrogenase 1, or MDS with a mutation in isocitrate dehydrogenase 2); reducing the severity of MDS (e.g., MDS with a splicing factor mutation, NMS with a mutation in isocitrate dehydrogenase 1, or NMS with a mutation in isocitrate dehydrogenase 2); causing a regression of NMS (e.g., NMS with a splicing factor mutation, NMS with a mutation in isocitrate dehydrogenase 1, or MDS with a mutation in isocitrate dehydrogenase 2) or one or more of the symptoms associated with MDS (e.g., an increase in blood cell count); causing remission of NMS (e.g., NMS with a splicing factor mutation, NMS with a mutation in isocitrate dehydrogenase 1, or MDS with a mutation in isocitrate dehydrogenase 2); causing remission of NMS (e.g., NMS with a splicing factor mutation, NMS with a mutation in isocitrate dehydrogenase 1, or NMS with a mutation in isocitrate dehydrogenase 2) by preventing or minimizing FLT3 mutations (e.g., internal tandem duplication mutations or the D835Y mutation); preventing relapse of NMS (e.g., MDS with a splicing factor mutation, NMS with a mutation in isocitrate dehydrogenase 1, or NMS with a mutation in isocitrate dehydrogenase 2); or preventing relapse of MDS (e.g., MDS with a splicing factor mutation, NMS with a mutation in isocitrate dehydrogenase 1, or NMS with a mutation in isocitrate dehydrogenase 2) in animals/humans that have intrinsic or acquired resistance to other NMS treatments. In some embodiments, treating does not include prophylactic treatment of MDS (e.g., preventing or ameliorating future MDS).

As related to treating hematopoietic cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation (e.g., ABC DLBCL with MYD88 mutation L265P), follicular lymphoma, or marginal zone lymphoma, and combinations thereof, and the like), treating can include but is not limited to prophylactic treatment and therapeutic treatment. As such, treatment can include, but is not limited to: preventing cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); reducing the risk of cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); ameliorating or relieving symptoms of cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); eliciting a bodily response against cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); inhibiting the development or progression of cancer (e.g., acute myeloid leukemia, lymphoma, leukemia, chronic lymphocytic leukemia (CLL), chronic myeloid leukemia (CML), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); inhibiting or preventing the onset of symptoms associated with cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, or Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); reducing the severity of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); causing a regression of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like) or one or more of the symptoms associated with cancer (e.g., a decrease in tumor size); causing remission of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); causing remission of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like) by preventing or minimizing FLT3 mutations (e.g., internal tandem duplication mutations or the D835Y mutation); causing remission of acute myeloid leukemia by preventing or minimizing FLT3 mutations (e.g., internal tandem duplication mutations or the D835Y mutation); preventing relapse of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like); preventing relapse of cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like) in animals/humans that have intrinsic or acquired resistance to other cancer treatments (e.g., from some FLT3 inhibitors or from MLL); or preventing relapse of acute myeloid leukemia in animals/humans that have intrinsic or acquired resistance to other cancer treatments (e.g., from some FLT3 inhibitors or from MLL). In some embodiments, treating does not include prophylactic treatment of cancer (e.g., preventing or ameliorating future cancer).

Treatment of a subject can occur using any suitable administration method (such as those disclosed herein) and using any suitable amount of a compound of the disclosure (e.g., Formula (I)). In some embodiments, methods of treatment comprise treating an animal or human for MDS (e.g., MDS with a splicing factor mutation, NMS with a mutation in isocitrate dehydrogenase 1, or NMS with a mutation in isocitrate dehydrogenase 2). In some embodiments, methods of treatment comprise treating an animal or human for a hematopoietic cancer (e.g., acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like). Other embodiments include treatment after one or more of having a blood disorder, having myelodysplastic syndrome, having myeloproliferative disease, an occurrence of chemical exposure, an exposure to ionizing radiation, or a treatment for a hematopoietic cancer (e.g., with chemotherapy, ionizing radiation, or both). Some embodiments of the disclosure include a method for treating a subject (e.g., an animal such as a human or primate) with a composition comprising a compound of the disclosure (e.g., Formula (I)) (e.g., a pharmaceutical composition) which comprises one or more administrations of one or more such compositions; the compositions may be the same or different if there is more than one administration.

In some embodiments, the method of treatment includes administering to a subject an effective amount of a composition comprising a compound of the disclosure (e.g., Formula (I)). As used herein, the term "effective amount" refers to a dosage or a series of dosages sufficient to affect treatment (e.g., to treat MDS such as but not limited to MDS (e.g., MDS with a splicing factor mutation, MDS with a mutation in isocitrate dehydrogenase 1, or MDS with a mutation in isocitrate dehydrogenase 2); or to treat a hematopoietic cancer, such as but not limited to acute myeloid leukemia, lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL MYD88 mutation, follicular lymphoma, or marginal zone lymphoma, and combinations thereof, and the like) in a subject. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the disclosure (e.g., Formula (I) such as but not limited to Compounds 1-132, as listed in Tables 1-21) (which can be administered to a subject such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg body weight or about 6.5 mg/kg body weight. In some instances, an effective amount of at least one compound of the disclosure (e.g., Formula (I) such as but not limited to Compounds 1-132, as listed in Tables 1-21) (which can be administered to a subject such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the disclosure (e.g., Formula (I) such as but not limited to Compounds 1-132, as listed in Tables 1-21) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the disclosure (e.g., Formula (I) such as but not limited to Compounds 1-132, as listed in Tables 1-21) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; anti-estrogens, such as tamoxifen; high-dose progestogens; aromatase inhibitors; and/or adrenalectomy. Chemotherapy can be used as a single-agent or as a combination with known or new therapies.

In some embodiments, the administration to a subject of at least one compound of the disclosure (e.g., Formula (I)) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the disclosure (e.g., Formula (I)) can be used as adjuvant with other chemotherapeutic agents. The use of a compound of the disclosure (e.g., Formula (I)) may, in some instances, reduce the duration of the dose of both drugs and drug combinations reducing the side effects.

In some embodiments, the administration to a subject may decrease the incidence of one or more symptoms associated with MDS/AML/a type of hematopoietic cancer. In some embodiments, the administration may decrease marrow failure, immune dysfunction, transformation to overt leukemia, or combinations thereof in said subject, as compared to a subject not receiving said composition.

In some embodiments, the method may decrease a marker of viability of MDS cells AML cells, or cancer cells in a subject. In one aspect, the method may decrease a marker of viability of MDS, AML, and/or cancer cells. The marker may be selected from survival over time, proliferation, growth, migration, formation of colonies, chromatic assembly, DNA binding, RNA metabolism, cell migration, cell adhesion, inflammation, or a combination thereof.

Combination Therapies

In some embodiments, the treatments disclosed herein can include use of other drugs (e.g., antibiotics) or therapies for treating disease, e.g. MDS/AML/a type of hematopoietic cancer. For example, antibiotics can be used to treat infections and can be combined with a compound of the disclosure to treat disease (e.g., infections). In other embodiments, intravenous immunoglobulin (IVIG) therapy can be used as part of the treatment regime (i.e., in addition to administration of the compound(s) of the disclosure). For example, treatment regimens for various types of cancers can involve one or more elements selected from chemotherapy, targeted therapy, alternative therapy, immunotherapy, and the like.

Accordingly, in some embodiments, the compounds and/or compositions described herein can be used in one or more administrations to a subject, in combination with one or more BCL2 inhibitor, BTK inhibitor, chemotherapy, targeted therapy, alternative therapy, immunotherapy, DNA methyltransferase inhibitor/hypomethylating agent, anthracycline, histone deacetylase (HDAC) inhibitor, purine nucleoside analogue (antimetabolite), isocitrate dehydrogenase 1 or 2 (IDH1 and/or IDH2) inhibitor, antibody-drug conjugate, mAbs/immunotherapy, CAR-T cell therapy, P1k inhibitor, MEK inhibitor, CDK9 inhibitor, CDK8 inhibitor, retinoic acid receptor agonist, TP53 activator, smoothened receptor antagonist, ERK inhibitor, PI3K inhibitor, mTOR inhibitor, glucocorticoid receptor modulator, or EZH2 inhibitor, and the like, or one or more combinations thereof, where the compositions may be the same or different if there is more than one administration. In some embodiments, if there is more than one administration at least one composition used for at least one administration is different from the composition of at least one other administration.

In particular, IRAK inhibitors have been demonstrated to have synergistic effects when administered in combination with an apoptosis modulator/inhibitor, such as a BCL2 inhibitor. As described in U.S. patent application Ser. No. 16/804,518 (incorporated herein by reference in its entirety), an exemplary apoptosis/BCL2 inhibitor has been shown to have a synergistic effect when used in combination with an exemplary IRAK inhibitor in multiple AML cell lines. Venetoclax was used as a representative apoptosis/BCL2 inhibitor.

When a concentration of an exemplary IRAK inhibitor was combined with venetoclax, the potency of venetoclax was increased by an unexpectedly high ~50-fold. According to particular aspects of the disclosure, this synergistic combination allows for increased efficacy of venetoclax at lower doses, to provide for avoiding at least some of the toxicity observed in the clinic. According to particular aspects, the degree of interaction is dependent on the dose ratio combination that is used, with lower concentrations of the exemplary IRAK inhibitor providing larger shifts in the venetoclax IC50. This unexpected and dramatic shift in the venetoclax IC50 is substantially more than an additive response and demonstrates the unexpected synergistic interaction of the two drugs even in cell lines that do not express activated FLT3 mutants.

Accordingly, the present disclosure encompasses methods for treating a disease or disorder which is responsive to inhibition of IRAK, comprising administration to a subject of a composition comprising an IRAK inhibiting compound, wherein some embodiments of the method can further involve administration of an apoptotic modulator. The apoptotic modulator may comprise a BTK and/or a BCL2 inhibitor. BTK and BCL2 inhibitors may be, for example, those known in the art. In some embodiments, the method may comprise the step of administering to the subject an apoptotic modulator. In some embodiments, the apoptotic modulator may comprise a BCL2 inhibitor selected from ABT-263 (Navitoclax), ABT-737, ABT-199 (venetoclax), GDC-0199, GX15-070 (Obatoclax) (all available from Abbott Laboratories), HA14-1, Si, 2-methoxy antimycin A3, gossypol, AT-101, apogossypol, WEHI-539, A-1155463, BXI-61, BXI-72, TW37, MIM1, UMI-77, and the like, and combinations thereof. One skilled in the art would appreciate that there are many known BCL2 inhibitors which can be used in accordance with the present disclosure. In some embodiments, the BCL2 inhibitor comprises venetoclax.

In some embodiments, the administration step comprises administration to a subject of a composition comprising an IRAK inhibiting compound and a BCL2 inhibitor. In some embodiments, the administration step comprises administration of a composition comprising an IRAK inhibiting compound in combination with a composition comprising a BCL2 inhibitor.

In some embodiments, the IRAK inhibiting compound is selected from Compounds 1-132, or a salt, isomer, derivative or analog thereof, and the BCL2 inhibitor is venetoclax, or a salt, isomer, derivative or analog thereof.

In some embodiments, the method can further involve administration to a subject of an immune modulator. The immune modulator can include, for example, Lenalidomide (Revlamid; Celgene Corporation). In some embodiments, the method can involve administration of an epigenetic modulator. The epigenetic modulator can include, for example, a hypomethylating agent such as azacitidine, decitabine, or a combination thereof.

In some embodiments, the compounds and/or compositions described herein can be used in one or more administrations to a subject, together with or in combination with one or more BTK inhibitor, such as, for example, ibrutinib, or a salt, isomer, derivative or analog thereof.

For example, the compounds and/or compositions described herein can be used in one or more administrations, together with or in combination with a DNA methyltransferase inhibitor/hypomethylating agent, such as, for example, azacytidine, decitabine, cytarabine, and/or guadecitabine; an anthracycline, such as, for example, daunorubicin, idarubicin, doxorubicin, mitoxantrone, epirubicin, and/or CPX-351 (a combination cytarabine and daunorubicin in a fixed 5:1 molar ratio), and the like; a histone deacetylase (HDAC) inhibitor, such as, for example, vorinostat, panobinostat, valproic acid, and/or pracinostat, and the like; a purine nucleoside analogue (antimetabolite), such as, for example, fludarabine, cladribine, and/or clofarabine, and the like; an isocitrate dehydrogenase 1 or 2 (IDH1 and/or IDH2) inhibitor, such as, for example, ivosidenib and/or enasidenib, and the like; an antibody-drug conjugate, such as, for example, Anti-CD33 (e.g. Ac225-lintuzumab, vadastuximab, or gemtuzumab-ozogamicin) and/or Anti-CD45 (e.g. $I^{131}$-apamistamab), and the like; an mAbs/Immunotherapy, such as, for example, Anti-CD70 (e.g. ARGX-110, cusatuzumab), a bispecific antibody (e.g. floteuzumab (CD123×CD3)), Anti-CTLA4 (e.g. ipilimumab), Anti-PD1/PDL1 (e.g. nivolumab, pembrolizumab, atezolizumab, avelumab, PDR001, MBG453), and/or Anti-CD47 (e.g. 5F9 (Magrolimab)), and the like; a Plk inhibitor, such as, for example, volasertib and/or rigosertib, and the like; a MEK inhibitor, such as, for example, trametinib, cobimetinib, selumetinib, pimasertib, and/or refametinib, and the like; a CDK9 inhibitor, such as, for example, alvocidib and/or voruciclib, and the like; a CDK8 inhibitor, such as, for example, SEL120, and the like; a retinoic acid receptor agonist, such as, for example, ATRA (all-trans retinoic acid) and/or SY-1425 (a selective RARa agonist), and the like; a TP53 activator, such as, for example, APR-246 (Eprenetapopt), and the like; a smoothened receptor antagonist, such as, for example, glasdegib, and the like; an ERK inhibitor, such as, for example, an ERK2/MAPK1 or ERK1/MAPK3 inhibitor, such as, for example, ulixertinib, SCH772984, ravoxertinib, MK-8353, and/or VTX-11e, and the like; a PI3K inhibitor, such as, for example, fimepinostat (CUDC-907), alpelisib, leniolisib (CDZ-173), pilaralisib (XL147, SAR245408), and/or bimiralisib (PQR-309), and the like; an mTOR inhibitor, such as, for example, bimiralisib (PQR-309), sapanisertib (TAK-228, INK-128), ridaforolimus (MK-8669, AP-23573), everolimus, and/or vistusertib (AZD2014), and the like; a glucocorticoid receptor modulator, such as, for example, an agonist comprising prednisolone, beclometasone, methylprednisolone, prednisone, fluticasone, budesonide, dexamethasone, and/or cortisol, and/or an antagonist comprising mifepristone, miricorilant, and/or onapristone, and/or another binding ligand comprising vamorolone (VBP15), and the like; and/or an EZH2 inhibitor, such as, for example, tazemetostat, and the like. In some embodiments, compounds and pharmaceutical compositions including the same can be used in prevention of secondary malignancies when used in combination with an EZH2 inhibitor. Further therapies are described below and are contemplated in combination therapies in the context of the present disclosure.

Chemotherapy/Targeted Therapy/Alternative Therapy

Cancers are commonly treated with chemotherapy and/or targeted therapy and/or alternative therapy. Chemotherapies act by indiscriminately targeting rapidly dividing cells, including healthy cells as well as tumor cells, whereas targeted cancer therapies rather act by interfering with specific molecules, or molecular targets, which are involved in cancer growth and progression. Targeted therapy generally targets cancer cells exclusively, having minimal damage to normal cells. Chemotherapies and targeted therapies which are approved and/or in the clinical trial stage are known to those skilled in the art. Any such compound can be utilized in the practice of the present disclosure.

For example, approved chemotherapies include abitrexate (Methotrexate Injection), abraxane (Paclitaxel Injection), adcetris (Brentuximab Vedotin Injection), adriamycin (Doxorubicin), adrucil Injection (5-FU (fluorouracil)), afinitor (Everolimus), afinitor Disperz (Everolimus), alimta (PEMETREXED), alkeran Injection (Melphalan Injection), alkeran Tablets (Melphalan), aredia (Pamidronate), arimidex (Anastrozole), aromasin (Exemestane), arranon (Nelarabine), arzerra (Ofatumumab Injection), avastin (Bevacizumab), beleodaq (Belinostat Injection), bexxar (Tositumomab), BiCNU (Carmustine), blenoxane (Bleomycin), blincyto (Blinatumoma b Injection), bosulif (Bosutinib), busulfex Injection (Busulfan Injection), campath (Alemtuzumab), camptosar (Irinotecan), caprelsa (Vandetanib), casodex (Bicalutamide), CeeNU (Lomustine), CeeNU Dose Pack (Lomustine), cerubidine (Daunorubicin), clolar (Clofarabine Injection), cometriq (Cabozantinib), cosmegen (Dactinomycin), cotellic (Cobimetinib), cyramza (Ramucirumab Injection), cytosarU (Cytarabine), cytoxan (Cytoxan), cytoxan Injection (Cyclophosphamide Injection), dacogen (Decitabine), daunoXome (Daunorubicin Lipid Complex Injection), decadron (Dexamethasone), depoCyt (Cytarabine Lipid Complex Injection), dexamethasone Intensol (Dexamethasone), dexpak Taperpak (Dexamethasone), docefrez (Docetaxel), doxil (Doxorubicin Lipid Complex Injection), droxia (Hydroxyurea), DTIC (Decarbazine), eligard (Leuprolide), ellence (Ellence (epirubicin)), eloxatin (Eloxatin (oxaliplatin)), el spar (Asparaginase), emcyt (Estramustine), erbitux (Cetuximab), erivedge (Vismodegib), erwinaze (Asparaginase *Erwinia chrysanthemi*), ethyol (Amifostine), etopophos (Etoposide Injection), eulexin (Flutamide), fareston (Toremifene), farydak (Panobinostat), faslodex (Fulvestrant), femara (Letrozole), firmagon (Degarelix Injection), fludara (Fludarabine), folex (Methotrexate Injection), folotyn (Pralatrexate Injection), FUDR (FUDR (floxuridine)), gazyva (Obinutuzumab Injection), gemzar (Gemcitabine), gilotrif (Afatinib), gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Ibrance (Palbociclib), Iclusig (Ponatinib), Idamycin PFS (Idarubicin), Ifex (Ifosfamide), Imbruvica (Ibrutinib), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Keytruda (Pembrolizumab Injection), Kyprolis (Carfilzomib), Lanvima (Lenvatinib), Leukeran (Chlorambucil), Leukine (Sargramostim), Leustatin (Cladribine), Lonsurf (Trifluridine and Tipiracil), Lupron (Leuprolide), Lupron Depot (Leuprolide), Lupron Depot-PED (Leuprolide), Lynparza (Olaparib), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Odomzo (Sonidegib), Oncaspar (Pegaspargase), Oncovin (Vincristine), Ontak (Denileukin Diftitox), onxol (Paclitaxel Injection), opdivo (Nivolumab Injection), panretin (Alitretinoin), paraplatin (Carboplatin), perjeta (Pertuzumab Injection), platinol (Cisplatin), platinol (Cisplatin Injection), platinolAQ (Cisplatin), platinolAQ (Cisplatin Injection), pomalyst (Pomalidomide), prednisone Intensol (Prednisone), proleukin (Aldesleukin), purinethol (Mercaptopurine), reclast (Zoledronic acid), revlimid (Lenalidomide), rheumatrex (Methotrexate), rituxan (Rituximab), roferonA alfaa (Interferon alfa-2a), rubex (Doxorubicin), sandostatin (Octreotide), sandostatin LAR Depot (Octreotide), soltamox (Tamoxifen), sprycel (Dasatinib), sterapred (Prednisone), sterapred DS (Prednisone), stivarga (Regorafenib), supprelin LA (Histrelin Implant), sutent (Sunitinib), sylatron (Peginterferon Alfa-2b Injection (Sylatron)), sylvant (Siltuximab Injection), synribo (Omacetaxine Injection), tabloid (Thioguanine), taflinar (Dabrafenib), tarceva (Erlotinib), targretin Capsules (Bexarotene), tasigna (Decarbazine), taxol (Paclitaxel Injection), taxotere (Docetaxel), temodar (Temozolomide), temodar (Temozolomide Injection), tepadina (Thiotepa), thalomid (Thalidomide), theraCys BCG (BCG), thioplex (Thiotepa), TICE BCG (BCG), toposar (Etoposide Injection), torisel (Temsirolimus), treanda (Bendamustine hydrochloride), trelstar (Triptorelin Injection), trexall (Methotrexate), trisenox (Arsenic trioxide), tykerb (lapatinib), unituxin (Dinutuximab Injection), valstar (Valrubicin Intravesical), vantas (Histrelin Implant), vectibix (Panitumumab), velban (Vinblastine), velcade (Bortezomib), vepesid (Etoposide), vepesid (Etoposide Injection), vesanoid (Tretinoin), vidaza (Azacitidine), vincasar PFS (Vincristine), vincrex (Vincristine), votrient (Pazopanib), vumon (Teniposide), wellcovorin IV (Leucovorin Injection), xalkori (Crizotinib), xeloda (Capecitabine), xtandi (Enzalutamide), yervoy (Ipilimumab Injection), yondelis (Trabectedin Injection), zaltrap (Ziv-aflibercept Injection), zanosar (Streptozocin), zelboraf (Vemurafenib), zevalin (Ibritumomab Tiuxetan), zoladex (Goserelin), zolinza (Vorinostat), zometa (Zoledronic acid), zortress (Everolimus), zydelig (Idelalisib), zykadia (Ceritinib), zytiga (Abiraterone), and the like, in addition to analogs and derivatives thereof. For example, approved targeted therapies include ado-trastuzumab emtansine (Kadcyla), afatinib (Gilotrif), aldesleukin (Proleukin), alectinib (Alecensa), alemtuzumab (Campath), axitinib (Inlyta), belimumab (Benlysta), belinostat (Beleodaq), bevacizumab (Avastin), bortezomib (Velcade), bosutinib (Bosulif), brentuximab vedotin (Adcetris), cabozantinib (Cabometyx, Cometriq), canakinumab (Ilaris), carfilzomib (Kyprolis), ceritinib (Zykadia), cetuximab (Erbitux), cobimetinib (Cotellic), crizotinib (Xalkori), dabrafenib (Tafinlar), daratumumab (Darzalex), dasatinib (Sprycel), denosumab (Xgeva), dinutuximab (Unituxin), elotuzumab (Empliciti), erlotinib (Tarceva), everolimus (Afinitor), gefitinib (Iressa), ibritumomab tiuxetan (Zevalin), ibrutinib (Imbruvica), idelalisib (Zydelig), imatinib (Gleevec), ipilimumab (Yervoy), ixazomib (Ninlaro), lapatinib (Tykerb), lenvatinib (Lenvima), necitumumab (Portrazza), nilotinib (Tasigna), nivolumab (Opdivo), obinutuzumab (Gazyva), ofatumumab (Arzerra, HuMax-CD20), olaparib (Lynparza), osimertinib (Tagrisso), palbociclib (Ibrance), panitumumab (Vectibix), panobinostat (Farydak), pazopanib (Votrient), pembrolizumab (Keytruda), pertuzumab (Perj eta), ponatinib (Iclusig), ramucirumab (Cyramza), rapamycin, regorafenib (Stivarga), rituximab (Rituxan, Mabthera), romidepsin (Istodax), ruxolitinib (Jakafi), siltuximab (Sylvant), sipuleucel-T (Provenge), sirolimus, sonidegib (Odomzo), sorafenib (Nexavar), sunitinib, tamoxifen, temsirolimus (Torisel), tocilizumab (Actemra), tofacitinib (Xeljanz), tositumomab (Bexxar), trametinib (Mekinist), trastuzumab (Herceptin), vandetanib (Caprelsa), vemurafenib (Zelboraf), venetoclax (Venclexta), vismodegib (Erivedge), vorinostat (Zolinza), ziv-aflibercept (Zaltrap), and the like, in addition to analogs and derivatives thereof.

Those skilled in the art can determine appropriate chemotherapy and/or targeted therapy and/or alternative therapy options, including treatments that have been approved and those that in clinical trials or otherwise under development. Some targeted therapies are also immunotherapies. Any relevant chemotherapy, target therapy, and alternative therapy treatment strategies can be utilized, alone or in combination with one or more additional cancer therapy, in the practice of the present disclosure.

Immunotherapy

In some embodiments, immunotherapies include cell-based immunotherapies, such as those involving cells which effect an immune response (such as, for example, lymphocytes, macrophages, natural killer (NK) cells, dendritic cells, cytotoxic T lymphocytes (CTL), antibodies and antibody derivatives (such as, for example, monoclonal antibodies, conjugated monoclonal antibodies, polyclonal antibodies, antibody fragments, radiolabeled antibodies, chemolabeled antibodies, etc.), immune checkpoint inhibitors, vaccines (such as, for example, cancer vaccines (e.g. tumor cell vaccines, antigen vaccines, dendritic cell vaccines, vector-based vaccines, etc.), e.g. oncophage, sipuleucel-T, and the like), immunomodulators (such as, for example, interleukins, cytokines, chemokines, etc.), topical immunotherapies (such as, for example, imiquimod, and the like), injection immunotherapies, adoptive cell transfer, oncolytic virus therapies (such as, for example, talimogene laherparepvec (T-VEC), and the like), immunosuppressive drugs, helminthic therapies, other non-specific immunotherapies, and the like. Immune checkpoint inhibitor immunotherapies are those that target one or more specific proteins or receptors, such as PD-1, PD-Li, CTLA-4, and the like. Immune checkpoint inhibitor immunotherapies include ipilimumab (Yervoy), nivolumab (Opdivo), pembrolizumab (Keytruda), and the like. Non specific immunotherpaies include cytokines, interleukins, interferons, and the like. In some embodiments, an immunotherapy assigned or administered to a subject can include an interleukin, and/or interferon (IFN), and/or one or more suitable antibody-based reagent, such as denileukin diftitox and/or administration of an antibody-based reagent selected from the group consisting of ado-trastuzumab emtansine, alemtuzumab, atezolizumab, bevacizumab, blinatumomab, brentuximab vedotin, cetuximab, catumaxomab, gemtuzumab, ibritumomab tiuxetan, ilipimumab, natalizumab, nimotuzumab, nivolumab, ofatumumab, panitumumab, pembrolizumab, rituximab, tositumomab, trastuzumab, vivatuxin, and the like. In some embodiments, an immunotherapy assigned or administered to a subject can include an indoleamine 2,3-dioxygenase (IDO) inhibitor, adoptive T-cell therapy, virotherapy (T-VEC), and/or any other immunotherapy whose efficacy extensively depends on anti-tumor immunity.

Those skilled in the art can determine appropriate immunotherapy options, including treatments that have been approved and those that in clinical trials or otherwise under development. Any relevant immunotherapy treatment strategies, alone or in combination with one or more additional cancer therapy, can be utilized in the practice of the present disclosure.

Other Cancer Treatments

In addition to chemotherapies, targeted therapies, alternative therapies, and immunotherapies, cancer can additionally be treated by other strategies. These include surgery, radiation therapy, hormone therapy, stem cell transplant, precision medicine, and the like; such treatments and the compounds and compositions utilized therein are known to those skilled in the art. Any such treatment strategies can be utilized in the practice of the present disclosure.

Alternative treatment strategies have also been used with various types of cancers. Such treatment can be used alone or in combination with any other treatment modality. These include exercise, massage, relaxation techniques, yoga, acupuncture, aromatherapy, hypnosis, music therapy, dietary changes, nutritional and dietary supplements, and the like; such treatments are known to those skilled in the art. Any such treatment strategies can be utilized, alone or in combination with one or more additional cancer therapy, in the practice of the present disclosure.

Dosage and Administration Routes

Other embodiments of the disclosure can include methods of administering or treating an animal/human, which can involve treatment with an amount of at least one compound of the disclosure (e.g., Formula (I)) that is effective to treat the disease, condition, or disorder that the organism has, or is suspected of having, or is susceptible to, or to bring about a desired physiological effect. In some embodiments, the composition or pharmaceutical composition comprises at least one compound of the disclosure (e.g., Formula (I)) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some subjects (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present disclosure, and using, in part, the guidance provided herein, will be able to adjust and test any number of concentrations in order to find one that achieves the desired result in a given circumstance. In some embodiments, a dose or a therapeutically effective dose of a compound disclosed herein will be that which is sufficient to achieve a plasma concentration of the compound or its active metabolite(s) within a range set forth herein, e.g., 1-10 nM, 10-100 nM, 1-100 nM, 0.1-1 nM, 0.1-100 nM, 0.1-200 nM, 1-200 nM, 10-200 nM, 100-200 nM, 200-500 nM, 0.1-500 nM, 1-500 nM, 10-500 nM, 500-1000 nM, 0.1-1000 nM, 1-1000 nM, 10-1000 nM, or 100-1000 nM. In some embodiments, the inhibitory activity is less than 0.1 nM, less than 1 nM, less than 10 nM, less than 100 nM, or less than 1000 nM, 0.1-1 μM, 1-10 μM, 10-100 μM, 100-200 μM, 200-500 μM, or even 500-1000 μM, preferably about 1-10 nM, 10-100 nM, or 0.1-1 μM. Without wishing to be bound by any theory, it is believed that such compounds are indicated in the treatment or management of hematopoietic cancers, such as, for example, MDS and/or AML and/or DLBCL, etc., other types of cancers, inflammatory conditions, and/or autoimmune diseases, as described herein.

In other embodiments, the compounds and/or pharmaceutical compounds of the disclosure (e.g., compounds of Formula (I) and pharmaceutical compositions including the same) can be administered in combination with one or more other therapeutic agents for a given disease, condition, or disorder.

The compounds and pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The compounds and pharmaceutical compositions contemplated herein can be administered locally or systemically in a therapeutically effective dose. Amounts effective for this use will, of course, depend on the severity of the disease or disorder and the weight and general state of the subject. Typically, dosages used in vitro can provide useful guidance in the amounts useful for in situ administration of the pharmaceutical composition, and animal models can be used to determine effective dosages for treatment of particular disorders.

Various considerations are described, e. g., in Langer, 1990, *Science,* 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/mL times 1.8=the corresponding oral dosage in milligrams ("mg"). As to oncology applications, the parenteral dosage in mg/mL times 1.6=the corresponding oral dosage in mg. An average adult weighs about 70 kg. See e.g., Miller-Keane, 1992, Encyclopedia & Dictionary of Medicine, Nursing & Allied Health, 5th Ed., (W. B. Saunders Co.), pp. 1708 and 1651.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In some embodiments, the compounds and/or pharmaceutical compositions can include a unit dose of one or more compounds of the disclosure (e.g., compounds of Formula (I) and pharmaceutical compositions including the same) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The compounds of the disclosure (e.g., compounds according to Formula (I)) can be administered to subjects by any number of suitable administration routes or formulations. The compounds of the disclosure (e.g., Formula (I)) of the disclosure can also be used to treat subjects for a variety of diseases. Subjects include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject", unless stated otherwise, encompasses both human and non-human subjects.

The route of administration of the compounds of the disclosure (e.g., Formula (I)) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal/human, the particular disease (e.g., cancer or MDS), and the severity of the disease (e.g., stage or severity of cancer or MDS). Of course, combinations of administration routes can be administered, as desired.

Some embodiments of the disclosure include a method for providing a subject with a composition comprising one or more compounds of the disclosure (e.g., Formula (I)) described herein (e.g., a pharmaceutical composition) which comprises one or more administrations of one or more such compositions; the compositions may be the same or different if there is more than one administration.

Toxicity

The ratio between toxicity and therapeutic effect for a particular compound is its therapeutic index and can be expressed as the ratio between LD50 (the amount of compound lethal in 50% of the population) and ED50 (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the ED50 with little or no toxicity. The dosage can vary within this range depending upon the dosage form employed and the route of administration utilized. See, e.g., Fingl et al., In: The Pharmacological Basis of Therapeutics, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

Having described the disclosure in detail, it will be apparent that modifications, variations, and equivalent embodiments are possible without departing from the scope of the disclosure defined in the appended claims. Furthermore, it should be appreciated that all examples in the present disclosure are provided as non-limiting examples.

The following clauses describe certain embodiments.

Clause 1. A compound selected from Formula (I)

(I)

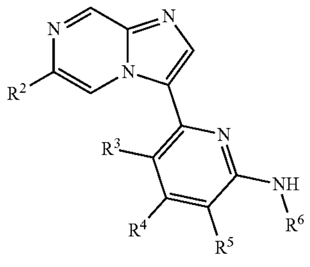

or a salt, ester, solvate, optical isomer, geometric isomer, salt of an isomer, prodrug, or derivative thereof, wherein:

$R^2$ is H, halogen, hydroxy, oxo, —CN, amino, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, heterocyclyl, spiro-fused cycloalkyl, aryl, heteroaryl, or fused ring heteroaryl, which amino, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, heterocyclyl, spiro-fused cycloalkyl, heterocyclyl, aryl, heteroaryl, or fused ring heteroaryl is optionally substituted with one or more of halogen, hydroxy, oxo (=O), —$O^-$, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ heteroalkyl, $C_1$-$C_7$ haloalkyl, $C_1$-$C_7$ perfluorinated alkyl, $C_1$-$C_7$ alkoxy, $C_1$-$C_7$ haloalkoxy, cycloalkyl, heterocyclyl, spiro-fused cycloalkyl, aryl, or fused ring aryl, heteroaryl, fused ring heteroaryl, or $C_1$-$C_7$ alkyl which is substituted with cycloalkyl wherein two adjacent optional substituents can bond or fuse to form a ring;

$R^3$, $R^4$, and $R^5$ are independently selected from H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more of halogen, hydroxy, oxo, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, $CONH_2$, —$CONHCH_3$, —CON$(CH_3)_2$, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl;

$R^6$ is (Ia)

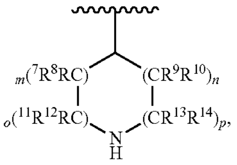

or (Ib)

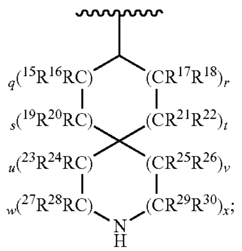

;

$R^7$, $R^8$, $R^9$, $R^{10}$, $R^{11}$, $R^{12}$, $R^{13}$, $R^{14}$ are independently selected from H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are independently selected from H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen; and m, n, o, p, q, r, s, t, u, v, w, and x are independently selected from 0, 1, 2, 3, 4, or 5, where q+r+s+t is at least 1, and where u+v+w+x is at least 1.

Clause 2. The compound of clause 1, wherein $R^2$ is H, halogen, hydroxy, O-aryl, amino, $C_1$-$C_7$ alkyl, $C_2$-$C_7$ alkenyl, $C_2$-$C_7$ alkynyl, $C_1$-$C_7$ alkoxy, cycloalkyl, heterocyclyl, aryl, fused ring aryl, heteroaryl, or fused ring heteroaryl, which O-aryl, amino, $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, fused ring aryl, heteroaryl, or fused ring heteroaryl is optionally substituted with one or more of halogen, hydroxy, —CN, amino, cycloalkyl, spiro-fused cycloalkyl, heterocyclyl, aryl, heteroaryl, fused ring aryl, fused ring heteroaryl, pyrrolyl, piperidyl, piperazinyl, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

Clause 3. The compound of clause 1 or clause 2, wherein $R^2$ is H, halogen, hydroxy, O-aryl, amino, $C_1$-$C_7$ alkyl, $C_1$-$C_7$ alkoxy, cycloalkyl, heterocyclyl, aryl, fused ring aryl, heteroaryl, or fused ring heteroaryl which O-aryl, amino, $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, heteroaryl, or fused ring heteroaryl is optionally substituted with one or more of halogen, hydroxy, amino, cycloalkyl, spiro-fused cycloalkyl, heterocyclyl, aryl, heteroaryl, pyrrolyl, piperidyl, piperazinyl, $C_1$-$C_7$ alkyl, $C_1$-$C_7$ haloalkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

Clause 4. The compound of any of clauses 1-3, wherein $R^2$ is H, $C_1$, hydroxy, —$NHCH_3$, —$N(CH_3)_2$, —$OCH_3$, —$OCF_3$, —$OCHF_2$, —OPh, —$CF_3$, —$CHF_2$, unsubstituted $C_1$-$C_7$ alkyl, substituted amino, substituted $C_1$-$C_7$ alkyl, substituted cycloalkyl, unsubstituted cycloalkyl, unsubstituted heterocyclyl, substituted pyrazolyl, substituted fused ring heteroaryl, or unsubstituted fused ring heteroaryl.

Clause 5. The compound of any of clauses 1-4, wherein $R^2$ is not H.

Clause 6. The compound of any of clauses 1-5, wherein $R^3$ is H, halogen, hydroxy, —CN, methanoyl (—COH), carboxy (—$CO_2$H), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

Clause 7. The compound of any of clauses 1-6, wherein $R^3$ is H, halogen, hydroxy, —CN, methyl, —$CF_3$, or methoxy.

Clause 8. The compound of any of clauses 1-5, wherein $R^4$ is H, halogen, hydroxy, —CN, methanoyl (—COH), carboxy (—$CO_2$H), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

Clause 9. The compound of any of clauses 1-8, wherein $R^4$ is H, halogen, hydroxy, —CN, methyl, —$CF_3$, or methoxy.

Clause 10. The compound of any of clauses 1-9, wherein $R^5$ is H, halogen, hydroxy, —CN, methanoyl (—COH), carboxy (—$CO_2$H), $C_1$-$C_7$ alkyl, or $C_1$-$C_7$ alkoxy, which $C_1$-$C_7$ alkyl, or $C_2$-$C_6$ alkoxy, is optionally substituted with one or more of halogen, hydroxy, methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl.

Clause 11. The compound of any of clauses 1-10, wherein $R^5$ is H, halogen, hydroxy, —CN, methyl, —$CF_3$, or methoxy.

Clause 12. The compound of any of clauses 1-11, wherein $R^4$ is methyl or —$CF_3$, and wherein at least one of $R^3$ and $R^5$ is H or halogen.

Clause 13. The compound of any of clauses 1-12, wherein $R^6$ is (Ia)

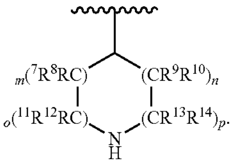

Clause 14. The compound of any of clauses 1-13, wherein m is 0 or 1, wherein n is 0 or 1, wherein o is 0 or 1, and wherein p is 0 or 1.

Clause 15. The compound of any of clauses 1-14, wherein $R^7$, $R^8$, $R^9$, and $R^{10}$ are H, and wherein at least one of $R^{11}$, $R^{12}$, $R^{13}$, and $R^{14}$ is not H.

Clause 16. The compound of any of clauses 1-15, wherein $R^{11}$, $R^{12}$, $R^{13}$, and $R^{14}$ are H, and wherein at least one of $R^7$, $R^8$, $R^9$, and $R^{10}$ is not H.

Clause 17. The compound of any of clauses 1-14, wherein all of $R^7$, $R^8$, $R^9$, $R^{10}$, $R^{11}$, $R^{12}$, $R^{13}$, and $R^{14}$ are H.

Clause 18. The compound of any of clauses 1-17, wherein $R^7$, $R^8$, $R^9$, $R^{10}$, $R^{11}$, $R^{12}$, $R^{13}$, and $R^{14}$ are independently selected from H, halogen, hydroxy, oxo, methanoyl (—COH), carboxy (—$CO_2$H), $C_1$-$C_7$ alkyl, $C_1$-$C_7$ alkoxy, cycloalkyl, or spiro-fused cycloalkyl, which methanoyl (—COH), carboxy (—$CO_2$H), $C_1$-$C_7$ alkyl, $C_2$-$C_7$ alkenyl, $C_2$-$C_7$ alkynyl, $C_2$-$C_6$ alkoxy, cycloalkyl, or spiro-fused cycloalkyl is optionally substituted with one or more halogen.

Clause 19. The compound of clause 18, wherein $R^7$, $R^8$, $R^9$, and $R^{10}$ are H, and wherein at least one of $R^{11}$, $R^{12}$, $R^{13}$, and $R^{14}$ is halogen, hydroxy, oxo, methanoyl (—COH), carboxy (—$CO_2$H), $C_1$-$C_7$ alkyl, $C_1$-$C_7$ alkoxy, cycloalkyl, or spiro-fused cycloalkyl, which methanoyl (—COH), carboxy (—$CO_2$H), $C_1$-$C_7$ alkyl, $C_2$-$C_7$ alkenyl, $C_2$-$C_7$ alkynyl, $C_2$-$C_6$ alkoxy, cycloalkyl, or spiro-fused cycloalkyl is optionally substituted with one or more halogen.

Clause 20. The compound of clause 18, wherein $R^{11}$, $R^{12}$, $R^{13}$, and $R^{14}$ are H, and wherein at least one of $R^7$, $R^8$, $R^9$, and $R^{10}$ is halogen, hydroxy, oxo, methanoyl (—COH), carboxy (—$CO_2$H), $C_1$-$C_7$ alkyl, $C_1$-$C_7$ alkoxy, cycloalkyl, or spiro-fused cycloalkyl, which methanoyl (—COH), carboxy (—$CO_2$H), $C_1$-$C_7$ alkyl, $C_2$-$C_7$ alkenyl, $C_2$-$C_7$ alkynyl, $C_2$—$C_6$ alkoxy, cycloalkyl, or spiro-fused cycloalkyl is optionally substituted with one or more halogen.

Clause 21. The compound of any of clauses 1-20, wherein at least one of $R^7$, $R^8$, $R^9$, and $R^{10}$ is halogen, hydroxyl, $C_1$-$C_7$ alkyl, $C_1$-$C_7$ haloalkyl, $C_1$-$C_7$ alkoxy, cycloalkyl, or spiro-fused cycloalkyl.

Clause 22. The compound of clause 20, wherein at least one of $R^7$, $R^8$, $R^9$, and $R^{10}$ is F, hydroxyl, methyl, methoxy, —$CHF_2$, —$CF_3$, spiro-fused cyclopropyl, spiro-fused cyclobutyl, or spiro-fused cyclopentyl.

Clause 23. The compound of clause 22, wherein both of $R^7$ and $R^8$ or both of $R^9$ and $R^{10}$ are F, or wherein both of $R^7$ and $R^8$ or both of $R^9$ and $R^{10}$ are methyl.

Clause 24. The compound of any of clauses 1-23, wherein at least one of $R^{11}$, $R^{12}$, $R^{13}$, and $R^{14}$ is halogen, hydroxyl, $C_1$-$C_7$ alkyl, $C_1$-$C_7$ haloalkyl, $C_1$-$C_7$ alkoxy, cycloalkyl, or spiro-fused cycloalkyl.

Clause 25. The compound of clause 24, wherein at least one of $R^{11}$, $R^{12}$, $R^{13}$, and $R^{14}$ is F, hydroxyl, methyl, methoxy, —$CHF_2$, —$CF_3$, spiro-fused cyclopropyl, spiro-fused cyclobutyl, or spiro-fused cyclopentyl.

Clause 26. The compound of clause 25, wherein both of $R^{11}$ and $R^{12}$ or both of $R^{13}$ and $R^{14}$ are F, or wherein both of $R^{11}$ and $R^{12}$ or both of $R^{13}$ and $R^{14}$ are methyl.

Clause 27. The compound of any of clauses 1-12, wherein $R^6$ is (Ib)

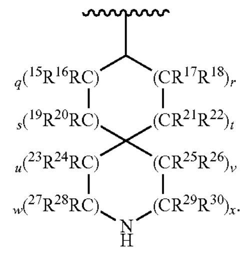

Clause 28. The compound of clause 27, wherein q, r, s, t, u, v, w, and x are independently 0, 1, or 2.

Clause 29. The compound of clause 27 or clause 28, wherein q is 0 or 1, wherein r is 0 or 1, wherein s is 0 or 1, wherein t is 0 or 1, wherein u is 0 or 1, wherein v is 0 or 1, wherein w is 0 or 1, and wherein x is 0 or 1.

Clause 30. The compound of any of clauses 27-29, wherein $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are independently selected from H, halogen, hydroxy, oxo, methanoyl (—COH), carboxy (—$CO_2H$), $C_1$-$C_7$ alkyl, $C_1$-$C_7$ alkoxy, or spiro-fused cycloalkyl, which methanoyl (—COH), carboxy (—$CO_2H$), $C_1$-$C_7$ alkyl, $C_2$-$C_7$ alkenyl, $C_2$-$C_7$ alkynyl, $C_2$-$C_6$ alkoxy, or spiro-fused cycloalkyl is optionally substituted with one or more halogen.

Clause 31. The compound of any of clauses 27-30, wherein one or more of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are H, or wherein all of $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are H.

Clause 32. The compound of any of clauses 27-31, wherein $R^6$ is:

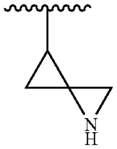 , 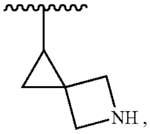 , 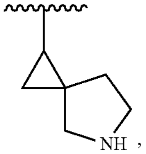 ,

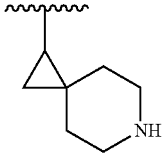 , 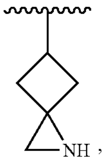 , 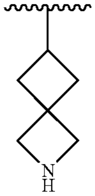 , 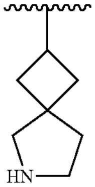 ,

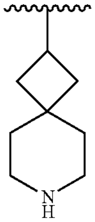 , 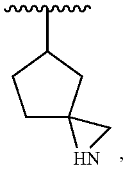 , 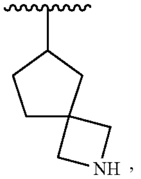 ,

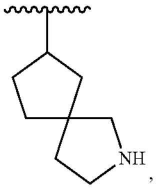 , 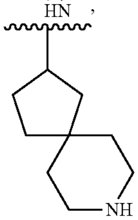 , 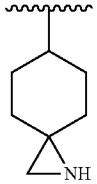 ,

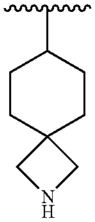 , 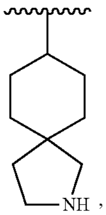 , or 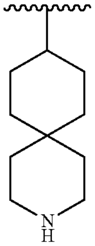 .

Clause 33. The compound of any of clauses 27-32, wherein $R^6$ is:

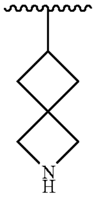 , 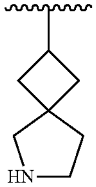 , 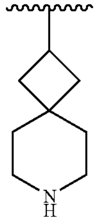 ,

-continued

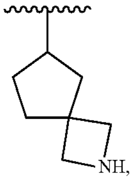 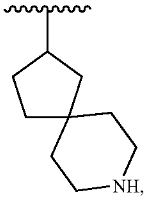 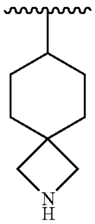 , or

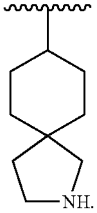

Clause 34. The compound of any of clauses 1-33, wherein the compound is selected from Compounds 1-64, as listed in Examples 1-14 and Tables 1-10.

Clause 35. The compound of any of clauses 1-34, wherein the compound is selected from Compound 1, Compound 5, Compound 6, Compound 8, Compound 12, Compound 14, Compound 16, Compound 35, Compound 40, Compound 44, Compound 45, Compound 46, Compound 47, Compound 51, and Compound 55.

Clause 36. The compound of any of clauses 1-35, wherein the compound is selected from Compound 1, Compound 5, Compound 8, Compound 12, Compound 14, Compound 16, Compound 35, Compound 44, Compound 45, Compound 46, Compound 47, Compound 51, and Compound 55.

Clause 37. A composition comprising a compound of any of clauses 1-36.

Clause 38. The composition of clause 37, wherein the amount of the compound is from about 0.0001% (by weight total composition) to about 99%.

Clause 39. The composition of clause 37 or clause 38, further comprising a formulary ingredient, an adjuvant, or a carrier.

Clause 40. The composition of any of clauses 37-39, wherein the composition further comprises a BCL2 inhibitor.

Clause 41. The composition of any of clauses 37-40, wherein the composition is used in combination with a second composition comprising a BCL2 inhibitor.

Clause 42. The composition of any of clauses 37-41, wherein the BCL2 comprises venetoclax, or a salt, isomer, derivative or analog thereof.

Clause 43. The composition of any of clauses 37-42, wherein the composition is used in combination with one or more chemotherapy, DNA methyltransferase inhibitor/hypomethylating agent, anthracycline, histone deacetylase (HDAC) inhibitor, purine nucleoside analogue (antimetabolite), isocitrate dehydrogenase 1 or 2 (IDH1 and/or IDH2) inhibitor, antibody-drug conjugate, mAbs/immunotherapy, CAR-T cell therapy, Plk inhibitor, MEK inhibitor, CDK9 inhibitor, CDK8 inhibitor, retinoic acid receptor agonist, TP53 activator, smoothened receptor antagonist, ERK inhibitor, PI3K inhibitor, mTOR inhibitor, glucocorticoid receptor modulator, or EZH2 inhibitor, or one or more combinations thereof.

Clause 44. The composition of clause 43, wherein the DNA methyltransferase inhibitor/hypomethylating agent comprises azacytidine, decitabine, cytarabine, and/or guadecitabine; wherein the anthracycline comprises daunorubicin, idarubicin, doxorubicin, mitoxantrone, epirubicin, and/or CPX-351 (a combination cytarabine and daunorubicin in a fixed 5:1 molar ratio); wherein the histone deacetylase (HDAC) inhibitor comprises vorinostat, panobinostat, valproic acid, and/or pracinostat; wherein the purine nucleoside analogue (antimetabolite) comprises fludarabine, cladribine, and/or clofarabine; wherein the isocitrate dehydrogenase 1 or 2 (IDH1 and/or IDH2) inhibitor comprises ivosidenib and/or enasidenib; wherein the antibody-drug conjugate comprises Anti-CD33 (e.g. Ac225-lintuzumab, vadastuximab, or gemtuzumab-ozogamicin) and/or Anti-CD45 (e.g. $I^{131}$-apamistamab); wherein the mAbs/Immunotherapy comprises Anti-CD70 (e.g. ARGX-110, cusatuzumab), a bispecific antibody (e.g. floteuzumab (CD123×CD3)), Anti-CTLA4 (e.g. ipilimumab), Anti-PD1/PDL1 (e.g. nivolumab, pembrolizumab, atezolizumab, avelumab, PDR001, MBG453), and/or Anti-CD47 (e.g. 5F9 (Magrolimab)); wherein the Plk inhibitor comprises volasertib and/or rigosertib; wherein the MEK inhibitor comprises trametinib, cobimetinib, selumetinib, pimasertib, and/or refametinib; wherein the CDK9 inhibitor comprises alvocidib and/or voruciclib; wherein the CDK8 inhibitor comprises SEL120; wherein the retinoic acid receptor agonist comprises ATRA (all-trans retinoic acid) and/or SY-1425 (a selective RARa agonist); wherein the TP53 activator comprises APR-246 (Eprenetapopt); wherein the smoothened receptor antagonist comprises glasdegib; wherein the ERK inhibitor comprises an ERK2/MAPK1 or ERK1/MAPK3 inhibitor comprising ulixertinib, SCH772984, ravoxertinib, MK-8353, and/or VTX-11e; wherein the PI3K inhibitor comprises fimepinostat (CUDC-907), alpelisib, leniolisib (CDZ-173), pilaralisib (XL147, SAR245408), and/or bimiralisib (PQR-309); wherein the mTOR inhibitor comprises bimiralisib (PQR-309), sapanisertib (TAK-228, INK-128), ridaforolimus (MK-8669, AP-23573), everolimus, and/or vistusertib (AZD2014); wherein the glucocorticoid receptor modulator comprises an agonist comprising prednisolone, beclometasone, methylprednisolone, prednisone, fluticasone, budesonide, dexamethasone, and/or cortisol, and/or an antagonist comprising mifepristone, miricorilant, and/or onapristone, and/or another binding ligand comprising vamorolone (VBP15); and/or wherein the EZH2 inhibitor comprises tazemetostat.

Clause 45. A method for providing a subject with a compound comprising one or more administrations of one or more compositions comprising the compound of any of clauses 1-36, wherein the compositions may be the same or different if there is more than one administration.

Clause 46. The method of clause 45, wherein at least one of the one or more compositions further comprises a formulary ingredient.

Clause 47. The method of clause 45 or clause 46, wherein at least one of the one or more compositions comprises the composition of any of clauses 37-44.

Clause 48. The method of any of clauses 45-47, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

Clause 49. The method of any of clauses 45-48, wherein if there is more than one administration at least one composition used for at least one administration is different from the composition of at least one other administration.

Clause 50. The method of any of clauses 45-49, wherein the compound of at least one of the one or more compositions is administered to the subject in an amount of from about 0.005 mg/kg subject body weight to about 50 mg/kg subject body weight.

Clause 51. The method of any of clauses 45-50, wherein the subject is a mammal, preferably wherein the subject is a human, a rodent, or a primate.

Clause 52. A method for treating a disease or disorder, comprising one or more administrations to a subject of one or more compositions comprising the compound of any of clauses 1-36, wherein the compositions may be the same or different if there is more than one administration.

Clause 53. The method of clause 52, wherein the disease or disorder is responsive to at least one of interleukin-1 receptor-associated kinase (IRAK) inhibition or fms-like tyrosine kinase 3 (FLT3) inhibition.

Clause 54. The method of clause 52 or clause 53, wherein at least one of the one or more compositions further comprises a formulary ingredient.

Clause 55. The method of clause 53 or clause 54, wherein at least one of the one or more compositions comprises the composition of any of clauses 37-44.

Clause 56. The method of any of clauses 52-55, wherein at least one of the one or more administrations comprises parenteral administration, a mucosal administration, intravenous administration, subcutaneous administration, topical administration, intradermal administration, transdermal administration, oral administration, sublingual administration, intranasal administration, or intramuscular administration.

Clause 57. The method of any of clauses 52-56, wherein at least one of the one or more administrations comprises an oral administration.

Clause 58. The method of any of clauses 52-57, wherein if there is more than one administration at least one composition used for at least one administration is different from the composition of at least one other administration.

Clause 59. The method of any of clauses 52-58, wherein the compound of at least one of the one or more compositions is administered to the subject in an amount of from about 0.005 mg/kg subject body weight to about 50 mg/kg subject body weight.

Clause 60. The method of any of clauses 52-59, wherein the subject is a mammal, preferably wherein the subject is a human, a rodent, or a primate.

Clause 61. The method of any of clauses 52-60, wherein the subject is in need of the treatment.

Clause 62. The method of any of clauses 52-61, wherein the method is for treating a hematopoietic cancer.

Clause 63. The method of any of clauses 52-62, wherein the method is for treating a myelodysplastic syndrome (MDS) and/or acute myeloid leukemia (AML).

Clause 64. The method of any of clauses 52-62, wherein the method is for treating at least one of lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL with MYD88 mutation, follicular lymphoma, or marginal zone lymphoma.

Clause 65. The method of any of clauses 52-61, wherein the method is for treating at least one cancer selected from glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, or one or more inflammatory diseases or autoimmune disease characterized by overactive IRAK1 and/or IRAK4, or combinations thereof.

Clause 66. The method of clause 65, wherein the method is for treating one or more inflammatory diseases or autoimmune disease selected from chronic inflammation (i.e., associated with viral and bacterial infection), sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, or combinations thereof.

Clause 67. The method of any of clauses 52-63, wherein the method is for treating NMS, MDS with a splicing factor mutation, MDS with a mutation in isocitrate dehydrogenase 1, MDS with a mutation in isocitrate dehydrogenase 2, or wherein the method is for treating AML having enhanced IRAK4-Long expression and/or activity relative to IRAK4-Short, and/or wherein the AML is not driven by FLT3 mutations but expresses IRAK4-Long.

Clause 68. The method of clause 64, wherein the method is for treating DLBCL, and wherein the DLBCL comprises a L265P MYD88 mutant (ABC) subtype of DLBCL.

Clause 69. The method of clause 68, wherein the method further comprises administration of a composition comprising a BTK inhibitor.

Clause 70. The method of clause 69, wherein the BTK inhibitor comprises ibrutinib.

Clause 71. The method of any of clauses 52-70, wherein the subject is susceptible to AML and/or NMS, and/or wherein the method prevents or ameliorates future AML and/or NMS.

Clause 72. The method of any of clauses 52-71, wherein the method occurs after one or more of having MDS, having myeloproliferative disease, an occurrence of chemical exposure, an exposure to ionizing radiation, or a treatment for cancer.

Clause 73. The method of any of clauses 52-71, wherein the method further comprises administration of a composition comprising a BCL2 inhibitor, or wherein the at least one or more compositions comprises the compound of any of clauses 1-36 and further comprises a BCL2 inhibitor.

Clause 74. The method of clause 73 wherein the compound of any of clauses 1-36 and the BCL2 inhibitor may be administered together or separately, in one or more administrations of one or more compositions.

Clause 75. The method of clause 73 or clause 74, wherein the BCL2 inhibitor comprises venetoclax, or a salt, isomer, derivative or analog thereof.

Clause 76. The method of any of clauses 52-75, wherein the method further comprises administration of one or more additional therapy selected from one or more chemotherapy, DNA methyltransferase inhibitor/hypomethylating agent, anthracycline, histone deacetylase (HDAC) inhibitor, purine nucleoside analogue (antimetabolite), isocitrate dehydrogenase 1 or 2 (IDH1 and/or IDH2) inhibitor, antibody-drug conjugate, mAbs/immunotherapy, CAR-T cell therapy, Plk inhibitor, MEK inhibitor, CDK9 inhibitor, CDK8 inhibitor, retinoic acid receptor agonist, TP53 activator, smoothened receptor antagonist, ERK inhibitor, PI3K inhibitor, mTOR inhibitor, glucocorticoid receptor modulator, or EZH2 inhibitor, or one or more combinations thereof.

Clause 77. The method of clause 76, wherein the DNA methyltransferase inhibitor/hypomethylating agent comprises azacytidine, decitabine, cytarabine, and/or guadecitabine; wherein the anthracycline comprises daunorubicin, idarubicin, doxorubicin, mitoxantrone, epirubicin, and/or CPX-351 (a combination cytarabine and daunorubicin in a fixed 5:1 molar ratio); wherein the histone deacetylase (HDAC) inhibitor comprises vorinostat, panobinostat, valproic acid, and/or pracinostat; wherein the purine nucleoside analogue (antimetabolite) comprises fludarabine, cladribine, and/or clofarabine; wherein the isocitrate dehydrogenase 1 or 2 (IDH1 and/or IDH2) inhibitor comprises ivosidenib and/or enasidenib; wherein the antibody-drug conjugate comprises Anti-CD33 (e.g. Ac225-lintuzumab, vadastuximab, or gemtuzumab-ozogamicin) and/or Anti-CD45 (e.g. $I^{131}$-apamistamab); wherein the mAbs/Immunotherapy comprises Anti-CD70 (e.g. ARGX-110, cusatuzumab), a bispecific antibody (e.g. floteuzumab (CD123×CD3)), Anti-CTLA4 (e.g. ipilimumab), Anti-PD1/PDL1 (e.g. nivolumab, pembrolizumab, atezolizumab, avelumab, PDR001, MBG453), and/or Anti-CD47 (e.g. 5F9 (Magrolimab)); wherein the Plk inhibitor comprises volasertib and/or rigosertib; wherein the MEK inhibitor comprises trametinib, cobimetinib, selumetinib, pimasertib, and/or refametinib; wherein the CDK9 inhibitor comprises alvocidib and/or voruciclib; wherein the CDK8 inhibitor comprises SEL120; wherein the retinoic acid receptor agonist comprises ATRA (all-trans retinoic acid) and/or SY-1425 (a selective RARa agonist); wherein the TP53 activator comprises APR-246 (Eprenetapopt); wherein the smoothened receptor antagonist comprises glasdegib; wherein the ERK inhibitor comprises an ERK2/MAPK1 or ERK1/MAPK3 inhibitor comprising ulixertinib, SCH772984, ravoxertinib, MK-8353, and/or VTX-11e; wherein the PI3K inhibitor comprises fimepinostat (CUDC-907), alpelisib, leniolisib (CDZ-173), pilaralisib (XL147, SAR245408), and/or bimiralisib (PQR-309); wherein the mTOR inhibitor comprises bimiralisib (PQR-309), sapanisertib (TAK-228, INK-128), ridaforolimus (MK-8669, AP-23573), everolimus, and/or vistusertib (AZD2014); wherein the glucocorticoid receptor modulator comprises an agonist comprising prednisolone, beclometasone, methylprednisolone, prednisone, fluticasone, budesonide, dexamethasone, and/or cortisol, and/or an antagonist comprising mifepristone, miricorilant, and/or onapristone, and/or another binding ligand comprising vamorolone (VBP15); and/or wherein the EZH2 inhibitor comprises tazemetostat.

Clause 78. A compound according to any one of clauses 1-36, for use in a method for treating a disease or disorder, the method comprising inhibiting at least one of IRAK and FLT3 by administering one or more compositions comprising the compound, wherein the compositions may be the same or different if there is more than one administration.

Clause 79. The compound for use of clause 78, wherein the disease or disorder is responsive to at least one of interleukin-1 receptor-associated kinase (IRAK) inhibition or fms-like tyrosine kinase 3 (FLT3) inhibition.

Clause 80. The compound for use of clause 78 or clause 79, wherein at least one of the one or more compositions further comprises a formulary ingredient.

Clause 81. The compound for use of any one of clauses 78-80, wherein at least one of the one or more compositions comprises the composition of any of clauses 37-44.

Clause 82. The compound for use of any one of clauses 78-81, wherein at least one of the one or more administrations comprises parenteral administration, a mucosal administration, intravenous administration, subcutaneous administration, topical administration, intradermal administration, transdermal administration, oral administration, sublingual administration, intranasal administration, or intramuscular administration.

Clause 83. The compound for use of any one of clauses 78-82, wherein at least one of the one or more administrations comprises an oral administration.

Clause 84. The compound for use of any one of clauses 78-83, wherein if there is more than one administration at least one composition used for at least one administration is different from the composition of at least one other administration.

Clause 85. The compound for use of any one of clauses 78-84, wherein the compound is administered to the subject in an amount of from about 0.005 mg/kg subject body weight to about 50 mg/kg subject body weight.

Clause 86. The compound for use of any one of clauses 78-85, wherein the subject is a mammal, preferably wherein the subject is a human, a rodent, or a primate.

Clause 87. The compound for use of any one of clauses 78-86, wherein the subject is in need of the treatment.

Clause 88. The compound for use of any one of clauses 78-87, wherein the method is for treating a hematopoietic cancer.

Clause 89. The compound for use of any one of clauses 78-88, wherein the method is for treating MDS and/or AML.

Clause 90. The compound for use of any one of clauses 78-88, wherein the method is for treating at least one of lymphoma, leukemia, chronic lymphocytic leukemia (CLL), chronic myeloid leukemia (CIVIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL with MYD88 mutation, follicular lymphoma, or marginal zone lymphoma.

Clause 91. The compound for use of any one of clauses 78-87, wherein the method is for treating at least one cancer selected from glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, or one or more inflammatory diseases or autoimmune disease characterized by overactive IRAK1 and/or IRAK4, or combinations thereof.

Clause 92. The compound for use of clause 91, wherein the method is for treating one or more inflammatory diseases or autoimmune disease selected from chronic inflammation (i.e., associated with viral and bacterial infection), sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, or combinations thereof.

Clause 93. The compound for use of any one of clauses 78-89, wherein the method is for treating MDS, MDS with a splicing factor mutation, MDS with a mutation in isocitrate dehydrogenase 1, MDS with a mutation in isocitrate dehydrogenase 2, or wherein the method is for treating AML having enhanced IRAK4-Long expression and/or activity relative to IRAK4-Short, and/or wherein the AML is not driven by FLT3 mutations but expresses IRAK4-Long.

Clause 94. The compound for use of clause 90, wherein the method is for treating DLBCL, and wherein the DLBCL comprises a L265P MYD88 mutant (ABC) subtype of DLBCL.

Clause 95. The compound for use of clause 94, wherein the method further comprises administration of a composition comprising a BTK inhibitor.

Clause 96. The compound for use of clause 95, wherein the BTK inhibitor comprises ibrutinib.

Clause 97. The compound for use of any one of clauses 78-96, wherein the subject is susceptible to AML and/or NMS, and/or wherein the method prevents or ameliorates future AML and/or NMS.

Clause 98. The compound for use of any one of clauses 78-97, wherein the method occurs after one or more of having NMS, having myeloproliferative disease, an occurrence of chemical exposure, an exposure to ionizing radiation, or a treatment for cancer.

Clause 99. The compound for use of any one of clauses 78-98, wherein the method further comprises administration of a composition comprising a BCL2 inhibitor, or wherein the at least one or more compositions comprises the compound of any of clauses 1-36 and further comprises a BCL2 inhibitor.

Clause 100. The compound for use of clause 99, wherein the compound of any of clauses 1-36 and the BCL2 inhibitor may be administered together or separately, in one or more administrations of the one or more compositions.

Clause 101. The compound for use of clause 99 or clause 100, wherein the BCL2 inhibitor comprises venetoclax, or a salt, isomer, derivative or analog thereof.

Clause 102. The compound for use of any one of clauses 78-101, wherein the method further comprises administration of one or more additional therapy selected from one or more chemotherapy, DNA methyltransferase inhibitor/hypomethylating agent, anthracycline, histone deacetylase (HDAC) inhibitor, purine nucleoside analogue (antimetabolite), isocitrate dehydrogenase 1 or 2 (IDH1 and/or IDH2) inhibitor, antibody-drug conjugate, mAbs/immunotherapy, CAR-T cell therapy, Plk inhibitor, MEK inhibitor, CDK9 inhibitor, CDK8 inhibitor, retinoic acid receptor agonist, TP53 activator, smoothened receptor antagonist, ERK inhibitor, PI3K inhibitor, mTOR inhibitor, glucocorticoid receptor modulator, or EZH2 inhibitor, or one or more combinations thereof.

Clause 103. The compound for use of any one of clauses 78-102, wherein the DNA methyltransferase inhibitor/hypomethylating agent comprises azacytidine, decitabine, cytarabine, and/or guadecitabine; wherein the anthracycline comprises daunorubicin, idarubicin, doxorubicin, mitoxantrone, epirubicin, and/or CPX-351 (a combination cytarabine and daunorubicin in a fixed 5:1 molar ratio); wherein the histone deacetylase (HDAC) inhibitor comprises vorinostat, panobinostat, valproic acid, and/or pracinostat; wherein the purine nucleoside analogue (antimetabolite) comprises fludarabine, cladribine, and/or clofarabine; wherein the isocitrate dehydrogenase 1 or 2 (IDH1 and/or IDH2) inhibitor comprises ivosidenib and/or enasidenib; wherein the antibody-drug conjugate comprises Anti-CD33 (e.g. Ac225-lintuzumab, vadastuximab, or gemtuzumab-ozogamicin) and/or Anti-CD45 (e.g. $I^{131}$-apamistamab); wherein the mAbs/Immunotherapy comprises Anti-CD70 (e.g. ARGX-110, cusatuzumab), a bispecific antibody (e.g. floteuzumab (CD123×CD3)), Anti-CTLA4 (e.g. ipilimumab), Anti-PD1/PDL1 (e.g. nivolumab, pembrolizumab, atezolizumab, avelumab, PDR001, MBG453), and/or Anti-CD47 (e.g. 5F9 (Magrolimab)); wherein the Plk inhibitor comprises volasertib and/or rigosertib; wherein the MEK inhibitor comprises trametinib, cobimetinib, selumetinib, pimasertib, and/or refametinib; wherein the CDK9 inhibitor comprises alvocidib and/or voruciclib; wherein the CDK8 inhibitor comprises SEL120; wherein the retinoic acid receptor agonist comprises ATRA (all-trans retinoic acid) and/or SY-1425 (a selective RARa agonist); wherein the TP53 activator comprises APR-246 (Eprenetapopt); wherein the smoothened receptor antagonist comprises glasdegib; wherein the ERK inhibitor comprises an ERK2/MAPK1 or ERK1/MAPK3 inhibitor comprising ulixertinib, SCH772984, ravoxertinib, MK-8353, and/or VTX-11e; wherein the PI3K inhibitor comprises fimepinostat (CUDC-907), alpelisib, leniolisib (CDZ-173), pilaralisib (XL147, SAR245408), and/or bimiralisib (PQR-309); wherein the mTOR inhibitor comprises bimiralisib (PQR-309), sapanisertib (TAK-228, INK-128), ridaforolimus (MK-8669, AP-23573), everolimus, and/or vistusertib (AZD2014); wherein the glucocorticoid receptor modulator comprises an agonist comprising prednisolone, beclometasone, methylprednisolone, prednisone, fluticasone, budesonide, dexamethasone, and/or cortisol, and/or an antagonist comprising mifepristone, miricorilant, and/or onapristone, and/or another binding ligand comprising vamorolone (VBP15); and/or wherein the EZH2 inhibitor comprises tazemetostat.

Clause 201. A compound of Formula (I):

(I)

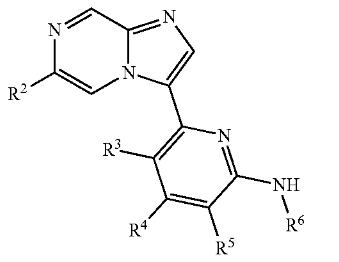

or a salt, ester, solvate, optical isomer, geometric isomer, salt of an isomer, prodrug, or derivative thereof, wherein:

$R^2$, $R^3$, $R^4$, and $R^5$ are each independently selected from H, halogen, hydroxy, oxo (=O), —CN, amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, spiro-fused cycloalkyl, heterocyclyl, aryl, heteroaryl, or fused ring heteroaryl, wherein amino, amido, —O-aryl, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more of halogen, hydroxy, oxo, methanoyl (—COH), carboxy (—$CO_2$H), nitro (—$NO_2$), —$NH_2$, —$NHCH_3$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl, wherein two adjacent optional substituents can bond or fuse to form a ring;

$R^6$ is selected from (Ia)

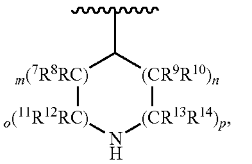

or (Ib)

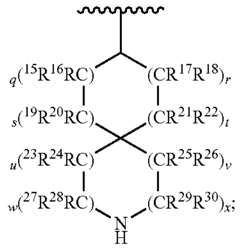

$R^7$, $R^8$, $R^9$, $R^{10}$, $R^{11}$, $R^{12}$, $R^{13}$, and $R^{14}$ are each independently selected from H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are each independently selected from H, halogen, hydroxy, oxo, —CN, methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2$H), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl; and m, n, o, p, q, r, s, t, u, v, w, and x are each independently selected from 0, 1, 2, 3, 4, or 5; where q+r+s+t is at least 1, and where u+v+w+x is at least 1.

Clause 202. The compound of clause 201, wherein the compound of Formula (I) is a compound of Formula (IIf):

Formula (IIf)

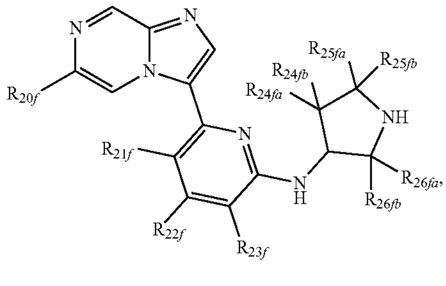

or a salt, ester, solvate, optical isomer, geometric isomer, or salt of an isomer thereof;

wherein:

$R_{20f}$ is selected from H, halogen, $C_1$-$C_6$ alkyl, $C_1$-$C_6$ alkoxy, $C_3$-$C_6$ cycloalkyl, —O—$(CH_2)_a$—($C_3$-$C_6$ cycloalkyl), and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocyclyl is optionally substituted with one or more substituents selected from halogen, $C_1$-$C_6$ alkyl, $C_1$-$C_6$ alkoxy, —OH, and =O wherein two adjacent optional substituents can bond or fuse to form a ring;

$R_{21f}$, $R_{22f}$, and $R_{23f}$ are each independently selected from H and halogen;

$R_{24fa}$, $R_{24fb}$, $R_{25fa}$, $R_{25fb}$, $R_{26fa}$, and $R_{26fa}$ are each independently selected from H, halogen, —OH, $C_1$-$C_6$ alkyl, and $C_1$-$C_6$ alkoxy, wherein $C_1$-$C_6$ alkyl and $C_1$-$C_6$ alkoxy are each optionally substituted with one or more halogen atoms; and a is selected from 0, 1, 2, 3, 4, 5, and 6.

Clause 203. The compound of clause 2, wherein one or more of $R_{24fa}$, $R_{24fb}$, $R_{25fa}$, $R_{25fb}$, $R_{26fa}$, and $R_{26fb}$ is independently selected from halogen, —OH, optionally substituted $C_1$-$C_6$ alkyl, and optionally substituted $C_1$-$C_6$ alkoxy.

Clause 204. The compound of clause 202 or 203, wherein $R_{20f}$ is H.

Clause 205. The compound of clause 202 or 203, wherein at least one of (i)-(viii) applies:

(i) $R_{20f}$ is selected from t-butyl, unsubstituted $C_3$ cycloalkyl, pyrrolidinyl, —$OCH_3$, —$OCH_2CH_3$,

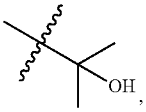, 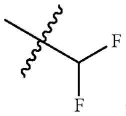, 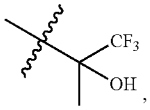,

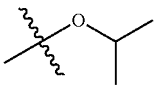, 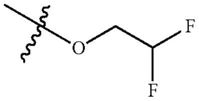,

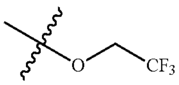, 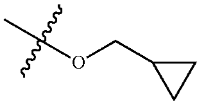,

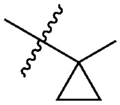, 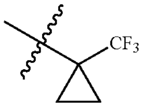, 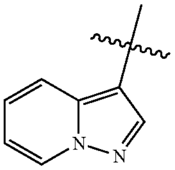,

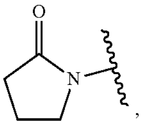, 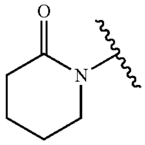, 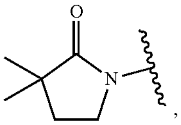,

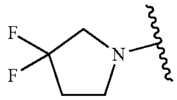, 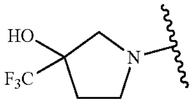,

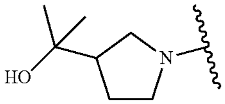, 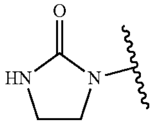,

-continued

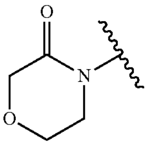, and 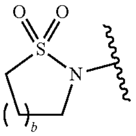

wherein b is 1 or 2;

(ii) $R_{20f}$ is

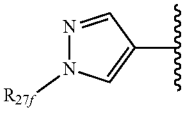

wherein $R_{27f}$ is selected from —$CH_3$,

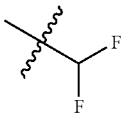, and 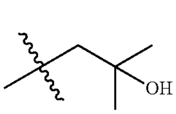;

(iii) $R_{20f}$ is

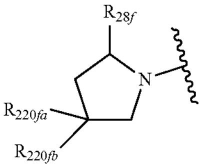

wherein $R_{28f}$ is =O and $R_{220fa}$ and $R_{220fb}$ are each —$CH_3$ or $R_{220fa}$ and $R_{220fb}$ bond or fuse to form oxetanyl;

(iv) $R_{21f}$, $R_{22f}$, and $R_{23f}$ are each H;

(v) $R_{21f}$ and $R_{23f}$ are each F and $R_{22f}$ is H;

(vi) $R_{21f}$ and $R_{23f}$ are each H and $R_{22f}$ is F;

(vii) $R_{24fa}$, $R_{24fb}$, $R_{25fa}$, $R_{25fb}$, $R_{26fa}$, and $R_{26fb}$ are each H;

(viii) $R_{25fa}$, $R_{25fb}$, $R_{26fa}$, and $R_{26fb}$ are each H and $R_{24fa}$ and/or $R_{24fb}$ are selected from F, —$CH_3$, and —$CF_3$.

Clause 206. The compound of any one of clauses 202-205, wherein the compound is selected from:

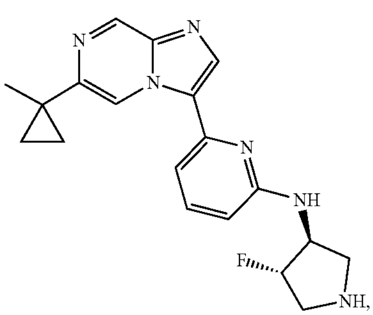

-continued
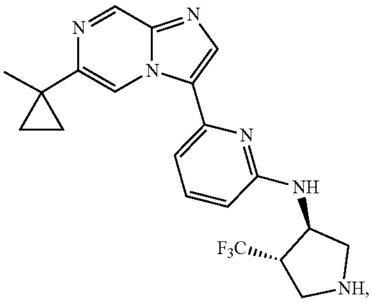
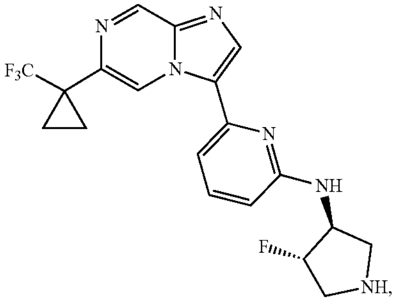
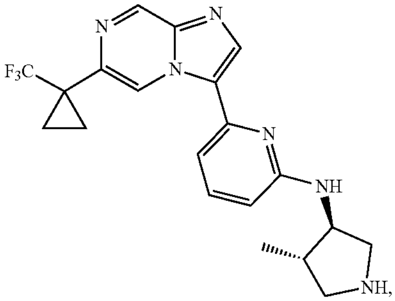
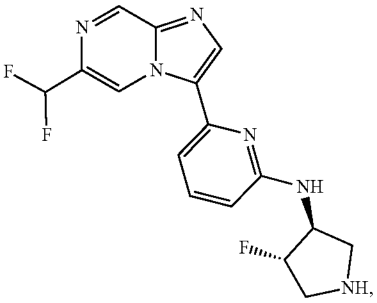
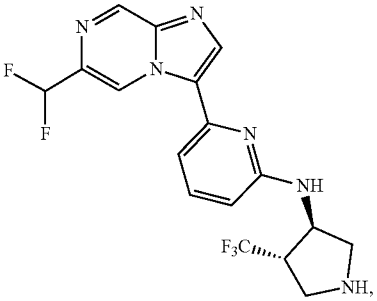
-continued
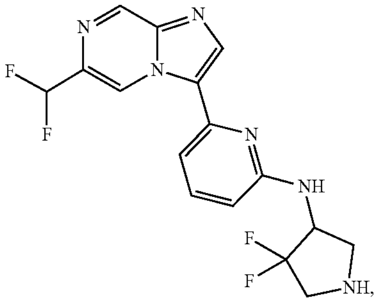
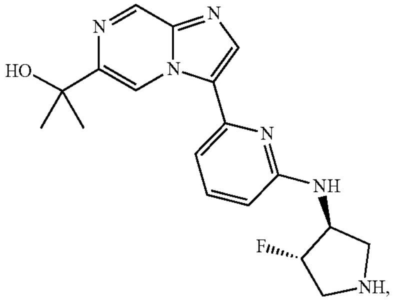
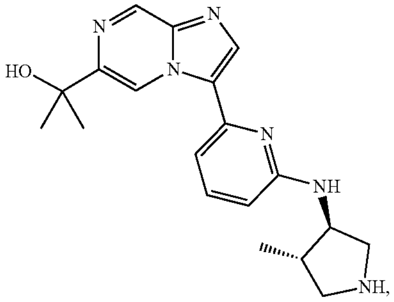
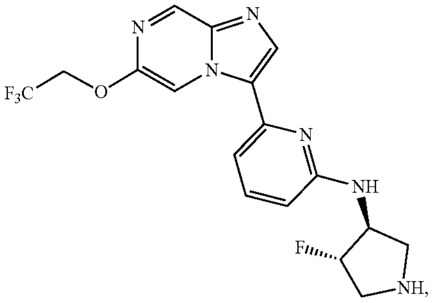
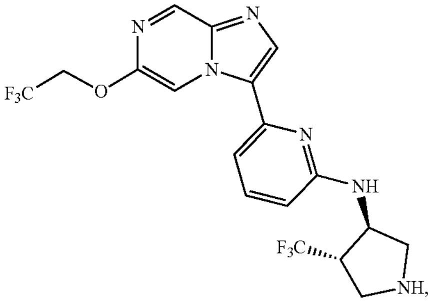

-continued
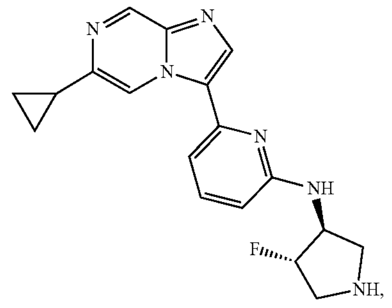
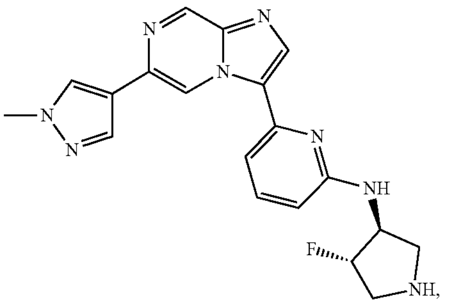
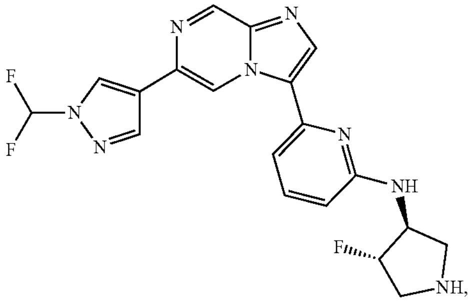
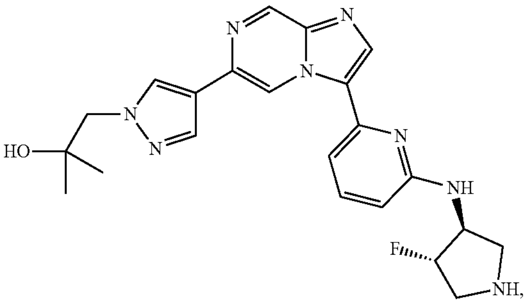
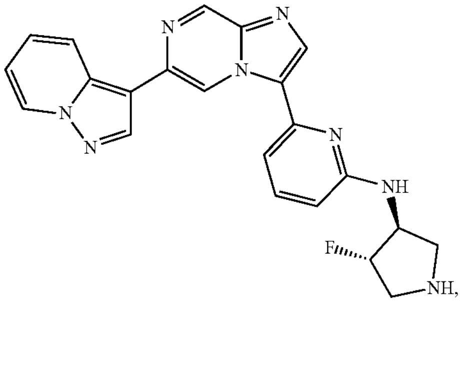
-continued
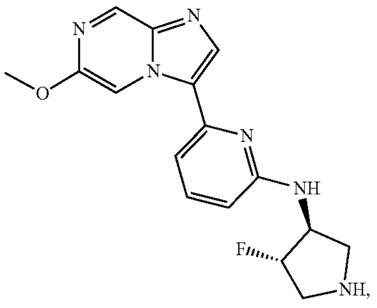
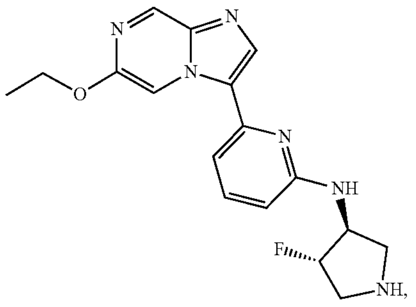
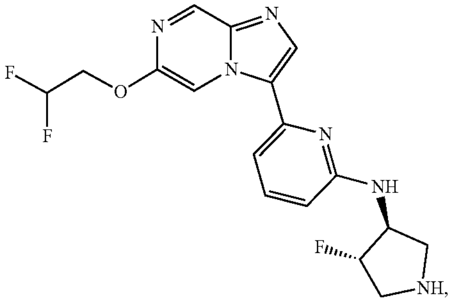
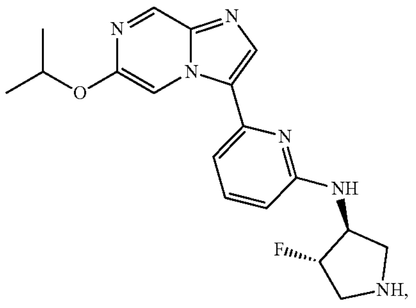
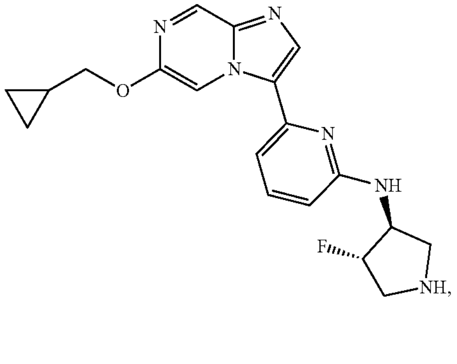

-continued
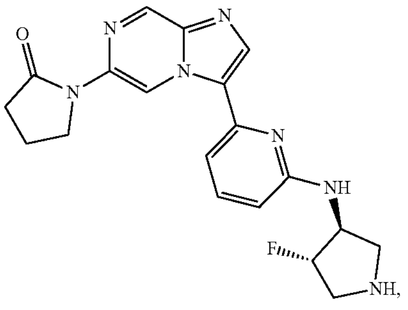
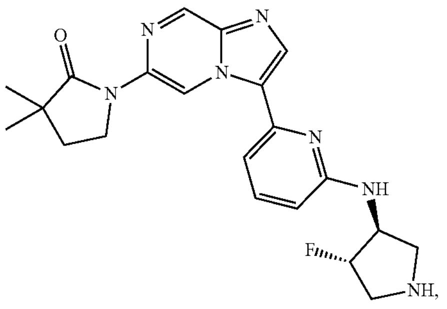
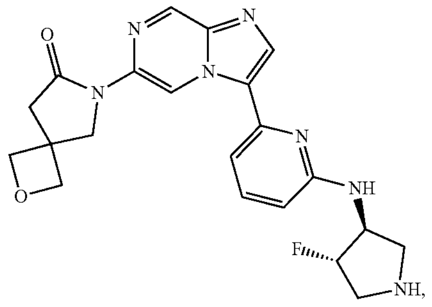
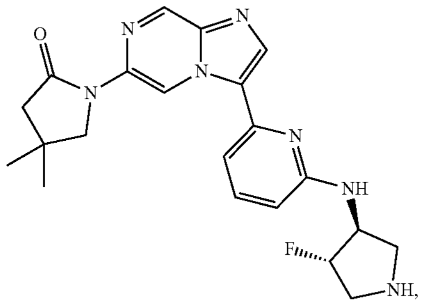
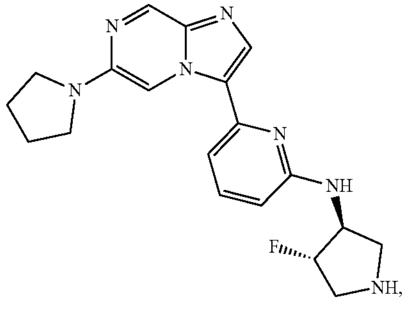
-continued
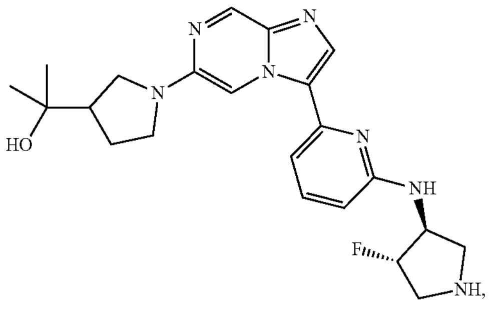
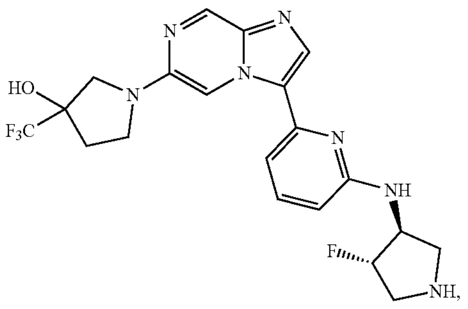
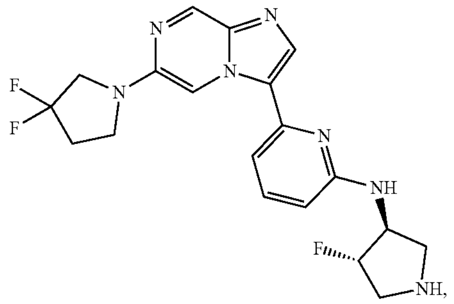
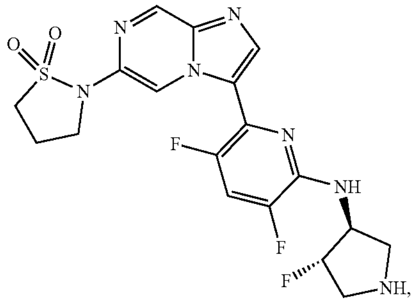
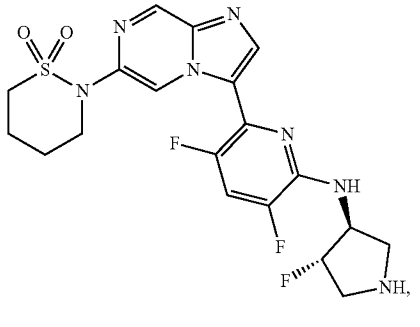

-continued
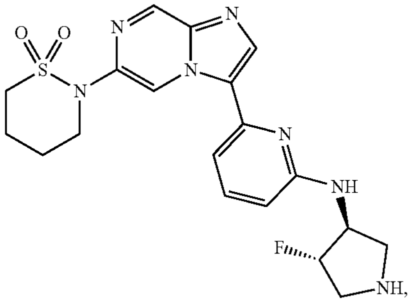
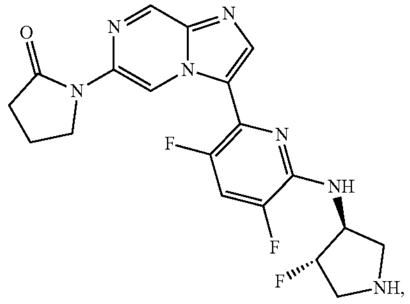
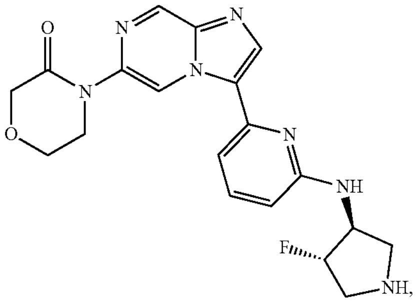
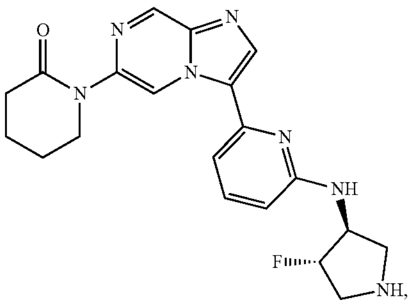
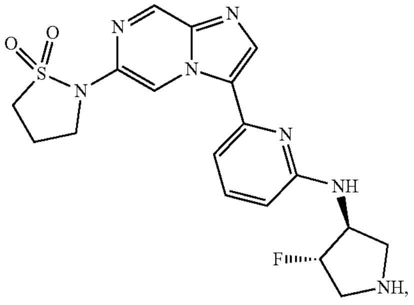
-continued
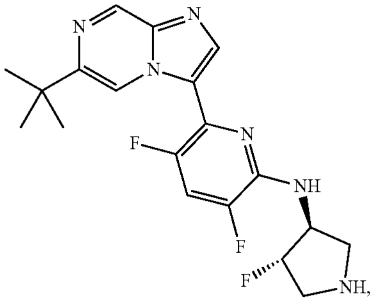
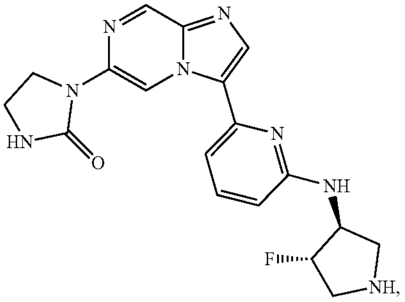
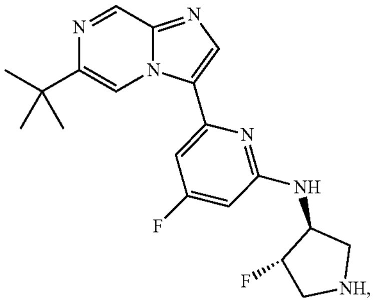
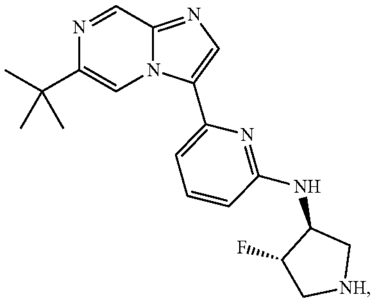
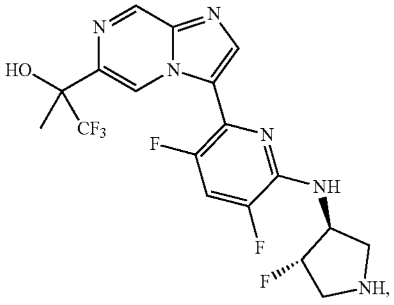

-continued
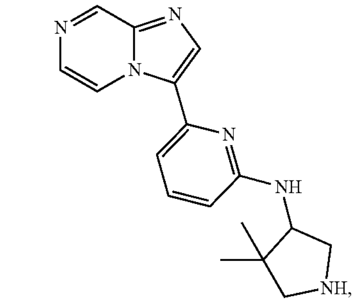
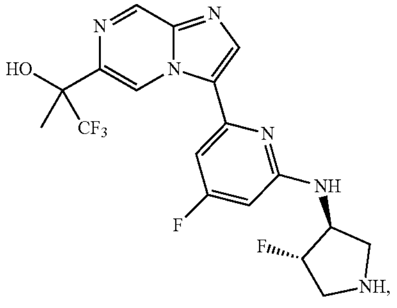
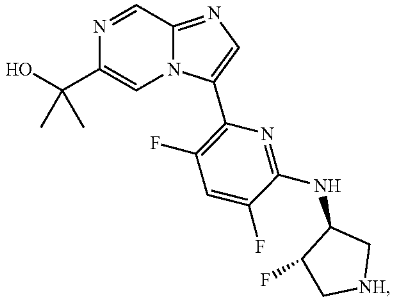
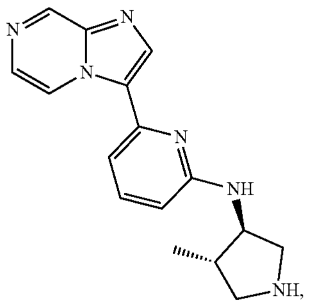
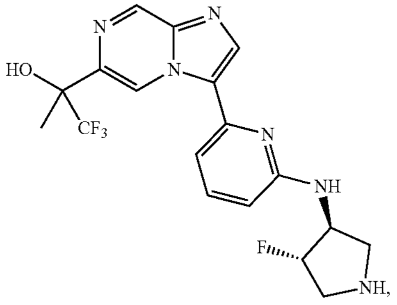
-continued
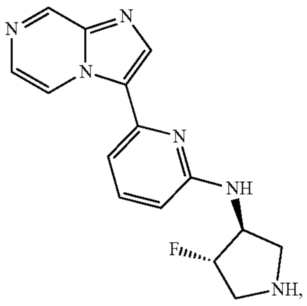
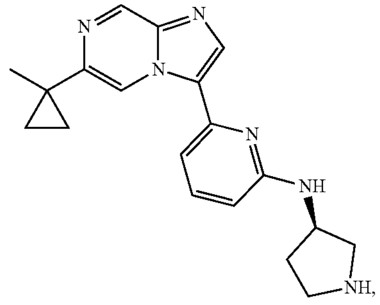
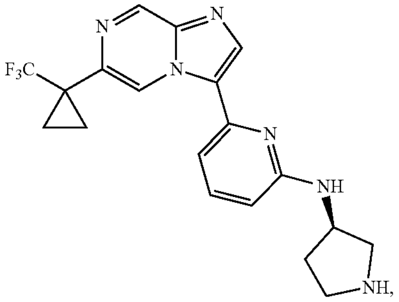
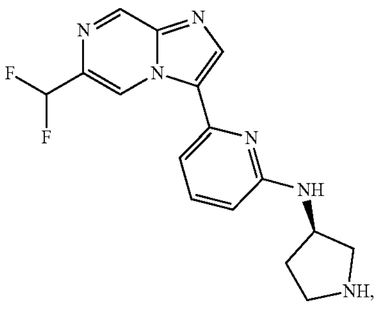
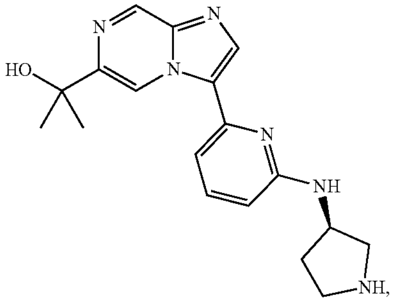

-continued

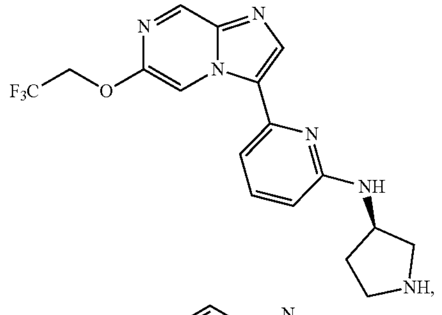

and

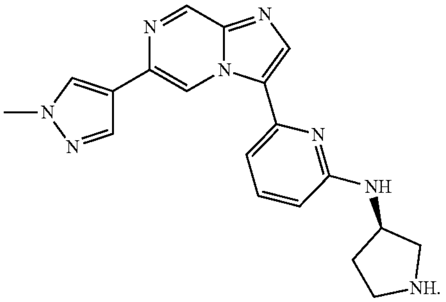

Clause 207. The compound of clause 201, wherein the compound of Formula (I) is a compound of Formula (IIg):

Formula (IIg)

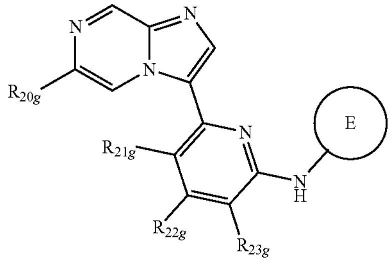

, or a salt, ester, solvate, optical isomer, geometric isomer, or salt of an isomer thereof;
wherein:

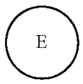

is selected from

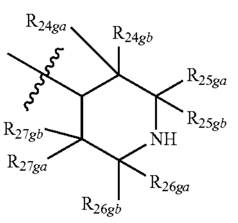

and

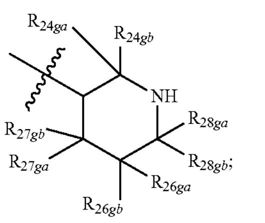

$R_{20g}$ is selected from H, $C_1$-$C_6$ alkyl, $C_1$-$C_6$ alkoxy, $C_3$-$C_6$ cycloalkyl, and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocyclyl is optionally substituted with one or more substituents selected from halogen, $C_1$-$C_6$ alkyl, $C_3$-$C_6$-cycloalkyl, —OH, and =O;

$R_{21g}$, $R_{22g}$, and $R_{23g}$ are each independently selected from H and halogen; and $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ are each independently selected from H, halogen, —OH, and $C_1$-$C_6$ alkyl.

Clause 208. The compound of clause 207, wherein one or more of $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ is independently selected from halogen, —OH, and $C_1$-$C_6$ alkyl.

Clause 209. The compound of clause 207 or 208, wherein $R_{20g}$ is H.

Clause 210. The compound of any one of clauses 207-209, wherein at least one of (i)-(xi) applies:

(i) $R_{20g}$ is selected from t-butyl, unsubstituted $C_3$ cycloalkyl,

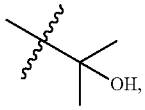

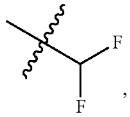

,

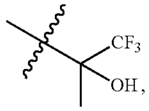

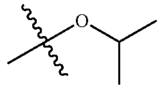

,

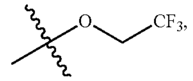

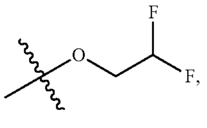

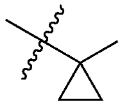

,

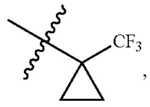

,

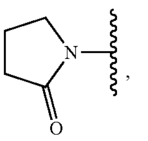

,

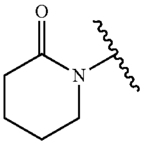

,

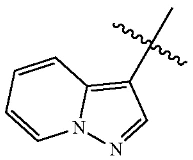

,

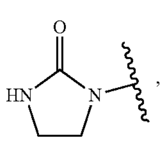

,

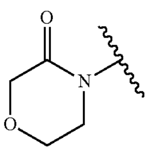

, and

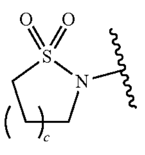

wherein c is 1 or 2;

(ii) $R_{20g}$ is

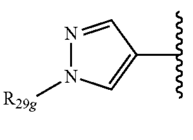

wherein $R_{29g}$ is selected from unsubstituted $C_3$ cycloalkyl, —$CH_3$,

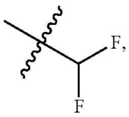
and
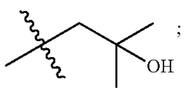
;

(iii) $R_{21g}$, $R_{22g}$, and $R_{23g}$ are each H;
(iv) $R_{21g}$ and $R_{23g}$ are each F and $R_{22g}$ is H;
(v) $R_{21g}$ and $R_{23g}$ are each H and $R_{22g}$ is F;
(vi)

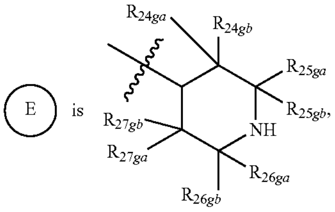

each of $R_{24ga}$, $R_{24gb}$, $R_{25ga}$, $R_{25gb}$, $R_{26ga}$, $R_{26gb}$, $R_{27ga}$, and $R_{27gb}$ is H;
(vii)

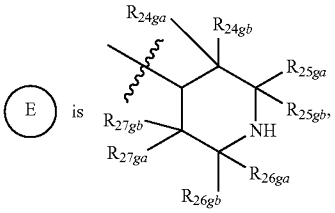

each of $R_{24ga}$, $R_{25ga}$, $R_{25gb}$, $R_{26ga}$, $R_{26gb}$, $R_{27ga}$, and $R_{27gb}$ is H and $R_{24gb}$ is F;
(viii)

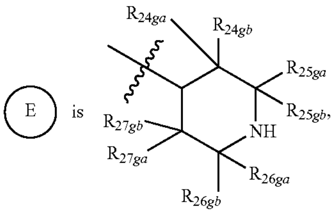

each of $R_{24ga}$, $R_{24gb}$, $R_{25ga}$, $R_{26ga}$, $R_{26gb}$, $R_{27ga}$, and $R_{27gb}$ is H and $R_{25gb}$ is —$CH_3$;
(ix)

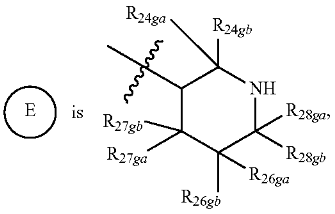

each of $R_{24ga}$, $R_{24gb}$, $R_{26ga}$, $R_{26gb}$, $R_{27ga}$, $R_{27gb}$, $R_{28ga}$, and $R_{28gb}$ is H;
(x)

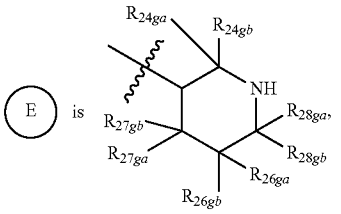

each of $R_{24ga}$, $R_{24gb}$, $R_{26ga}$, $R_{26gb}$, $R_{28ga}$, and $R_{28gb}$ is H and $R_{27g}$a and/or $R_{27g}$b is F or —$CH_3$;
(xi)

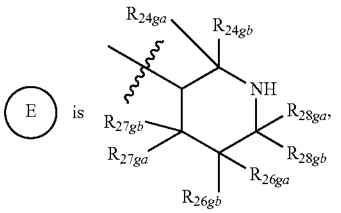

each of $R_{24ga}$, $R_{24gb}$, $R_{27ga}$, $R_{27gb}$, $R_{26ga}$, $R_{28ga}$, and $R_{28gb}$ is H and $R_{26gb}$ is F or —$CH_3$.

Clause 211. The compound of any one of clauses 207-210, wherein the compound is selected from:

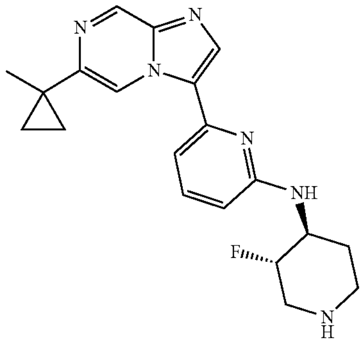
,

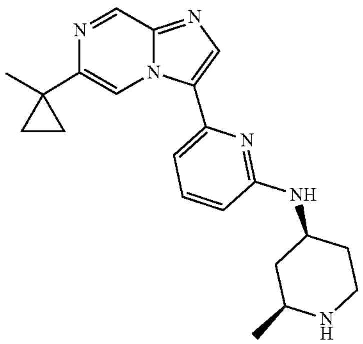
,

-continued
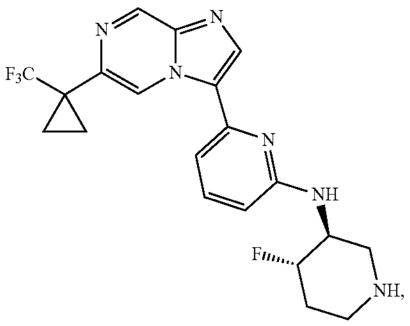
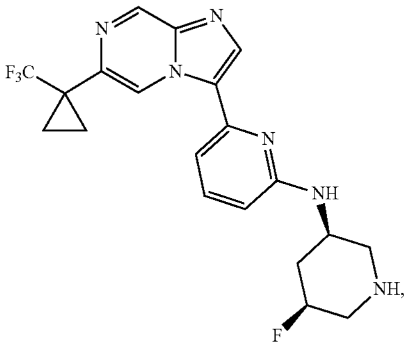
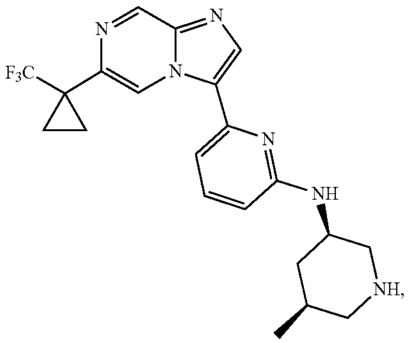
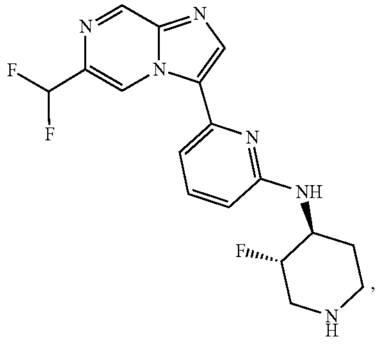
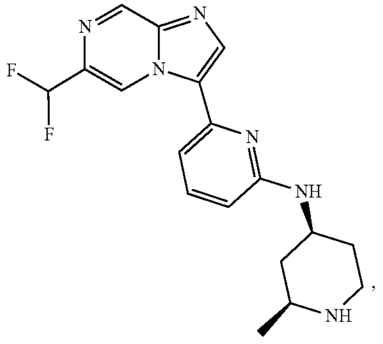
-continued
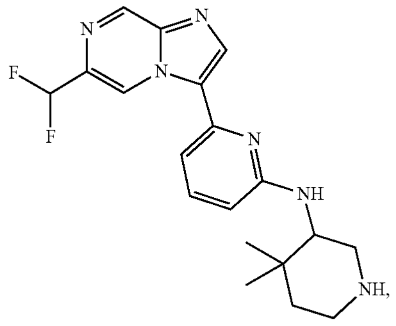
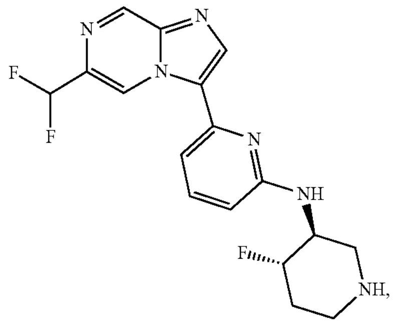
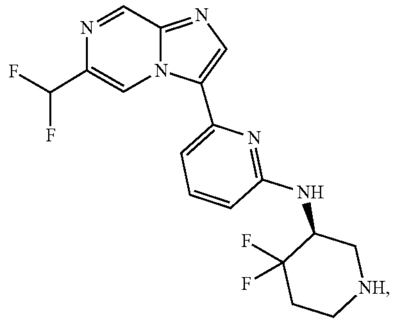
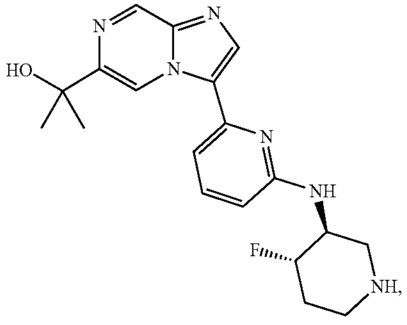
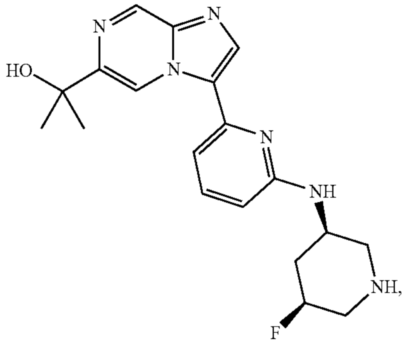

-continued
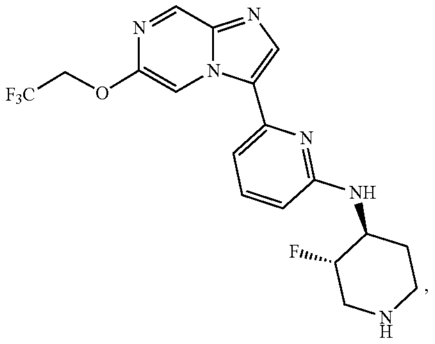
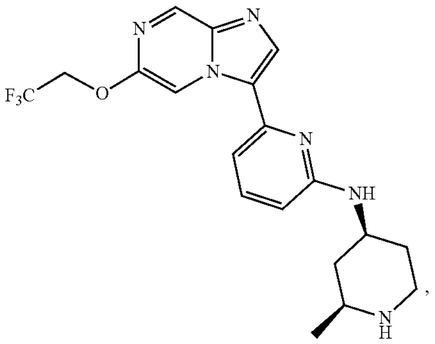
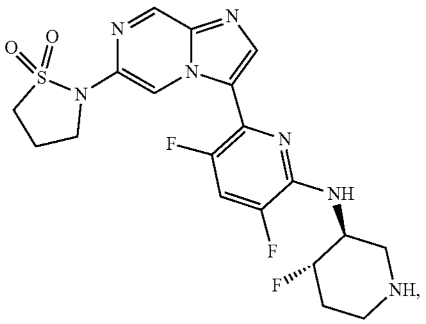
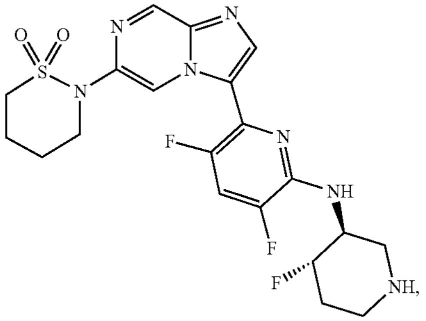
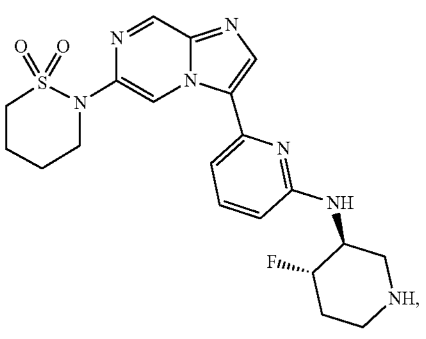
-continued
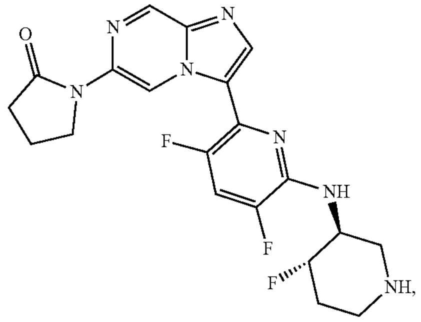
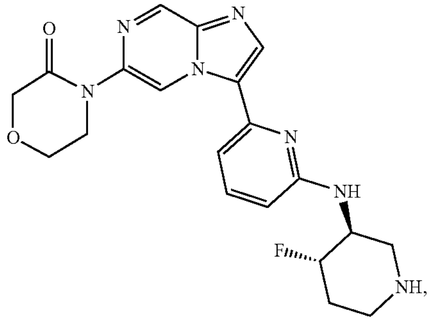
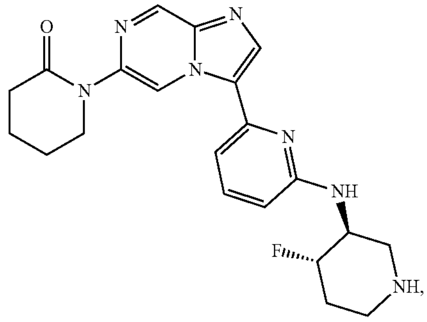
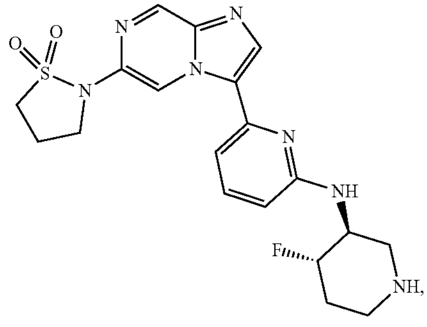
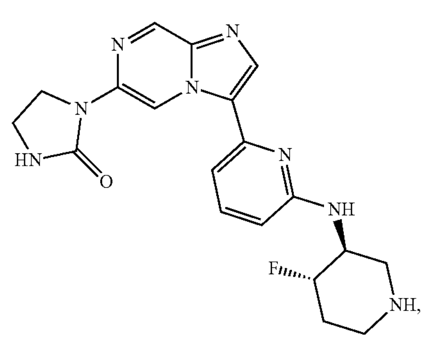

-continued
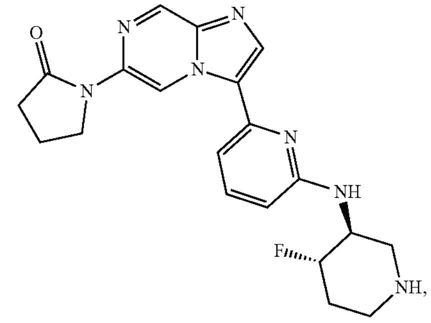
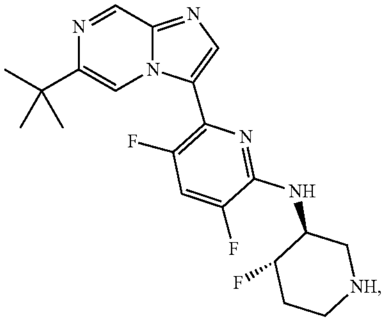
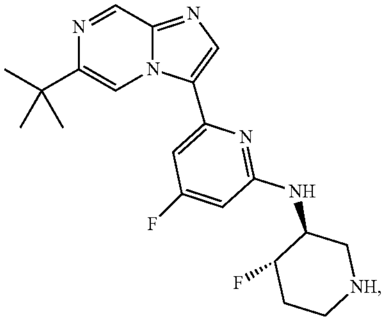
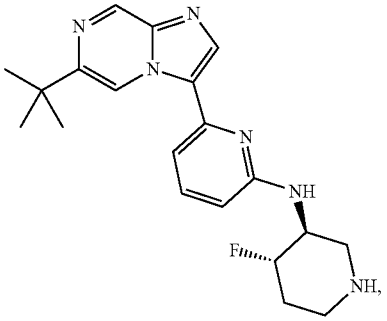
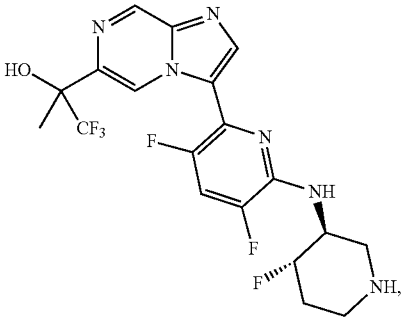
-continued
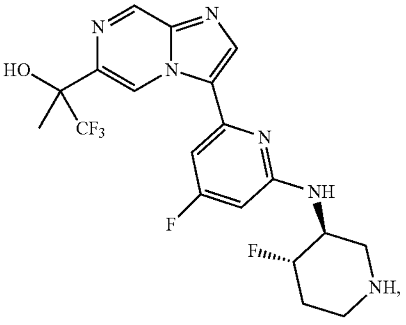
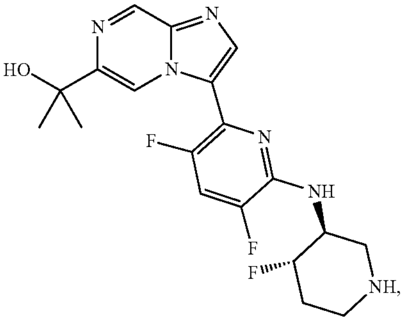
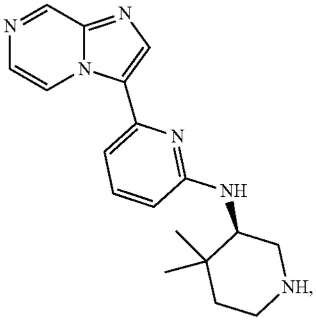
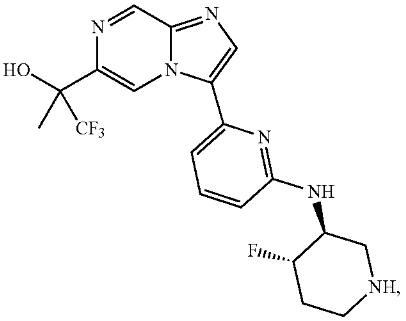
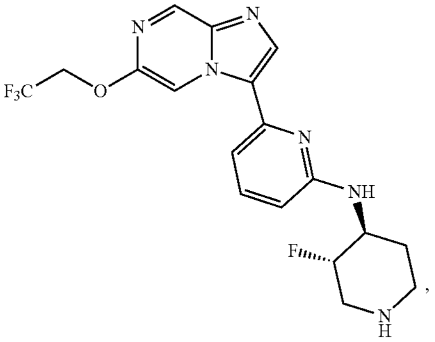

-continued
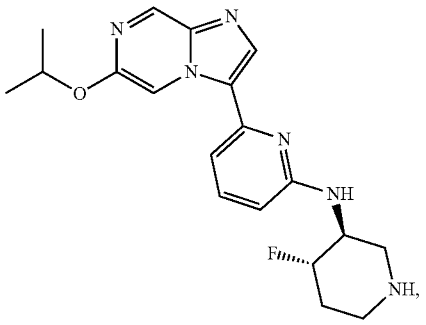
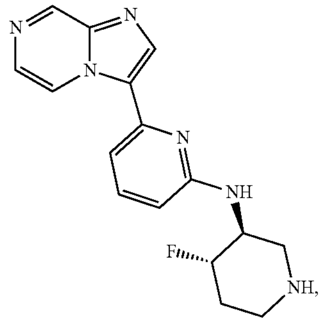
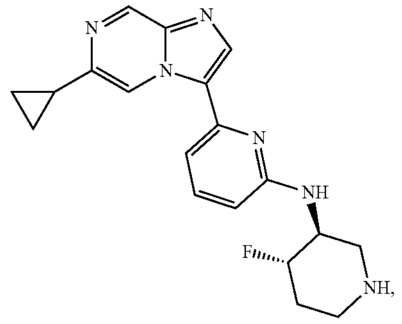
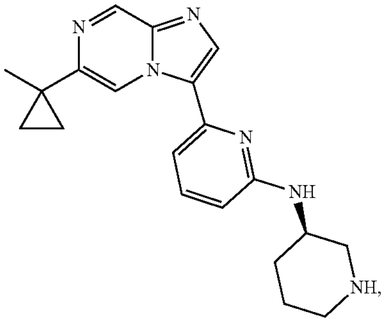
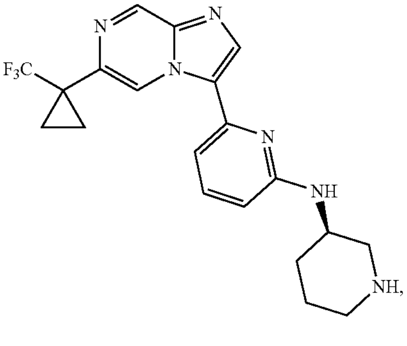
-continued
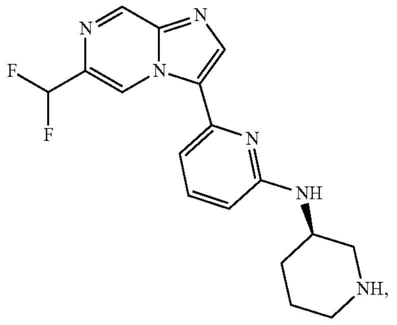
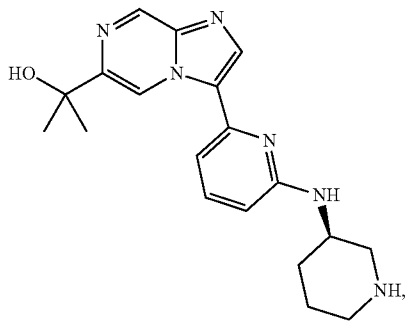
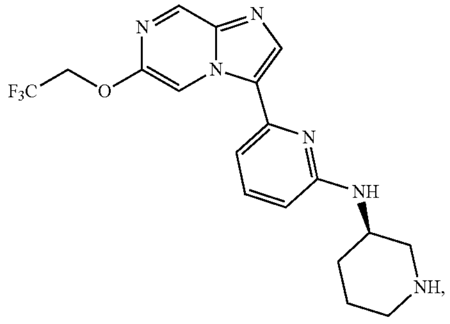
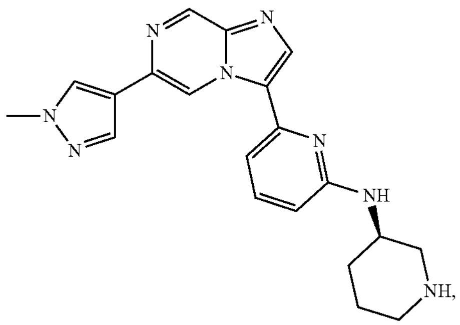
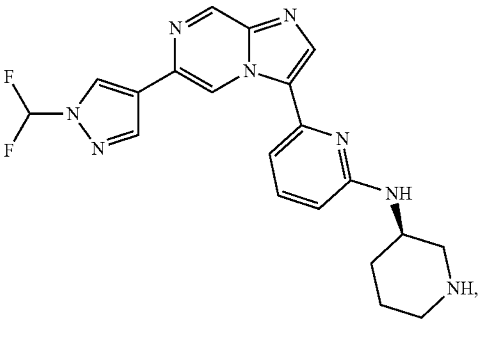

-continued
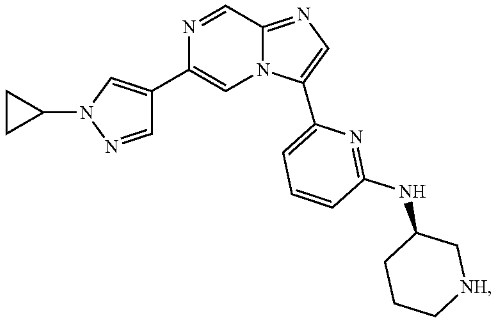
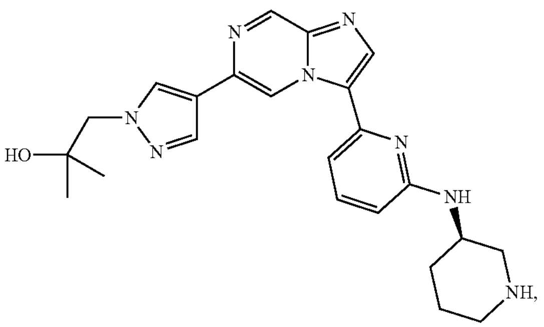
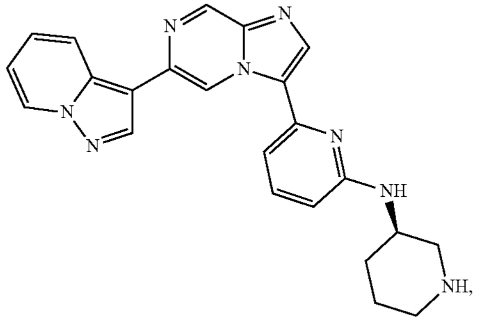
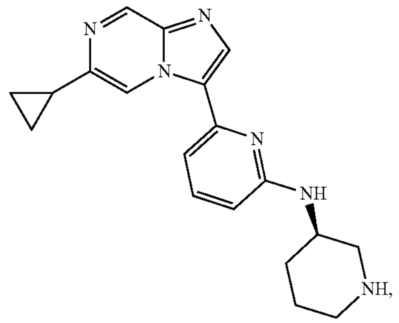
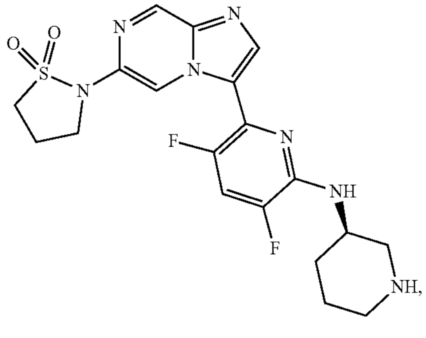
-continued
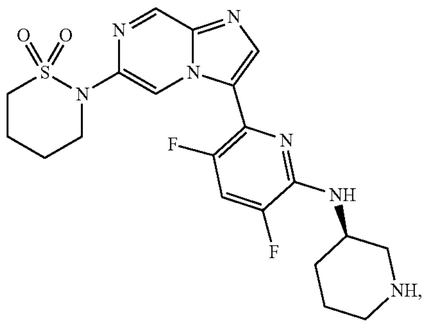
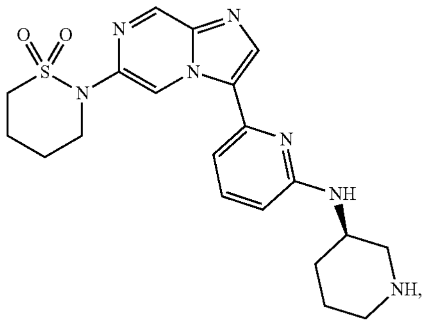
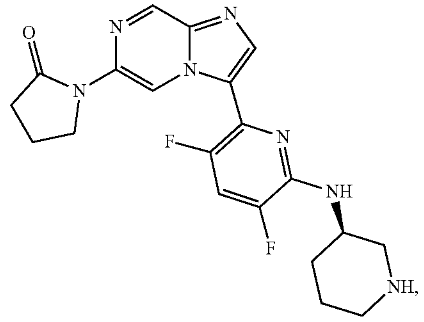
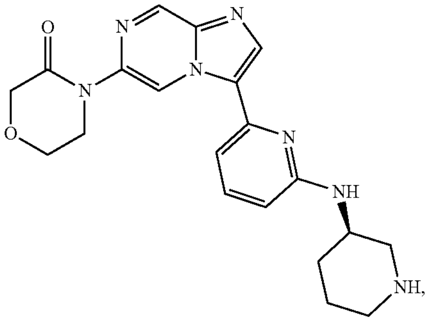
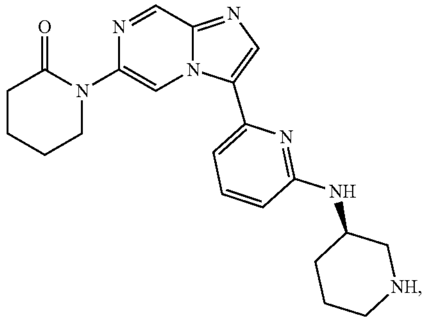

-continued
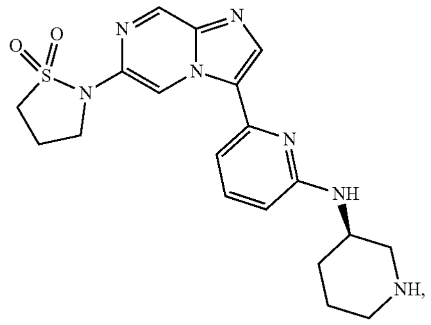
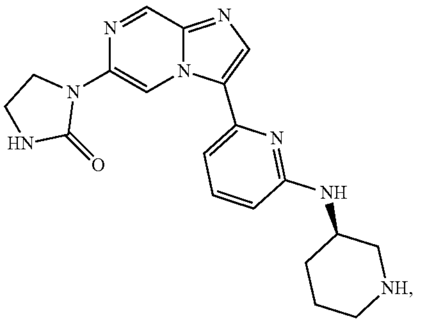
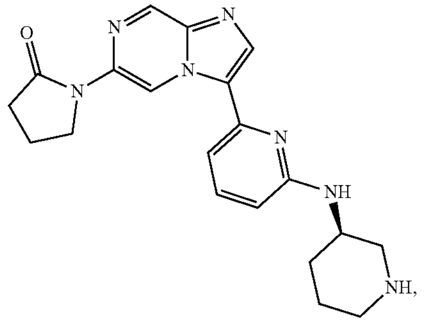
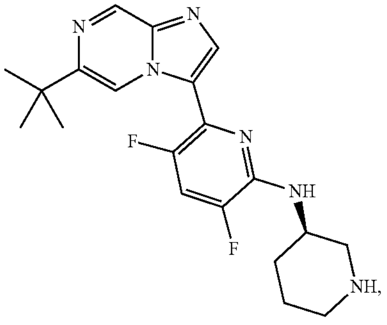
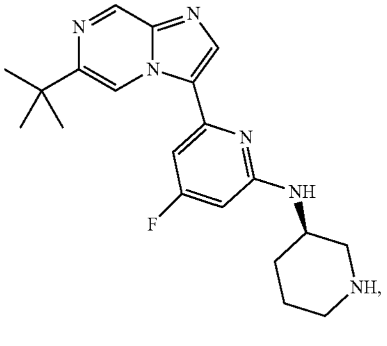
-continued
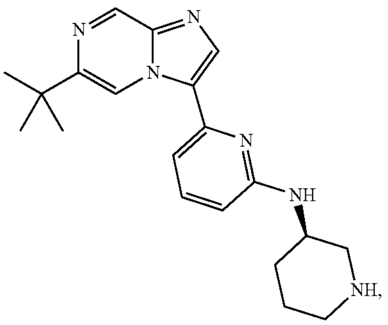
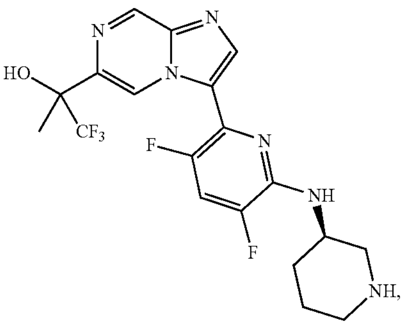
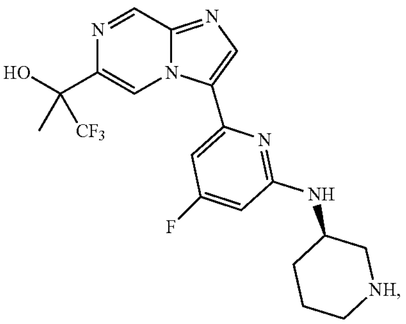
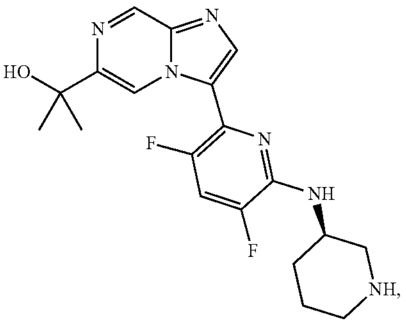
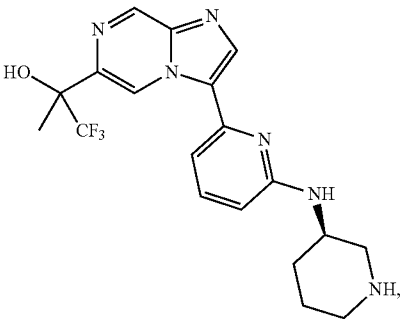

-continued

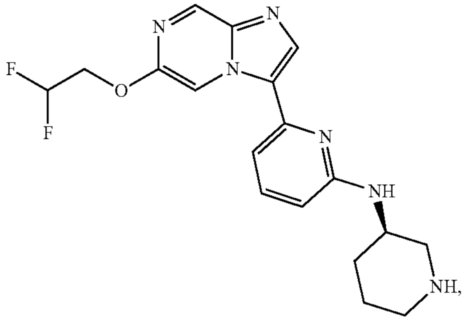

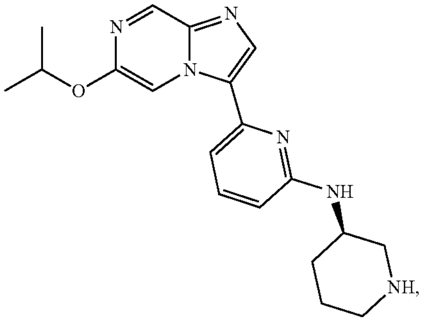

and

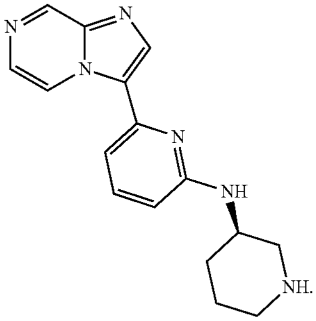

Clause 212. The compound of clause 201, wherein the compound of Formula (I) is a compound of Formula (IIh):

Formula (IIh)

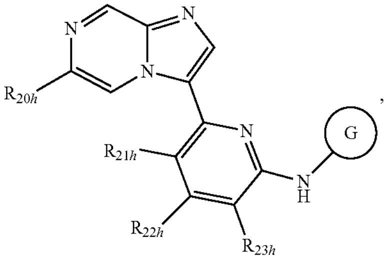

or a salt, ester, solvate, optical isomer, geometric isomer, or salt of an isomer thereof;

wherein:

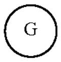

is selected from

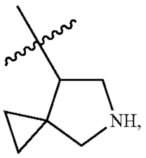

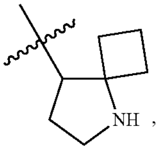

and

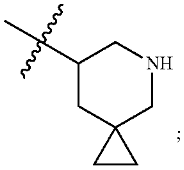

;

$R_{20h}$ is selected from H, $C_1$-$C_6$ alkyl, $C_1$-$C_6$ alkoxy, and $C_3$-$C_6$ cycloalkyl, wherein $C_1$-$C_6$ alkyl and $C_1$-$C_6$ alkoxy are each optionally substituted with one or more substituents selected from halogen and —OH, and wherein $C_3$-$C_6$ cycloalkyl is optionally substituted with one or more substituents selected from $C_1$-$C_6$ alkyl and halogen; and $R_{21h}$, $R_{22h}$, and $R_{23h}$ are each independently selected from H and halogen.

Clause 213. The compound of clause 212, wherein $R_{20h}$ is H.

Clause 214. The compound of clause 212 or 213, wherein at least one of (i)-(v) applies:

(i) $R_{20h}$ is selected from

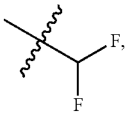

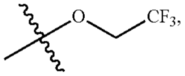

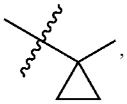

, and

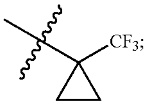

(ii) $R_{21h}$, $R_{22h}$, and $R_{23h}$ are each H;

(iii) $R_{21h}$ and $R_{23h}$ are each F and $R_{22h}$ is H;

(iv) $R_{21h}$ and $R_{23h}$ are each H and $R_{22h}$ is F;

(v)

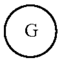

is

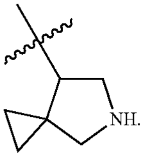

Clause 215. The compound of any one of clauses 212-214, wherein the compound is selected from:

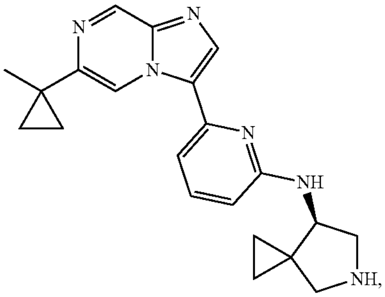

-continued

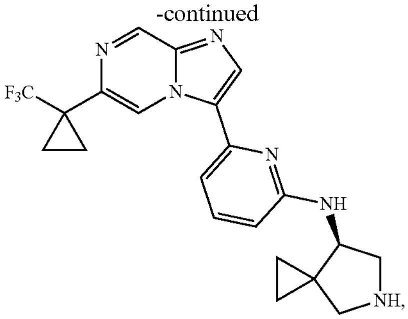

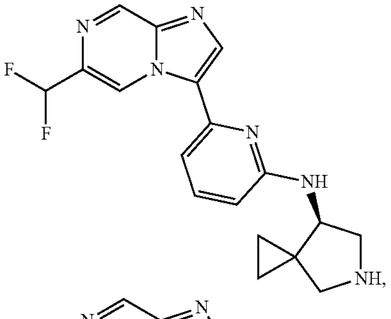

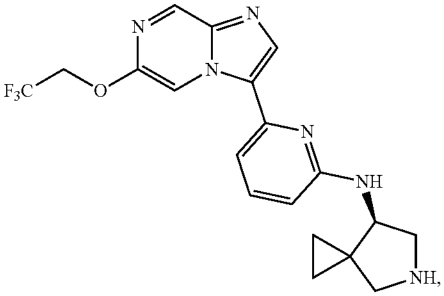

and

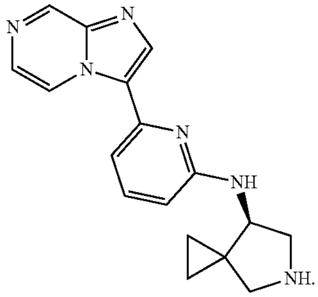

Clause 216. The compound of any one of clauses 201-215, wherein the compound is an inhibitor of at least one of IRAK1, IRAK4, and FLT3.

Clause 217. The compound of any one of clauses 201-216, wherein the compound is an inhibitor of at least two of IRAK1, IRAK4, and FLT3.

Clause 218. The compound of any one of clauses 201-217, wherein the compound is an inhibitor of IRAK1 and IRAK4.

Clause 219. The compound of any one of clauses 201-217, wherein the compound is an inhibitor of IRAK1, IRAK4, and FLT3.

Clause 220. The compound of any one of clauses 216, 217, or 219, wherein FLT3 is selected from WT FLT3, activated FLT3, and mutated FLT3.

Clause 221. The compound of clause 220, wherein the mutated FLT3 is D835Y mutated FLT3 or F691L mutated FLT3.

Clause 222. A composition comprising a compound of any one of clauses 201-221, wherein the composition further comprises a formulary ingredient, an adjuvant, or a carrier.

Clause 223. The composition of clause 222, wherein the composition is used in combination with one or more of: a chemotherapy agent, a BCL2 inhibitor, an immune modulator, a BTK inhibitor, a DNA methyltransferase inhibitor/hypomethylating agent, an anthracycline, a histone deacetylase (HDAC) inhibitor, a purine nucleoside analogue (antimetabolite), an isocitrate dehydrogenase 1 or 2 (IDH1 and/or IDH2) inhibitor, an antibody-drug conjugate, an mAbs/immunotherapy, a Plk inhibitor, a MEK inhibitor, a CDK inhibitor, a CDK9 inhibitor, a CDK8 inhibitor, a retinoic acid receptor agonist, a TP53 activator, a CELMoD, a smoothened receptor antagonist, an ERK inhibitor including an ERK2/MAPK1 or ERK1/MAPK3 inhibitor, a PI3K inhibitor, an mTOR inhibitor, a steroid or glucocorticoid receptor modulator, an EZH2 inhibitor, a hedgehog (Hh) inhibitor, a Topoisomerase I inhibitor, a Topoisomerase II inhibitor, an aminopeptidase/Leukotriene A4 hydrolase inhibitor, a FLT3/Axl/ALK inhibitor, a FLT3/KIT/PDGFR, PKC, and/or KDR inhibitor, a Syk inhibitor, an E-selectin inhibitor, an NEDD8-activator, an MDM2 inhibitor, a PLK1 inhibitor, an Aura A inhibitor, an aurora kinase inhibitor, an EGFR inhibitor, an AuroraB/C/VEGFR1/2/3/FLT3/CSF-1R/Kit/PDGFRA/B inhibitor, an AKT 1, 2, and/or 3 inhibitor, a ABL1/2/SRC/EPHA2/LCK/YES1/KIT/PDGFRB/FYN inhibitor, a farnesyltransferase inhibitor, a BRAF/MAP2K1/MAP2K2 inhibitor, a Menin-KMT2A/MLL inhibitor, and a multikinase inhibitor.

Clause 224. The composition of clause 223, wherein the composition is used in combination with a BCL2 inhibitor.

Clause 225. The composition of clause 224, wherein the BCL2 inhibitor is venetoclax or a pharmaceutically acceptable salt therof.

Clause 226. A method of treating a disease or disorder in a subject, the method comprising administering to the subject a therapeutically effective amount of a compound of any one of clauses 201-221 or a composition of any one of clauses 222-225.

Clause 227. The method of clause 226, wherein the method comprises administering to the subject a composition comprising the therapeutically effective amount of the compound of clause 1 and a formulary ingredient, an adjuvant, or a carrier.

Clause 228. The method of clause 226 or 227, wherein the disease or disorder is responsive to at least one of interleukin-1 receptor-associated kinase (IRAK) inhibition and fms-like tyrosine kinase 3 (FLT3) inhibition.

Clause 229. The method of any one of clauses 226-228, wherein the administration comprises parenteral administration, a mucosal administration, intravenous administration, subcutaneous administration, topical administration, intradermal administration, oral administration, sublingual administration, intranasal administration, or intramuscular administration.

Clause 230. The method of any one of clauses 226-229, wherein the compound is administered to the subject in an amount of from about 0.005 mg/kg subject body weight to about 1,000 mg/kg subject body weight.

Clause 231. The method of any one of clauses 226-230, wherein the disease or disorder comprises a hematopoietic cancer.

Clause 232. The method of any one of clauses 226-230, wherein the disease or disorder comprises myelodysplastic syndrome (MDS) and/or acute myeloid leukemia (AML).

Clause 233. The method of any one of clauses 226-230, wherein the disease or disorder comprises lymphoma, leukemia, chronic lymphocytic leukemia (CLL), chronic myeloid leukemia (CMIL), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL with MYD88 mutation, follicular lymphoma, or marginal zone lymphoma.

Clause 234. The method of any one of clauses 226-230, wherein the disease or disorder comprises at least one cancer selected from glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer, or one or more inflammatory diseases or autoimmune disease characterized by overactive IRAK1 and/or IRAK4, or combinations thereof.

Clause 235. The method of any one of clauses 226-230, wherein the disease or disorder comprises one or more inflammatory diseases or autoimmune disease selected from chronic inflammation, sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, or combinations thereof.

Clause 236. The method of any one of clauses 226-230, wherein the disease or disorder comprises:

(i) MDS, MDS with a splicing factor mutation, MDS with a mutation in isocitrate dehydrogenase 1, MDS with a mutation in isocitrate dehydrogenase 2; or (ii) AML with a splicing factor mutation, AML having enhanced IRAK4-Long expression and/or activity relative to IRAK4-Short, and/or wherein the AML is not driven by FLT3 mutations but expresses IRAK4-Long.

Clause 237. The method of clause 236, wherein the MDS with a splicing factor mutation comprises MDS with a splicing factor mutation in U2AF1 or SF3B1 and the AML splicing factor mutation comprises AML with a splicing factor mutation in U2AF1 or SF3B1.

Clause 238. The method of any one of clauses 226-230, wherein the disease or disorder comprises DLBCL, and wherein the DLBCL comprises a L265P MYD88 mutant (ABC) subtype of DLBCL or a S219C MYD88 mutant (GCB) subtype of DLBCL.

Clause 239. The method of any one of clauses 226-238, further comprising administering to the subject one or more additional therapies selected from: a chemotherapy agent, a BCL2 inhibitor, an immune modulator, a BTK inhibitor, a DNA methyltransferase inhibitor/hypomethylating agent, an anthracycline, a histone deacetylase (HDAC) inhibitor, a purine nucleoside analogue (antimetabolite), an isocitrate dehydrogenase 1 or 2 (IDH1 and/or IDH2) inhibitor, an antibody-drug conjugate, an mAbs/immunotherapy, a Plk inhibitor, a MEK inhibitor, a CDK inhibitor, a CDK9 inhibitor, a CDK8 inhibitor, a retinoic acid receptor agonist, a TP53 activator, a CELMoD, a smoothened receptor antagonist, an ERK inhibitor including an ERK2/MAPK1 or ERK1/MAPK3 inhibitor, a PI3K inhibitor, an mTOR inhibitor, a steroid or glucocorticoid receptor modulator, an EZH2 inhibitor, a hedgehog (Hh) inhibitor, a Topoisomerase I inhibitor, a Topoisomerase II inhibitor, an aminopeptidase/Leukotriene A4 hydrolase inhibitor, a FLT3/Axl/ALK inhibitor, a FLT3/KIT/PDGFR, PKC, and/or KDR inhibitor, a Syk inhibitor, an E-selectin inhibitor, an NEDD8-activator, an MDM2 inhibitor, a PLK1 inhibitor, an Aura A inhibitor, an aurora kinase inhibitor, an EGFR inhibitor, an AuroraB/C/VEGFR1/2/3/FLT3/CSF-1R/Kit/PDGFRA/B inhibitor, an AKT 1, 2, and/or 3 inhibitor, a ABL1/2/SRC/EPHA2/LCK/YES1/KIT/PDGFRB/FYN inhibitor, a farnesyltransferase inhibitor, a BRAF/MAP2K1/MAP2K2 inhibitor, a Menin-KMT2A/MLL inhibitor, and a multikinase inhibitor.

Clause 240. The method of clause 239, wherein the additional therapy is a BCL2 inhibitor.

Clause 241. The method of clause 240, wherein the BCL2 inhibitor is venetoclax or a pharmaceutically acceptable salt thereof.

Clause 242. The method of any one of clauses 226-241, wherein the disease or disorder is a BCL2 inhibitor resistant disease or disorder.

Clause 243. The method of any one of clauses 226-241, wherein the disease or disorder is a venetoclax resistant disease or disorder.

Clause 244. The method of any one of clauses 226-241, wherein the disease or disorder is a FLT3 inhibitor resistant disease or disorder.

Clause 245. The method of any one of clauses 226-241, wherein the disease or disorder is BCL2 inhibitor resistant acute myeloid leukemia (AML).

Clause 246. The method of any one of clauses 226-241, wherein the disease or disorder is venetoclax resistant acute myeloid leukemia (AML).

Clause 247. The method of any one of clauses 226-241, wherein the disease or disorder is FLT3 inhibitor resistant acute myeloid leukemia (AML).

Clause 248. The method of any one of clauses 226-241, wherein the disease or disorder is BCL2 inhibitor resistant refractory acute myeloid leukemia (AML).

Clause 249. The method of any one of clauses 226-241, wherein the disease or disorder is venetoclax resistant refractory acute myeloid leukemia (AML).

Clause 250. The method of any one of clauses 226-241, wherein the disease or disorder is FLT3 inhibitor resistant refractory acute myeloid leukemia (AML).

Clause 251. The method of any one of clauses 226-241, wherein the disease or disorder is BCL2 inhibitor resistant relapsed acute myeloid leukemia (AML).

Clause 252. The method of any one of clauses 226-241, wherein the disease or disorder is venetoclax resistant relapsed acute myeloid leukemia (AML).

Clause 253. The method of any one of clauses 226-241, wherein the disease or disorder is FLT3 inhibitor resistant relapsed acute myeloid leukemia (AML).

Clause 254. The method of clause 239, wherein the compound of any one of clauses 201-221 or the composition of any one of clauses 222-225 and the one or more additional therapies are administered together in one administration or composition.

Clause 255. The method of clause 239, wherein the compound of any one of clauses 201-221 or the composition of any one of clauses 222-225 and the one or more additional therapies are administered separately in more than one administration or more than one composition.

Clause 256. The method of any one of clauses 226-255, wherein the disease or disorder is alleviated by inhibiting at least one of IRAK1, IRAK4, and FLT3 in the subject.

Clause 257. The method of any one of clauses 226-256, wherein the disease or disorder is alleviated by inhibiting at least two of IRAK1, IRAK4, and FLT3 in the subject.

Clause 258. The method of any one of clauses 226-255, wherein the disease or disorder is alleviated by inhibiting IRAK1 and IRAK4 in the subject.

Clause 259. The method of any one of clauses 226-255, wherein the disease or disorder is alleviated by inhibiting IRAK1, IRAK4, and FLT3 in the subject.

Clause 260. The method of any one of clauses 256, 257, or 259, wherein FLT3 is selected from WT FLT3, activated FLT3, and mutated FLT3.

Clause 261. The method of clause 260, wherein the mutated FLT3 is D835Y mutated FLT3 or F691L mutated FLT3.

EXAMPLES

The following non-limiting examples are provided to further illustrate embodiments of the disclosure disclosed herein. It should be appreciated by those of skill in the art that the techniques disclosed in the examples that follow represent approaches that have been found to function well in the practice of the disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the disclosure.

LIST OF ABBREVIATIONS

In the accompanying procedures and schemes, abbreviations are used with the following meanings unless otherwise indicated: Ac=acetate; aq, aq.=aqueous; Ar=aryl; BOC, Boc=t-butyloxycarbonyl; Bn=benzyl; BSA=bovine serum albumin; Bu=butyl, t-Bu=tert-butyl; BuLi, n-BuLi=n-butyllithium; CBZ, Cbz=Benzyloxycarbonyl; conc, conc.=concentrated; c-Bu=cyclobutyl; c-Pr=cyclopropyl; Cy=cyclohexyl; DAST=(diethylamino)sulfur trifluoride; dba=dibenzylideneacetone; DCM=dichloromethane; DIAD=diisopropylazodicarboxylate; DIBAL, DIBAL-H=diisobutylaluminum hydried; DIEA=diisopropy- lethylamine; DMAC, DMA=dimethylacetamide; DME=1,2-dimethoxyethane; DMEM=Dulbecco's modified eagle medium; DMAP=4-dimethylaminopyridine; DMF=N,N-dimethylformamide; DMSO=dimethylsulfoxide; eq.=equivalent(s); EDC=N-[3-(dimethylamino)propyl]-N-ethylcarbodiimide; EDTA=ethylenediaminetetraacetic acid; ESI=electrospray ionization; Et=ethyl; EtOAc=ethyl acetate; EtOH=ethanol; FBS=Fetal Bovine Serum; h, hr=hour; HATU=N-[(dimethylamino)-1H-1,2,3-triazolo[4,5-b]pyridin-1-ylmethylene]-N-methylmethanaminium hexafluorophosphate N-oxide; HOAc=acetic acid; HOAt=3H-[1,2,3]-triazolo[4,5-b]pyridin-3-ol; HOBt=1H-benzotriazol-1-ol; HPLC=High pressure liquid chromatography; HTRF=homogenous time resolved fluorescence; IPA, i-PrOH=isopropanol; iPr=isopropyl; LAH=lithium aluminum hydried; LCMS=liquid chromatography—mass spectroscopy; LHMIDS=lithium bis(trimethylsilyl)amide; Me=methyl; MeOH=methanol; min, min.=minute; W=microwave; NaHMDS=sodium bis(trimethylsilyl) amide; NBS=1-bromopyrrolidine-2,5-dione; NCS=1-chloropyrrolidine-2,5-dione; NMP=N-methylpyrrolidinone; NMR=nuclear magnetic resonance; OMs, mesyl=methanesulfonyl; Oxone, OXONE=potassium peroxymonosulfate; PBS=phosphate buffered saline; Pd2dba$_3$=tris(dibenzylidineacetone)dipalladium; Pd/C=palladium on activated carbon; Ph=phenyl; PMB=4-methoxybenzyl; PMBCI=1-(chloromethyl)-4-methoxybenzene; Pr=propyl; Py=pyridyl; RT, rt=room temperature; RuPhos Pd G3=(2-dicyclohexylphosphino-2',6'-diisopropoxy-1,1'-biphenyl)[2-(2'-amino-1,1'-biphenyl)]palladium(II)methanesulfonate; sat.=saturated; TBAF=tetrabutylammonium fluoride; TBAI=tetrabutylammonium iodide; t-Bu=tert-butyl; TFA=trifluoroacetic acid; THE=tetrahydrofuran; TLC=thin layer chromatography; prep TLC=preparative thin layer chromatography; Tosyl=toluenesulfonyl; triflate, OTf=trifluoromethanesulfonate; triflic=trifluoromethanesulfonic; Xantphos=4,5-bis(diphenylphosphino)-9,9-dimethylxanthene; XPhos Pd G2 or XPhos-PD-G2=chloro(2-dicyclohexylphosphino-2',4',6'-triisopropyl-1,1'-biphenyl)[2-(2'-amino-1,1'-biphenyl)] palladium(II).

General Methods

Unless otherwise stated, all reactions were carried out under an atmosphere of dry nitrogen in dried glassware. Indicated reaction temperatures refer to those of the reaction bath, while room temperature (rt) is noted as 25° C. Unless otherwise noted, all solvents were of anhydrous quality purchased from Aldrich Chemical Co. and were used as received. Commercially available starting materials and reagents were purchased from commercial suppliers and were used as received.

Analytical thin layer chromatography (TLC) was performed with Sigma Aldrich TLC plates (5×20 cm, 60 Å, 250 m). Visualization was accomplished by irradiation under a 254 nm UV lamp. Chromatography on silica gel was performed using forced flow (liquid) of the indicated solvent system on Biotage KP-Sil pre-packed cartridges and using the Biotage SP-1 automated chromatography system. $^1$H NMR spectra were recorded on a Varian Inova 400 MHz spectrometer. Chemical shifts are reported in ppm with the solvent resonance as the internal standard (DMSO-d6 2.50 ppm for $^1$H). Data are reported as follows: chemical shift, multiplicity (s=singlet, d=doublet, t=triplet, q=quartet, quint=quintet, spt=septet, br=broad, m=multiplet), coupling constants, and number of protons. Low resolution mass spectra (electrospray ionization) were acquired on an Agilent Technologies 6130 quadrupole spectrometer coupled to the HPLC system. Unless otherwise noted, all LCMS ions listed are [M+H]. If needed, products were purified via semi-preparative HPLC using the columns and mobile phases noted. Samples were analyzed for purity on an Agilent 1200 series LC/MS equipped with a Luna® $C_{18}$ reverse phase (3 micron, 3×75 mm) column having a flow rate of 0.8-1.0 mL/min over a 7 minute gradient and an 8.5 minute run time (Method 1). Unless otherwise noted, the mobile phase was a mixture of acetonitrile (0.025% TFA) and $H_2O$ (0.05% TFA), with temperature maintained at 50° C. Purity of final compounds was determined to be >95% using a 3 μL injection with quantitation by AUC at 220 and 254 nm (Agilent Diode Array Detector).

Example 1

Exemplary Synthetic Procedure #1 (Compounds 1-7)

Compound 1, N-((3S,4S)-4-fluoropyrrolidin-3-yl)-6-(6-(1-methylcyclopropyl)imidazo[1,2-a]pyrazin-3-yl)pyridin-2-amine

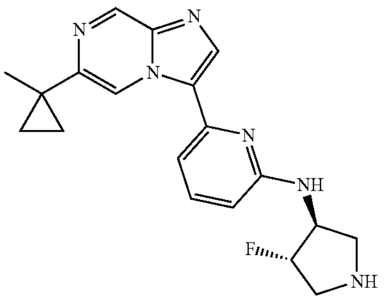 [SMILES: CC1(c2cn3c(-c4cccc(N[C@H]5CNC[C@@H]5F)n4)cnc3cn2)CC1]

Step A. 5-bromo-N,N-bis(4-methoxybenzyl)pyridin-2-amine

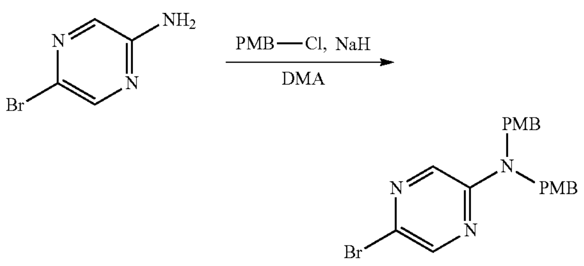

To a stirred 0° C. mixture of 5-bromopyrazin-2-amine (27.00 g, 155.2 mmol) and sodium hydried (15.52 g, 387.9 mmol, 60% purity) in N,N-dimethylacetamide (200 mL) was added 1-(chloromethyl)-4-methoxy-benzene (60.75 g, 387.9 mmol, 52.83 mL). The resulting reaction mixture was stirred at 0° C. for 2 hours, and was then poured into ice water and extracted with ethyl acetate (3×300 mL). The organic extracts were combined, washed with saturated aqueous sodium chloride solution (2×250 mL), dried over anhydrous sodium sulfate, filtered, and concentrated under reduced pressure. The resulting crude product was purified by flash chromatography on silica gel (0-15% ethyl acetate in petroleum ether) to provide the title compound.

Step B. 5-isopropenyl-N,N-bis[(4-methoxyphenyl) methyl]pyrazin-2-amine

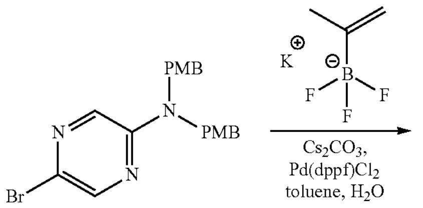

-continued

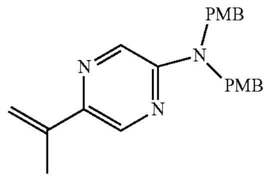

To a solution of 5-bromo-N,N-bis[(4-methoxyphenyl) methyl]pyrazin-2-amine (60.00 g, 144.8 mmol) in toluene (250 mL), tetrahydrofuran (250 mL), and water (100 mL) were added potassium isopropenyltrifluoroborate (25.72 g, 173.8 mmol), cesium carbonate (141.56 g, 434.47 mmol), and [1,1-bis(diphenylphosphino)ferrocene]dichloropalladium(II) (10.60 g, 14.48 mmol). The resulting mixture was heated at 80° C. for 2 hours, and was then cooled to room temperature, poured into water (200 mL), and extracted with ethyl acetate (2×200 mL). The organic extracts were combined, washed with saturated aqueous sodium chloride solution (100 mL), dried over anhydrous sodium sulfate, and concentrated under reduced pressure. The resulting crude product was purified by flash chromatography on silica gel (0-10% ethyl acetate in petroleum ether) to provide the title compound: LCMS m/z 376.2 $[M+H]^+$.

Step C. N,N-bis[(4-methoxyphenyl)methyl]-5-(1-methylcyclopropyl)pyrazin-2-amine

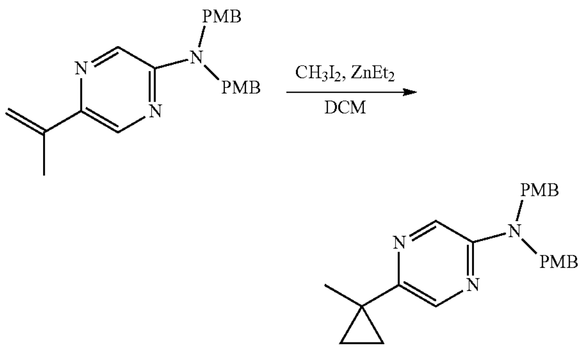

A solution of diethylzinc in hexanes (1 M, 103.87 mL, 103.87 mmol) was added to dichloromethane (100 mL) at 0° C. Diiodomethane (46.37 g, 173.1 mmol, 13.97 mL) was added dropwise, and the resulting reaction mixture was stirred at 0° C. for 30 minutes. A solution of 5-isopropenyl-N,N-bis[(4-methoxyphenyl)methyl]pyrazin-2-amine (13.0 g, 34.6 mmol) in dichloromethane (50 mL) was added, and the reaction was then stirred for 5 hours while warming to room temperature. The reaction mixture was then quenched by addition of water (100 mL) and extracted with dichloromethane (2×200 mL). The organic extracts were combined, washed with saturated aqueous sodium chloride solution (200 mL), dried over anhydrous sodium sulfate, filtered, and concentrated under reduced pressure. The resulting crude product was purified by flash chromatography on silica gel (0-20% ethyl acetate in petroleum ether) to provide the title compound: LCMS m/z 390.3 $[M+H]^+$.

Step D. 5-(1-methylcyclopropyl)pyrazin-2-amine

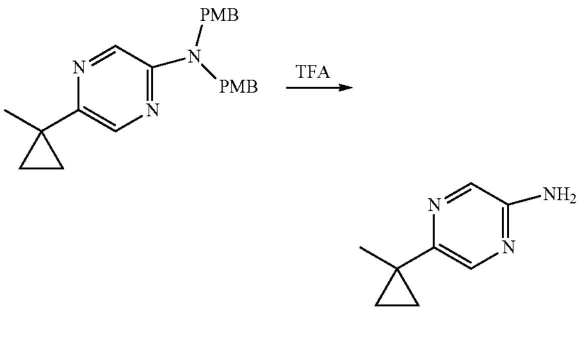

A solution of N,N-bis[(4-methoxyphenyl)methyl]-5-(1-methylcyclopropyl)pyrazin-2-amine (8.00 g, 20.5 mmol) in trifluoroacetic acid (100 mL) was stirred at room temperature for 5 hours. The reaction was then diluted with methanol (100 mL), and the resulting mixture was filtered and concentrated under reduced pressure. The residue thus obtained was basified to pH=8-9 by addition of aqueous 1 N sodium hydroxide solution at 0° C., and was then extracted with ethyl acetate (2×20 mL). The organic extracts were combined, washed with saturated aqueous sodium chloride solution (2×15 mL), dried over anhydrous sodium sulfate, filtered, and concentrated under reduced pressure to provide the title compound: LCMS m/z 150.0 $[M+H]^+$.

Step E. 6-(1-methylcyclopropyl)imidazo[1,2-a]pyrazine

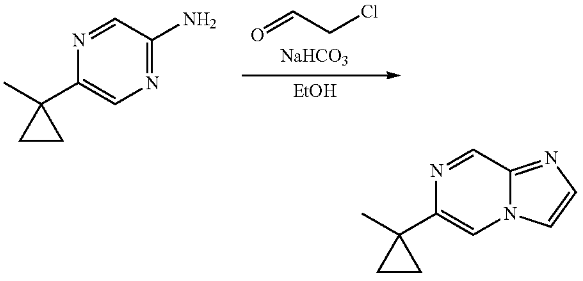

To a solution of 5-(1-methylcyclopropyl)pyrazin-2-amine (1.50 g, 10.1 mmol) and 2-chloroacetaldehyde (19.73 g, 100.5 mmol, 16.17 mL, 40% purity) in ethyl alcohol (15 mL) was added sodium hydrogen carbonate (1.44 g, 17.1 mmol). The resulting mixture was heated at 80° C. for 5 hours, and was then cooled to room temperature, concentrated under reduced pressure, diluted with water (30 mL), and extracted with ethyl acetate (2×20 mL). The organic extracts were combined, washed with saturated aqueous sodium chloride solution (2×10 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 174.1 $[M+H]^+$.

Step F. 3-(6-bromo-2-pyridyl)-6-(1-methylcyclopropyl)imidazo[1,2-a]pyrazine

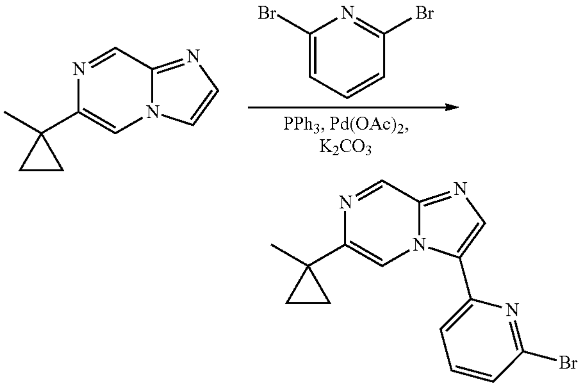

A mixture of 6-(1-methylcyclopropyl)imidazo[1,2-a]pyrazine (0.901 g, 5.20 mmol), 2,6-dibromopyridine (3.69 g, 15.6 mmol), triphenylphosphine (0.136 g, 0.520 mmol), palladium acetate (0.117 g, 0.520 mol) and potassium carbonate (2.15 g, 15.6 mmol) in ethyl alcohol (2 mL) and dioxane (4 mL) was purged with nitrogen, and then heated at 100° C. for 10 hours under nitrogen atmosphere. The reaction mixture was then cooled to room temperature, filtered, and concentrated under reduced pressure. The resulting crude product was purified by flash chromatography on silica gel (0-10% methanol in dichloromethane) to provide the title compound: LCMS m/z 329.1 $[M+H]^+$.

Step G. tert-butyl (3S,4S)-3-fluoro-4-[[6-[6-(1-methylcyclopropyl)imidazo[1,2-a]pyrazin-3-yl]-2-pyridyl]amino]pyrrolidine-1-carboxylate

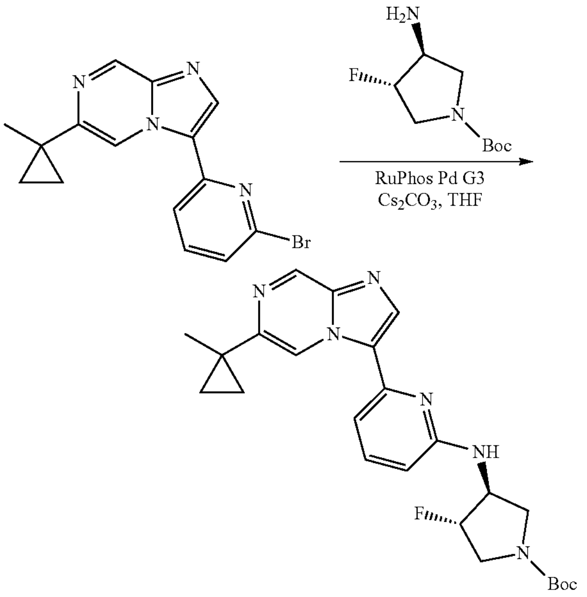

A mixture of 3-(6-bromo-2-pyridyl)-6-(1-methylcyclopropyl)imidazo[1,2-a]pyrazine (0.501 g, 1.52 mmol), tert-butyl (3S,4S)-3-amino-4-fluoro-pyrrolidine-1-carboxylate (0.310 g, 1.52 mmol), cesium carbonate (1.24 g, 3.80 mmol), and (2-dicyclohexylphosphino-2',6'-diisopropoxy-1,1'-biphenyl)[2-(2'-amino-1,1'-biphenyl)]palladium(II)methanesulfonate (0.127 g, 0.152 mmol) in tetrahydrofuran (10 mL) was degassed and purged with nitrogen, and then heated at 80° C. for 5 hours under nitrogen atmosphere. The reaction mixture was then cooled to room temperature, filtered, and concentrated under reduced pressure to provide the title compound: LCMS m/z 453.4 $[M+H]^+$.

Step H. N-[(3S,4S)-4-fluoropyrrolidin-3-yl]-6-[6-(1-methylcyclopropyl)imidazo[1,2-a]pyrazin-3-yl]pyridin-2-amine

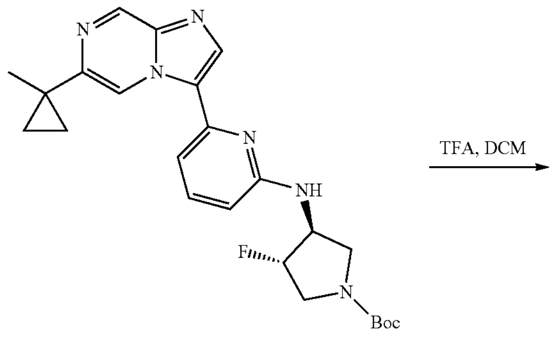

-continued

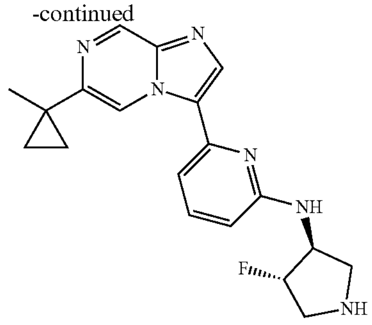

To a solution of tert-butyl (3S,4S)-3-fluoro-4-[[6-[6-(1-methylcyclopropyl)imidazo[1,2-a]pyrazin-3-yl]-2-pyridyl]amino]pyrrolidine-1-carboxylate (0.400 g, 0.884 mmol,) in dichloromethane (15 mL) was added trifluoroacetic acid (2.31 g, 20.3 mmol, 1.50 mL). The resulting mixture was stirred at room temperature for 2 hours, and was then filtered and concentrated under reduced pressure. The resulting crude product was purified by HPLC (Phenomenex Luna $C_{18}$ column, 10 micron, 250×50 mm; 10-40% acetonitrile in water containing 0.1% trifluoroacetic acid) to provide the title compound: LCMS m/z 353.0 $[M+H]^+$; $^1$H NMR (400 MHz, $CD_3OD$) δ 9.61 (d, J=1.3 Hz, 1H), 9.09 (d, J 1.1 Hz, 1H), 8.41 (s, 1H), 7.68 (t, J 7.9 Hz, 1H), 7.34 (d, J=7.4 Hz, 1H), 6.69 (d, J 8.4 Hz, 1H), 5.62-5.37 (m, 1H), 5.01-4.96 (m, 1H), 3.92-3.62 (m, 4H), 1.60 (s, 3H), 1.35-1.20 (m, 2H), 1.00-0.84 (m, 2H).

The compounds in Table 1 were all prepared using the synthetic procedures described in Example 1.

TABLE 1

Additional compounds prepared according to Example 1.

| Compound # | Structure | IUPAC Name | LCMS |
|---|---|---|---|
| 2 | 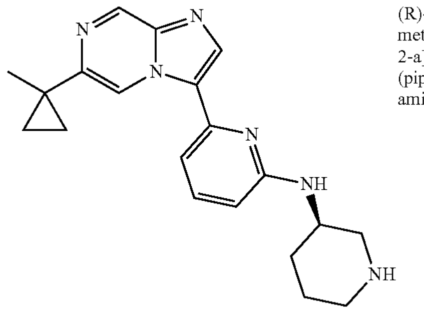 | (R)-6-(6-(1-methylcyclopropyl)imidazo[1,2-a]pyrazin-3-yl)-N-(piperidin-3-yl)pyridin-2-amine | 349.1 |
| 3 | 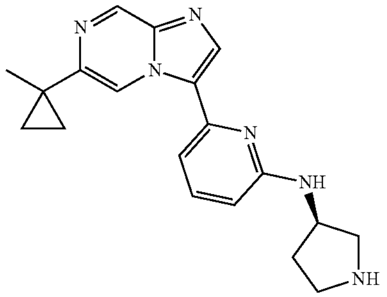 [SMILES: CC1(c2cn3c(-c4cccc(N[C@@H]5CCNC5)n4)cnc3cn2)CC1] | (R)-6-(6-(1-methylcyclopropyl)imidazo[1,2-a]pyrazin-3-yl)-N-(pyrrolidin-3-yl)pyridin-2-amine | 335.1 |

TABLE 1-continued

| Additional compounds prepared according to Example 1. | | | |
|---|---|---|---|
| Compound # | Structure | IUPAC Name | LCMS |
| 4 | 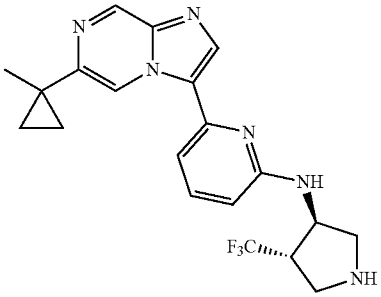 | 6-(6-(1-methylcyclopropyl)imidazo[1,2-a]pyrazin-3-yl)-N-((3R,4S)-4-(trifluoromethyl)pyrrolidin-3-yl)pyridin-2-amine | 403.0 |
| 5 | 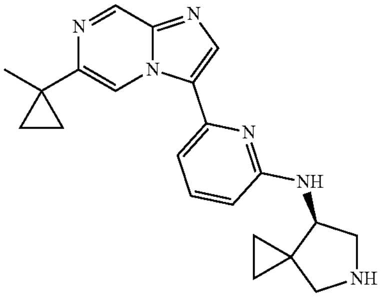 [SMILES: CC1(c2cn3c(-c4cccc(N[C@H]5CNCC56CC6)n4)cnc3cn2)CC1] | (R)-N-(6-(6-(1-methylcyclopropyl)imidazo[1,2-a]pyrazin-3-yl)pyridin-2-yl)-5-azaspiro[2.4]heptan-7-amine | 361.3 |
| 6 | 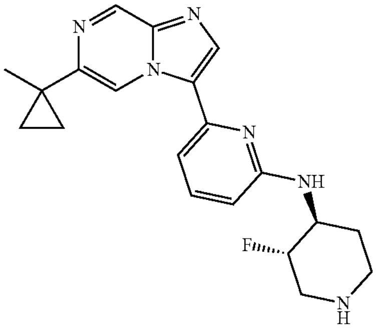 [SMILES: CC1(c2cn3c(-c4cccc(N[C@H]5CCNC[C@@H]5F)n4)cnc3cn2)CC1] | N-((3S,4S)-3-fluoropiperidin-4-yl)-6-(6-(1-methylcyclopropyl)imidazo[1,2-a]pyrazin-3-yl)pyridin-2-amine | 367.2 |
| 7 | 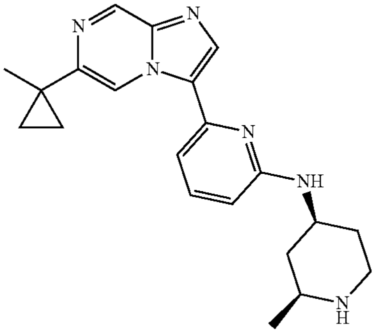 [SMILES: C[C@H]1C[C@@H](Nc2cccc(-c3cnc4cnc(C5(C)CC5)cn34)n2)CCN1] | 6-(6-(1-methylcyclopropyl)imidazo[1,2-a]pyrazin-3-yl)-N-((2S,4S)-2-methylpiperidin-4-yl)pyridin-2-amine | 363.2 |

Example 2

Exemplary Synthetic Procedure #2 (Compounds 8-15)

Compound 8, N-((3S,4S)-4-fluoropyrrolidin-3-yl)-6-(6-(1-(trifluoromethyl)cyclopropyl)imidazo[1,2-a]pyrazin-3-yl)pyridin-2-amine

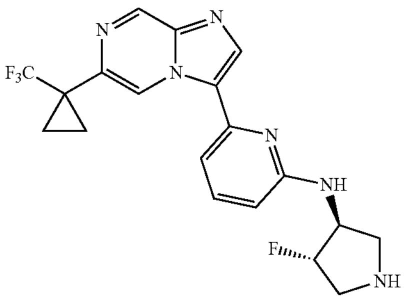

Step A. 6-[1-(trifluoromethyl)vinyl]imidazo[1,2-a]pyrazine

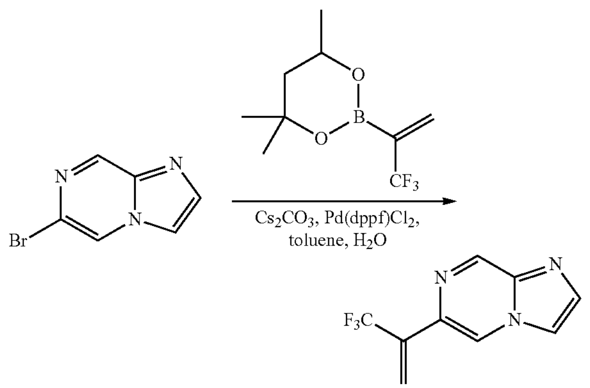

A mixture of 6-bromoimidazo[1,2-a]pyrazine (2.00 g, 10.1 mmol), 4,4,6-trimethyl-2-[1-(trifluoromethyl)vinyl]-1,3,2-dioxaborinane (2.47 g, 11.1 mmol), cesium carbonate (9.87 g, 30.3 mmol), and [1,1-bis(diphenylphosphino)ferrocene]dichloropalladium(II) (0.739 g, 1.01 mmol) in toluene (40 mL) and water (15 mL) was purged with nitrogen, and was then heated at 110° C. for 10 hours under nitrogen atmosphere. The reaction mixture was then cooled to room temperature, diluted with water (20 mL), and extracted with ethyl acetate (3×15 mL). The organic extracts were combined, washed with saturated aqueous sodium chloride solution (20 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 214.1 $[M+H]^+$; $^1H$ NMR (400 MHz, $CDCl_3$) δ 9.04 (s, 1H), 8.20 (s, 1H), 7.78-7.65 (m, 2H), 6.70 (q, J=2.0 Hz, 1H), 6.10 (d, J=0.8 Hz, 1H).

Step B. 6-[1-(trifluoromethyl)cyclopropyl]imidazo[1,2-a]pyrazine

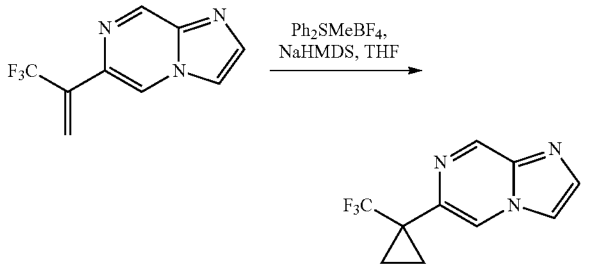

To a cooled 0° C. solution of 6-[1-(trifluoromethyl)vinyl]imidazo[1,2-a]pyrazine (2.00 g, 9.38 mmol) and methyl(diphenyl)sulfonium tetrafluoroborate (2.27 g, 11.3 mmol) in tetrahydrofuran (30 mL) was added a solution of sodium bis(trimethylsilyl)amide in tetrahydrofuran (1 M, 18.77 mL). The resulting mixture was stirred for 10 hours while warming to room temperature. The reaction was then quenched by addition of water (20 mL) and extracted with ethyl acetate (2×20 mL). The organic extracts were combined, washed with saturated aqueous sodium chloride solution (2×10 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 228.1 $[M+H]^+$.

Step C. 3-(6-bromo-2-pyridyl)-6-[1-(trifluoromethyl)cyclopropyl]imidazo[1,2-a]pyrazine

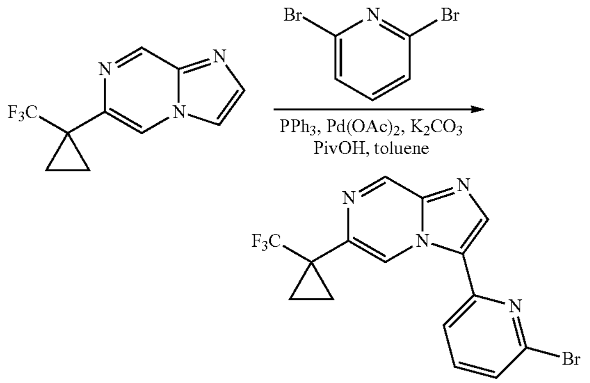

A mixture of 6-[1-(trifluoromethyl)cyclopropyl]imidazo[1,2-a]pyrazine (1.30 g, 5.72 mmol), 2,6-dibromopyridine (4.07 g, 17.2 mmol), triphenylphosphine (0.300 g, 1.14 mmol), palladium acetate (0.128 g, 0.572 mmol), potassium carbonate (2.37 g, 17.2 mmol), and 2,2-dimethylpropanoic acid (0.175 g, 1.72 mmol, 0.197 mL) in toluene (50 mL) was purged with nitrogen, and was then heated at 100° C. for 16 hours under nitrogen atmosphere. The reaction mixture was then cooled to room temperature, filtered, and concentrated under reduced pressure. The resulting crude product was purified by flash chromatography on silica gel (0-100% ethyl acetate in petroleum ether) to provide the title compound: LCMS m/z 383.0 $[M+H]^+$.

Step D. tert-butyl (3S,4S)-3-fluoro-4-[[6-[6-[1-(trifluoromethyl)cyclopropyl]imidazo[1,2-a]pyrazin-3-yl]-2-pyridyl]amino]pyrrolidine-1-carboxylate

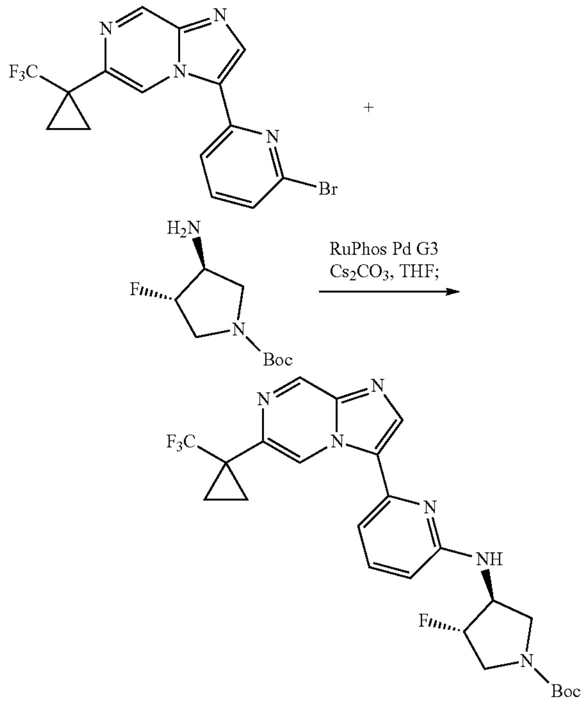

A mixture of 3-(6-bromo-2-pyridyl)-6-[1-(trifluoromethyl)cyclopropyl]imidazo[1,2-a]pyrazine (0.060 g, 0.157 mmol), tert-butyl (3S,4S)-3-amino-4-fluoro-pyrrolidine-1-carboxylate (0.032 g, 0.157 mmol), (2-dicyclohexylphosphino-2',6'-diisopropoxy-1,1'-biphenyl)[2-(2'-amino-1,1'-biphenyl)]palladium(II)methanesulfonate (0.013 g, 0.016 mmol), and cesium carbonate (0.128 g, 0.391 mmol) in tetrahydrofuran (3 mL) was purged with nitrogen, and was then heated at 80° C. for 5 hours under nitrogen atmosphere. The reaction mixture was then cooled to room temperature, filtered, and concentrated under reduced pressure to provide the title compound: LCMS m/z 507.3 $[M+H]^+$ Step E. 5-(tert-butyl)-N,N-bis(4-methoxybenzyl) pyridin-2-amine

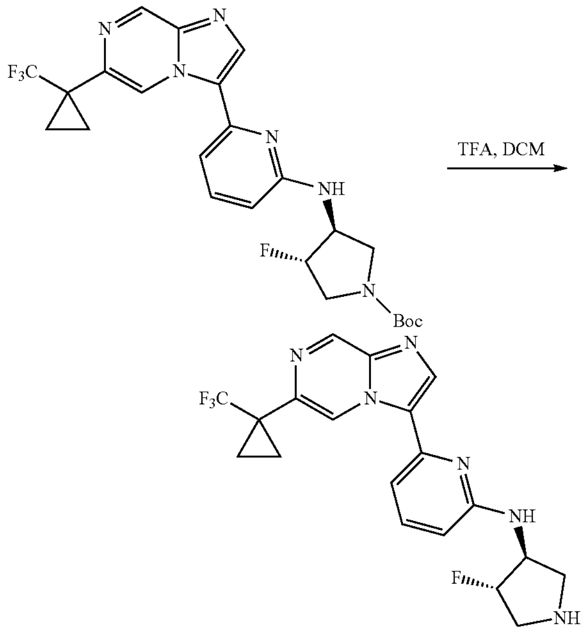

To a solution of tert-butyl (3S,4S)-3-fluoro-4-[[6-[6-[1-(trifluoromethyl)cyclopropyl]imidazo[1,2-a]pyrazin-3-yl]-2-pyridyl]amino]pyrrolidine-1-carboxylate (0.070 g, 0.138 mmol) in dichloromethane (5 mL) was added trifluoroacetic acid (0.770 g, 6.75 mmol, 0.500 mL). The resulting mixture was stirred at room temperature for 3 hours, and was then filtered and concentrated under reduced pressure. The resulting crude product was purified by HPLC (Phenomenex Gemini-NX $C_{18}$ column, 5 micron, 150x30 mm; 10-40% acetonitrile in water containing 0.1% trifluoroacetic acid) to provide the title compound: LCMS m/z 407.0 $[M+H]^+$; $^1H$ NMR (400 MHz, $CD_3OD$) δ 9.87 (s, 1H), 9.07 (s, 1H), 8.40 (s, 1H), 7.67 (t, J 7.9 Hz, 1H), 7.38 (d, J=7.5 Hz, 1H), 6.66 (d, J=8.3 Hz, 1H), 5.63-5.35 (m, 1H), 4.97 (br dd, J=5.5, 12.6 Hz, 1H), 3.92-3.62 (m, 4H), 1.56-1.48 (m, 2H), 1.47-1.38 (m, 2H).

The compounds in Table 2 were all prepared using the synthetic procedures described in Example 2.

TABLE 2

Additional compounds prepared according to Example 2.

| Compound # | Structure | IUPAC Name | LCMS |
|---|---|---|---|
| 9 | 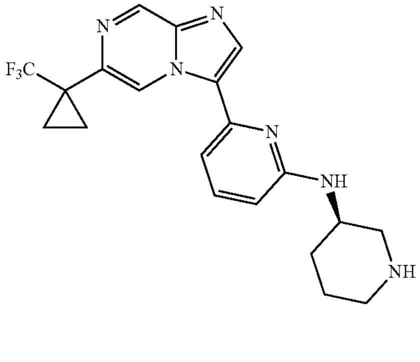 [SMILES: FC(F)(F)C1(c2cn3c(-c4cccc(N[C@@H]5CCCNC5)n4)cnc3cn2)CC1] | (R)-N-(piperidin-3-yl)-6-(6-(1-(trifluoromethyl)cyclopropyl) imidazo[1,2-a]pyrazin-3-yl)pyridin-2-amine | 403.0 |

TABLE 2-continued

| Additional compounds prepared according to Example 2. | | | |
|---|---|---|---|
| Compound # | Structure | IUPAC Name | LCMS |
| 10 | 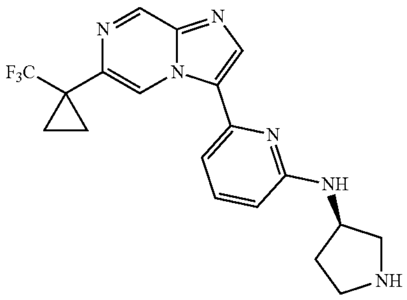 [SMILES: FC(F)(F)C1(c2cn3c(-c4cccc(N[C@@H]5CCNC5)n4)cnc3cn2)CC1] | (R)-N-(pyrrolidin-3-yl)-6-(6-(1-(trifluoromethyl)cyclopropyl) imidazo[1,2-a]pyrazin-3-yl)pyridin-2-amine | 389.1 |
| 11 | 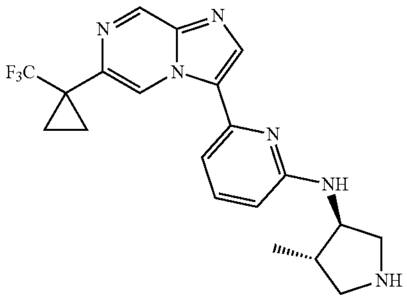 [SMILES: C[C@H]1CNC[C@@H]1Nc1cccc(-c2cnc3cnc(C4(C(F)(F)F)CC4)cn23)n1] | N-((3R,4S)-4-methylpyrrolidin-3-yl)-6-(6-(1-(trifluoromethyl)cyclopropyl) imidazo[1,2-a]pyrazin-3-yl)pyridin-2-amine | 403.1 |
| 12 | 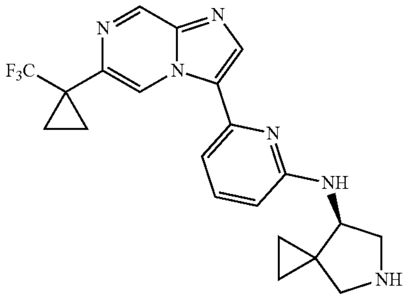 [SMILES: FC(F)(F)C1(c2cn3c(-c4cccc(N[C@H]5CNCC56CC6)n4)cnc3cn2)CC1] | (R)-N-(6-(6-(1-(trifluoromethyl)cyclopropyl) imidazo[1,2-a]pyrazin-3-yl)pyridin-2-yl)-5-azaspiro[2.4]heptan-7-amine | 415.2 |
| 13 | 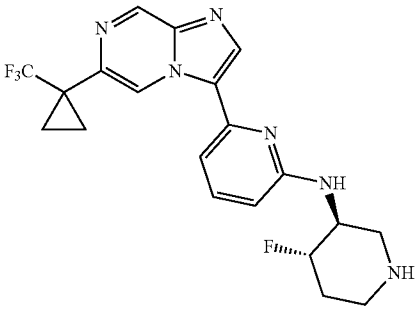 [SMILES: F[C@H]1CCNC[C@@H]1Nc1cccc(-c2cnc3cnc(C4(C(F)(F)F)CC4)cn23)n1] | N-((3S,4S)-4-fluoropiperidin-3-yl)-6-(6-(1-(trifluoromethyl)cyclopropyl) imidazo[1,2-a]pyrazin-3-yl)pyridin-2-amine | 421.0 |
| 14 | 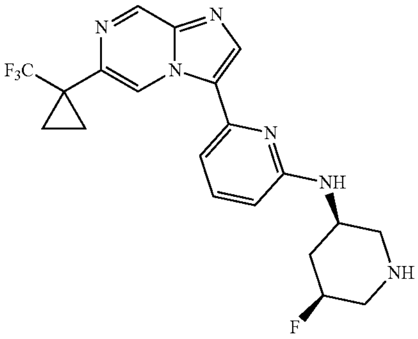 [SMILES: F[C@@H]1CNC[C@H](Nc2cccc(-c3cnc4cnc(C5(C(F)(F)F)CC5)cn34)n2)C1] | N-((3R,5S)-5-fluoropiperidin-3-yl)-6-(6-(1-(trifluoromethyl)cyclopropyl) imidazo[1,2-a]pyrazin-3-yl)pyridin-2-amine | 421.1 |

TABLE 2-continued

Additional compounds prepared according to Example 2.

| Compound # | Structure | IUPAC Name | LCMS |
|---|---|---|---|
| 15 | 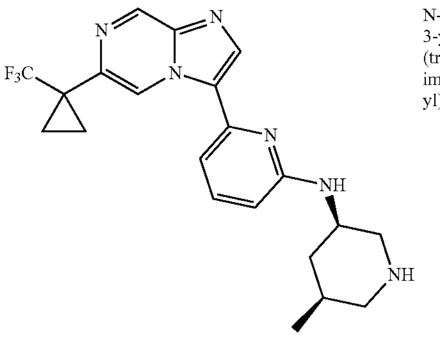 | N-((3R,5S)-5-methylpiperidin-3-yl)-6-(6-(1-(trifluoromethyl)cyclopropyl)imidazo[1,2-a]pyrazin-3-yl)pyridin-2-amine | 417.2 |

Example 3

Exemplary Synthetic Procedure #3 (Compounds 16-26)

Compound 16, 6-(6-(difluoromethyl)imidazo[1,2-a]pyrazin-3-yl)-N-((3S,4S)-4-fluoropyrrolidin-3-yl)pyridin-2-amine

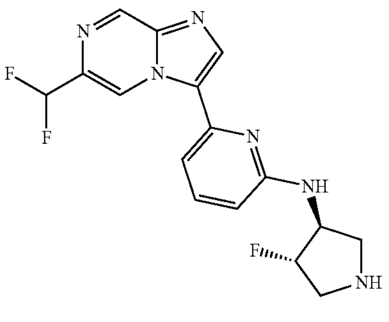 [SMILES: FC(F)c1cn2c(-c3cccc(N[C@H]4CNC[C@@H]4F)n3)cnc2cn1]

Step A. 6-vinylimidazo[1,2-a]pyrazine

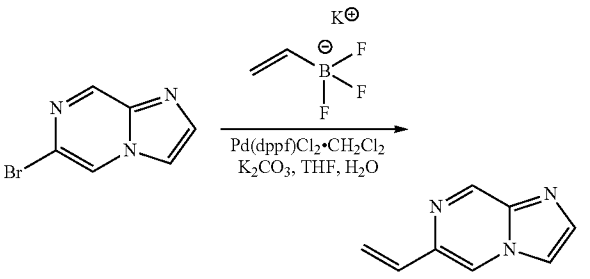

A mixture of 6-bromoimidazo[1,2-a]pyrazine (10.0 g, 50.5 mmol), potassium vinyltrifluoroborate (16.91 g, 126.3 mmol), [1,1-bis(diphenylphosphino)ferrocene]palladium(II) chloride dichloromethane complex (4.12 g, 5.05 mmol), and aqueous potassium carbonate solution (1.0 M, 152 mL, 152 mmol) in tetrahydrofuran (150 mL) was purged with nitrogen, and was then heated at 80° C. for 15 hours under nitrogen atmosphere. The reaction mixture was then cooled to room temperature, diluted with water (100 mL), and extracted with ethyl acetate (2×150 mL). The organic extracts were combined, washed with saturated aqueous sodium chloride solution (2×75 mL), dried over anhydrous sodium sulfate, filtered, and concentrated under reduced pressure. The resulting crude product was purified by flash chromatography on silica gel (0-10% methanol in dichloromethane) to provide the title compound: LCMS m/z 146.1 $[M+H]^+$; $^1$H NMR (400 MHz, $CDCl_3$) δ 9.21-8.78 (m, 1H), 7.95 (s, 1H), 7.73 (s, 1H), 7.62 (s, 1H), 6.66 (dd, J=10.6, 17.0 Hz, 1H), 6.27 (d, J=16.9 Hz, 1H), 5.43 (d, J=10.7 Hz, 1H).

Step B. imidazo[1,2-a]pyrazine-6-carbaldehyde

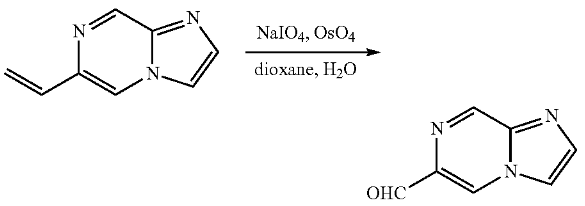

To a solution of 6-vinylimidazo[1,2-a]pyrazine (6.00 g, 41.3 mmol) in 1,4-dioxane (300 mL) and water (150 mL) were added sodium periodate (13.26 g, 62.00 mmol), 2,6-dimethylpyridine (8.86 g, 82.7 mmol), and osmium tetroxide (1.05 g, 4.13 mmol). The resulting reaction mixture was stirred at room temperature for 10 hours, and was then quenched by addition of saturated aqueous sodium sulfite solution (150 mL) and extracted with ethyl acetate (3×100 mL). The organic extracts were combined, washed with saturated aqueous sodium chloride solution (2×50 mL), dried over anhydrous sodium sulfate, filtered, and concentrated under reduced pressure. The resulting crude product was purified by flash chromatography on silica gel (0-100% ethyl acetate in petroleum ether) to provide the title compound: $^1$H NMR (400 MHz, $CDCl_3$) δ 10.21-9.98 (m, 1H), 9.16 (s, 1H), 8.81 (d, J=1.5 Hz, 1H), 8.02-7.77 (m, 2H).

Step C. 6-(difluoro methyl)imidazo[1,2-a]pyrazine

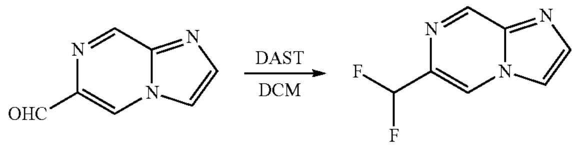

To a cooled 0° C. solution of imidazo[1,2-a]pyrazine-6-carbaldehyde (2.00 g, 13.6 mmol) in dichloromethane (60 mL) was added diethylaminosulfur trifluoride (4.38 g, 27.2 mmol, 3.59 mL). The resulting reaction mixture was stirred at room temperature for 10 hours, and was then filtered and concentrated under reduced pressure. The crude product thus obtained was purified by flash chromatography on silica gel (0-100% ethyl acetate in petroleum ether) to provide the title compound: LCMS m/z 170.2 $[M+H]^+$.

Step D. 3-(6-bromo-2-pyridyl)-6-(difluoromethyl) imidazo[1,2-a]pyrazine

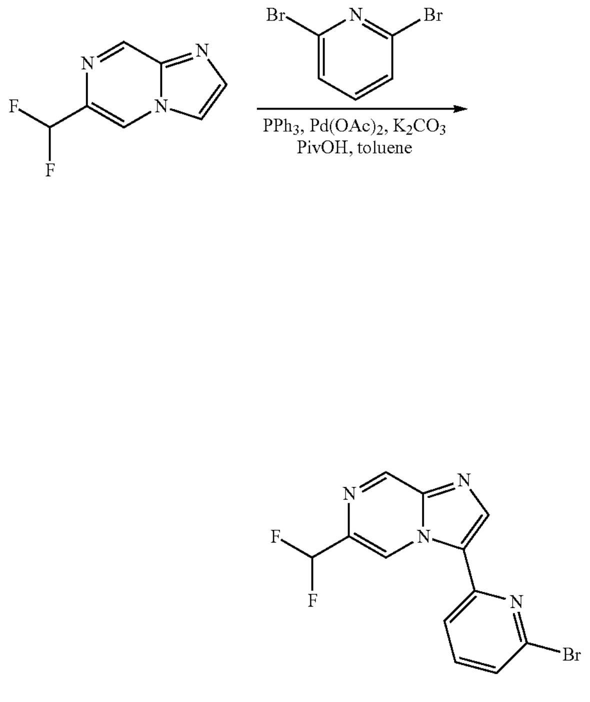

A mixture of 6-(difluoromethyl)imidazo[1,2-a]pyrazine (1.00 g, 5.91 mmol), 2,6-dibromopyridine (4.20 g, 17.7 mmol), triphenylphosphine (0.310 g, 1.18 mmol), palladium acetate (0.133 g, 0.591 mmol), potassium carbonate (2.45 g, 17.7 mmol), and 2,2-dimethylpropanoic acid (0.181 g, 1.77 mmol) in toluene (40 mL) was purged with nitrogen, and was then heated at 100° C. for 10 hours under nitrogen atmosphere. The reaction mixture was then cooled to room temperature, filtered, and concentrated under reduced pressure. The resulting crude product was purified by flash chromatography on silica gel (0-100% ethyl acetate in petroleum ether) to provide the title compound.

Step E. 5-(tert-butyl)-N,N-bis(4-methoxybenzyl) pyridin-2-amine

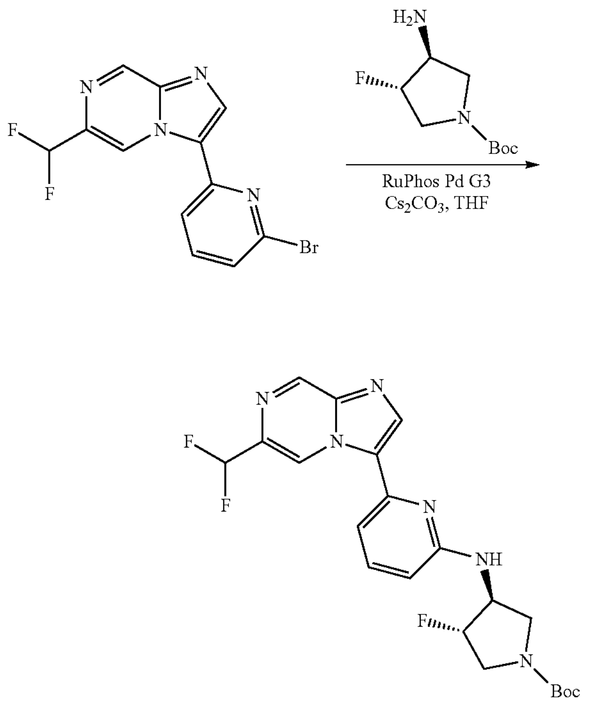

A mixture of 3-(6-bromo-2-pyridyl)-6-(difluoromethyl) imidazo[1,2-a]pyrazine (0.070 g, 0.215 mmol), tert-butyl (3S,4S)-3-amino-4-fluoro-pyrrolidine-1-carboxylate (0.044 g, 0.215 mmol), cesium carbonate (0.175 g, 0.538 mmol), and (2-dicyclohexylphosphino-2',6'-diisopropoxy-1,1'-biphenyl)[2-(2'-amino-1,1'-biphenyl)]palladium(II)methanesulfonate (0.018 g, 0.022 mmol) in tetrahydrofuran (5 mL) was degassed and purged with nitrogen, and was then heated at 80° C. for 5 hours under nitrogen atmosphere. The reaction mixture was then cooled to room temperature, filtered, and concentrated under reduced pressure to give the title compound: LCMS m/z 449.2 $[M+H]^+$.

Step F. 6-[6-(difluoromethyl)imidazo[1,2-a]pyrazin-3-yl]-N-[(3S,4S)-4-fluoropyrrolidin-3-yl]pyridin-2-amine

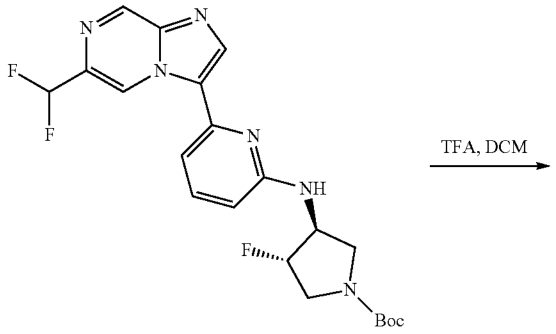

-continued

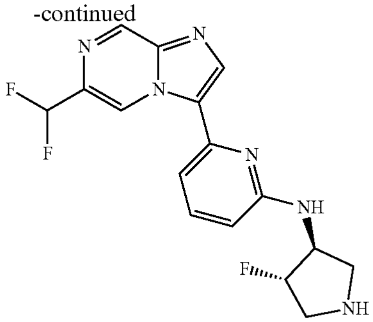

To a solution of tert-butyl (3S,4S)-3-[[6-[6-(difluoromethyl)imidazo[1,2-a]pyrazin-3-yl]-2-pyridyl]amino]-4-fluoro-pyrrolidine-1-carboxylate (0.100 g, 0.223 mmol) in dichloromethane (3 mL) was added trifluoroacetic acid (0.770 g, 6.75 mmol, 0.500 mL). The resulting reaction mixture was stirred at room temperature for 3 hours, and was then filtered and concentrated under reduced pressure. The crude product thus obtained was purified by HPLC (Phenomenex Gemini-NX $C_{18}$ column, 5 micron, 150x30 mm; 5-35% acetonitrile in water containing 0.1% trifluoroacetic acid) to provide the title compound: LCMS m/z 349.0 $[M+H]^+$; $^1H$ NMR (400 MHz, $CD_3OD$) δ 10.10 (d, J=1.1 Hz, 1H), 9.13 (s, 1H), 8.45 (s, 1H), 7.71-7.51 (m, 1H), 7.40 (d, J=7.5 Hz, 1H), 7.10-6.72 (m, 1H), 6.64 (d, J=8.2 Hz, 1H), 5.63-5.41 (m, 1H), 4.95-4.88 (m, 1H), 3.89 (dd, J=6.1, 12.2 Hz, 1H), 3.79-3.73 (m, 1H), 3.72-3.60 (m, 2H).

The compounds in Table 3 were all prepared using the synthetic procedures described in Example 3.

TABLE 3

Additional compounds prepared according to Example 3.

| Compound # | Structure | IUPAC Name | LCMS |
|---|---|---|---|
| 17 | 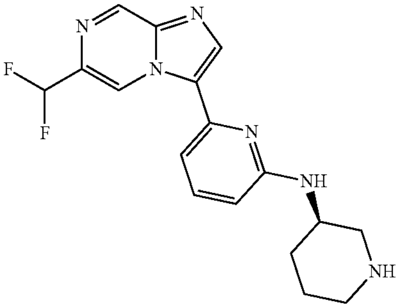 [SMILES: FC(F)c1cn2c(-c3cccc(N[C@@H]4CCCNC4)n3)cnc2cn1] | (R)-6-(6-(difluoromethyl)imidazo[1,2-a]pyrazin-3-yl)-N-(piperidin-3-yl)pyridin-2-amine | 345.1 |
| 18 | 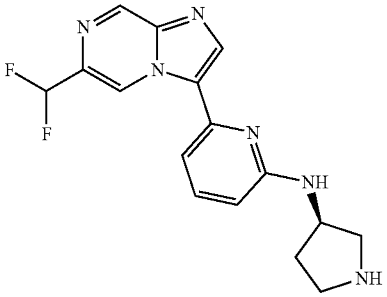 [SMILES: FC(F)c1cn2c(-c3cccc(N[C@@H]4CCNC4)n3)cnc2cn1] | (R)-6-(6-(difluoromethyl)imidazo[1,2-a]pyrazin-3-yl)-N-(pyrrolidin-3-yl)pyridin-2-amine | 331.1 |
| 19 | 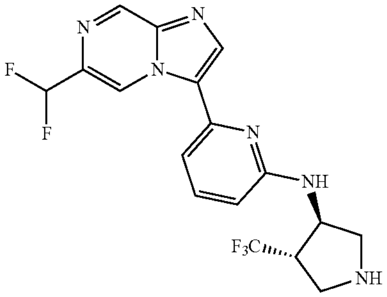 [SMILES: FC(F)c1cn2c(-c3cccc(N[C@H]4CNC[C@@H]4C(F)(F)F)n3)cnc2cn1] | 6-(6-(difluoromethyl)imidazo[1,2-a]pyrazin-3-yl)-N-((3R,4S)-4-(trifluoromethyl)pyrrolidin-3-yl)pyridin-2-amine | 399.0 |

TABLE 3-continued

| Additional compounds prepared according to Example 3. | | | |
|---|---|---|---|
| Compound # | Structure | IUPAC Name | LCMS |
| 20 | 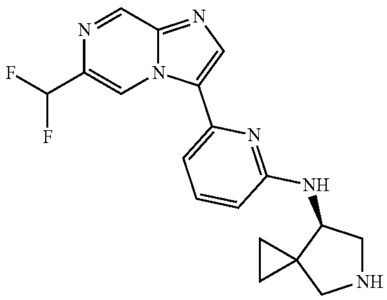 [SMILES: FC(F)c1cn2c(-c3cccc(N[C@H]4CNCC45CC5)n3)cnc2cn1] | (R)-N-(6-(6-(difluoromethyl)imidazo[1,2-a]pyrazin-3-yl)pyridin-2-yl)-5-azaspiro[2.4]heptan-7-amine | 357.1 |
| 21 | 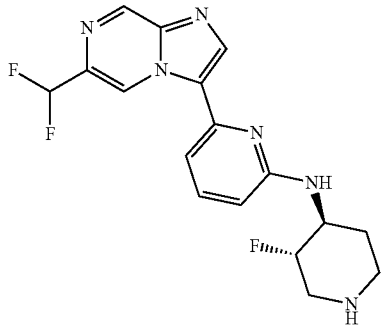 [SMILES: FC(F)c1cn2c(-c3cccc(N[C@H]4CCNC[C@@H]4F)n3)cnc2cn1] | 6-(6-(difluoromethyl)imidazo[1,2-a]pyrazin-3-yl)-N-((3S,4S)-3-fluoropiperidin-4-yl)pyridin-2-amine | 363.2 |
| 22 | 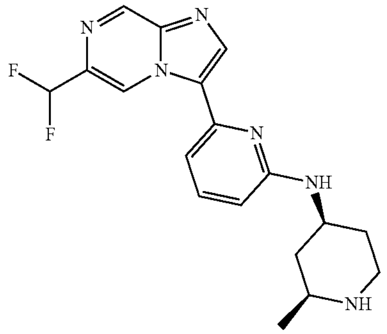 [SMILES: C[C@H]1C[C@@H](Nc2cccc(-c3cnc4cnc(C(F)F)cn34)n2)CCN1] | 6-(6-(difluoromethyl)imidazo[1,2-a]pyrazin-3-yl)-N-((2S,4S)-2-methylpiperidin-4-yl)pyridin-2-amine | 359.1 |
| 23 | 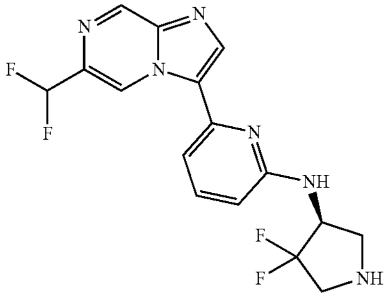 [SMILES: FC(F)c1cn2c(-c3cccc(N[C@H]4CNCC4(F)F)n3)cnc2cn1] | 6-(6-(difluoromethyl)imidazo[1,2-a]pyrazin-3-yl)-N-(4,4-difluoropyrrolidin-3-yl)pyridin-2-amine | 367.0 |

TABLE 3-continued

Additional compounds prepared according to Example 3.

| Compound # | Structure | IUPAC Name | LCMS |
| --- | --- | --- | --- |
| 24 | 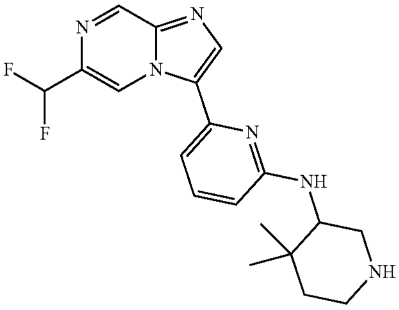 [SMILES: CC1(C)CCNCC1Nc1cccc(-c2cnc3cnc(C(F)F)cn23)n1] | 6-(6-(difluoromethyl)imidazo[1,2-a]pyrazin-3-yl)-N-(4,4-dimethylpiperidin-3-yl)pyridin-2-amine | 373.1 |
| 25 | 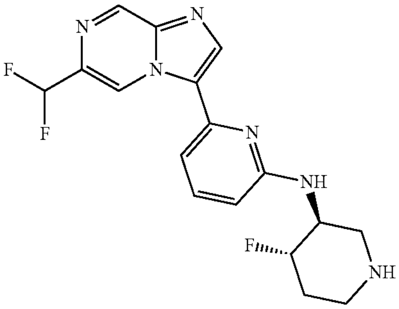 [SMILES: FC(F)c1cn2c(-c3cccc(N[C@H]4CNCC[C@@H]4F)n3)cnc2cn1] | 6-(6-(difluoromethyl)imidazo[1,2-a]pyrazin-3-yl)-N-((3S,4S)-4-fluoropiperidin-3-yl)pyridin-2-amine | 363.0 |
| 26 | 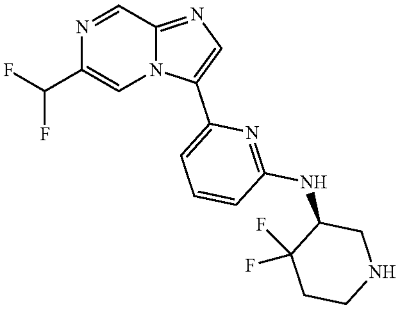 [SMILES: FC(F)c1cn2c(-c3cccc(N[C@H]4CNCCC4(F)F)n3)cnc2cn1] | (S)-6-(6-(difluoromethyl)imidazo[1,2-a]pyrazin-3-yl)-N-(4,4-difluoropiperidin-3-yl)pyridin-2-amine | 381.1 |

Example 4

Exemplary Synthetic Procedure #4 (Compounds 27-35)

Compound 27, (R)-2-(3-(6-(pyrrolidin-3-ylamino)pyridin-2-yl)imidazo[1,2-a]pyrazin-6-yl)propan-2-ol

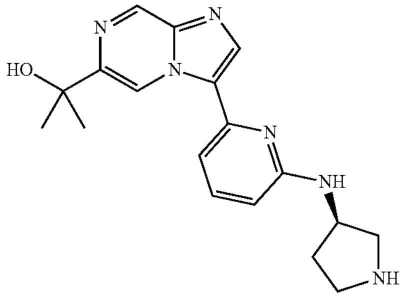 [SMILES: CC(C)(O)c1cn2c(-c3cccc(N[C@@H]4CCNC4)n3)cnc2cn1]

Step A. 1-imidazo[1,2-a]pyrazin-6-ylethanone

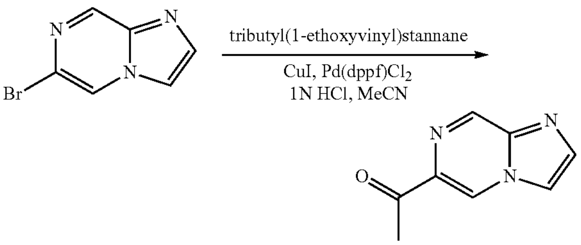

A mixture of 6-bromoimidazo[1,2-a]pyrazine (5.00 g, 25.3 mmol), tributyl(1-ethoxyvinyl)stannane (13.68 g, 37.87 mmol, 12.78 mL), [1,1-bis(diphenylphosphino)ferrocene] dichloropalladium(II) (1.85 g, 2.52 mmol), and copper iodide (0.721 g, 3.79 mmol) in acetonitrile (100 mL) was purged with nitrogen, and was then heated at 80° C. for 5 hours under nitrogen atmosphere. The reaction was then cooled to room temperature. Hydrochloric acid (1.0 M, 25.25 mL) was added, and the reaction was then stirred at room temperature for 2 hours. Saturated aqueous potassium fluoride solution (30 mL) was added, giving a mixture that was then cooled to 0° C., basified to pH=8-9 by addition of saturated aqueous sodium hydroxide solution, and extracted with ethyl acetate (3×50 mL). The organic extracts were combined, washed with saturated aqueous sodium chloride solution (2×40 mL), dried over anhydrous sodium sulfate, filtered, and concentrated under reduced pressure. The resulting crude product was purified by flash chromatography on silica gel (0-100% ethyl acetate) to provide the title compound: $^1$H NMR (400 MHz, $CDCl_3$) δ 9.15 (br s, 1H), 8.94 (br s, 1H), 8.03-7.81 (m, 2H), 2.79 (s, 3H).

Step B. 5-isopropenyl-N,N-bis[(4-methoxyphenyl) methyl]pyrazin-2-amine

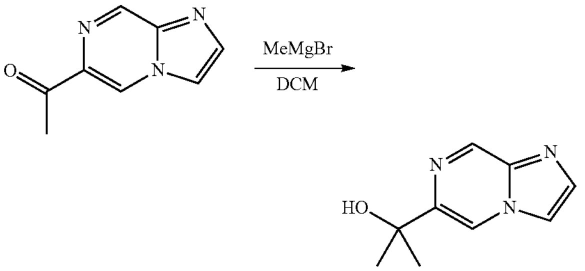

To a cooled 0° C. solution of 1-imidazo[1,2-a]pyrazin-6-ylethanone (0.901 g, 5.58 mmol) in dichloromethane (20 mL) was added a solution of methylmagnesium bromide in diethyl ether (3 M, 9.31 mL). The resulting reaction mixture was stirred at 0° C. for 1 hour, and was then quenched by addition of water (10 mL) and extracted with dichloromethane (3×10 mL). The organic extracts were combined, washed with saturated aqueous sodium chloride solution (10 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 178.2 $[M+H]^+$.

Step C. 2-(6-(bis(4-methoxybenzyl)amino)pyridin-3-yl)-2-methylpropan-1-ol

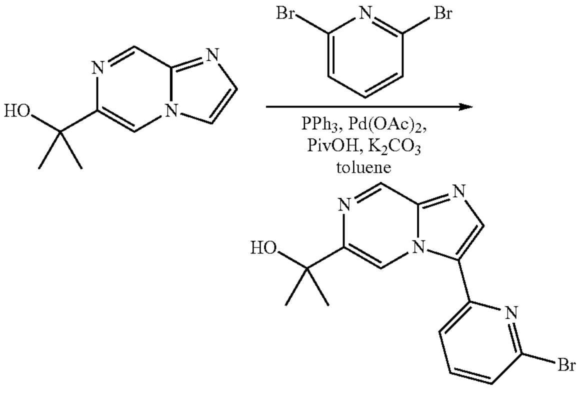

A mixture of 2-imidazo[1,2-a]pyrazin-6-ylpropan-2-ol (0.300 g, 1.69 mmol), 2,6-dibromopyridine (1.20 g, 5.08 mmol), triphenylphosphine (0.089 g, 0.339 mmol), palladium acetate (0.038 g, 0.169 mmol), potassium carbonate (0.702 g, 5.08 mmol), and 2,2-dimethylpropanoic acid (0.052 g, 0.508 mmol) in toluene (5 mL) was purged with nitrogen, and was then heated at 100° C. for 10 hours under nitrogen atmosphere. The reaction mixture was then cooled to room temperature, filtered, and concentrated under reduced pressure. The resulting crude product was purified by flash chromatography on silica gel (0-50% ethyl acetate in petroleum ether) to provide the title compound: LCMS m/z 333.2 $[M+H]^+$.

Step D. tert-butyl (3R)-3-[[6-[6-(1-hydroxy-1-methyl-ethyl)imidazo[1,2-a]pyrazin-3-yl]-2-pyridyl] amino]pyrrolidine-1-carboxylate

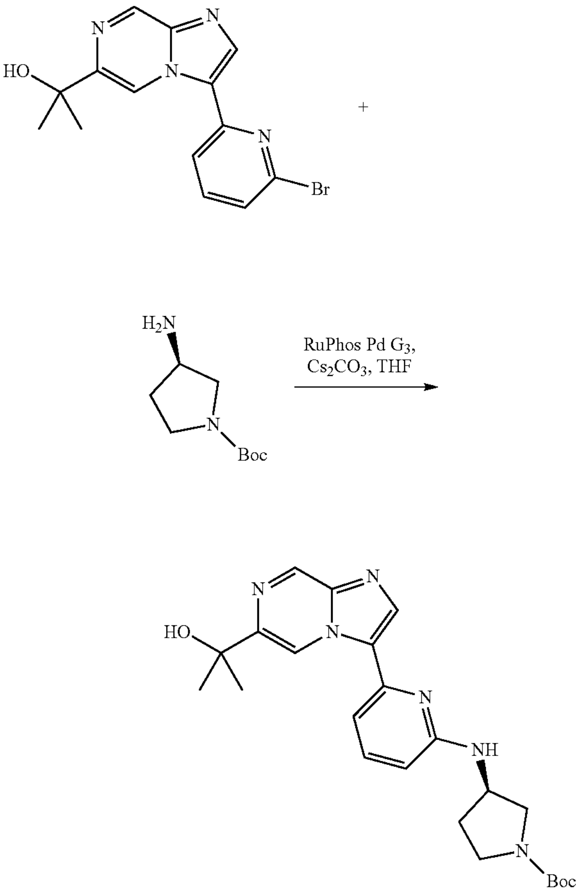

A mixture of 2-[3-(6-bromo-2-pyridyl)imidazo[1,2-a] pyrazin-6-yl]propan-2-ol (0.030 g, 0.090 mmol), tert-butyl (3R)-3-aminopyrrolidine-1-carboxylate (0.017 g, 0.090 mmol), (2-dicyclohexylphosphino-2',6'-diisopropoxy-1,1'-biphenyl)[2-(2'-amino-1,1'-biphenyl)]palladium(II)methanesulfonate (0.008 g, 0.009 mmol), and cesium carbonate (0.073 g, 0.225 mmol) in tetrahydrofuran (3 mL) was purged with nitrogen, and was then heated at 80° C. for 3 hours under nitrogen atmosphere. The reaction mixture was then cooled to room temperature, filtered, and concentrated under reduced pressure to g provide the title compound: LCMS m/z 439.2 $[M+H]^+$.

Step E. 2-[3-[6-[[(3R)-pyrrolidin-3-yl]amino]-2-pyridyl]imidazo[1,2-a]pyrazin-6-yl]propan-2-ol

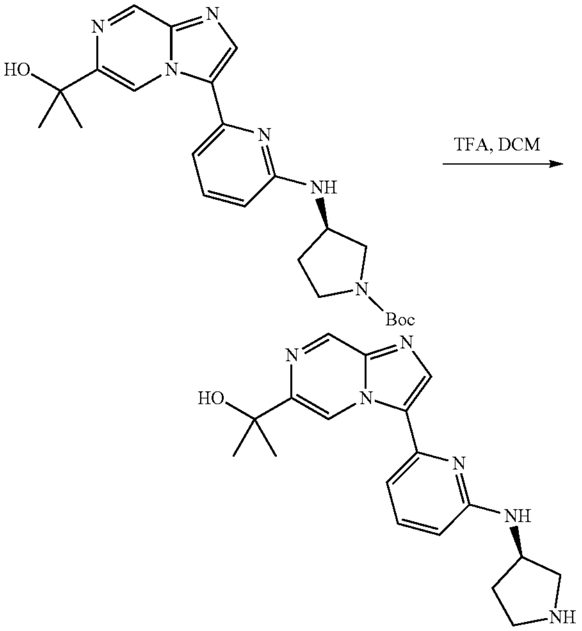

To a solution of tert-butyl (3R)-3-[[6-[6-(1-hydroxy-1-methyl-ethyl)imidazo[1,2-a]pyrazin-3-yl]-2-pyridyl]amino] pyrrolidine-1-carboxylate (0.030 g, 0.068 mmol) in dichloromethane (3 mL) was added trifluoroacetic acid (0.770 g, 6.75 mmol, 0.500 mL). The resulting reaction mixture was stirred at room temperature for 2 hours, and was then filtered and concentrated under reduced pressure. The crude product thus obtained was purified by HPLC (Phenomenex Luna $C_{18}$ column, 3 micron, 75x30 mm; 6-36% acetonitrile in water containing 0.1% trifluoroacetic acid) to provide the title compound: LCMS m/z 339.1 $[M+H]^+$; $^1H$ NMR (400 MHz, $CD_3OD$) δ 10.20 (d, J=1.3 Hz, 1H), 9.06 (d, J=1.3 Hz, 1H), 8.40 (s, 1H), 7.59 (dd, J=7.6, 8.3 Hz, 1H), 7.30 (d, J=7.5 Hz, 1H), 6.58 (d, J=8.2 Hz, 1H), 4.96-4.88 (m, 1H), 3.81 (dd, J=5.8, 12.0 Hz, 1H), 3.61-3.44 (m, 2H), 3.36 (dd, J=4.2, 11.9 Hz, 1H), 2.56-2.44 (m, 1H), 2.22-2.12 (m, 1H), 1.65 (d, J=9.0 Hz, 6H).

The compounds in Table 4 were all prepared using the synthetic procedures described in Example 4.

TABLE 4

Additional compounds prepared according to Example 4.

| Compound # | Structure | IUPAC Name | LCMS |
|---|---|---|---|
| 28 | 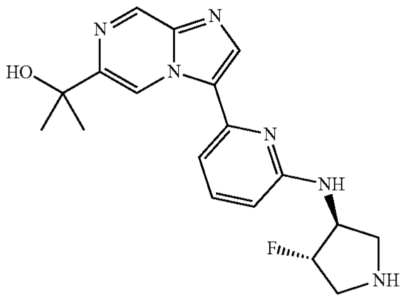 | 2-(3-(6-(((3S,4S)-4-fluoropyrrolidin-3-yl)amino)pyridin-2-yl)imidazo[1,2-a]pyrazin-6-yl)propan-2-ol | 357.0 |
| 29 | 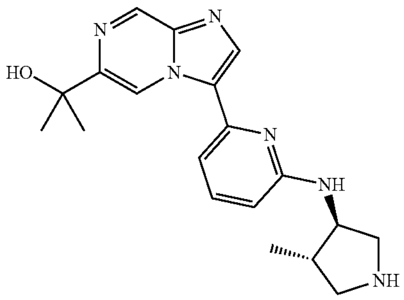 [SMILES: C[C@H]1CNC[C@@H]1Nc1cccc(-c2cnc3cnc(C(C)(C)O)cn23)n1] | 2-(3-(6-(((3R,4S)-4-methylpyrrolidin-3-yl)amino)pyridin-2-yl)imidazo[1,2-a]pyrazin-6-yl)propan-2-ol | 353.1 |

TABLE 4-continued

| Additional compounds prepared according to Example 4. | | | |
|---|---|---|---|
| Compound # | Structure | IUPAC Name | LCMS |
| 30 | 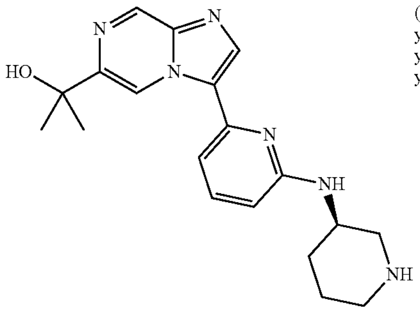 | (R)-2-(3-(6-(piperidin-3-ylamino)pyridin-2-yl)imidazo[1,2-a]pyrazin-6-yl)propan-2-ol | 353.1 |
| 31 | 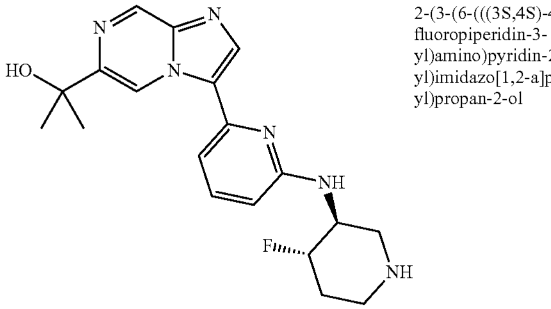 | 2-(3-(6-(((3S,4S)-4-fluoropiperidin-3-yl)amino)pyridin-2-yl)imidazo[1,2-a]pyrazin-6-yl)propan-2-ol | 371.0 |
| 32 | 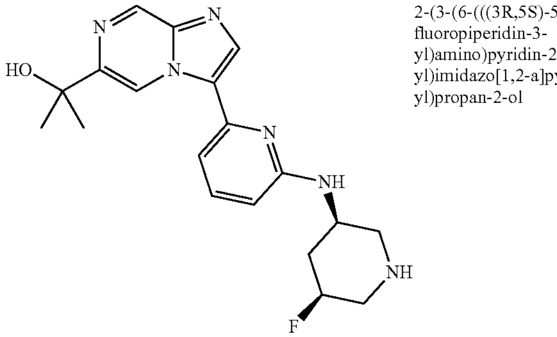 | 2-(3-(6-(((3R,5S)-5-fluoropiperidin-3-yl)amino)pyridin-2-yl)imidazo[1,2-a]pyrazin-6-yl)propan-2-ol | 371.0 |
| 33 | 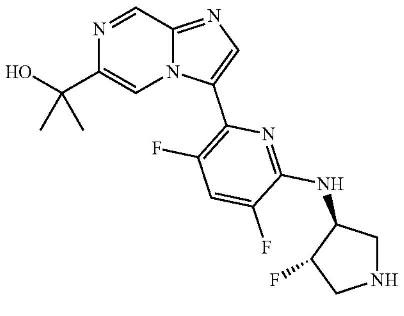 [SMILES: CC(C)(O)c1cn2c(-c3nc(N[C@H]4CNC[C@@H]4F)c(F)cc3F)cnc2cn1] | 2-(3-(3,5-difluoro-6-(((3S,4S)-4-fluoropyrrolidin-3-yl)amino)pyridin-2-yl)imidazo[1,2-a]pyrazin-6-yl)propan-2-ol | 393.3 |

TABLE 4-continued

Additional compounds prepared according to Example 4.

| Compound # | Structure | IUPAC Name | LCMS |
| --- | --- | --- | --- |
| 34 | 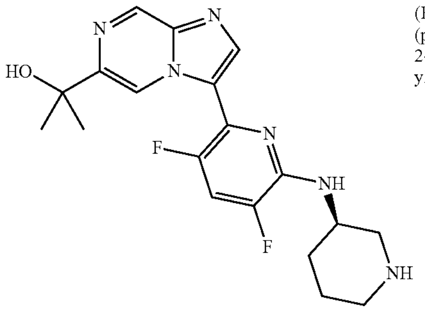 | (R)-2-(3-(3,5-difluoro-6-(piperidin-3-ylamino)pyridin-2-yl)imidazo[1,2-a]pyrazin-6-yl)propan-2-ol | 389.1 |
| 35 | 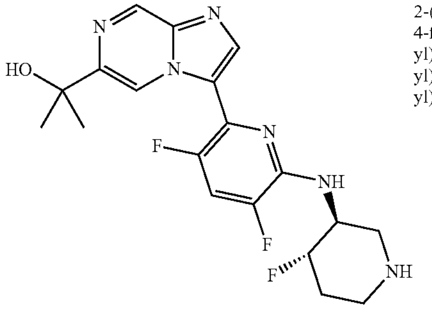 | 2-(3-(3,5-difluoro-6-(((3S,4S)-4-fluoropiperidin-3-yl)amino)pyridin-2-yl)imidazo[1,2-a]pyrazin-6-yl)propan-2-ol | 407.1 |

Example 5

Exemplary Synthetic Procedure #5 (Compounds 36-42)

Compound 36, N-((3S,4S)-4-fluoropyrrolidin-3-yl)-6-(6-(2,2,2-trifluoroethoxy)imidazo[1,2-a]pyrazin-3-yl)pyridin-2-amine

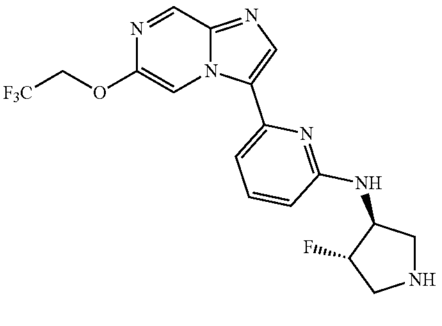 [SMILES: F[C@H]1CNC[C@@H]1Nc1cccc(-c2cnc3cnc(OCC(F)(F)F)cn23)n1]

Step A. 6-(2,2,2-trifluoroethoxy)imidazo[1,2-a]pyrazine

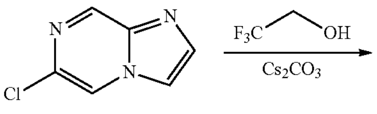

-continued

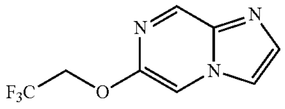

A mixture of 6-chloroimidazo[1,2-a]pyrazine (1.60 g, 10.4 mmol) and cesium carbonate (16.97 g, 52.09 mmol) in 2,2,2-trifluoroethanol (15 mL) was stirred at 100° C. for 16 hours. The reaction mixture was then cooled to room temperature, diluted with water (30 mL), and extracted with ethyl acetate (3×20 mL). The organic extracts were combined, washed with saturated aqueous sodium chloride solution (15 mL), dried over anhydrous sodium sulfate, filtered, and concentrated under reduced pressure. The resulting crude product was purified by flash chromatography on silica gel (0-20% ethyl acetate in petroleum ether) to provide the title compound: $^1H$ NMR (400 MHz, DMSO-d6) δ 8.90 (s, 1H), 8.46 (s, 1H), 8.12 (s, 1H), 7.87 (s, 1H), 4.99 (q, J=9.0 Hz, 2H).

Step B. 3-(6-bromopyridin-2-yl)-6-(2,2,2-trifluoroethoxy)imidazo[1,2-a]pyrazine

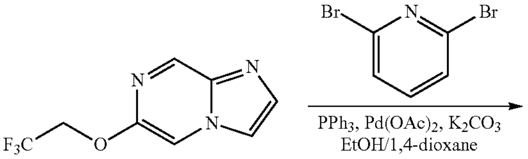

-continued

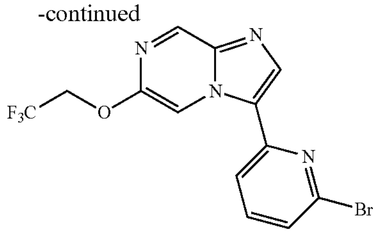

A mixture of 6-(2,2,2-trifluoroethoxy)imidazo[1,2-a]pyrazine (1.00 g, 4.61 mmol), 2,6-dibromopyridine (3.27 g, 13.8 mmol), triphenylphosphine (0.121 g, 0.461 mmol), potassium carbonate (1.91 g, 13.8 mmol), and palladium acetate (0.103 g, 0.461 mmol) in 1,4-dioxane (10 mL) and ethyl alcohol (5 mL) was purged with nitrogen, and was then heated at 100° C. for 16 hours under nitrogen atmosphere. The reaction mixture was then cooled to room temperature and concentrated under reduced pressure. The resulting crude product was purified by flash chromatography on silica gel (0-20% ethyl acetate in petroleum ether) to provide the title compound:

Step C. tert-butyl (3S,4S)-3-fluoro-4-[[6-[6-(2,2,2-trifluoroethoxy)imidazo[1,2-a]pyrazin-3-yl]-2-pyridyl]amino]pyrrolidine-1-carboxylate

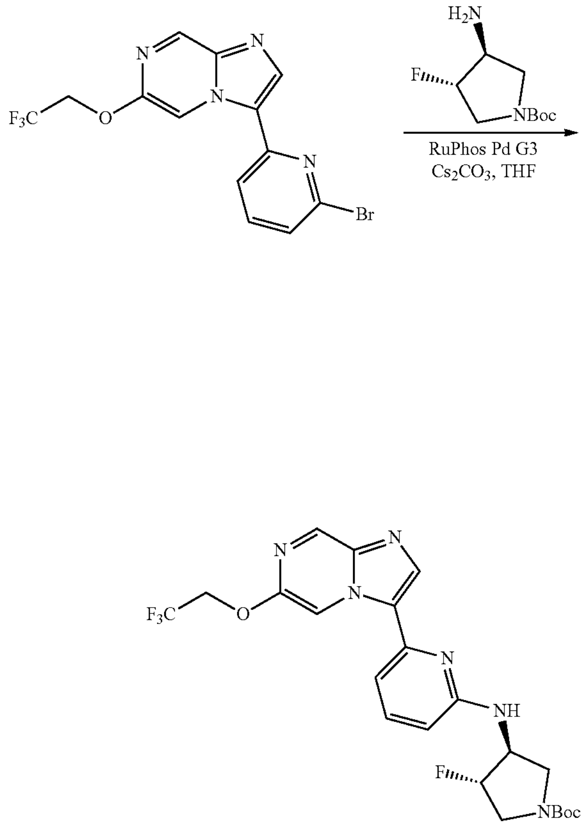

A mixture of 3-(6-bromo-2-pyridyl)-6-(2,2,2-trifluoroethoxy)imidazo[1,2-a]pyrazine (0.060 g, 0.161 mmol), tert-butyl (3S,4S)-3-amino-4-fluoro-pyrrolidine-1-carboxylate (0.036 g, 0.177 mmol), cesium carbonate (0.131 g, 0.402 mmol), and (2-dicyclohexylphosphino-2',6'-diisopropoxy-1,1'-biphenyl)[2-(2'-amino-1,1'-biphenyl)]palladium(II)methanesulfonate (0.013 g, 0.016 mmol) in tetrahydrofuran (1 mL) was heated at 80° C. for 10 hours. The reaction mixture was then cooled to room temperature and concentrated under reduced pressure to provide the title compound: LCMS m/z 497.2 $[M+H]^+$.

Step D. N-[(3S,4S)-4-fluoropyrrolidin-3-yl]-6-[6-(2,2,2-trifluoroethoxy)imidazo[1,2-a]pyrazin-3-yl]pyridin-2-amine

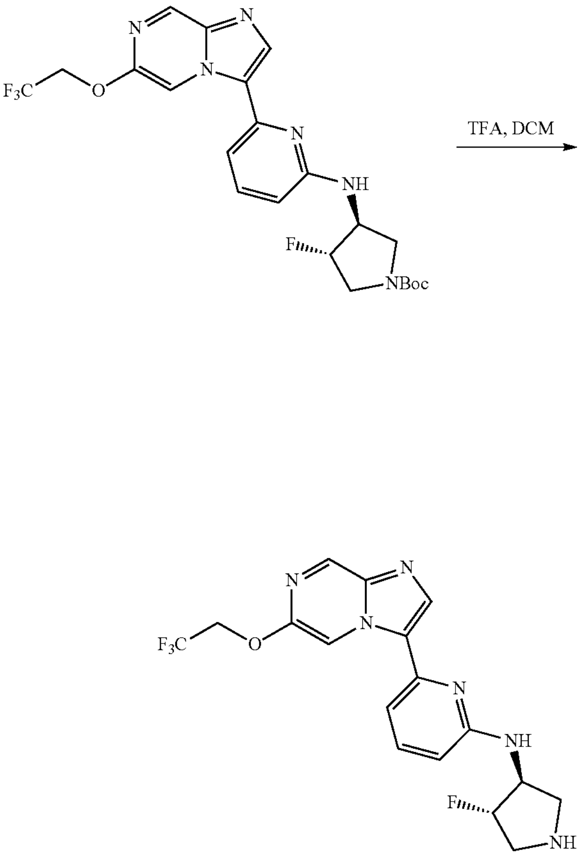

To a solution of tert-butyl (3S,4S)-3-fluoro-4-[[6-[6-(2,2,2-trifluoroethoxy)imidazo[1,2-a]pyrazin-3-yl]-2-pyridyl]amino]pyrrolidine-1-carboxylate (0.050 mg, 0.101 mmol) in dichloromethane (2 mL) was added trifluoroacetic acid (0.770 g, 6.75 mmol, 0.500 mL). The resulting reaction mixture was stirred at room temperature for 1 hour, and was then concentrated under reduced pressure. The crude product thus obtained was purified by HPLC (Phenomenex Luna $C_{18}$ column, 3 micron, 80x30 mm; 10-40% acetonitrile in water containing 0.1% trifluoroacetic acid) to provide the title compound: LCMS m/z 397.1 $[M+H]^+$; $^1H$ NMR (400 MHz, $CD_3OD$) δ 9.54 (s, 1H), 8.86 (d, J=1.1 Hz, 1H), 8.40 (s, 1H), 7.64 (t, J 7.9 Hz, 1H), 7.36 (d, J=7.5 Hz, 1H), 6.61 (d, J=8.3 Hz, 1H), 5.58-5.43 (m, 1H), 4.94 (q, J=8.7 Hz, 2H), 4.89 (br s, 1H), 3.89 (dd, J=6.2, 12.8 Hz, 1H), 3.78-3.74 (m, 1H), 3.72-3.65 (m, 1H), 3.65-3.59 (m, 1H).

The compounds in Table 5 were all prepared using the synthetic procedures described in Example 5.

TABLE 5

| Additional compounds prepared according to Example 5. | | | |
|---|---|---|---|
| Compound # | Structure | IUPAC Name | LCMS |
| 37 | 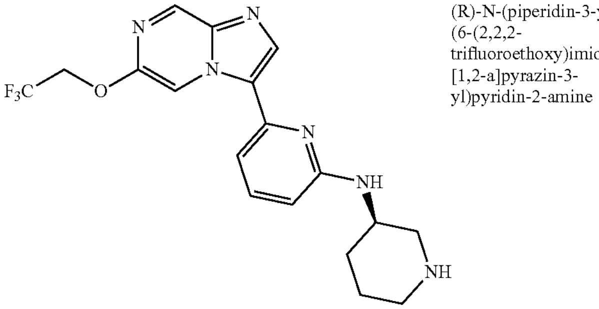 | (R)-N-(piperidin-3-yl)-6-(6-(2,2,2-trifluoroethoxy)imidazo[1,2-a]pyrazin-3-yl)pyridin-2-amine | 393.1 |
| 38 | 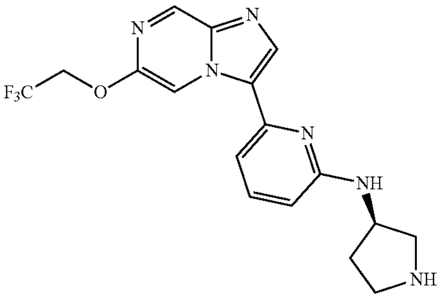 [SMILES: FC(F)(F)COc1cn2c(-c3cccc(N[C@@H]4CCNC4)n3)cnc2cn1] | (R)-N-(pyrrolidin-3-yl)-6-(6-(2,2,2-trifluoroethoxy)imidazo[1,2-a]pyrazin-3-yl)pyridin-2-amine | 379.0 |
| 39 | 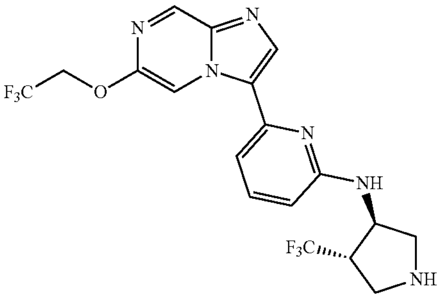 [SMILES: FC(F)(F)COc1cn2c(-c3cccc(N[C@H]4CNC[C@@H]4C(F)(F)F)n3)cnc2cn1] | 6-(6-(2,2,2-trifluoroethoxy)imidazo[1,2-a]pyrazin-3-yl)-N-((3R,4S)-4-(trifluoromethyl)pyrrolidin-3-yl)pyridin-2-amine | 447.2 |
| 40 | 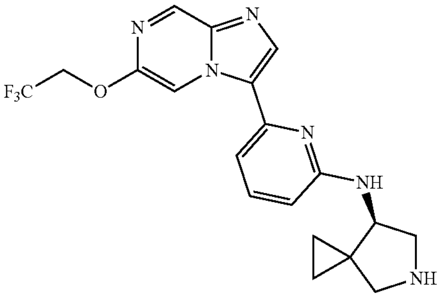 [SMILES: FC(F)(F)COc1cn2c(-c3cccc(N[C@H]4CNCC45CC5)n3)cnc2cn1] | (R)-N-(6-(6-(2,2,2-trifluoroethoxy)imidazo[1,2-a]pyrazin-3-yl)pyridin-2-yl)-5-azaspiro[2.4]heptan-7-amine | 405.1 |
| 41 | 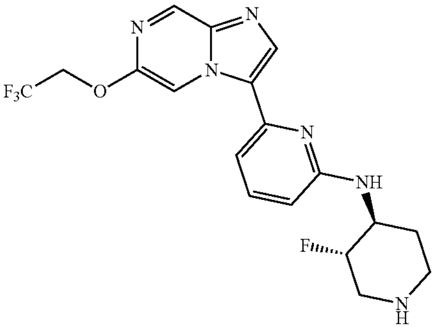 [SMILES: F[C@H]1CNCC[C@@H]1Nc1cccc(-c2cnc3cnc(OCC(F)(F)F)cn23)n1] | N-((3S,4S)-3-fluoropiperidin-4-yl)-6-(6-(2,2,2-trifluoroethoxy)imidazo[1,2-a]pyrazin-3-yl)pyridin-2-amine | 411.2 |

TABLE 5-continued

| Additional compounds prepared according to Example 5. | | | |
|---|---|---|---|
| Compound # | Structure | IUPAC Name | LCMS |
| 42 | 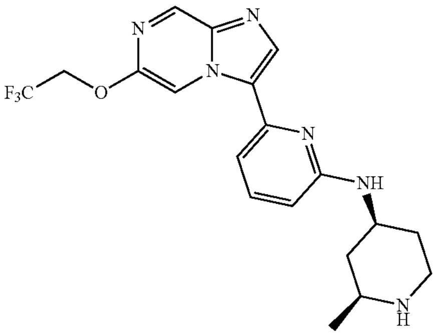 [SMILES: C[C@H]1C[C@@H](Nc2cccc(-c3cnc4cnc(OCC(F)(F)F)cn34)n2)CCN1] | N-((2S,4S)-2-methylpiperidin-4-yl)-6-(6-(2,2,2-trifluoroethoxy)imidazo[1,2-a]pyrazin-3-yl)pyridin-2-amine | 407.0 |

Example 6

Exemplary Synthetic Procedure #6 (Compounds 43-55)

Compound 43, (R)-6-(6-(1-methyl-1H-pyrazol-4-yl)imidazo[1,2-a]pyrazin-3-yl)-N-(piperidin-3-yl)pyridin-2-amine

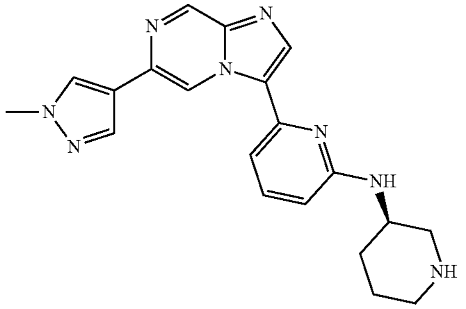 [SMILES: Cn1cc(-c2cn3c(-c4cccc(N[C@@H]5CCCNC5)n4)cnc3cn2)cn1]

Step A. tert-butyl (3R)-3-[[6-(6-chloroimidazo[1,2-a]pyrazin-3-yl)-2-pyridyl]amino]piperidine-1-carboxylate

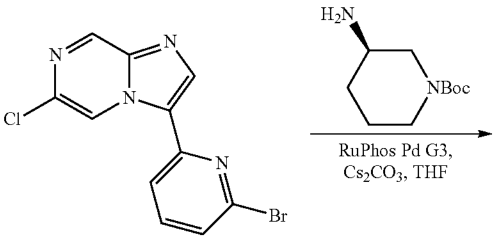

-continued

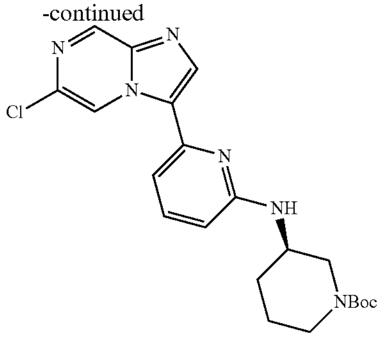

A mixture of 3-(6-bromo-2-pyridyl)-6-chloro-imidazo[1,2-a]pyrazine (1.00 g, 3.23 mmol), tert-butyl (3R)-3-aminopiperidine-1-carboxylate (0.647 g, 3.23 mmol), (2-dicyclohexylphosphino-2',6'-diisopropoxy-1,1'-biphenyl)[2-(2'-amino-1,1'-biphenyl)]palladium(II)methanesulfonate (0.270 g, 0.323 mmol), and cesium carbonate (3.16 g, 9.69 mmol) in tetrahydrofuran (20 mL) was purged with nitrogen, and was then heated at 80° C. for 5 hours under nitrogen atmosphere. The reaction mixture was then cooled to room temperature, filtered, and concentrated under reduced pressure. The resulting crude product was purified by flash chromatography on silica gel (0-30% ethyl acetate in petroleum ether) to provide the title compound: LCMS m/z 429.1 $[M+H]^+$.

Step B. tert-butyl (3R)-3-[[6-[6-(1-methylpyrazol-4-yl)imidazo[1,2-a]pyrazin-3-yl]-2-pyridyl]amino]piperidine-1-carboxylate

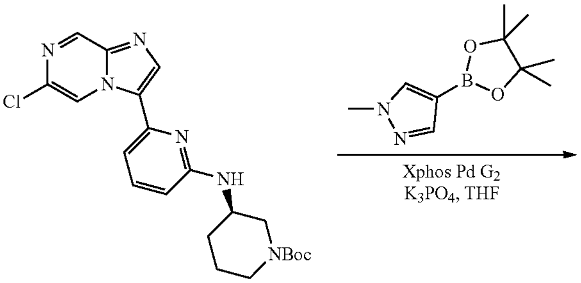

-continued

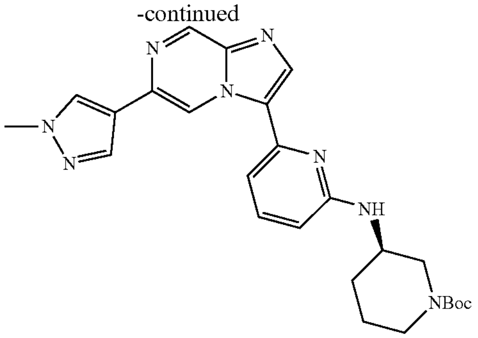

A mixture of tert-butyl (3R)-3-[[6-(6-chloroimidazo[1,2-a]pyrazin-3-yl)-2-pyridyl]amino]piperidine-1-carboxylate (0.080 g, 0.187 mmol), 1-methyl-4-(4,4,5,5-tetramethyl-1,3,2-dioxaborolan-2-yl)pyrazole (0.039 g, 0.187 mmol), chloro(2-dicyclohexylphosphino-2',4',6'-triisopropyl-1,1'-biphenyl)[2-(2'-amino-1,1'-biphenyl)]palladium(II) (0.015 g, 0.019 mmol), and aqueous potassium phosphate solution (1.0 M, 0.560 mL, 0.560 mmol) in tetrahydrofuran (3 mL) was purged with nitrogen, and was then stirred at 90° C. for 3 hours under nitrogen atmosphere. The reaction mixture was then cooled to room temperature, filtered, and concentrated under reduced pressure to provide the title compound: LCMS m/z 475.2 $[M+H]^+$.

Step C. 6-[6-(1-methylpyrazol-4-yl)imidazo[1,2-a]pyrazin-3-yl]-N-[(3R)-3-piperidyl]pyridin-2-amine

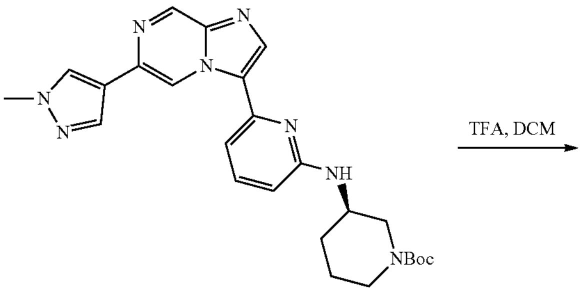

-continued

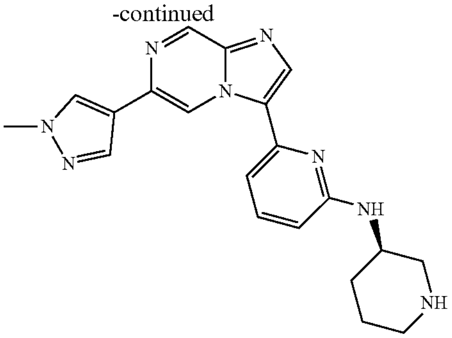

To a solution of tert-butyl (3R)-3-[[6-[6-(1-methylpyrazol-4-yl)imidazo[1,2-a]pyrazin-3-yl]-2-pyridyl]amino]piperidine-1-carboxylate (0.065 g, 0.137 mmol) in dichloromethane (2 mL) was added trifluoroacetic acid (0.770 g, 6.75 mmol, 0.500 mL). The resulting reaction mixture was stirred at room temperature for 1 hour, and was then concentrated under reduced pressure. The resulting crude product was purified by HPLC (Phenomenex Gemini-NX $C_{18}$ column, 5 micron, 150x30 mm; 2-32% acetonitrile in water containing 0. #% trifluoroacetic acid) to provide the title compound: LCMS m/z 375.2 $[M+H]^+$; $^1H$ NMR (400 MHz, $CD_3OD$) δ 9.64 (d, J=1.3 Hz, 1H), 9.09 (d, J=1.3 Hz, 1H), 8.29 (s, 1H), 8.14 (s, 1H), 7.96 (s, 1H), 7.61 (t, J 7.9 Hz, 1H), 7.18 (d, J=7.5 Hz, 1H), 6.64 (d, J=8.4 Hz, 1H), 4.34 (td, J=4.0, 7.8 Hz, 1H), 3.97 (s, 3H), 3.38 (dd, J=3.3, 12.6 Hz, 1H), 3.28-3.21 (m, 1H), 3.17 (dd, J=8.4, 12.1 Hz, 1H), 3.11-3.03 (m, 1H), 2.28-2.17 (m, 1H), 2.15-2.06 (m, 1H), 1.90-1.73 (m, 2H).

The compounds in Table 6 were all prepared using the synthetic procedures described in Example 6.

TABLE 6

Additional compounds prepared according to Example 6.

| Compound # | Structure | IUPAC Name | LCMS |
|---|---|---|---|
| 44 | 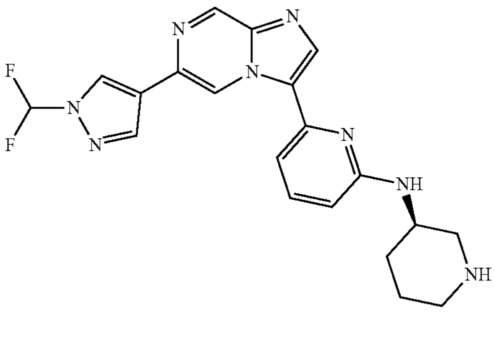 [SMILES: FC(F)n1cc(-c2cn3c(-c4cccc(N[C@@H]5CCCNC5)n4)cnc3cn2)cn1] | (R)-6-(6-(1-(difluoromethyl)-1 H-pyrazol-4-yl)imidazo[1,2-a]pyrazin-3-yl)-N-(piperidin-3-yl)pyridin-2-amine | 411.0 |

TABLE 6-continued

| Additional compounds prepared according to Example 6. | | | |
|---|---|---|---|
| Compound # | Structure | IUPAC Name | LCMS |
| 45 | 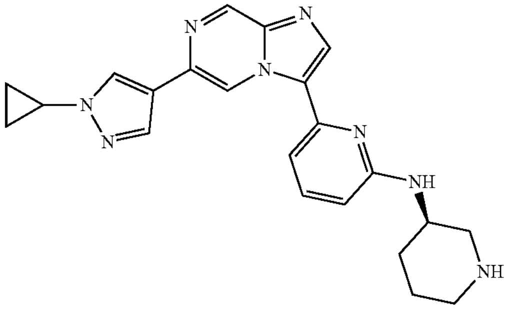 [SMILES: c1cc(N[C@@H]2CCCNC2)nc(-c2cnc3cnc(-c4cnn(C5CC5)c4)cn23)c1] | (R)-6-(6-(1-cyclopropyl-1H-pyrazol-4-yl)imidazo[1,2-a]pyrazin-3-yl)-N-(piperidin-3-yl)pyridin-2-amine | 401.0 |
| 46 | 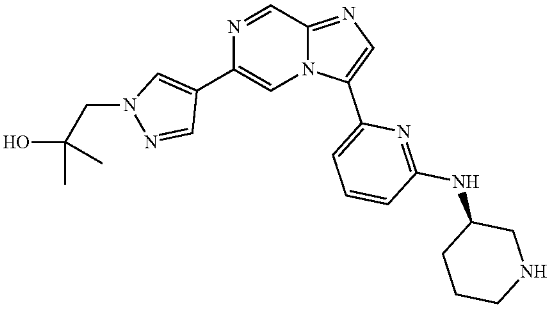 [SMILES: CC(C)(O)Cn1cc(-c2cn3c(-c4cccc(N[C@@H]5CCCNC5)n4)cnc3cn2)cn1] | (R)-2-methyl-1-(4-(3-(6-(piperidin-3-ylamino)pyridin-2-yl)imidazo[1,2-a]pyrazin-6-yl)-1 H-pyrazol-1-yl)propan-2-ol | 433.1 |
| 47 | 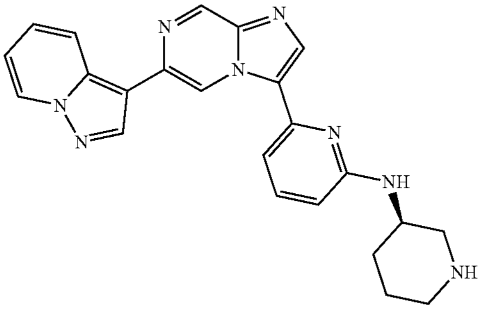 [SMILES: c1cc(N[C@@H]2CCCNC2)nc(-c2cnc3cnc(-c4cnn5ccccc45)cn23)c1] | (R)-N-(piperidin-3-yl)-6-(6-(pyrazolo[1,5-alpyridin-3-yl)imidazo[1,2-a]pyrazin-3-yl)pyridin-2-amine | 411.2 |
| 48 | 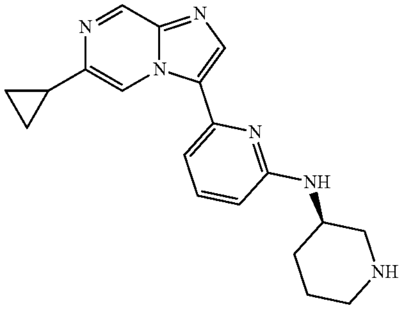 [SMILES: c1cc(N[C@@H]2CCCNC2)nc(-c2cnc3cnc(C4CC4)cn23)c1] | (R)-6-(6-cyclopropylimidazo[1,2-a]pyrazin-3-yl)-N-(piperidin-3-yl)pyridin-2-amine | 335.1 |
| 49 | 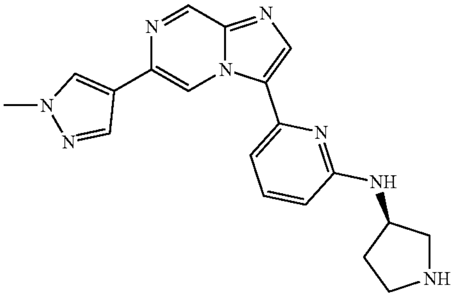 [SMILES: Cn1cc(-c2cn3c(-c4cccc(N[C@@H]5CCNC5)n4)cnc3cn2)cn1] | (R)-6-(6-(1-methyl-1 H-pyrazol-4-yl)imidazo[1,2-a]pyrazin-3-yl)-N-(pyrrolidin-3-yl)pyridin-2-amine | 361.1 |

TABLE 6-continued

Additional compounds prepared according to Example 6.

| Compound # | Structure | IUPAC Name | LCMS |
|---|---|---|---|
| 50 | 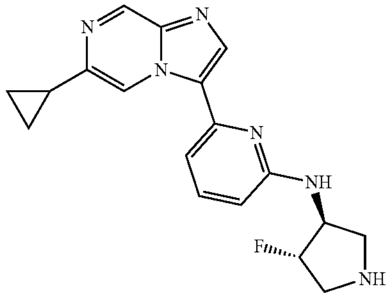 [SMILES: F[C@H]1CNC[C@@H]1Nc1cccc(-c2cnc3cnc(C4CC4)cn23)n1] | 6-(6-cyclopropylimidazo[1,2-a]pyrazin-3-yl)-N-((3S,4S)-4-fluoropyrrolidin-3-yl)pyridin-2-amine | 339.1 |
| 51 | 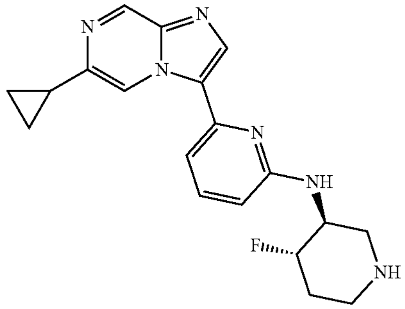 [SMILES: F[C@H]1CCNC[C@@H]1Nc1cccc(-c2cnc3cnc(C4CC4)cn23)n1] | 6-(6-cyclopropylimidazo[1,2-a]pyrazin-3-yl)-N-((3S,4S)-4-fluoropiperidin-3-yl)pyridin-2-amine | 353.2 |
| 52 | 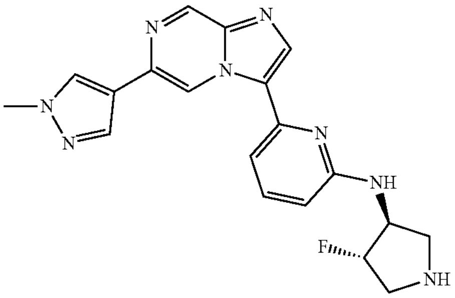 [SMILES: Cn1cc(-c2cn3c(-c4cccc(N[C@H]5CNC[C@@H]5F)n4)cnc3cn2)cn1] | N-((3S,4S)-4-fluoropyrrolidin-3-yl)-6-(6-(1-methyl-1 H-pyrazol-4-yl)imidazo[1,2-a]pyrazin-3-yl)pyridin-2-amine | 379.1 |
| 53 | 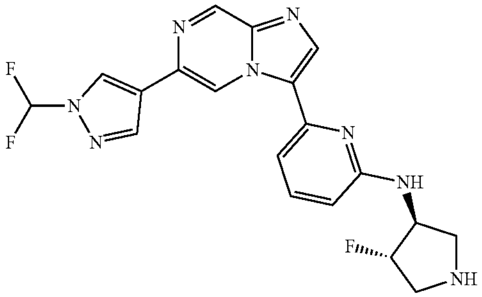 [SMILES: FC(F)n1cc(-c2cn3c(-c4cccc(N[C@H]5CNC[C@@H]5F)n4)cnc3cn2)cn1] | 6-(6-(1-(difluoromethyl)-1 H-pyrazol-4-yl)imidazo[1,2-a]pyrazin-3-yl)-N-((3S,4S)-4-fluoropyrrolidin-3-yl)pyridin-2-amine | 415.0 |
| 54 | 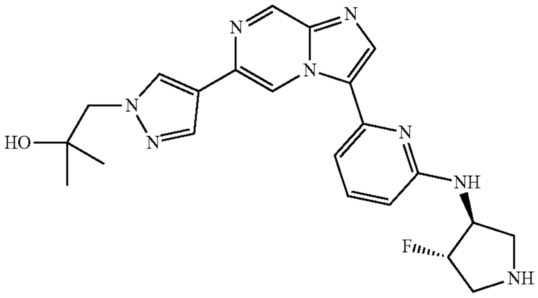 [SMILES: CC(C)(O)Cn1cc(-c2cn3c(-c4cccc(N[C@H]5CNC[C@@H]5F)n4)cnc3cn2)cn1] | 1-(4-(3-(6-(((3S,4S)-4-fluoropyrrolidin-3-yl)amino)pyridin-2-yl)imidazo[1,2-a]pyrazin-6-yl)-1 H-pyrazol-1-yl)-2-methylpropan-2-ol | 437.2 |

TABLE 6-continued

Additional compounds prepared according to Example 6.

| Compound # | Structure | IUPAC Name | LCMS |
|---|---|---|---|
| 55 | 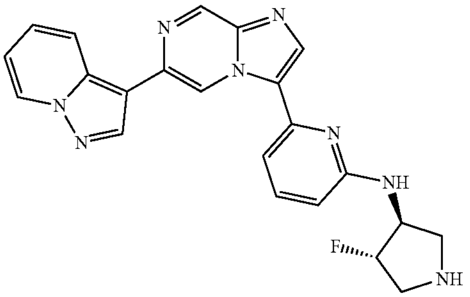 [SMILES: F[C@H]1CNC[C@@H]1Nc1cccc(-c2cnc3cnc(-c4cnn5ccccc45)cn23)n1] | N-((3S,4S)-4-fluoropyrrolidin-3-yl)-6-(6-(pyrazolo[1,5-a]pyridin-3-yl)imidazo[1,2-a]pyrazin-3-yl)pyridin-2-amine | 415.2 |

Example 7

Exemplary Synthetic Procedure #7 (Compounds 56-57)

Compound 56, N-((3S,4S)-4-fluoropyrrolidin-3-yl)-6-(6-methoxyimidazo[1,2-a]pyrazin-3-yl)pyridin-2-amine

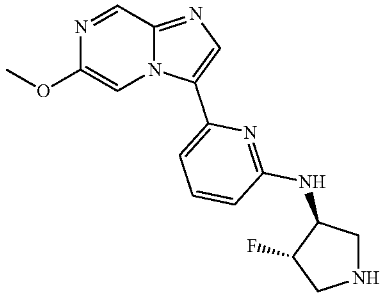 [SMILES: COc1cn2c(-c3cccc(N[C@H]4CNC[C@@H]4F)n3)cnc2cn1]

Step A. (3S,4S)-tert-butyl 3-fluoro-4-((6-(6-methoxyimidazo[1,2-a]pyrazin-3-yl)pyridin-2-yl)amino)pyrrolidine-1-carboxylate

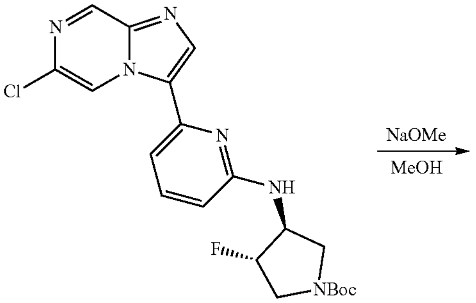

-continued

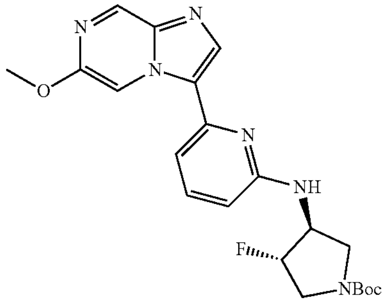

To a solution of tert-butyl (3S,4S)-3-[[6-(6-chloroimidazo[1,2-a]pyrazin-3-yl)-2-pyridyl]amino]-4-fluoro-pyrrolidine-1-carboxylate (0.070 g, 0.162 mmol) in methanol (1 mL) was added sodium methoxide (0.087 g, 1.62 mmol). The resulting reaction mixture was heated at 80° C. for 16 hours, and was then cooled to room temperature, diluted with water (3 mL), and extracted with ethyl acetate (3×5 mL). The organic extracts were combined, dried over sodium sulfate, filtered, and concentrated under reduced pressure to provide the title compound: LCMS m/z 429.2[M+H]$^+$.

Step B. N-((3S,4S)-4-fluoropyrrolidin-3-yl)-6-(6-methoxyimidazo[1,2-a]pyrazin-3-yl)pyridin-2-amine

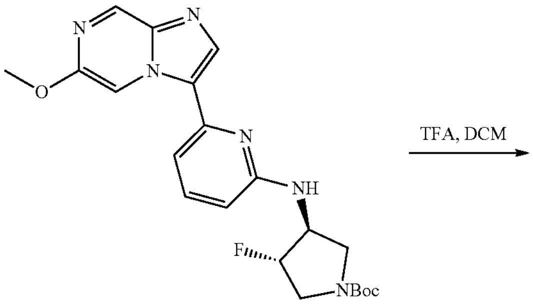

-continued

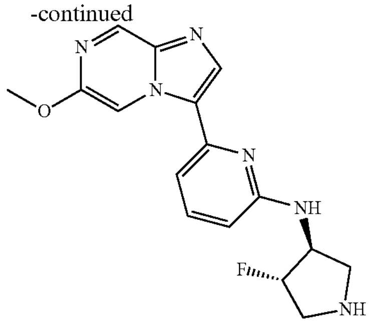

To a solution of tert-butyl (3S,4S)-3-fluoro-4-[[6-(6-methoxyimidazo[1,2-a]pyrazin-3-yl)-2-pyridyl]amino]pyrrolidine-1-carboxylate (0.080 g, 0.187 mmol) in dichloromethane (3 mL) was added trifluoroacetic acid (1.23 g, 10.8 mmol, 0.800 mL). The resulting reaction was stirred at room temperature for 1 hour, and was then filtered and concentrated under reduced pressure. The crude product thus obtained was purified by HPLC (Phenomenex Luna $C_{18}$ column, 5 micron, 100×40 mm; 5-30% acetonitrile in water containing 0.1% trifluoroacetic acid) to provide the title compound: LCMS m/z 329.1 $[M+H]^+$; $^1H$ NMR (400 MHz, $CD_3OD$) δ 9.37 (s, 1H), 8.87 (d, J=1.0 Hz, 1H), 8.37 (s, 1H), 7.66 (t, J 7.9 Hz, 1H), 7.35 (d, J=7.4 Hz, 1H), 6.62 (d, J=8.4 Hz, 1H), 5.59-5.40 (m, 1H), 4.96-4.90 (m, 1H), 4.03 (s, 3H), 3.92 (dd, J=6.1, 12.7 Hz, 1H), 3.79-3.76 (m, 1H), 3.72-3.57 (m, 2H).

The compound in Table 7 were all prepared using the synthetic procedures described in Example 7.

TABLE 7

Additional compounds prepared according to Example 7.

| Compound # | Structure | IUPAC Name | LCMS |
|---|---|---|---|
| 57 | 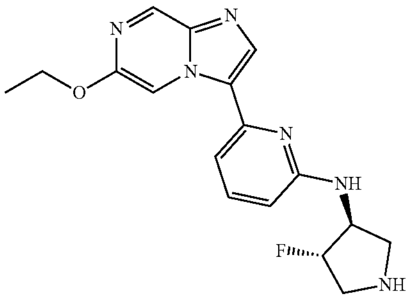 [SMILES: CCOc1cn2c(-c3cccc(N[C@H]4CNC[C@@H]4F)n3)cnc2cn1] | 6-(6-ethoxyimidazo[1,2-a]pyrazin-3-yl)-N-((3S,4S)-4-fluoropyrrolidin-3-yl)pyridin-2-amine | 343.1 |

Example 8

Exemplary Synthetic Procedure #8 (Compound 58)

Compound 58, 6-(6-(2,2-difluoroethoxy)imidazo[1,2-a]pyrazin-3-yl)-N-((3S,4S)-4-fluoropyrrolidin-3-yl)pyridin-2-amine

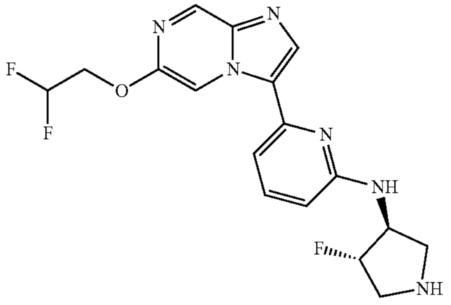 [SMILES: FC(F)COc1cn2c(-c3cccc(N[C@H]4CNC[C@@H]4F)n3)cnc2cn1]

Step A. (3S,4S)-tert-butyl 3-((6-(6-(2,2-difluoroethoxy)imidazo[1,2-a]pyrazin-3-yl)pyridin-2-yl)amino)-4-fluoropyrrolidine-1-carboxylate

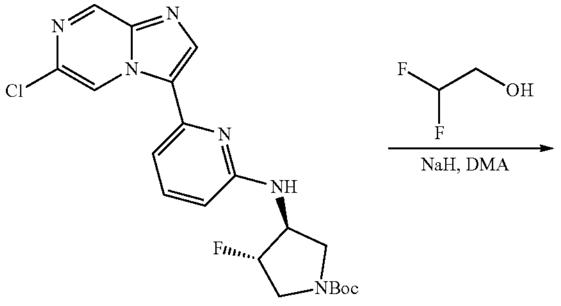

-continued

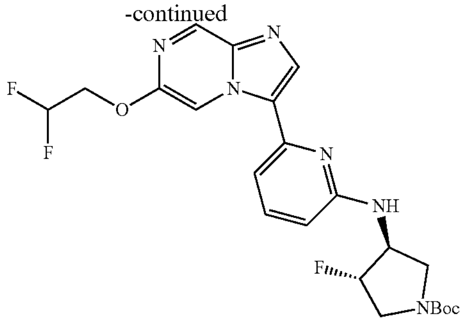

To a cooled 0° C. solution of 2,2-difluoroethanol (0.057 g, 0.693 mmol) in N,N-dimethylacetamide (2 mL) was added sodium hydried (0.017 g, 0.416 mmol, 60% purity). The resulting reaction mixture was removed from the cold bath and stirred for 30 minutes while warming to room temperature. A solution of tert-butyl(3S,4S)-3-[[6-(6-chloroimidazo[1,2-a]pyrazin-3-yl)-2-pyridyl]amino]-4-fluoro-pyrrolidine-1-carboxylate (0.060 g, 0.139 mmol) in N,N-dimethylacetamide (1 mL) was then added, giving a mixture that was then heated at 80° C. for 12 hours. The reaction was then cooled to room temperature, diluted with water (3 mL), and extracted with ethyl acetate (3×5 mL). The organic extracts were combined, washed with saturated aqueous sodium chloride solution (4 mL), dried over sodium sulfate, filtered, and concentrated under reduced pressure to provide the title compound: LCMS m/z 479.3[M+H]$^+$.

Step B. 6-(6-(2,2-difluoroethoxy)imidazo[1,2-a]pyrazin-3-yl)-N-((3S,4S)-4-fluoropyrrolidin-3-yl)pyridin-2-amine

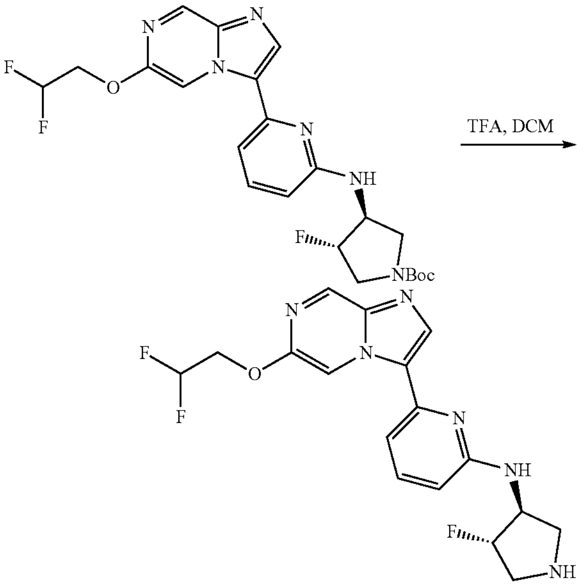

To a solution of tert-butyl (3S,4S)-3-[[6-[6-(2,2-difluoroethoxy)imidazo[1,2-a]pyrazin-3-yl]-2-pyridyl]amino]-4-fluoro-pyrrolidine-1-carboxylate (0.050 g, 0.105 mmol) in dichloromethane (2 mL) was added trifluoroacetic acid (1.54 g, 13.5 mmol, 1.00 mL). The resulting reaction was stirred at room temperature for 1 hour, and was then concentrated under reduced pressure. The crude product thus obtained was purified by HPLC (Xtimate $C_{18}$ column, 3 micron, 100×30 mm; 1-31% acetonitrile in water containing 0.1% trifluoroacetic acid) to provide the title compound: LCMS m/z 379.2 [M+H]$^+$; $^1$H NMR (400 MHz, $CD_3OD$) δ 9.81 (d, J=1.4 Hz, 1H), 9.24 (d, J=1.4 Hz, 1H), 8.88 (s, 1H), 7.75 (dd, J=7.6, 8.4 Hz, 1H), 7.43 (d, J=7.5 Hz, 1H), 6.79 (d, J=8.5 Hz, 1H), 6.03 (d, J=2.5 Hz, 1H), 5.59-5.41 (m, 1H), 4.90-4.84 (m, 1H), 4.75 (dt, J 3.7, 14.0 Hz, 2H), 3.94 (dd, J=6.4, 12.8 Hz, 1H), 3.82-3.76 (m, 1H), 3.74-3.61 (m, 2H).

Example 9

Exemplary Synthetic Procedure #9 (Compounds 59-60)

Compound 59, N-((3S,4S)-4-fluoropyrrolidin-3-yl)-6-(6-isopropoxyimidazo[1,2-a]pyrazin-3-yl)pyridin-2-amine

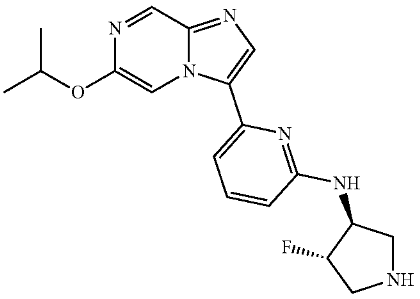 [SMILES: CC(C)Oc1cn2c(-c3cccc(N[C@H]4CNC[C@@H]4F)n3)cnc2cn1]

Step A. tert-butyl (3S,4S)-3-fluoro-4-[[6-(6-isopropoxyimidazo[1,2-a]pyrazin-3-yl)-2-pyridyl]amino]pyrrolidine-1-carboxylate

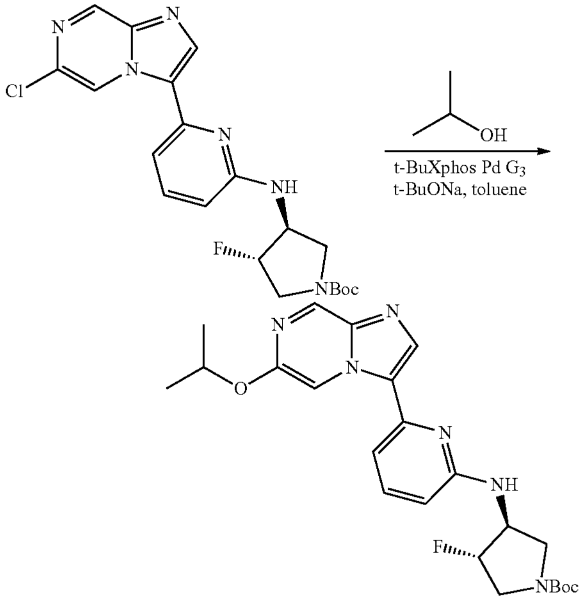

A mixture of tert-butyl (3S,4S)-3-[[6-(6-chloroimidazo[1,2-a]pyrazin-3-yl)-2-pyridyl]amino]-4-fluoro-pyrrolidine-1-carboxylate (0.060 g, 0.139 mmol), propan-2-ol (0.042 g, 0.693 mmol, 0.053 mL), sodium tert-butoxide (0.027 g, 0.277 mmol), and [2-(2-aminophenyl)phenyl]-methylsulfonyloxy-palladium-di-tert-butyl-[2-(2,4,6-triisopropylphenyl)phenyl]phosphane (0.011 g, 0.014 mmol) in toluene (2 mL) was purged with nitrogen, and was then heated at 80° C. for 16 hours under nitrogen atmosphere. The reaction was then cooled to room temperature, filtered, and concentrated under reduced pressure to provide the title compound: LCMS m/z 457.2 $[M+H]^+$.

-continued

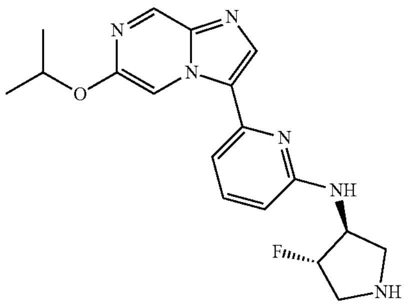

Step B. N-[(3S,4S)-4-fluoropyrrolidin-3-yl]-6-(6-isopropoxyimidazo[1,2-a]pyrazin-3-yl)pyridin-2-amine

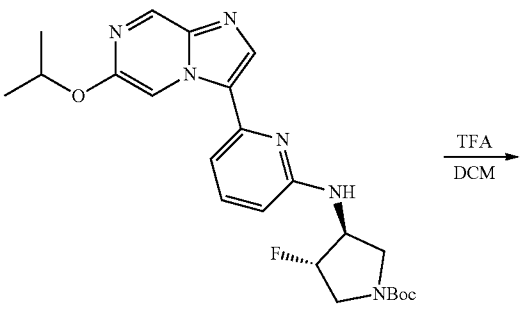

To a solution of tert-butyl (3S,4S)-3-fluoro-4-[[6-(6-isopropoxyimidazo[1,2-a]pyrazin-3-yl)-2-pyridyl]amino]pyrrolidine-1-carboxylate (0.015 g, 0.033 mmol) in dichloromethane (1 mL) was added trifluoroacetic acid (0.232 g, 2.03 mmol, 0.150 mL). The resulting reaction was stirred at room temperature for 1 hour, and was then filtered and concentrated under reduced pressure. The crude product thus obtained was purified by HPLC (Phenomenex Gemini-NX $C_{18}$ column, 5 micron, 150×30 mm; 1-26% acetonitrile in water containing 0.1% trifluoroacetic acid) to provide the title compound: LCMS m/z 357.1 $[M+H]^+$; $^1H$ NMR (400 MHz, $CD_3OD$) δ 9.34 (s, 1H), 8.84 (s, 1H), 8.34 (s, 1H), 7.63 (t, J 7.94 Hz, 1H), 7.33 (d, J=7.50 Hz, 1H), 6.60 (d, J=8.25 Hz, 1H), 5.37-5.63 (m, 1H), 5.20 (spt, J 6.13 Hz, 1H), 4.91-5.02 (m, 1H), 3.90 (dd, J=12.69, 6.07 Hz, 1H), 3.74-3.80 (m, 1H), 3.65-3.74 (m, 1H), 3.60-3.65 (m, 1H), 1.36 (t, J 6.50 Hz, 6H).

The compounds in Table 8 were all prepared using the synthetic procedures described in Example 9.

TABLE 8

Additional compounds prepared according to Example 9.

| Compound # | Structure | IUPAC Name | LCMS |
|---|---|---|---|
| 60 | 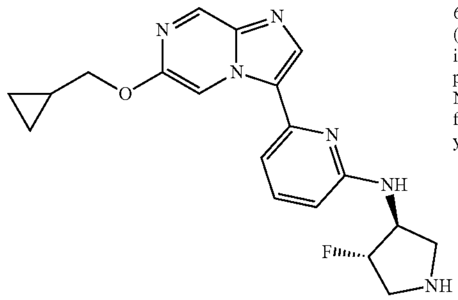 | 6-(6-(cyclopropylmethoxy)imidazo[1,2-a]pyrazin-3-yl)-N-((3S,4S)-4-fluoropyrrolidin-3-yl)pyridin-2-amine | 369.2 |

Example 10

Exemplary Synthetic Procedure #10 (Compounds 61-62)

Compound 61, 1-(3-(6-(((3S,4S)-4-fluoropyrrolidin-3-yl)amino)pyridin-2-yl)imidazo[1,2-a]pyrazin-6-yl)-3,3-dimethylpyrrolidin-2-one

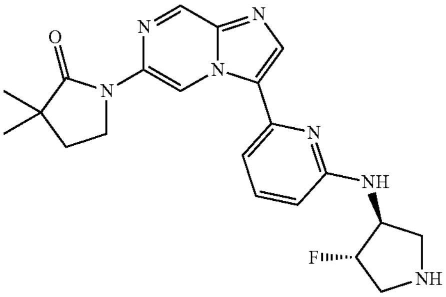 [SMILES: CC1(C)CCN(c2cn3c(-c4cccc(N[C@H]5CNC[C@@H]5F)n4)cnc3cn2)C1=O]

Step A. tert-butyl (3S,4S)-3-((6-(6-(3,3-dimethyl-2-oxopyrrolidin-1-yl)imidazo[1,2-a]pyrazin-3-yl)pyridin-2-yl)amino)-4-fluoropyrrolidine-1-carboxylate

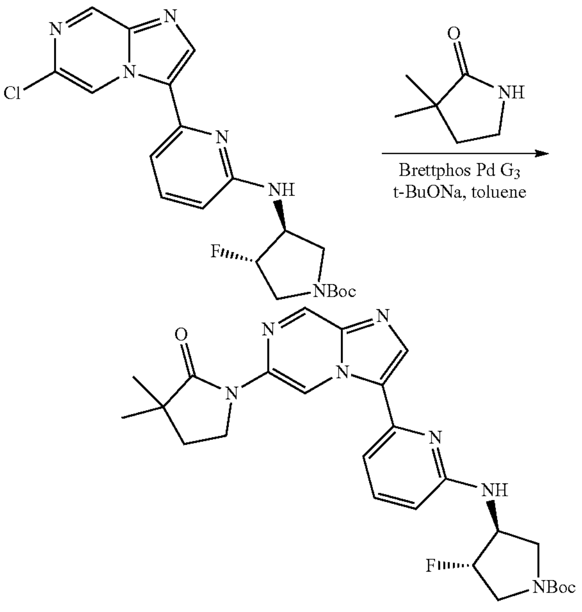

A mixture of tert-butyl (3S,4S)-3-[[6-(6-chloroimidazo[1,2-a]pyrazin-3-yl)-2-pyridyl]amino]-4-fluoro-pyrrolidine-1-carboxylate (0.020 g, 0.046 mmol), 3,3-dimethylpyrrolidin-2-one (0.010 g, 0.092 mmol), methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (0.004 g, 0.005 mmol), and sodium tert-butoxide (0.009 g, 0.092 mmol) in toluene (1 mL) was purged with nitrogen, and was then heated at 100° C. for 16 hours under nitrogen atmosphere. The reaction mixture was then cooled to room temperature, filtered, and concentrated under reduced pressure to provide the title compound: LCMS m/z 510.2 $[M+H]^+$.

Step B. 1-(3-(6-(((3S,4S)-4-fluoropyrrolidin-3-yl)amino)176yridine-2-yl)imidazo[1,2-a]pyrazin-6-yl)-3,3-dimehtylpyrrolidin-2-one

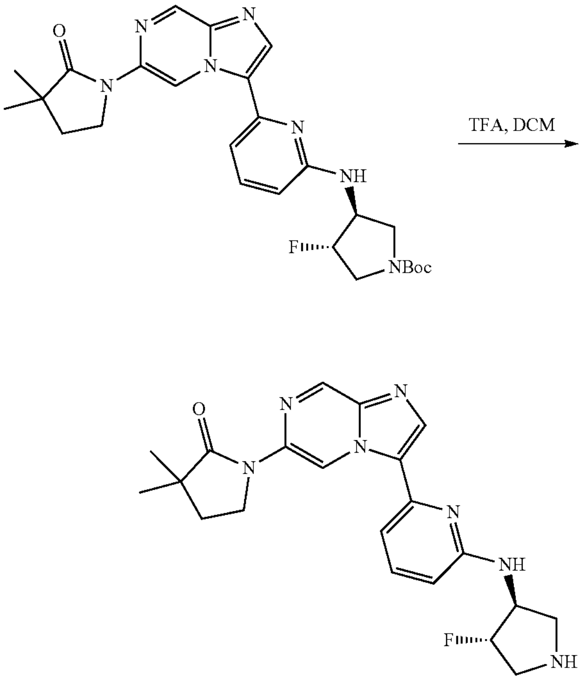

To a solution of tert-butyl (3S,4S)-3-[[6-[6-(3,3-dimethyl-2-oxo-pyrrolidin-1-yl)imidazo[1,2-a]pyrazin-3-yl]-2-pyridyl]amino]-4-fluoro-pyrrolidine-1-carboxylate (0.060 g, 0.118 mmol) in dichloromethane (3 mL) was added trifluoroacetic acid (0.578 g, 5.06 mmol, 0.375 mL). The resulting reaction was stirred at room temperature for 1 hour, and was then filtered and concentrated under reduced pressure. The crude product thus obtained was purified by HPLC (Phenomenex Luna $C_{18}$ column, 5 micron, 100×40 mm; 1-30% acetonitrile in water containing 0.1% trifluoroacetic acid) to provide the title compound: LCMS m/z 410.2 $[M+H]^+$; $^1H$ NMR (400 MHz, $CD_3OD$) δ 10.63 (s, 1H), 8.97 (s, 1H), 8.35 (s, 1H), 7.62 (t, J 7.9 Hz, 1H), 7.30 (d, J=7.5 Hz, 1H), 6.61 (d, J=8.3 Hz, 1H), 5.37 (br s, 1H), 5.26 (br dd, J=4.8, 13.1 Hz, 1H), 4.20-4.01 (m, 2H), 3.88 (br dd, J=5.7, 12.5 Hz, 1H), 3.81-3.55 (m, 3H), 2.08 (t, J 6.9 Hz, 2H), 1.27 (d, J=2.9 Hz, 6H).

The compounds in Table 9 were all prepared using the synthetic procedures described in Example 10.

TABLE 9

| Additional compounds prepared according to Example 10. | | | |
|---|---|---|---|
| Compound # | Structure | IUPAC Name | LCMS |
| 62 | 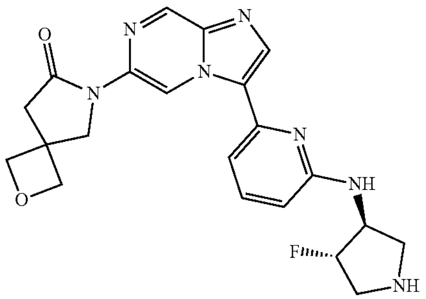 [SMILES: O=C1CC2(COC2)CN1c1cn2c(-c3cccc(N[C@H]4CNC[C@@H]4F)n3)cnc2cn1] | 6-(3-(6-(((3S,4S)-4-fluoropyrrolidin-3-yl)amino)pyridin-2-yl)imidazo[1,2-a]pyrazin-6-yl)-2-oxa-6-azaspiro[3.4]octan-7-one | 424.2 |

Example 11

Exemplary Synthetic Procedure #11 (Compound 63)

Compound 63, 1-(3-(6-(((3S,4S)-4-fluoropyrrolidin-3-yl)amino)pyridin-2-yl)imidazo[1,2-a]pyrazin-6-yl)-4,4-dimethylpyrrolidin-2-one

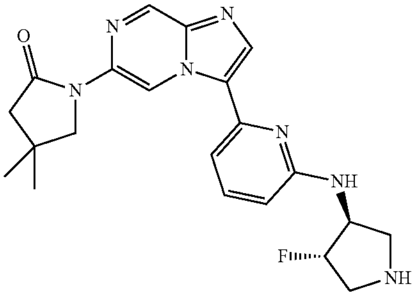 [SMILES: CC1(C)CC(=O)N(c2cn3c(-c4cccc(N[C@H]5CNC[C@@H]5F)n4)cnc3cn2)C1]

Step A. (3S,4S)-tert-butyl 3-((6-(6-(4,4-dimethyl-2-oxopyrrolidin-1-yl)imidazo[1,2-a]pyrazin-3-yl)pyridin-2-yl)amino)-4-fluoropyrrolidine-1-carboxylate -continued

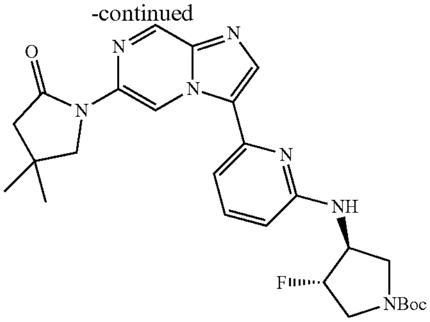

A mixture of tert-butyl (3S,4S)-3-[[6-(6-chloroimidazo[1,2-a]pyrazin-3-yl)-2-pyridyl]amino]-4-fluoro-pyrrolidine-1-carboxylate (0.070 g, 0.162 mmol), 4,4-dimethylpyrrolidin-2-one (0.055 g, 0.485 mmol), sodium tert-butoxide (0.047 g, 0.485 mmol), and [2-(2-aminophenyl)phenyl]-methylsulfonyloxy-palladium-di-tert-butyl-[2-(2,4,6-triisopropylphenyl)phenyl]phosphane (0.026 g, 0.032 mmol) in tert-amyl alcohol (1 mL) was purged with nitrogen, and was then heated at 100° C. for 16 hours under nitrogen atmosphere. The reaction mixture was then cooled to room temperature, filtered, and concentrated under reduced pressure to provide the title compound: LCMS m/z 510.2 $[M+H]^+$.

Step B. 1-(3-(6-(((3S,4S)-4-fluoropyrrolidin-3-yl)amino)pyridin-2-yl)imidazo[1,2-a]pyrazin-6-yl)-4,4-dimethylpyrrolidin-2-one

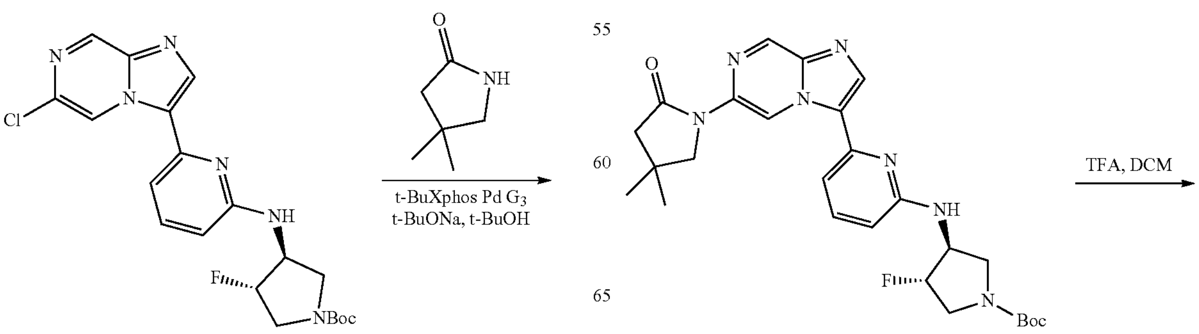

-continued

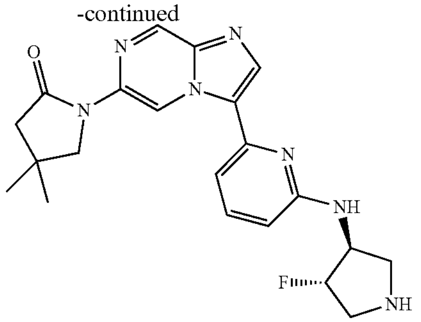

To a solution of tert-butyl (3S,4S)-3-[[6-[6-(4,4-dimethyl-2-oxo-pyrrolidin-1-yl)imidazo[1,2-a]pyrazin-3-yl]-2-pyridyl]amino]-4-fluoro-pyrrolidine-1-carboxylate (0.080 g, 0.157 mmol) in dichloromethane (3 mL) was added trifluoroacetic acid (1.23 g, 10.8 mmol, 0.800 mL). The resulting reaction was stirred at room temperature for 1 hour, and was then concentrated under reduced pressure. The crude product thus obtained was purified by HPLC (Phenomenex Gemini-NX $C_{18}$ column, 5 micron, 150×30 mm; 7-22% acetonitrile in water containing 0.1% trifluoroacetic acid) to provide the title compound: LCMS m/z 410.2 $[M+H]^+$; $^1H$ NMR (400 MHz, $CD_3OD$) δ 10.46 (s, 1H), 8.85 (s, 1H), 8.24 (s, 1H), 7.52 (t, J 7.8 Hz, 1H), 7.21 (d, J=7.5 Hz, 1H), 6.50 (d, J=8.3 Hz, 1H), 5.43-5.23 (m, 1H), 5.14 (br d, J=8.8 Hz, 1H), 3.91-3.74 (m, 3H), 3.69-3.52 (m, 2H), 3.41 (br d, J=12.4 Hz, 1H), 2.43 (d, J=2.3 Hz, 2H), 1.17 (d, J=7.0 Hz, 6H).

Example 12

Exemplary Synthetic Procedure #12 (Compounds 64-66)

Compound 64, N-((3S,4S)-4-fluoropyrrolidin-3-yl)-6-(6-(pyrrolidin-1-yl)imidazo[1,2-a]pyrazin-3-yl)pyridin-2-amine

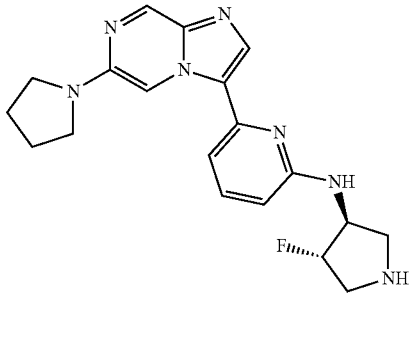 [SMILES: F[C@H]1CNC[C@@H]1Nc1cccc(-c2cnc3cnc(N4CCCC4)cn23)n1]

Step A. tert-butyl (3S,4S)-3-fluoro-4-((6-(6-(pyrrolidin-1-yl)imidazo[1,2-a]pyrazin-3-yl)pyridin-2-yl)amino)pyrrolidine-1-carboxylate

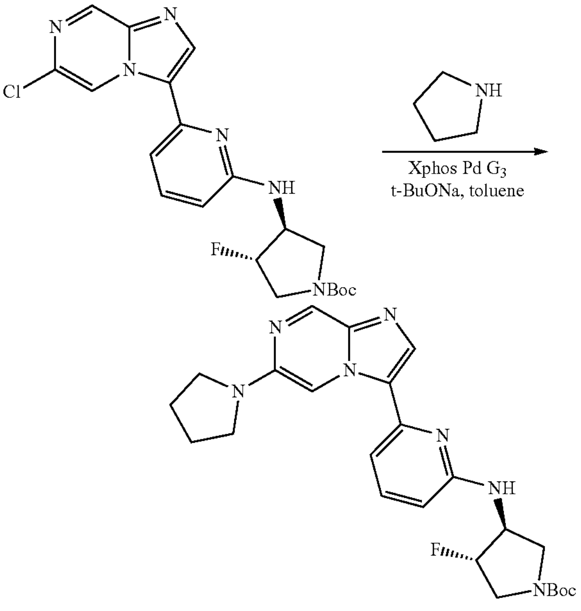

A mixture of tert-butyl (3S,4S)-3-[[6-(6-chloroimidazo[1,2-a]pyrazin-3-yl)-2-pyridyl]amino]-4-fluoro-pyrrolidine-1-carboxylate (0.070 g, 0.162 mmol), pyrrolidine (0.058 g, 0.809 mmol, 0.067 mL), sodium tert-butoxide (0.047 g, 0.485 mmol), and methanesulfonato(2-dicyclohexylphosphino-2,4,6-tri-I-propyl-1,1-biphenyl)(2-amino-1,1-biphenyl-2-yl)palladium(II) (0.014 g, 0.016 mmol) in toluene (1 mL) was purged with nitrogen, and was then heated by microwave at 110° C. for 2 hours under nitrogen atmosphere. The reaction mixture was then cooled to room temperature, filtered, and concentrated under reduced pressure. The resulting crude product was purified by prep-TLC (50% ethyl acetate in petroleum ether, $R_f$=0.41) to provide the title compound: LCMS m/z 468.2 $[M+H]^+$.

Step B. N-((3S,4S)-4-fluoropyrrolidin-3-yl)-6-(6-(pyrrolidin-1-yl)imidazo[1,2-a]pyrazin-3-yl)pyridin-2-amine

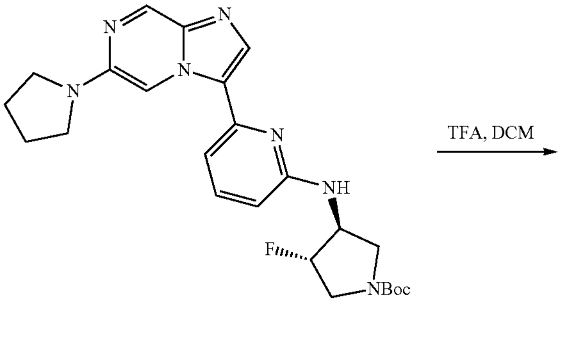

-continued

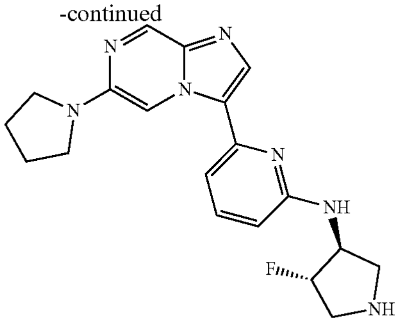

To a solution of tert-butyl (3S,4S)-3-fluoro-4-[[6-(6-pyrrolidin-1-ylimidazo[1,2-a]pyrazin-3-yl)-2-pyridyl]amino] pyrrolidine-1-carboxylate (0.020 g, 0.043 mmol) in dichloromethane (2 mL) was added trifluoroacetic acid (0.513 g, 4.50 mmol, 0.333 mL). The resulting reaction was stirred at room temperature for 1 hour, and was then concentrated under reduced pressure. The crude product thus obtained was purified by HPLC (Phenomenex Gemini-NX $C_{18}$ column, 5 micron, 150×30 mm; 1-28% acetonitrile in water containing 0.1% trifluoroacetic acid) to provide the title compound: LCMS m/z 368.1 $[M+H]^+$; $^1H$ NMR (400 MHz, $CD_3OD$) δ 9.14 (d, J=5.7 Hz, 1H), 8.28 (s, 1H), 7.69 (t, J 7.9 Hz, 1H), 7.38 (d, J=7.5 Hz, 1H), 7.18 (d, J=5.9 Hz, 1H), 6.71 (d, J=8.3 Hz, 1H), 5.62-5.37 (m, 1H), 5.02-4.96 (m, 1H), 4.72 (br s, 1H), 4.21 (br s, 3H), 3.92 (br dd, J 6.2, 12.9 Hz, 1H), 3.78-3.74 (m, 1H), 3.72-3.57 (m, 2H), 2.25-2.19 (m, 4H).

The compounds in Table 10 were all prepared using the synthetic procedures described in Example 12.

Compound 67, 6-(6-(3,3-difluoropyrrolidin-1-yl) imidazo[1,2-a]pyrazin-3-yl)-N-((3S,4S)-4-fluoropyrrolidin-3-yl)pyridin-2-amine

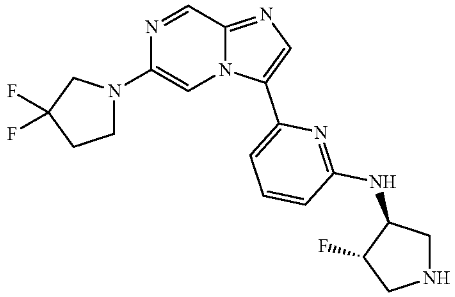

Step A. 6-(3,3-difluoropyrrolidin-1-yl)imidazo[1,2-a]pyrazine

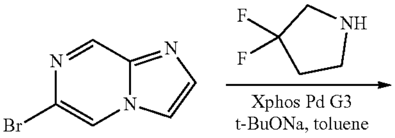

TABLE 10

Additional compounds prepared according to Example 12.

| Compound # | Structure | IUPAC Name | LCMS |
|---|---|---|---|
| 65 | 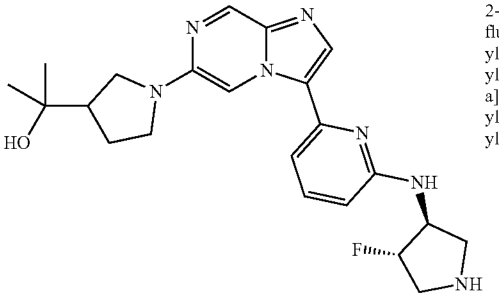 | 2-(1-(3-(6-(((3S,4S)-4-fluoropyrrolidin-3-yl)amino)180yridine-2-yl)imidazo[1,2-a]pyrazin-6-yl)pyrrolidin-3-yl)propan-2-ol | 426.2 |
| 66 | 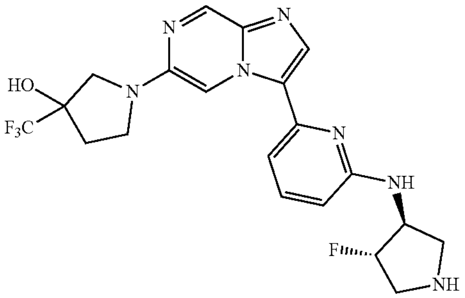 [SMILES: OC1(C(F)(F)F)CCN(c2cn3c(-c4cccc(N[C@H]5CNC[C@@H]5F)n4)cnc3cn2)C1] | 1-(3-(6-(((3S,4S)-4-fluoropyrrolidin-3-yl)amino)pyridin-2-yl)imidazo[1,2-a]pyrazin-6-yl)-3-(trifluoromethyl) pyrrolidin-3-ol | 452.2 |

-continued

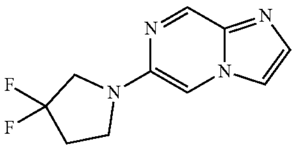

A mixture of 6-bromoimidazo[1,2-a]pyrazine (0.100 g, 0.505 mmol), 3,3-difluoropyrrolidine hydrochloride (0.145 g, 1.01 mmol), sodium tert-butoxide (0.146 g, 1.51 mmol), and methanesulfonato(2-dicyclohexylphosphino-2,4,6-tri-I-propyl-1,1-biphenyl)(2-amino-1,1-biphenyl-2-yl)palladium (II) (0.043 g, 0.051 mmol) in toluene (1 mL) was purged with nitrogen, and was then heated at 110° C. for 16 hours under nitrogen atmosphere. The reaction mixture was then cooled to room temperature, filtered, and concentrated under reduced pressure. The resulting crude product was purified by flash chromatography on silica gel (0-70% ethyl acetate in petroleum ether) to provide the title compound: LCMS m/z 255.1 $[M+H]^+$.

Step B. 3-(6-bromopyridin-2-yl)-6-(3,3-difluoropyrrolidin-1-yl)imidazo[1,2-a]

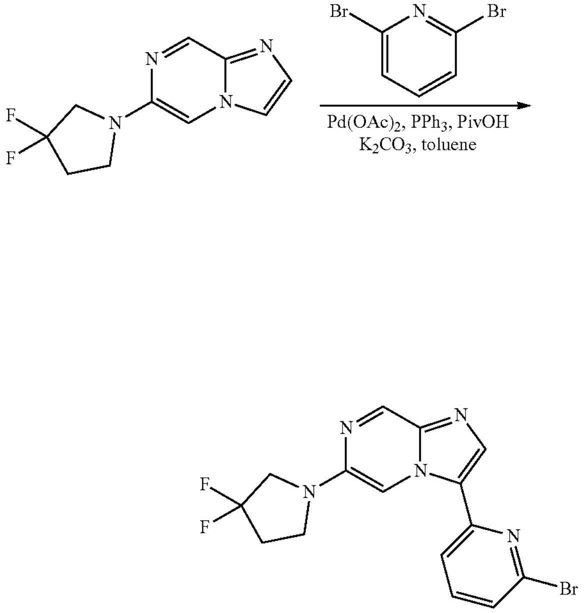

A mixture of 6-(3,3-difluoropyrrolidin-1-yl)imidazo[1,2-a]pyrazine (0.050 g, 0.223 mmol), 2,6-dibromopyridine (0.158 g, 0.669 mmol), potassium carbonate (0.092 g, 0.669 mmol), triphenylphosphine (0.009 g, 0.033 mmol), palladium(II)acetate (0.005 g, 0.022 mmol), and 2,2-dimethylpropanoic acid (0.007 g, 0.067 mmol) in toluene (3 mL) was purged with nitrogen, and was then heated at 100° C. for 16 hours under nitrogen atmosphere. The reaction mixture was then cooled to room temperature, filtered, and concentrated under reduced pressure. The resulting crude product was purified by prep-TLC (10% methanol in dichloromethane, $R_f$=0.45) to provide the title compound: LCMS m/z 380.0 $[M+H]^+$.

Step C. (3S,4S)-tert-butyl 3-((6-(6-(3,3-difluoropyrrolidin-1-yl)imidazo[1,2-a]pyrazin-3-yl)pyridin-2-yl)amino)-4-fluoropyrrolidine-1-carboxylate

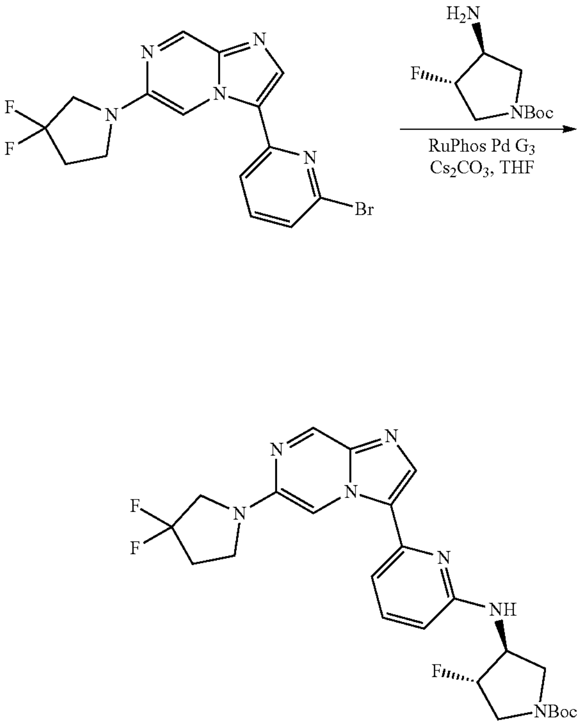

A mixture of 3-(6-bromo-2-pyridyl)-6-(3,3-difluoropyrrolidin-1-yl)imidazo[1,2-a]pyrazine (0.040 g, 0.105 mmol), tert-butyl (3S,4S)-3-amino-4-fluoro-pyrrolidine-1-carboxylate (0.021 g, 0.105 mmol), (2-dicyclohexylphosphino-2',6'-diisopropoxy-1,1'-biphenyl)[2-(2'-amino-1,1'-biphenyl)] palladium(II)methanesulfonate (0.009 g, 0.011 mmol), and cesium carbonate (0.103 g, 0.316 mmol) in tetrahydrofuran (3 mL) was purged with nitrogen, and was then heated at 80° C. for 2 hours under nitrogen atmosphere. The reaction mixture was then cooled to room temperature, filtered, and concentrated under reduced pressure to provide the title compound: LCMS m/z 504.2 $[M+H]^+$.

Step D. 6-(6-(3,3-difluoropyrrolidin-1-yl)imidazo[1,2-a]pyrazin-3-yl)-N-((3S,4S)-4-fluoropyrrolidin-3-yl)pyridin-2-amine

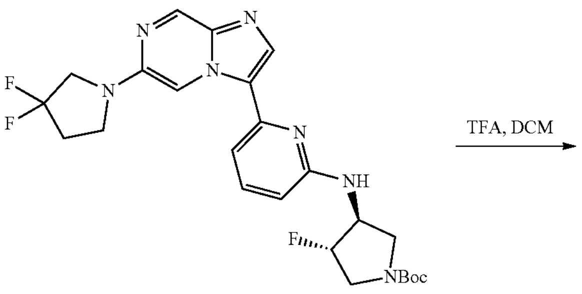

-continued

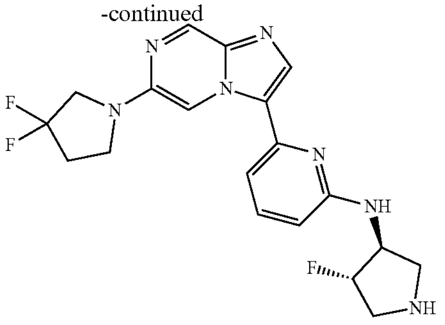

To a solution of tert-butyl (3S,4S)-3-[[6-[6-(3,3-difluoropyrrolidin-1-yl)imidazo[1,2-a]pyrazin-3-yl]-2-pyridyl]amino]-4-fluoro-pyrrolidine-1-carboxylate (0.050 g, 0.099 mmol) in dichloromethane (3 mL) was added trifluoroacetic acid (0.770 g, 6.75 mmol, 0.500 mL). The resulting reaction was stirred at room temperature for 1 hour, and was then concentrated under reduced pressure. The crude product thus obtained was purified by HPLC (Phenomenex Gemini-NX $C_{18}$ column, 5 micron, 150×30 mm; 1-30% acetonitrile in water containing 0.1% TFA) to provide the title compound: LCMS m/z 404.1 $[M+H]^+$; $^1H$ NMR (400 MHz, $CD_3OD$) δ 8.95 (s, 1H), 8.87 (s, 1H), 8.37 (s, 1H), 7.68 (t, J 7.9 Hz, 1 H), 7.32 (d, J=7.5 Hz, 1H), 6.67 (d, J=8.3 Hz, 1H), 5.60-5.43 (m, 1H), 5.02-4.93 (m, 1H), 4.00-3.86 (m, 3H), 3.81-3.68 (m, 4H), 3.65-3.58 (m, 1H), 2.71-2.52 (m, 2H).

Example 14

Exemplary Synthetic Procedure #14 (Compounds 68-74)

Compound 68, N-((3S,4S)-4-fluoropyrrolidin-3-yl)-6-(imidazo[1,2-a]pyrazin-3-yl)pyridin-2-amine

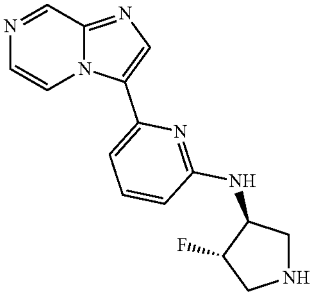 [SMILES: F[C@H]1CNC[C@@H]1Nc1cccc(-c2cnc3cnccn23)n1]

Step A. 3-(6-bromopyridin-2-yl)imidazo[1,2-a]pyrazine

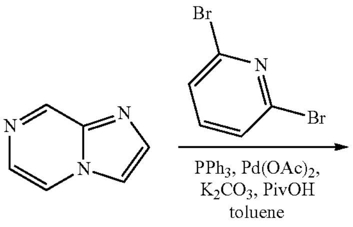

-continued

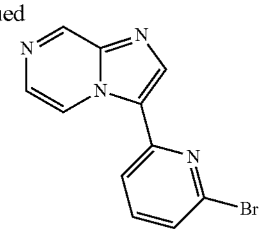

A mixture of imidazo[1,2-a]pyrazine (1.00 g, 8.39 mmol), 2,6-dibromopyridine (1.99 g, 8.39 mmol), palladium acetate (0.188 g, 0.839 mmol), triphenylphosphine (0.440 g, 1.68 mmol), 2,2-dimethylpropanoic acid (0.257 g, 2.52 mmol, 0.289 mL), and potassium carbonate (3.48 g, 25.2 mmol) in toluene (50 mL) was purged with nitrogen, and was then heated at 100° C. for 15 hours under nitrogen atmosphere. The reaction mixture was then cooled to room temperature, filtered, and concentrated under reduced pressure. The resulting crude product was purified by flash chromatography on silica gel (0-100% ethyl acetate in petroleum ether) to provide the title compound: LCMS m/z 275.1 $[M+H]^+$.

Step B. (3S,4S)-tert-butyl 3-fluoro-4-((6-(imidazo[1,2-a]pyrazin-3-yl)pyridin-2-yl)amino)pyrrolidine-1-carboxylate

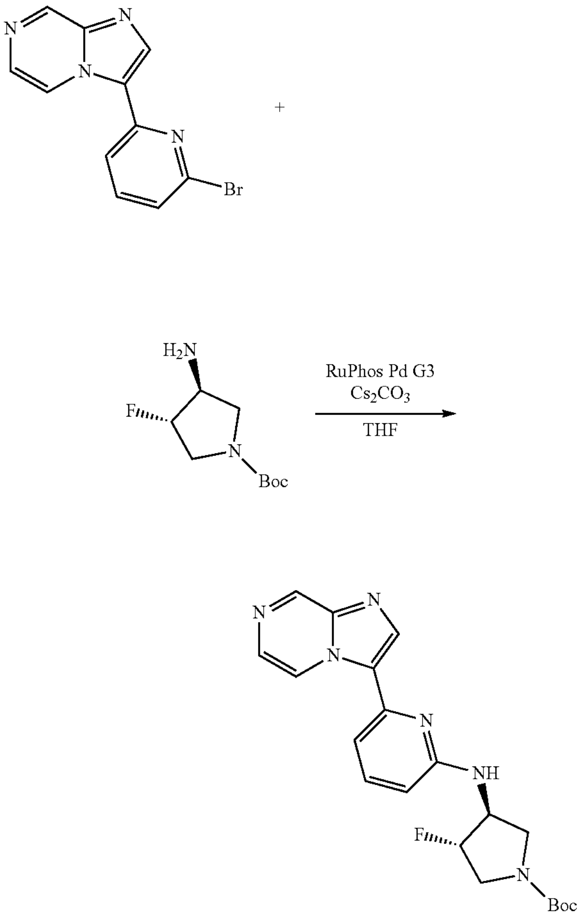 [SMILES: Brc1cccc(-c2cnc3cnccn23)n1 ; CC(C)(C)OC(=O)N1C[C@H](N)[C@@H](F)C1 ; "RuPhos Pd G3Cs2CO3" ; "THF" ; CC(C)(C)OC(=O)N1C[C@H](Nc2cccc(-c3cnc4cnccn34)n2)[C@@H](F)C1]

A mixture of 3-(6-bromo-2-pyridyl)imidazo[1,2-a]pyrazine (0.050 g, 0.181 mmol), tert-butyl (3S,4S)-3-amino-4-fluoro-pyrrolidine-1-carboxylate (0.037 g, 0.182 mmol), (2-dicyclohexylphosphino-2',6'-diisopropoxy-1,1'-biphenyl)[2-(2'-amino-1,1'-biphenyl)]palladium(II)methanesulfonate (0.015 g, 0.018 mmol), and cesium carbonate (0.148 g, 0.454 mmol) in tetrahydrofuran (3 mL) was purged with nitrogen, and was then heated at 80° C. for 2 hours under nitrogen atmosphere. The reaction mixture was then cooled to room temperature, filtered, and concentrated under reduced pressure to provide the title compound: LCMS m/z 399.3 $[M+H]^+$.

Step C. N-((3S,4S)-4-fluoropyrrolidin-3-yl)-6-(imidazo[1,2-a]pyrazin-3-yl)pyridin-2-amine

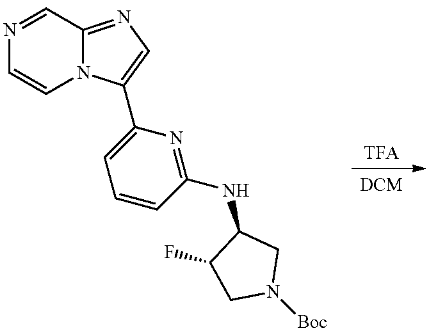

-continued

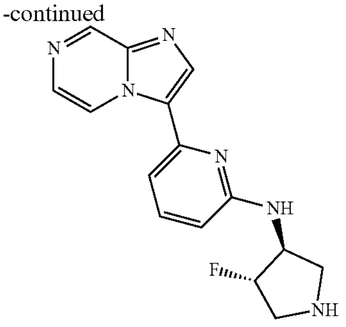

To a solution of tert-butyl (3S,4S)-3-fluoro-4-[(6-imidazo[1,2-a]pyrazin-3-yl-2-pyridyl)amino]pyrrolidine-1-carboxylate (0.080 g, 0.201 mmol) in dichloromethane (3 mL) was added trifluoroacetic acid (0.50 mL). The resulting reaction was stirred at room temperature for 1 hour, and was then filtered and concentrated under reduced pressure. The resulting crude product was purified by HPLC (Phenomenex Luna $C_{18}$ column, 5 micron, 100×40 mm; 1-20% acetonitrile in water containing 0.1% TFA) to provide the title compound: LCMS m/z 299.1 $[M+H]^+$; $^1H$ NMR (400 MHz, $CD_3OD$) δ 9.86 (d, J=4.9 Hz, 1H), 9.13 (s, 1H), 8.44 (s, 1H), 8.00 (d, J=4.9 Hz, 1H), 7.68-7.61 (m, 1H), 7.40-7.35 (m, 1H), 6.64 (d, J=8.2 Hz, 1H), 5.58-5.43 (m, 1H), 4.95-4.89 (m, 1H), 3.97-3.90 (m, 1H), 3.77-3.64 (m, 2H), 3.62-3.56 (m, 1H).

The compounds in Table 11 were all prepared using the synthetic procedures described in Example 14.

TABLE 11

Additional compounds prepared according to Example 14.

| Compound # | Structure | IUPAC Name | LCMS |
|---|---|---|---|
| 69 | 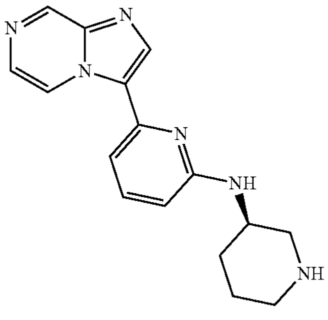 [SMILES: c1cc(N[C@@H]2CCCNC2)nc(-c2cnc3cnccn23)c1] | (R)-6-(imidazo [1,2-a] pyrazin-3-yl)-N-(piperidin-3-yl)pyridin-2-amine | 295.1 |
| 70 | 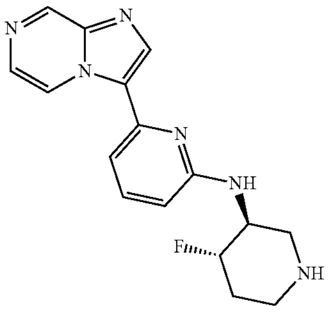 [SMILES: F[C@H]1CCNC[C@@H]1Nc1cccc(-c2cnc3cnccn23)n1] | N-((3S,4S)-4-fluoropiperidin-3-yl)-6-(imidazo[1,2-a]pyrazin-3-yl)pyridin-2-amine | 313.1 |

TABLE 11-continued
| Additional compounds prepared according to Example 14. | | | |
|---|---|---|---|
| Compound # | Structure | IUPAC Name | LCMS |
| 71 | 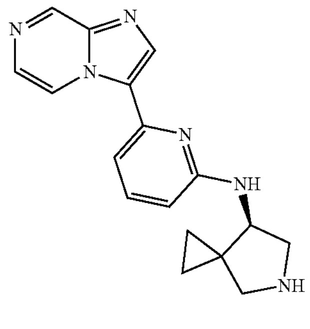 [SMILES: c1cc(N[C@H]2CNCC23CC3)nc(-c2cnc3cnccn23)c1] | (R)-N-(6-(imidazo[1,2-a]pyrazin-3-yl)pyridin-2-yl)-5-azaspiro[2.4]heptan-7-amine | 307.1 |
| 72 | 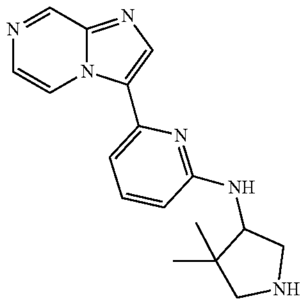 [SMILES: CC1(C)CNCC1Nc1cccc(-c2cnc3cnccn23)n1] | N-[(3S,4S)-4-fluoro-3-piperidyl]-6-(7-isopropoxyimidazo[1,2-a]pyridin-3-yl)pyridin-2-amine | 309.1 |
| 73 | 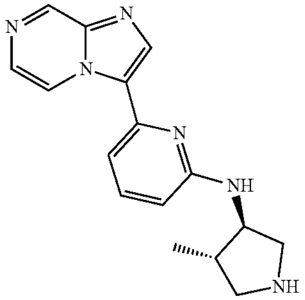 [SMILES: C[C@H]1CNC[C@@H]1Nc1cccc(-c2cnc3cnccn23)n1] | 6-(imidazo[1,2-a]pyrazin-3-yl)-N-((3R,4S)-4-methylpyrrolidin-3-yl)pyridin-2-amine | 295.1 |
| 74 | 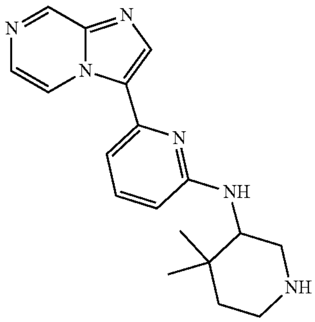 [SMILES: CC1(C)CCNCC1Nc1cccc(-c2cnc3cnccn23)n1] | N-(4,4-dimethylpiperidin-3-yl)-6-(imidazo[1,2-a]pyrazin-3-yl)pyridin-2-amine | 323.1 |

Example 15

Exemplary Synthetic Procedure #15 (Compound 75-76)

Compound 75, (R)-6-(6-(2,2-difluoroethoxy)imidazo[1,2-a]pyrazin-3-yl)-N-(piperidin-3-yl)pyridin-2-amine

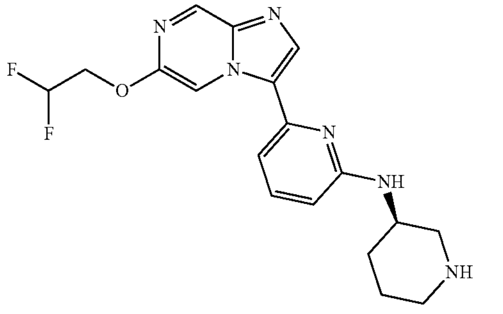 [SMILES: FC(F)COc1cn2c(-c3cccc(N[C@@H]4CCCNC4)n3)cnc2cn1]

Step A. 6-(2,2-difluoroethoxy)imidazo[1,2-a]pyrazine

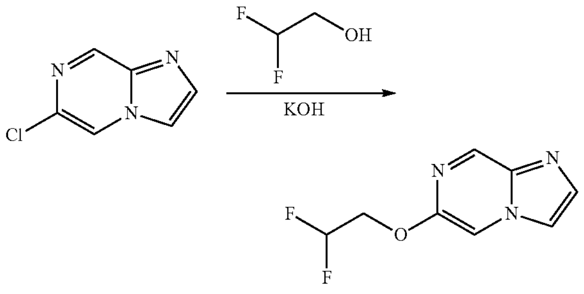

To a solution of 6-chloroimidazo[1,2-a]pyrazine (0.500 g, 3.26 mmol) in 2,2-difluoroethanol (5.34 g, 65.1 mmol, 5.00 mL) was added potassium hydroxide (1.10 g, 19.5 mmol). The resulting mixture was heated at 110° C. for 16 hours, and was then cooled to room temperature, filtered, and concentrated under reduced pressure. The resulting crude product was purified by flash chromatography on silica gel (0-50% ethyl acetate in petroleum ether) to provide the title compound: LCMS m/z 200.0 $[M+H]^+$.

Step B. 3-(6-bromopyridin-2-yl)-6-(2,2-difluoroethoxy)imidazo[1,2-a]pyrazine

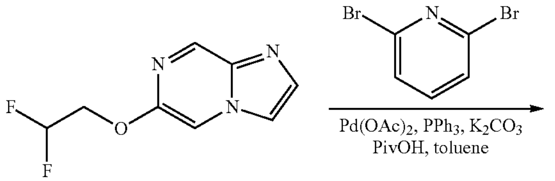

-continued

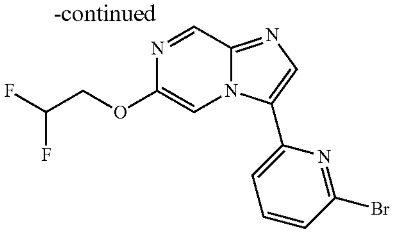

A mixture of 6-(2,2-difluoroethoxy)imidazo[1,2-a]pyrazine (0.230 g, 1.15 mmol), 2,6-dibromopyridine (0.273 g, 1.15 mmol), palladium acetate (0.026 g, 0.115 mmol), triphenylphosphine (0.060 g, 0.231 mmol), 2,2-dimethylpropanoic acid (0.035 g, 0.346 mmol, 0.040 mL), and potassium carbonate (0.487 g, 3.46 mmol) in toluene (10 mL) was purged with nitrogen, and was then heated at 100° C. for 15 hours under nitrogen atmosphere. The reaction mixture was then cooled to room temperature, filtered, and concentrated under reduced pressure. The resulting crude product was purified by flash chromatography on silica gel (0-100% ethyl acetate in petroleum ether) to provide the title compound: LCMS m/z 355.0$[M+H]^+$.

Step C. (R)-tert-butyl 3-((6-(6-(2,2-difluoroethoxy)imidazo[1,2-a]pyrazin-3-yl)pyridin-2-yl)amino)piperidine-1-carboxylate

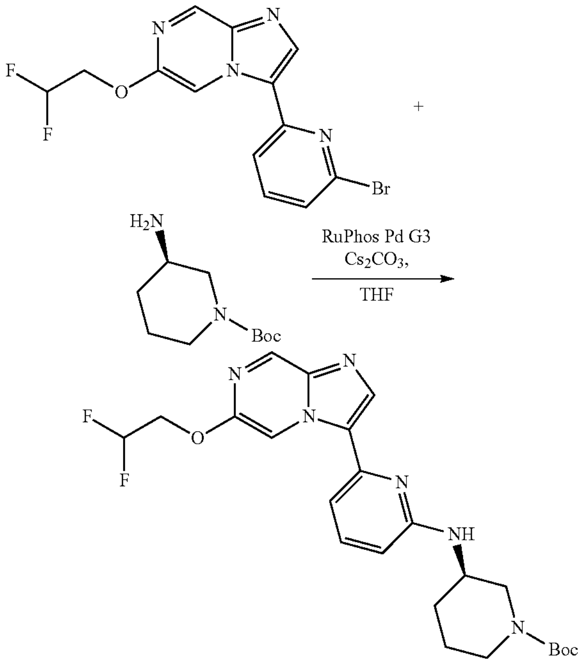

A mixture of 3-(6-bromo-2-pyridyl)-6-(2,2-difluoroethoxy)imidazo[1,2-a]pyrazine (0.050 g, 0.141 mmol), tert-butyl (3R)-3-aminopiperidine-1-carboxylate (0.028 g, 0.141 mmol), (2-dicyclohexylphosphino-2',6'-diisopropoxy-1,1'-biphenyl)[2-(2'-amino-1,1'-biphenyl)]palladium(II)methanesulfonate (0.012 g, 0.014 mmol), and cesium carbonate (0.114 g, 0.352 mmol) in tetrahydrofuran (3.0 mL) was purged with nitrogen, and was then heated at 80° C. for 2 hours under nitrogen atmosphere. The reaction mixture was then cooled to room temperature, filtered, and concentrated under reduced pressure to provide the title compound: LCMS m/z 475.2 $[M+H]^+$.

Step D. (R)-6-(6-(2,2-difluoroethoxy)imidazo[1,2-a]pyrazin-3-yl)-N-(piperidin-3-yl)pyridin-2-amine

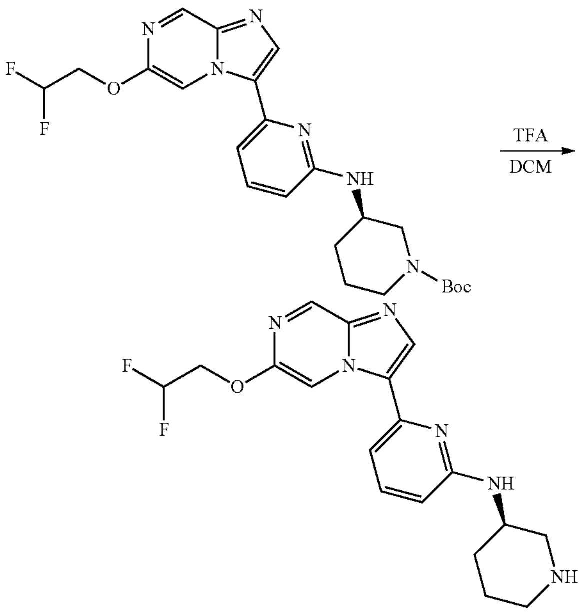

To a solution of tert-butyl (3R)-3-[[6-[6-(2,2-difluoroethoxy)imidazo[1,2-a]pyrazin-3-yl]-2-pyridyl]amino]piperidine-1-carboxylate (0.070 g, 0.148 mmol) in dichloromethane (3 mL) was added trifluoroacetic acid (0.500 mL). The resulting reaction was stirred at room temperature for 1 hour, and was then filtered and concentrated under reduced pressure. The resulting crude product was purified by HPLC (Phenomenex Luna $C_{18}$ column, 5 micron, 100×25 mm; 5-45% acetonitrile in water containing 0.1% TFA) to provide the title compound: LCMS m/z 375.1 $[M+H]^+$; $^1H$ NMR (400 MHz, $CD_3OD$) δ 9.64 (d, J=1.3 Hz, 1H), 8.81 (d, J=1.2 Hz, 1H), 8.31 (s, 1H), 7.51 (t, J=7.9 Hz, 1H), 7.14 (d, J=7.4 Hz, 1H), 6.47 (d, J=8.3 Hz, 1H), 6.30-6.12 (m, 1H), 4.64 (tt, J=3.5, 14.2 Hz, 2H), 4.05-3.96 (m, 1H), 3.39-3.34 (m, 1H), 3.12-3.04 (m, 1H), 2.80-2.69 (m, 2H), 2.29-2.21 (m, 1H), 1.96-1.76 (m, 2H), 1.66-1.55 (m, 1H).

The compounds in Table 12 were all prepared using the synthetic procedures described in Example 15.

TABLE 12

| Compound # | Structure | IUPAC Name | LCMS |
|---|---|---|---|
| Additional compounds prepared according to Example 15. | | | |
| 76 | 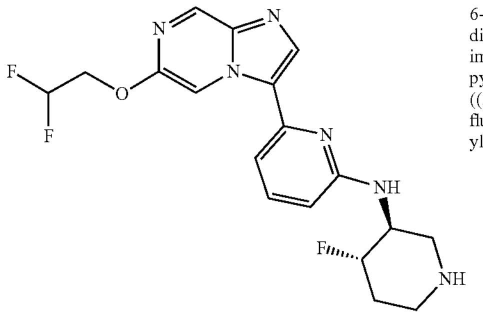 | 6-(6-(2,2-difluoroethoxy) imidazo[1,2-a] pyrazin-3-yl)-N-((3S,4S)-4-fluoropiperidin-3-yl)pyridin-2-amine | 393.1 |

Example 16

Exemplary Synthetic Procedure #16 (Compounds 77-82)

Compounds 77 and 78, Fast- and slow-eluting diastereomers of 1,1,1-trifluoro-2-(3-(6-((3S,4S)-4-fluoropyrrolidin-3-yl)amino)pyridin-2-yl)imidazo[1,2-a]pyrazin-6-yl)propan-2-ol

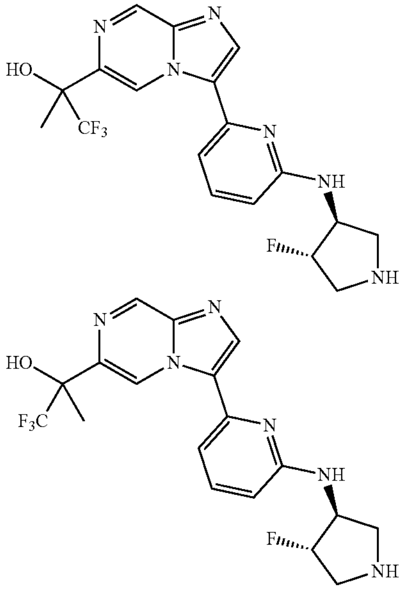

Step A. 6-(1-ethoxyvinyl)imidazo[1,2-a]pyrazine

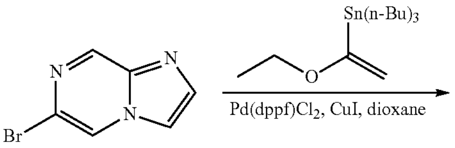

-continued

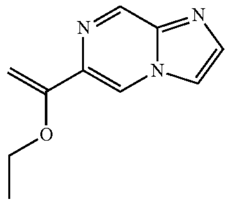

A mixture of 6-bromoimidazo[1,2-a]pyrazine (3.00 g, 15.2 mmol), tributyl(1-ethoxyvinyl)stannane (9.90 g, 27.4 mmol, 9.25 mL), [1,1-bis(diphenylphosphino)ferrocene]dichloropalladium(II) (1.11 g, 1.51 mmol), and cuprous iodide (0.288 g, 1.51 mmol) in dioxane (50 mL) was purged with nitrogen, and was then heated at 110° C. for 16 hours under nitrogen atmosphere. The reaction mixture was then cooled to room temperature, quenched by addition of saturated aqueous potassium fluoride solution (30 mL), poured into water (100 mL), and extracted with ethyl acetate (2×50 mL). The organic extracts were combined, washed with saturated aqueous sodium chloride solution (2×50 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 190.3 $[M+H]^+$.

Step B. 1-imidazo[1,2-a]pyrazin-6-ylethanone

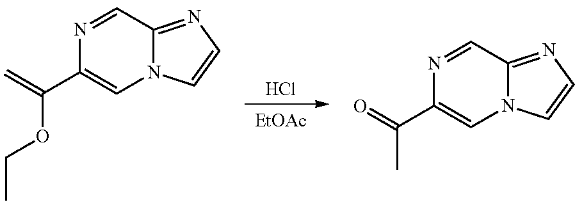

To a solution of 6-(1-ethoxyvinyl)imidazo[1,2-a]pyrazine (0.900 g, 4.76 mmol) in ethyl acetate (5.0 mL) was added hydrochloric acid (0.5 M, 9.51 mL). The resulting reaction was stirred at room temperature for 1 hour, and was then poured into water (20 mL) and extracted with ethyl acetate (3×20 mL). The organic extracts were combined, washed with saturated aqueous sodium chloride solution (10 mL), dried over anhydrous sodium sulfate, filtered, and concentrated under reduced pressure to provide the title compound: LCMS m/z 162.2 $[M+H]^+$; $^1H$ NMR (400 MHz, $CD_3OD$) δ 9.26-9.15 (m, 1H), 9.07-9.00 (m, 1H), 8.21-8.15 (m, 1H), 7.94-7.86 (m, 1H), 2.66 (s, 2H).

Step C. 1,1,1-trifluoro-2-(imidazo[1,2-a]pyrazin-6-yl)propan-2-ol

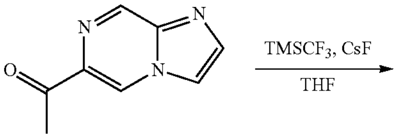

-continued

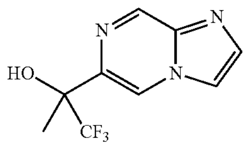

To a solution of 1-imidazo[1,2-a]pyrazin-6-ylethanone (0.900 g, 5.58 mmol) in tetrahydrofuran (10 mL) was added cesium fluoride (2.54 g, 16.8 mmol) and trimethyl(trifluoromethyl)silane (5.16 g, 36.3 mmol). The resulting reaction mixture was stirred at room temperature for 2 hours, and was then poured into water (10 mL) and extracted with ethyl acetate (3×10 mL). The organic extracts were combined, washed with saturated aqueous sodium chloride solution (10 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 232.2 $[M+H]^+$.

Step D. 2-(3-(6-bromopyridin-2-yl)imidazo[1,2-a]pyrazin-6-yl)-1,1,1-trifluoropropan-2-ol

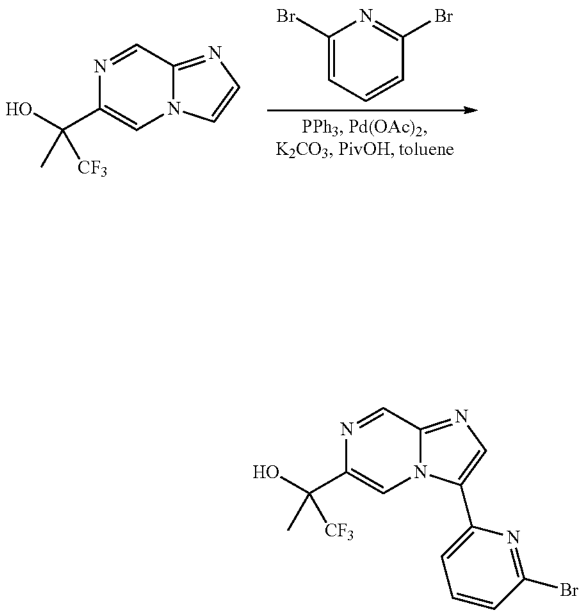

A mixture of 1,1,1-trifluoro-2-imidazo[1,2-a]pyrazin-6-yl-propan-2-ol (0.240 g, 1.04 mmol), 2,6-dibromopyridine (0.737 g, 3.11 mmol), palladium acetate (0.023 g, 0.104 mmol), triphenylphosphine (0.054 g, 0.208 mmol), 2,2-dimethylpropanoic acid (0.031 g, 0.311 mmol, 0.036 mL), and potassium carbonate (0.430 g, 3.11 mmol) in toluene (10 mL) was purged with nitrogen, and was then heated at 100° C. for 15 hours under nitrogen atmosphere. The reaction was then cooled to room temperature, filtered, and concentrated under reduced pressure. The resulting crude product was purified by flash chromatography on silica gel (0-100% ethyl acetate in petroleum ether) to provide the title compound: LCMS m/z 387.1 $[M+H]^+$.

Step E. (3S,4S)-tert-butyl 3-fluoro-4-((6-(6-(1,1,1-trifluoro-2-hydroxypropan-2-yl)imidazo[1,2-a]pyrazin-3-yl)pyridin-2-yl)amino)pyrrolidine-1-carboxylate

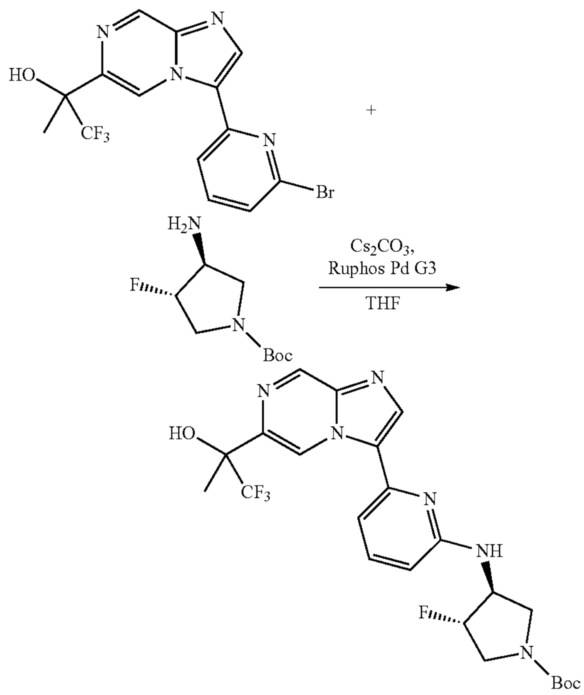

To a solution of 2-[3-(6-bromo-2-pyridyl)imidazo[1,2-a]pyrazin-6-yl]-1,1,1-trifluoro-propan-2-ol (0.080 g, 0.207 mmol) in tetrahydrofuran (3 mL) were added tert-butyl (3S,4S)-3-amino-4-fluoro-pyrrolidine-1-carboxylate (0.042 g, 0.207 mmol), (2-dicyclohexylphosphino-2',6'-diisopropoxy-1,1'-biphenyl)[2-(2'-amino-1,1'-biphenyl)]palladium(II)methanesulfonate (0.017 g, 0.021 mmol), and cesium carbonate (0.168 g, 0.517 mmol). The resulting mixture was purged with nitrogen, and was then heated at 80° C. for 2 hours under nitrogen atmosphere. The reaction was then cooled to room temperature, filtered, and concentrated under reduced pressure to provide the title compound: LCMS m/z 511.3[M+H]$^+$.

Step F. Fast- and slow-eluting diastereomers of 1,1,1-trifluoro-2-(3-(6-(((3S,4S)-4-fluoropyrrolidin-3-yl)amino)pyridin-2-yl)imidazo[1,2-a]pyrazin-6-yl)propan-2-ol

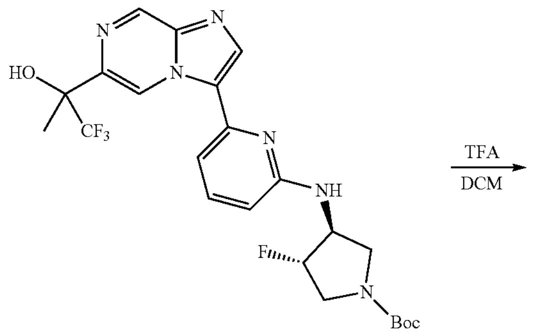

-continued

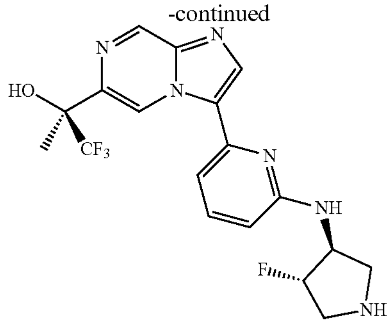

+

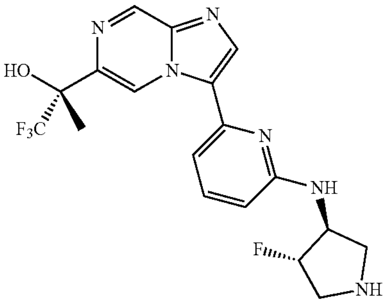

To a solution of tert-butyl (3S,4S)-3-fluoro-4-[[6-[6-(2,2,2-trifluoro-1-hydroxy-1-methyl-ethyl)imidazo[1,2-a]pyrazin-3-yl]-2-pyridyl]amino]pyrrolidine-1-carboxylate (0.080 g, 0.157 mmol) in dichloromethane (3.0 mL) was added trifluoroacetic acid (0.77 g, 6.8 mmol, 0.50 mL). The resulting reaction was stirred at room temperature for 1 hour, and was then filtered and concentrated under reduced pressure. The resulting crude product was purified by HPLC (Phenomenex Luna $C_{18}$ column, 5 micron, 100×40 mm; 5-27% acetonitrile in water containing 0.1% TFA) to provide the title compounds as diastereomers of unknown absolute configuration. Fast-eluting diastereomer: LCMS m/z 411.0 [M+H]$^+$; $^1$H NMR (400 MHz, $CD_3OD$) δ 10.31 (d, J=1.1 Hz, 1H), 9.10-9.06 (m, 1H), 8.47-8.43 (m, 1H), 7.67 (t, J=7.9 Hz, 1H), 7.45-7.40 (m, 1H), 6.69-6.62 (m, 1H), 5.58-5.42 (m, 1H), 4.99-4.94 (m, 1H), 4.04 (br dd, J=4.0, 12.0 Hz, 1H), 3.92-3.72 (m, 3H), 1.91 (s, 3H). Slow-eluting diastereomer: LCMS m/z 411.0 [M+H]$^+$; $^1$H NMR (400 MHz, $CD_3OD$) δ 10.05 (s, 1H), 9.06 (d, J=1.2 Hz, 1H), 8.36 (s, 1H), 7.65 (t, J=7.9 Hz, 1H), 7.35 (d, J=7.5 Hz, 1H), 6.63 (d, J=8.3 Hz, 1H), 5.52-5.37 (m, 1H), 4.96-4.91 (m, 1H), 3.93 (dd, J=5.0, 12.3 Hz, 1H), 3.85-3.75 (m, 1H), 3.74-3.66 (m, 2H), 1.88 (s, 3H).

The compounds in Table 13 were all prepared using the synthetic procedures described in Example 16.

TABLE 13

| Additional compounds prepared according to Example 16. | | | |
|---|---|---|---|
| Compound # | Structure | IUPAC Name | LCMS |
| 79 | 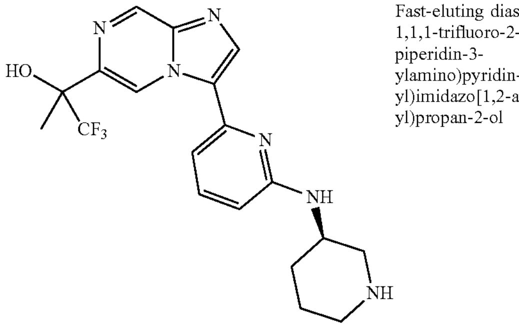 | Fast-eluting diastereomer of 1,1,1-trifluoro-2-(3-(6-((R)-piperidin-3-ylamino)pyridin-2-yl)imidazo[1,2-a]pyrazin-6-yl)propan-2-ol | 407.0 |
| 80 | 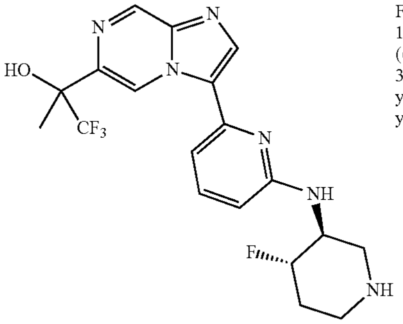 | Fast-eluting diastereomer of 1,1,1-trifluoro-2-(3-(6-(((3S,4S)-4-fluoropiperidin-3-yl)amino)pyridin-2-yl)imidazo[1,2-a]pyrazin-6-yl)propan-2-ol | 425.1 |
| 81 | 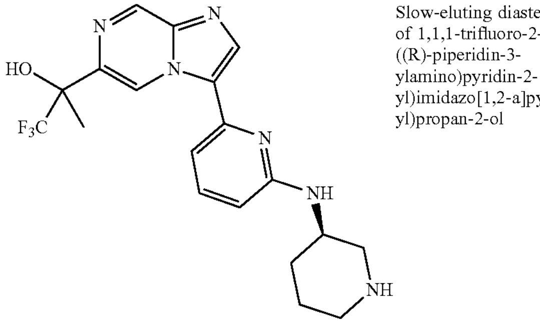 | Slow-eluting diastereomer of 1,1,1-trifluoro-2-(3-(6-((R)-piperidin-3-ylamino)pyridin-2-yl)imidazo[1,2-a]pyrazin-6-yl)propan-2-ol | 407.1 |
| 82 | 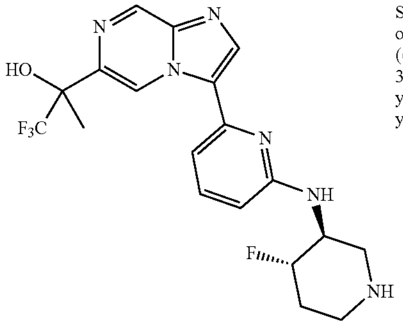 | Slow-eluting diastereomer of 1,1,1-trifluoro-2-(3-(6-(((3S,4S)-4-fluoropiperidin-3-yl)amino)pyridin-2-yl)imidazo[1,2-a]pyrazin-6-yl)propan-2-ol | 425.1 |

Example 17

Exemplary Synthetic Procedure #17 (Compounds 83-94)

Compounds 83 and 84, Fast- and slow-eluting diastereomers of 1,1,1-trifluoro-2-(3-(4-fluoro-6-(((3S,4S)-4-fluoropyrrolidin-3-yl)amino)pyridin-2-yl)imidazo[1,2-a]pyrazin-6-yl)propan-2-ol

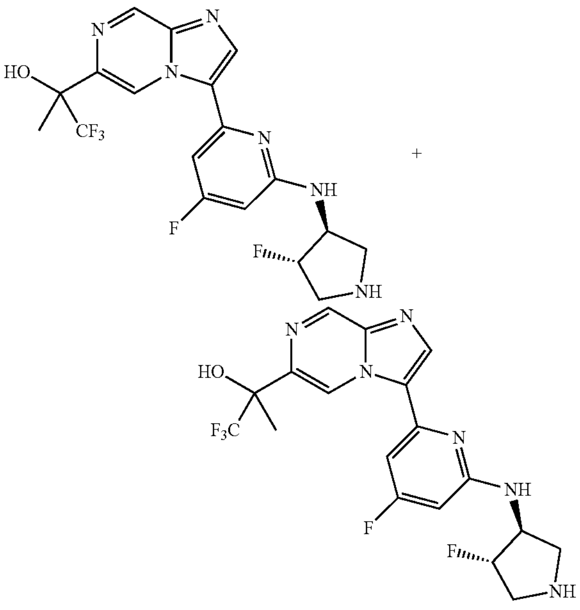

Step A. 2-(3-(6-bromo-4-fluoropyridin-2-yl)imidazo[1,2-a]pyrazin-6-yl)-1,1,1-trifluoropropan-2-ol

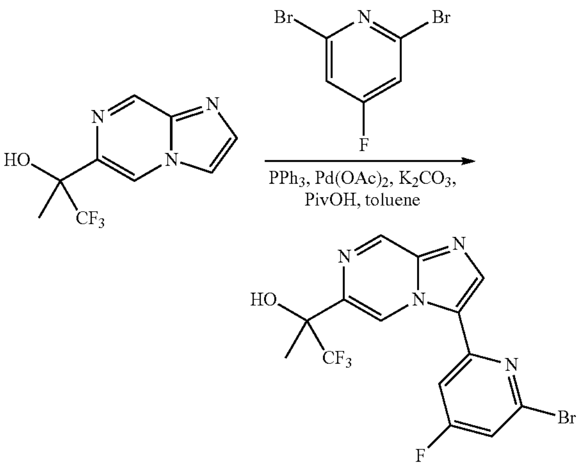

A mixture of 1,1,1-trifluoro-2-imidazo[1,2-a]pyrazin-6-yl-propan-2-ol (0.200 g, 0.865 mmol), 2,6-dibromo-4-fluoro-pyridine (0.243 g, 0.952 mmol), palladium acetate (0.019 g, 0.087 mmol), triphenylphosphine (0.045 g, 0.173 mmol), 2,2-dimethylpropanoic acid (0.027 g, 0.260 mmol, 0.030 mL), and potassium carbonate (0.359 g, 2.60 mmol) in toluene (5 mL) was purged with nitrogen, and was then heated at 120° C. for 18 hours under nitrogen atmosphere. The reaction was then cooled to room temperature, filtered, and concentrated under reduced pressure. The resulting crude product was purified by flash chromatography on silica gel (0-100% ethyl acetate in petroleum ether) to provide the title compound: LCMS m/z 405.1 $[M+H]^+$.

Step B. (3S,4S)-tert-butyl 3-fluoro-4-((4-fluoro-6-(6-(1,1,1-trifluoro-2-hydroxypropan-2-yl)imidazo[1,2-a]pyrazin-3-yl)pyridin-2-yl)amino)pyrrolidine-1-carboxylate

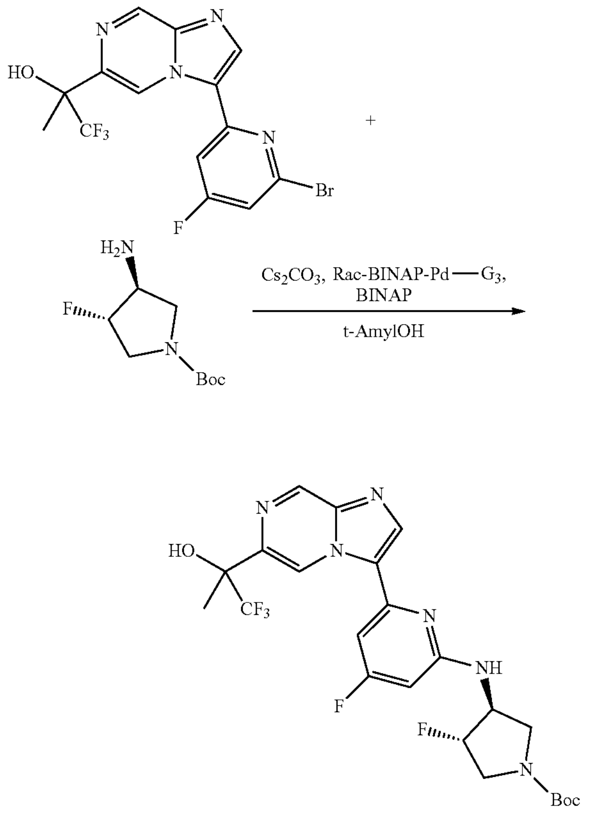

A mixture of 2-[3-(6-bromo-4-fluoro-2-pyridyl)imidazo[1,2-a]pyrazin-6-yl]-1,1,1-trifluoro-propan-2-ol (0.060 g, 0.148 mmol), tert-butyl (3R)-3-aminopiperidine-1-carboxylate (0.030 g, 0.148 mmol), [2-(2-aminophenyl)phenyl]-methylsulfonyloxy-palladium[1-(2-diphenylphosphanyl-1-naphthyl)-2-naphthyl]-diphenyl-phosphane (0.020 g, 0.020 mmol), cesium carbonate (0.129 g, 0.395 mmol), and [1-(2-diphenylphosphanyl-1-naphthyl)-2-naphthyl]-diphenyl-phosphane (0.012 g, 0.020 mmol) in 2-methylbutan-2-ol (3.0 mL) was purged with nitrogen, and was then heated at 100° C. for 5 hours under nitrogen atmosphere. The reaction was then cooled to room temperature, diluted with water (10 mL), and extracted with ethyl acetate (3x10 mL). The organic extracts were combined, washed with saturated aqueous sodium chloride solution (10 mL), dried over anhydrous sodium sulfate, filtered, and concentrated under reduced pressure to provide the title compound: LCMS m/z 525.4$[M+H]^+$.

Step C. Fast- and slow-eluting diastereomers of 1,1,1-trifluoro-2-(3-(4-fluoro-6-(((3S,4S)-4-fluoropyrrolidin-3-yl)amino)pyridin-2-yl)imidazo[1,2-a]pyrazin-6-yl)propan-2-ol

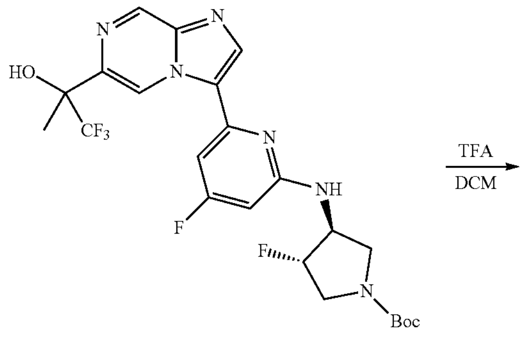

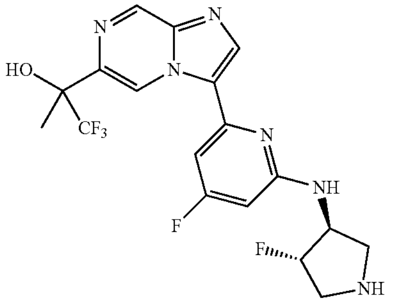

+

-continued

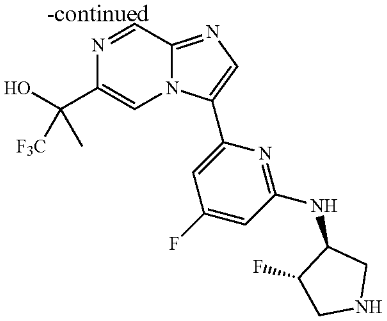

To a solution of tert-butyl (3R)-3-[[4-fluoro-6-[6-(2,2,2-trifluoro-1-hydroxy-1-methyl-ethyl)imidazo[1,2-a]pyrazin-3-yl]-2-pyridyl]amino]piperidine-1-carboxylate (0.050 g, 0.095 mmol) in dichloromethane (3.0 mL) was added trifluoroacetic acid (0.50 mL). The resulting reaction was stirred at room temperature for 1 hour, and was then filtered and concentrated under reduced pressure. The resulting crude product was purified by HPLC (Phenomenex Luna $C_{18}$ column, 3 micron, 100×40 mm; 1-30% acetonitrile in water containing 0.1% TFA) to provide the title compounds as diastereomers of unknown absolute configuration. Fast-eluting diastereomer: LCMS m/z 429.0 $[M+H]^+$; $^1H$ NMR (400 MHz, $CD_3OD$) δ 10.14 (s, 1H), 9.10 (s, 1H), 8.45 (s, 1H), 7.18 (br d, J=9.5 Hz, 1H), 6.37 (dd, J=1.7, 10.9 Hz, 1H), 4.50 (br s, 1H), 3.50-3.39 (m, 2H), 3.25 (br s, 2 H), 2.23-2.14 (i, 2H), 2.00-1.91 (F, 5H). Slow-eluting diastereomer: LCMS m/z 429.0 $[M+H]^+$; $^1H$ NMR (400 MHz, $CD_3OD$) δ 10.04 (d, J=1.0 Hz, 1H), 9.07 (d, J=1.4 Hz, 1H), 8.41 (s, 1H), 7.20 (br dd, J=1.9, 9.5 Hz, 1H), 6.34 (dd, J=1.8, 10.5 Hz, 1H), 5.50-5.35 (m, 1H), 4.96 (br dd, J=4.9, 13.6 Hz, 1H), 3.94 (dd, J=4.8, 12.0 Hz, 1H), 3.83-3.65 (Cp, 3H), 1.88 (s, 3H).

The compounds in Table 14 were all prepared using the synthetic procedures described in Example 17.

TABLE 14

Additional compounds prepared according to Example 17.

| Compound # | Structure | IUPAC Name | LCMS |
|---|---|---|---|
| 85 | 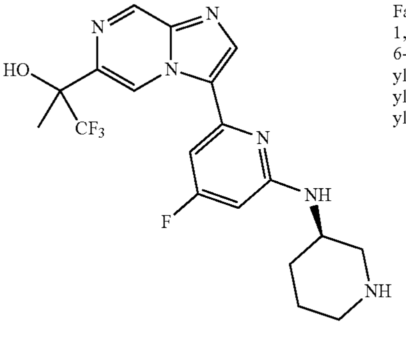 | Fast-eluting diastereomer of 1,1,1-trifluoro-2-(3-(4-fluoro-6-((R)-piperidin-3-ylamino)pyridin-2-yl)imidazo[1,2-a]pyrazin-6-yl)propan-2-ol | 425.1 |

TABLE 14-continued

| Additional compounds prepared according to Example 17. | | | |
|---|---|---|---|
| Compound # | Structure | IUPAC Name | LCMS |
| 86 | 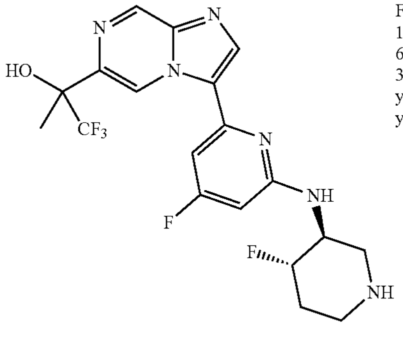 | Fast-eluting diastereomer of 1,1,1-trifluoro-2-(3-(4-fluoro-6-(((3S,4S)-4-fluoropiperidin-3-yl)amino)pyridin-2-yl)imidazo[1,2-a]pyrazin-6-yl)propan-2-ol | 443.0 |
| 87 | 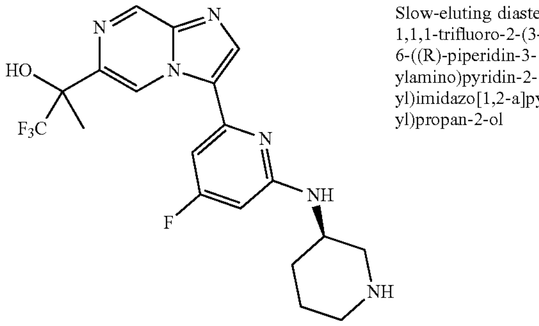 | Slow-eluting diastereomer of 1,1,1-trifluoro-2-(3-(4-fluoro-6-((R)-piperidin-3-ylamino)pyridin-2-yl)imidazo[1,2-a]pyrazin-6-yl)propan-2-ol | 425.0 |
| 88 | 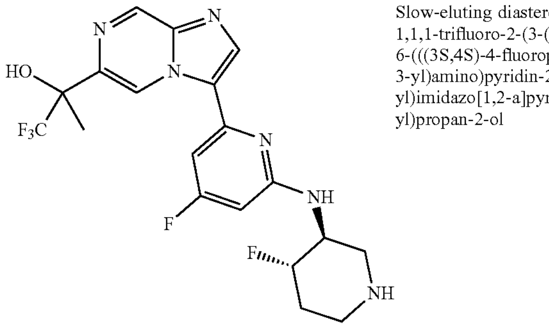 | Slow-eluting diastereomer of 1,1,1-trifluoro-2-(3-(4-fluoro-6-(((3S,4S)-4-fluoropiperidin-3-yl)amino)pyridin-2-yl)imidazo[1,2-a]pyrazin-6-yl)propan-2-ol | 443.0 |
| 89 | 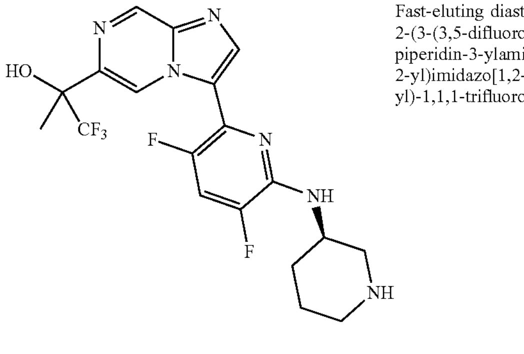 | Fast-eluting diastereomer of 2-(3-(3,5-difluoro-6-((R)-piperidin-3-ylamino)pyridin-2-yl)imidazo[1,2-a]pyrazin-6-yl)-1,1,1-trifluoropropan-2-ol | 443.0 |

TABLE 14-continued

| Additional compounds prepared according to Example 17. | | | |
|---|---|---|---|
| Compound # | Structure | IUPAC Name | LCMS |
| 90 | 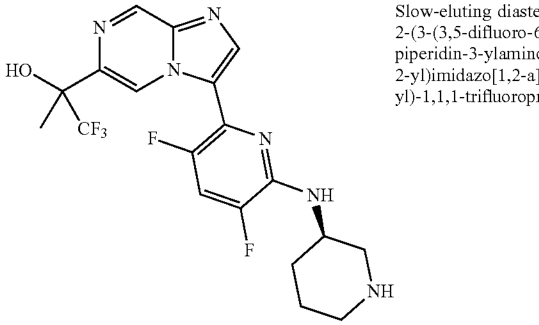 | Slow-eluting diastereomer of 2-(3-(3,5-difluoro-6-((R)-piperidin-3-ylamino)pyridin-2-yl)imidazo[1,2-a]pyrazin-6-yl)-1,1,1-trifluoropropan-2-ol | 443.0 |
| 91 | 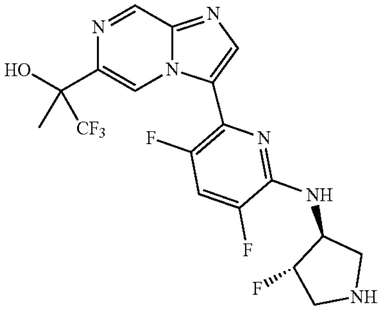 [SMILES: CC(O)(c1cn2c(-c3nc(N[C@H]4CNC[C@@H]4F)c(F)cc3F)cnc2cn1)C(F)(F)F] | Fast-eluting diastereomer of 2-(3-(3,5-difluoro-6-(((3S,4S)-4-fluoropyrrolidin-3-yl)amino)pyridin-2-yl)imidazo[1,2-a]pyrazin-6-yl)-1,1,1-trifluoropropan-2-ol | 447.0 |
| 92 | 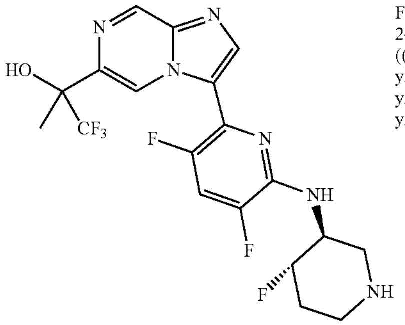 | Fast-eluting diastereomer of 2-(3-(3,5-difluoro-6-(((3S,4S)-4-fluoropiperidin-3-yl)amino)pyridin-2-yl)imidazo[1,2-a]pyrazin-6-yl)-1,1,1-trifluoropropan-2-ol | 461.0 |
| 93 | 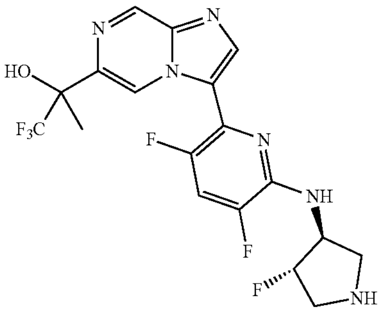 [SMILES: CC(O)(c1cn2c(-c3nc(N[C@H]4CNC[C@@H]4F)c(F)cc3F)cnc2cn1)C(F)(F)F] | Slow-eluting diastereomer of 2-(3-(3,5-difluoro-6-(((3S,4S)-4-fluoropyrrolidin-3-yl)amino)pyridin-2-yl)imidazo[1,2-a]pyrazin-6-yl)-1,1,1-trifluoropropan-2-ol | 447.0 |

TABLE 14-continued

| Additional compounds prepared according to Example 17. | | | |
|---|---|---|---|
| Compound # | Structure | IUPAC Name | LCMS |
| 94 | 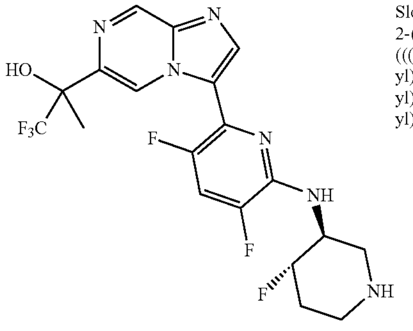 | Slow-eluting diastereomer of 2-(3-(3,5-difluoro-6-(((3S,4S)-4-fluoropiperidin-3-yl)amino)pyridin-2-yl)imidazo[1,2-a]pyrazin-6-yl)-1,1,1-trifluoropropan-2-ol | 461.1 |

Example 18

Exemplary Synthetic Procedure #18 (Compounds 95-106)

Compound 95, 2-(3-(6-(((3S,4S)-4-fluoropyrrolidin-3-yl)amino)pyridin-2-yl)imidazo[1,2-a]pyrazin-6-yl)isothiazolidine 1,1-dioxide

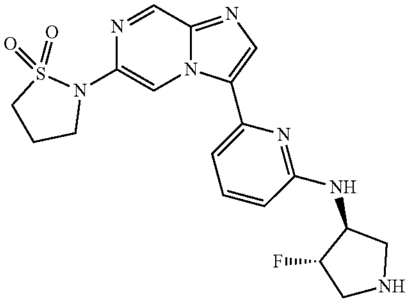 [SMILES: O=S1(=O)CCCN1c1cn2c(-c3cccc(N[C@H]4CNC[C@@H]4F)n3)cnc2cn1]

Step A. 2-(imidazo[1,2-a]pyrazin-6-yl)isothiazolidine 1,1-dioxide

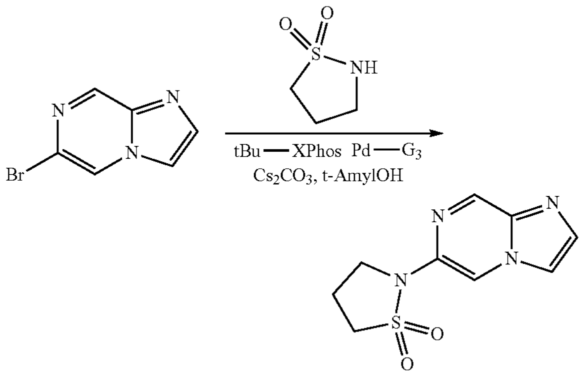

A mixture of 6-bromoimidazo[1,2-a]pyrazine (2.00 g, 10.1 mmol), 1,2-thiazolidine 1,1-dioxide (2.45 g, 20.2 mmol), [2-(2-aminophenyl)phenyl]-methylsulfonyloxy-palladium ditert-butyl-[2-(2,4,6-triisopropylphenyl)phenyl]phosphane (0.802 g, 1.01 mmol), and cesium carbonate (6.58 g, 20.2 mmol) in 2-methylbutan-2-ol (50 mL) was purged with nitrogen, and was then heated at 90° C. for 10 hours under nitrogen atmosphere. The reaction was then cooled to room temperature, diluted with water (50 mL), and extracted with ethyl acetate (3×25 mL). The organic extracts were combined, washed with saturated aqueous sodium chloride solution (50 mL), dried over anhydrous sodium sulfate, filtered, and concentrated under reduced pressure. The resulting crude product was purified by flash chromatography on silica gel (0-100% ethyl acetate in petroleum ether) to provide the title compound: LCMS m/z 239.2 $[M+H]^+$.

Step B. 2-(3-(6-bromopyridin-2-yl)imidazo[1,2-a]pyrazin-6-yl)isothiazolidine 1,1-dioxide

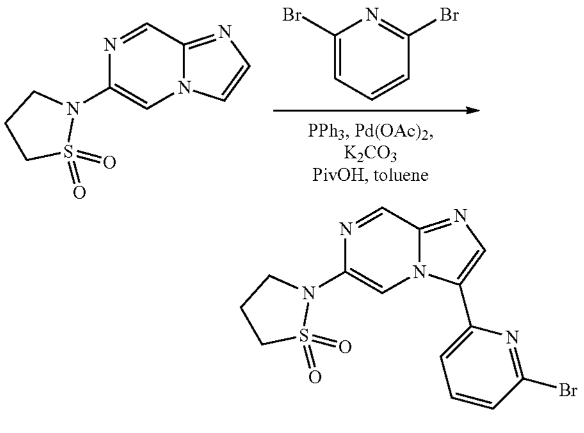

A mixture of 2-imidazo[1,2-a]pyrazin-6-yl-1,2-thiazolidine 1,1-dioxide (0.280 g, 1.18 mmol), 2,6-dibromopyridine (0.835 g, 3.53 mmol), palladium acetate (0.026 g, 0.118 mmol), triphenylphosphine (0.062 g, 0.235 mmol), 2,2-dimethylpropanoic acid (0.036 g, 0.353 mmol, 0.041 mL), and potassium carbonate (0.487 g, 3.53 mmol) in toluene (10 mL) was purged with nitrogen, and was then heated at 100° C. for 10 hours under nitrogen atmosphere. The reaction was then cooled to room temperature, filtered, and concentrated under reduced pressure. The crude product was purified by flash chromatography on silica gel (0-50% ethyl acetate in petroleum ether) to provide the title compound: LCMS m/z 394.1[M+H]$^+$.

Step C. (3S,4S)-tert-butyl 3-((6-(6-(1,1-dioxidoisothiazolidin-2-yl)imidazo[1,2-a]pyrazin-3-yl)pyridin-2-yl)amino)-4-fluoropyrrolidine-1-carboxylate

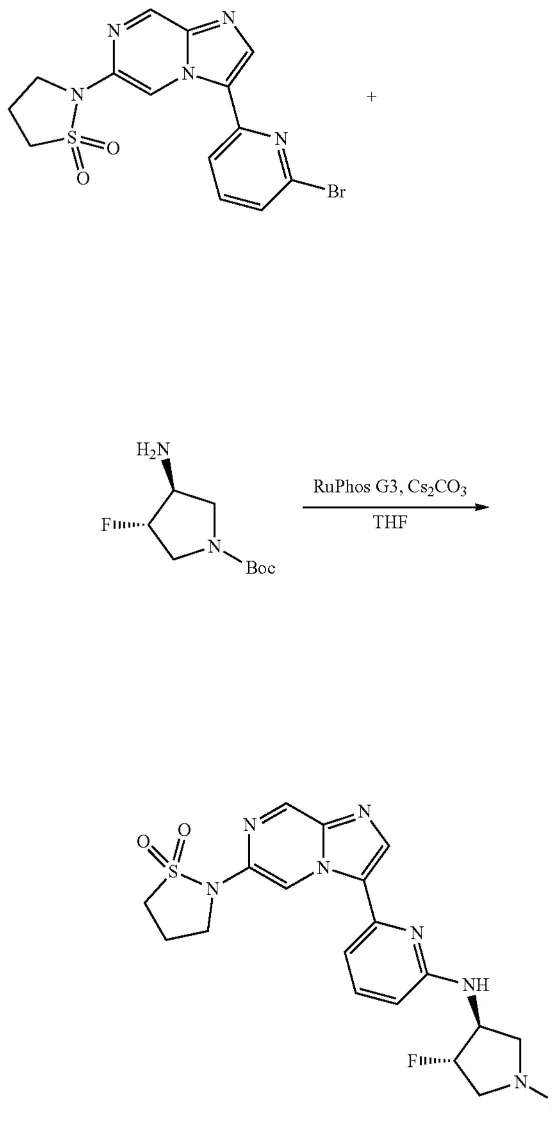

A mixture of 2-[3-(6-bromo-2-pyridyl)imidazo[1,2-a]pyrazin-6-yl]-1,2-thiazolidine 1,1-dioxide (0.050 g, 0.127 mmol), tert-butyl (3S,4S)-3-amino-4-fluoro-pyrrolidine-1-carboxylate (0.026 g, 0.127 mmol), (2-dicyclohexylphosphino-2',6'-diisopropoxy-1,1'-biphenyl)[2-(2'-amino-1,1'-biphenyl)]palladium(II)methanesulfonate (0.011 g, 0.013 mmol), and cesium carbonate (0.103 g, 0.317 mmol) in tetrahydrofuran (3 mL) was purged with nitrogen, and was then heated at 80° C. for 2 hours under nitrogen atmosphere. The reaction was then cooled to room temperature, filtered, and concentrated under reduced pressure to provide the title compound: LCMS m/z 518.3 [M+H]$^+$.

Step D. 2-(3-(6-(((3S,4S)-4-fluoropyrrolidin-3-yl)amino)pyridin-2-yl)imidazo[1,2-a]pyrazin-6-yl)isothiazolidine 1,1-dioxide

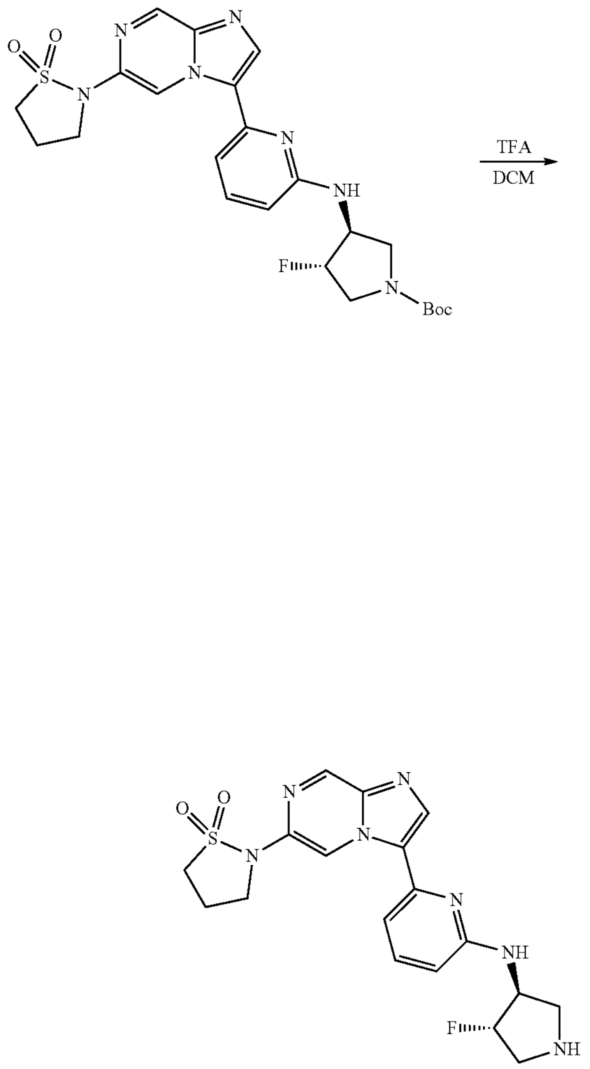

To a solution of tert-butyl (3S,4S)-3-[[6-[6-(1,1-dioxo-1,2-thiazolidin-2-yl)imidazo[1,2-a]pyrazin-3-yl]-2-pyridyl]amino]-4-fluoro-pyrrolidine-1-carboxylate (0.010 g, 0.019 mmol) in dichloromethane (2 mL) was added trifluoroacetic acid (0.50 mL). The mixture was stirred at room temperature for one hour, and was then filtered and concentrated under reduced pressure. The resulting crude product was purified by HPLC (Phenomenex Luna $C_{18}$ column, 5 micron, 100×40 mm; 10-40% acetonitrile in water containing 0.1% TFA) to provide the title compound: LCMS m/z 418.0 [M+H]$^+$; $^1$H NMR (400 MHz, $CD_3OD$) δ 9.69 (d, J=1.1 Hz, 1H), 8.97 (d, J=1.2 Hz, 1H), 8.34 (s, 1H), 7.62 (t, J=7.9 Hz, 1H), 7.31 (d, J=7.5 Hz, 1H), 6.61 (d, J=8.3 Hz, 1H), 5.47-5.32 (m, 1H), 5.10-5.04 (m, 1H), 4.19-4.12 (m, 1H), 4.06-3.99 (m, 2H), 3.79-3.67 (m, 2H), 3.58-3.47 (m, 3H), 2.58 (quin, J=6.9 Hz, 2H).

The compounds in Table 15 were all prepared using the synthetic procedures described in Example 18.

TABLE 15

| Additional compounds prepared according to Example 18. | | | |
|---|---|---|---|
| Compound # | Structure | IUPAC Name | LCMS |
| 96 | 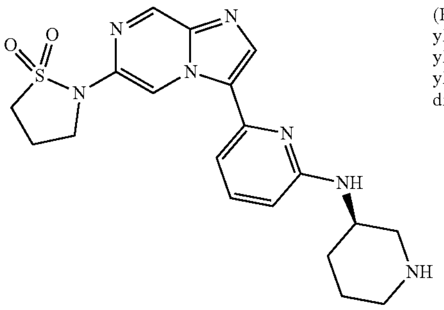 | (R)-2-(3-(6-(piperidin-3-ylamino)pyridin-2-yl)imidazo[1,2-a]pyrazin-6-yl)isothiazolidine 1,1-dioxide | 414.1 |
| 97 | 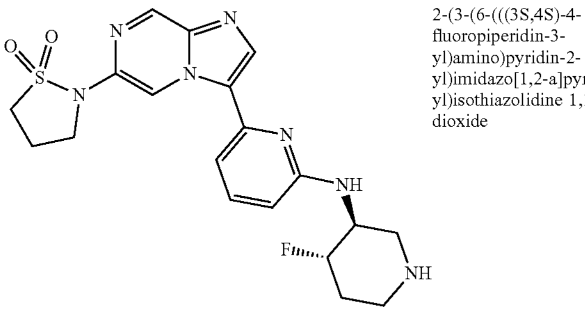 | 2-(3-(6-(((3S,4S)-4-fluoropiperidin-3-yl)amino)pyridin-2-yl)imidazo[1,2-a]pyrazin-6-yl)isothiazolidine 1,1-dioxide | 432.0 |
| 98 | 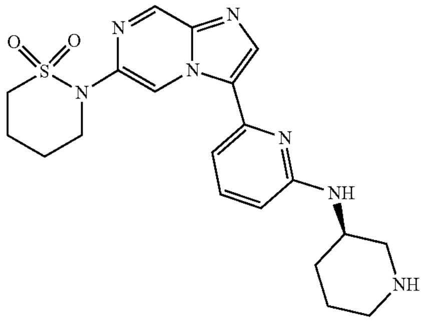 [SMILES: O=S1(=O)CCCCN1c1cn2c(-c3cccc(N[C@@H]4CCCNC4)n3)cnc2cn1] | (R)-2-(3-(6-(piperidin-3-ylamino)pyridin-2-yl)imidazo[1,2-a]pyrazin-6-yl)-1,2-thiazinane 1,1-dioxide | 428.1 |
| 99 | 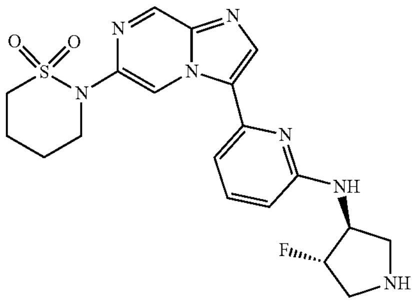 [SMILES: O=S1(=O)CCCCN1c1cn2c(-c3cccc(N[C@H]4CNC[C@@H]4F)n3)cnc2cn1] | 2-(3-(6-(((3S,4S)-4-fluoropyrrolidin-3-yl)amino)pyridin-2-yl)imidazo[1,2-a]pyrazin-6-yl)-1,2-thiazinane 1,1-dioxide | 431.15 |

TABLE 15-continued

| Additional compounds prepared according to Example 18. | | | |
|---|---|---|---|
| Compound # | Structure | IUPAC Name | LCMS |
| 100 | 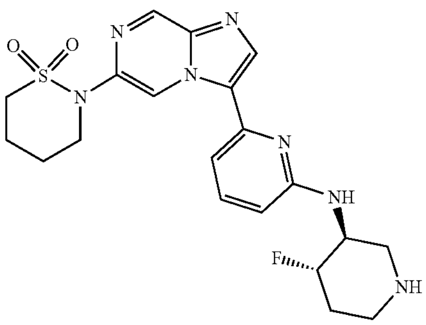 [SMILES: O=S1(=O)CCCCN1c1cn2c(-c3cccc(N[C@H]4CNCC[C@@H]4F)n3)cnc2cn1] | 2-(3-(6-(((3S,4S)-4-fluoropiperidin-3-yl)amino)pyridin-2-yl)imidazo[1,2-a]pyrazin-6-yl)-1,2-thiazinane 1,1-dioxide | 445.17 |
| 101 | 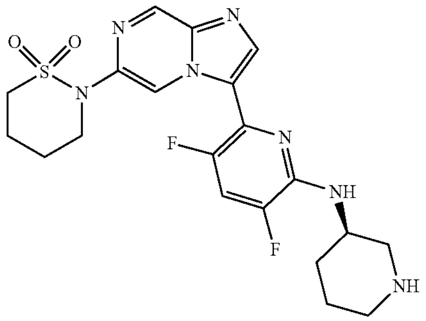 [SMILES: O=S1(=O)CCCCN1c1cn2c(-c3nc(N[C@@H]4CCCNC4)c(F)cc3F)cnc2cn1] | (R)-2-(3-(3,5-difluoro-6-(piperidin-3-ylamino)pyridin-2-yl)imidazo[1,2-a]pyrazin-6-yl)-1,2-thiazinane 1,1-dioxide | 464.1 |
| 102 | 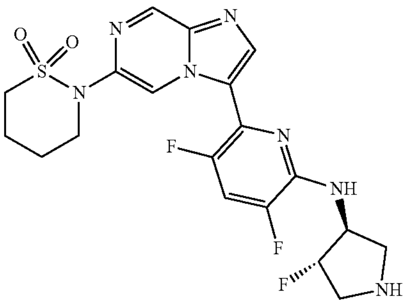 [SMILES: O=S1(=O)CCCCN1c1cn2c(-c3nc(N[C@H]4CNC[C@@H]4F)c(F)cc3F)cnc2cn1] | 2-(3-(3,5-difluoro-6-(((3S,4S)-4-fluoropyrrolidin-3-yl)amino)pyridin-2-yl)imidazo[1,2-a]pyrazin-6-yl)-1,2-thiazinane 1,1-dioxide | 468.2 |
| 103 | 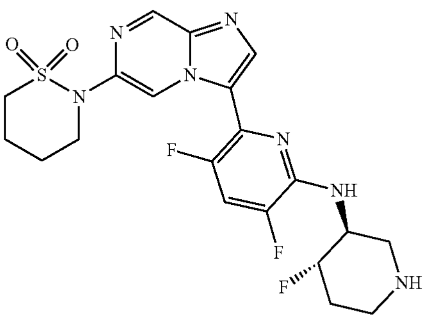 [SMILES: O=S1(=O)CCCCN1c1cn2c(-c3nc(N[C@H]4CNCC[C@@H]4F)c(F)cc3F)cnc2cn1] | 2-(3-(3,5-difluoro-6-(((3S,4S)-4-fluoropiperidin-3-yl)amino)pyridin-2-yl)imidazo[1,2-a]pyrazin-6-yl)-1,2-thiazinane 1,1-dioxide | 482.0 |

TABLE 15-continued

| Compound # | Structure | IUPAC Name | LCMS |
| --- | --- | --- | --- |
| Additional compounds prepared according to Example 18. | | | |
| 104 | 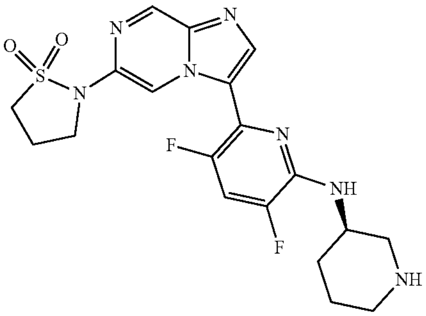 [SMILES: O=S1(=O)CCCN1c1cn2c(-c3nc(N[C@@H]4CCCNC4)c(F)cc3F)cnc2cn1] | (R)-2-(3-(3,5-difluoro-6-(piperidin-3-ylamino)pyridin-2-yl)imidazo[1,2-a]pyrazin-6-yl)isothiazolidine 1,1-dioxide | 450.2 |
| 105 | 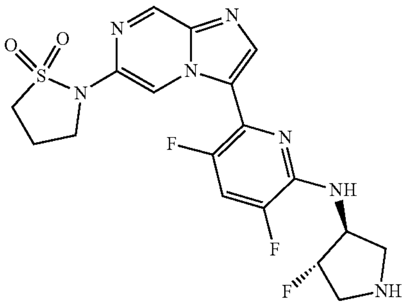 [SMILES: O=S1(=O)CCCN1c1cn2c(-c3nc(N[C@H]4CNC[C@@H]4F)c(F)cc3F)cnc2cn1] | 2-(3-(3,5-difluoro-6-(((3S,4S)-4-fluoropyrrolidin-3-yl)amino)pyridin-2-yl)imidazo[1,2-a]pyrazin-6-yl)isothiazolidine 1,1-dioxide | 454.2 |
| 106 | 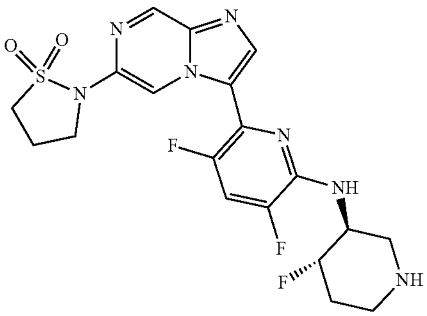 [SMILES: O=S1(=O)CCCN1c1cn2c(-c3nc(N[C@H]4CNCC[C@@H]4F)c(F)cc3F)cnc2cn1] | 2-(3-(3,5-difluoro-6-(((3S,4S)-4-fluoropiperidin-3-yl)amino)pyridin-2-yl)imidazo[1,2-a]pyrazin-6-yl)isothiazolidine 1,1-dioxide | 468.0 |

Example 19

Exemplary Synthetic Procedure #19 (Compounds 107-115)

Compound 107, 1-[3-[3,5-difluoro-6-[[(3 S,4 S)-4-fluoro-3-piperidyl]amino]-2-pyridyl]imidazo[1,2-a]pyrazin-6-yl]pyrrolidin-2-one

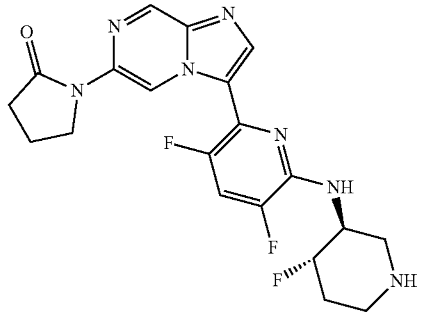 [SMILES: O=C1CCCN1c1cn2c(-c3nc(N[C@H]4CNCC[C@@H]4F)c(F)cc3F)cnc2cn1]

Step A. 1-(imidazo[1,2-a]pyrazin-6-yl)pyrrolidin-2-one

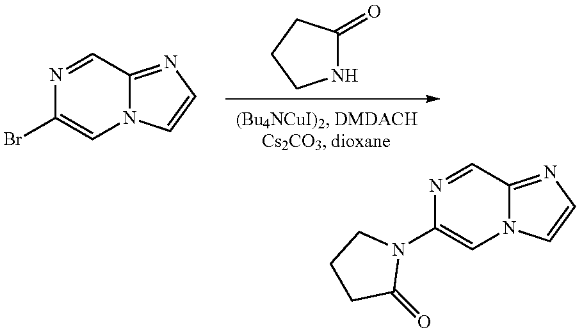

A mixture of 6-bromoimidazo[1,2-a]pyrazine (5.00 g, 25.3 mmol), pyrrolidin-2-one (2.58 g, 30.3 mmol), cesium carbonate (24.7 g, 75.8 mmol), (1R,2R)—N1,N2-dimethylcyclohexane-1,2-diamine (3.59 g, 25.4 mmol), and bis[(tetrabutylammonium iodide)copper(I) iodide] (1.41 g, 1.26 mmol) in dioxane (70 mL) was purged with nitrogen, and was then heated at 120° C. for 2 hours under nitrogen atmosphere. The reaction was then cooled to room temperature, diluted with water (50 mL), and extracted with ethyl acetate (3x50 mL). The organic extracts were combined, washed with saturated aqueous sodium chloride solution (20 mL), dried over sodium sulfate, filtered, and concentrated under reduced pressure. The resulting crude product was purified by flash silica gel chromatography on silica gel (0-80% ethyl acetate in petroleum ether) to provide the title compound: LCMS m/z 203.3 $[M+H]^+$; $^1H$ NMR (400 MHz, $CD_3OD$), δ 9.31-9.41 (m, 1H), 8.82-8.91 (m, 1H), 8.03-8.11 (m, 1H), 7.80 (d, 1H), 4.11-4.20 (m, 2H), 2.67 (t, 2H), 2.17-2.24 (m, 2H).

Step B. 1-(3-(6-bromo-3,5-difluoropyridin-2-yl)imidazo[1,2-a]pyrazin-6-yl)pyrrolidin-2-one

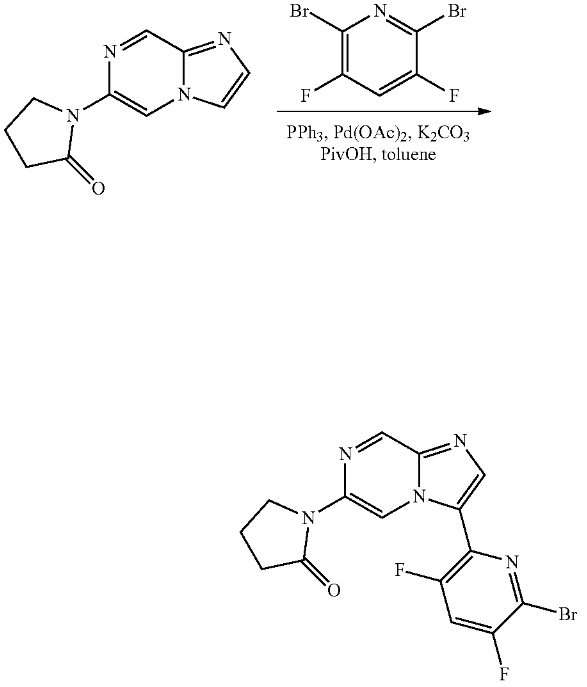

A mixture of 1-(imidazo[1,2-a]pyrazin-6-yl)pyrrolidin-2-one (0.300 g, 1.48 mmol), 2,6-dibromo-3,5-difluoropyridine (0.405 g, 1.48 mmol), triphenylphosphine (0.058 g, 0.223 mmol), palladuim(II)acetate (0.033 g, 0.148 mmol) 2,2-dimethylpropanoic acid (0.045 g, 0.445 mmol), and potassium carbonate (0.615 g, 4.45 mmol) in toluene (10 mL) was purged with nitrogen, and was heated at 100° C. for 16 hours under nitrogen atmosphere. The reaction was then cooled to room temperature, filtered, and concentrated under reduced pressure. The resulting crude product was purified by flash chromatography on silica gel (0-60% ethyl acetate in petroleum ether) to provide the title compound: LCMS m/z 396.1 $[M+H]^+$; $^1H$ NMR (400 MHz, $CD_3OD$), δ 10.74 (d, 1H), 9.03 (d, 1H), 8.42 (d, 1H), 7.94 (dd, 1H), 4.21 (d, 2H), 2.73 (t, 2H), 2.22-2.28 (m, 2H).

Step C. (3S,4S)-tert-butyl 3-((3,5-difluoro-6-(6-(2-oxopyrrolidin-1-yl)imidazo[1,2-a]pyrazin-3-yl)pyridin-2-yl)amino)-4-fluoropiperidine-1-carboxylate

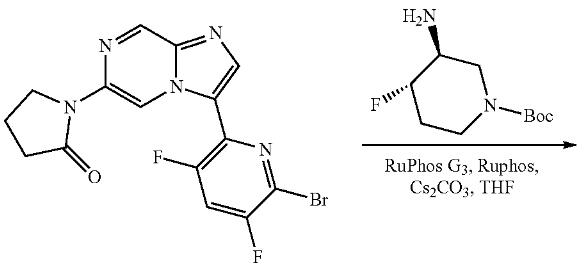

-continued

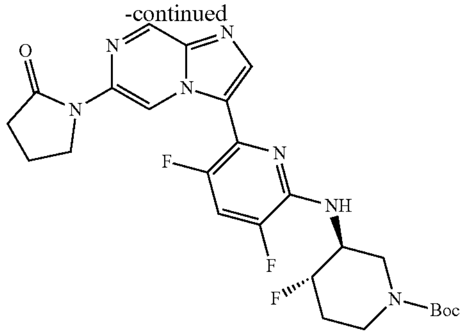

A mixture of 1-(3-(6-bromo-3,5-difluoropyridin-2-yl)imidazo[1,2-a]pyrazin-6-yl)pyrrolidin-2-one (0.050 g, 0.127 mmol), (3S,4S)-tert-butyl 3-amino-4-fluoropiperidine-1-carboxylate (0.028 g, 0.127 mmol), (2-dicyclohexylphosphino-2',6'-diisopropoxy-1,1'-biphenyl)[2-(2'-amino-1,1'-biphenyl)]palladium(II)methanesulfonate (0.011 g, 0.013 mmol), dicyclohexyl-[2-(2,6-diisopropoxyphenyl)phenyl] phosphane (0.012 g, 0.025 mmol), and cesium carbonate (0.124 g, 0.381 mmol) in tetrahydrofuran (1 mL) was purged with nitrogen, and was then heated at 80° C. for 16 hours under nitrogen atmosphere. The reaction was then cooled to room temperature, filtered, and concentrated under reduced pressure to provide the title compound: LCMS m/z 532.3 $[M+H]^+$.

Step D. 1-(3-(3,5-difluoro-6-(((3S,4S)-4-fluoropiperidin-3-yl)amino)pyridin-2-yl)imidazo[1,2-a]pyrazin-6-yl)pyrrolidin-2-one

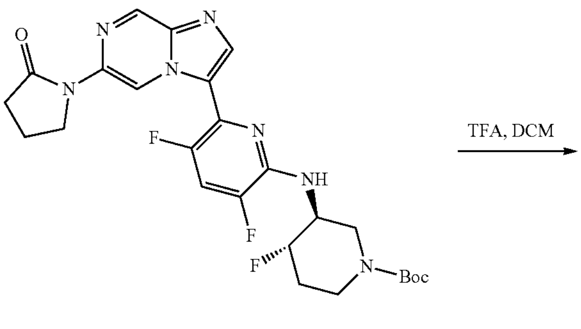

-continued

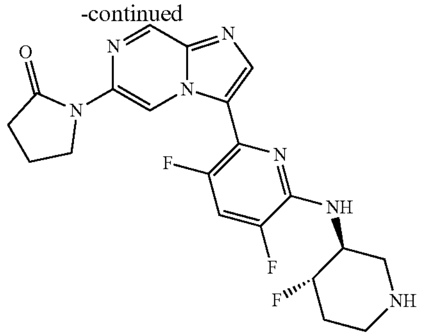

To a solution of (3S,4S)-tert-butyl 3-((3,5-difluoro-6-(6-(2-oxopyrrolidin-1-yl)imidazo[1,2-a]pyrazin-3-yl)pyridin-2-yl)amino)-4-fluoropiperidine-1-carboxylate (0.041 g, 0.077 mmol) in dichloromethane (1 mL) was added trifluoroacetic acid (0.50 mL). The resulting reaction was stirred at room temperature for 1 hour, and was then concentrated under reduced pressure. The resulting crude product was purified by HPLC (Phenomenex Luna $C_{18}$ column, 5 micron, 150×30 mm; 1-35% acetonitrile in water containing 0.04% trifluoroacetic acid) to provide the title compound: LCMS m/z 432.3 $[M+H]^+$; $^1H$ NMR (400 MHz, $CD_3OD$) δ 10.47 (s, 1H)), 9.01 (s, 1H), 8.36 (s, 1H), 7.64 (t, 1H), 5.21 (dd, 1H), 4.67-4.86 (m, 1H), 4.28 (t, 2H), 3.80 (d, 1H), 3.63 (d, 1H), 3.01 (t, 1H), 3.17 (t, 1H), 2.79-2.85 (m, 2H), 2.45 (s, 1H), 2.22-2.33 (m, 2H), 2.08-2.21 (m, 1H).

The compounds in Table 16 were all prepared using the synthetic procedures described in Example 19.

TABLE 16

Additional compounds prepared according to Example 19.

| Compound # | Structure | IUPAC Name | LCMS |
|---|---|---|---|
| 108 | 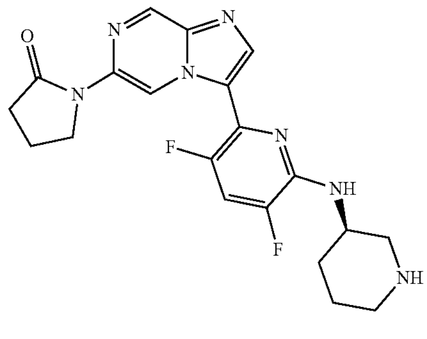 [SMILES: O=C1CCCN1c1cn2c(-c3nc(N[C@@H]4CCCNC4)c(F)cc3F)cnc2cn1] | (R)-1-(3-(3,5-difluoro-6-(piperidin-3-ylamino)pyridin-2-yl)imidazo[1,2-a]pyrazin-6-yl)pyrrolidin-2-one | 414.2 |

TABLE 16-continued

| Compound # | Structure | IUPAC Name | LCMS |
|---|---|---|---|
| Additional compounds prepared according to Example 19. | | | |
| 109 | 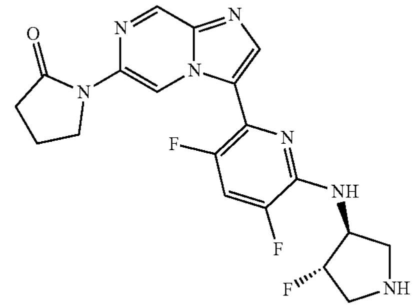 [SMILES: O=C1CCCN1c1cn2c(-c3nc(N[C@H]4CNC[C@@H]4F)c(F)cc3F)cnc2cn1] | 1-(3-(3,5-difluoro-6-(((3S,4S)-4-fluoropyrrolidin-3-yl)amino)pyridin-2-yl)imidazo[1,2-a]pyrazin-6-yl)pyrrolidin-2-one | 418.2 |
| 110 | 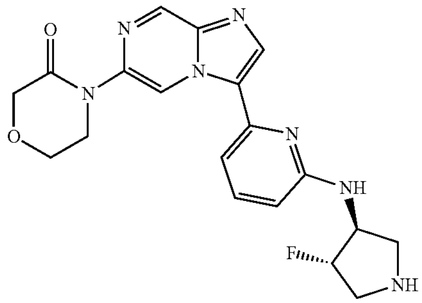 [SMILES: O=C1COCCN1c1cn2c(-c3cccc(N[C@H]4CNC[C@@H]4F)n3)cnc2cn1] | 4-(3-(6-(((3S,4S)-4-fluoropyrrolidin-3-yl)amino)pyridin-2-yl)imidazo[1,2-a]pyrazin-6-yl)morpholin-3-one | 398.17 |
| 111 | 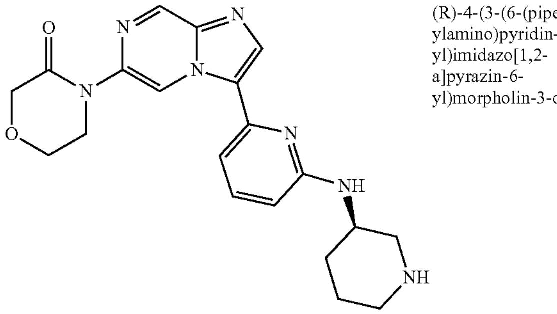 | (R)-4-(3-(6-(piperidin-3-ylamino)pyridin-2-yl)imidazo[1,2-a]pyrazin-6-yl)morpholin-3-one | 394.1 |
| 112 | 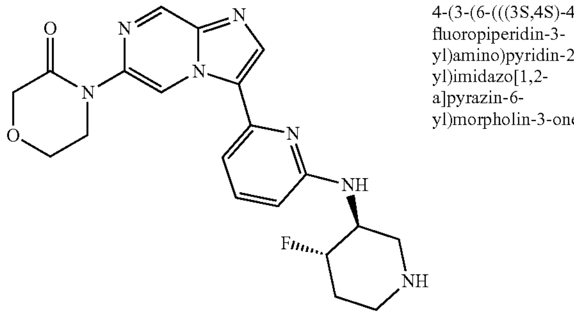 | 4-(3-(6-(((3S,4S)-4-fluoropiperidin-3-yl)amino)pyridin-2-yl)imidazo[1,2-a]pyrazin-6-yl)morpholin-3-one | 412.1 |
| 113 | 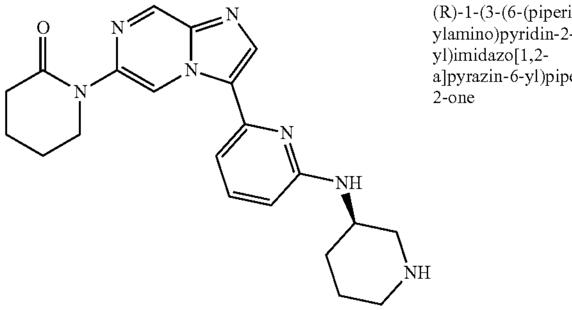 | (R)-1-(3-(6-(piperidin-3-ylamino)pyridin-2-yl)imidazo[1,2-a]pyrazin-6-yl)piperidin-2-one | 392.1 |

TABLE 16-continued

| Additional compounds prepared according to Example 19. | | | |
|---|---|---|---|
| Compound # | Structure | IUPAC Name | LCMS |
| 114 | 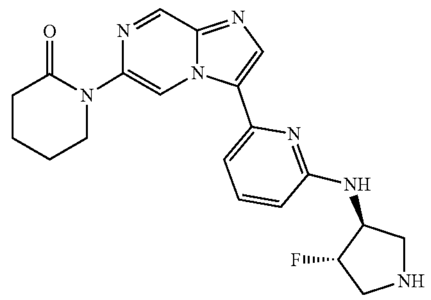 [SMILES: O=C1CCCCN1c1cn2c(-c3cccc(N[C@H]4CNC[C@@H]4F)n3)cnc2cn1] | 1-(3-(6-(((3S,4S)-4-fluoropyrrolidin-3-yl)amino)pyridin-2-yl)imidazo[1,2-a]pyrazin-6-yl)piperidin-2-one | 396.2 |
| 115 | 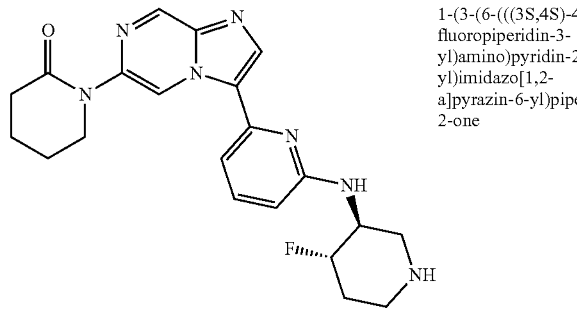 | 1-(3-(6-(((3S,4S)-4-fluoropiperidin-3-yl)amino)pyridin-2-yl)imidazo[1,2-a]pyrazin-6-yl)piperidin-2-one | 410.1 |

Example 20

Exemplary Synthetic Procedure #20 (Compound 116-118)

Compound 116, (R)-1-(3-(6-(piperidin-3-ylamino)pyridin-2-yl)imidazo[1,2-a]pyrazin-6-yl)imidazolidin-2-one

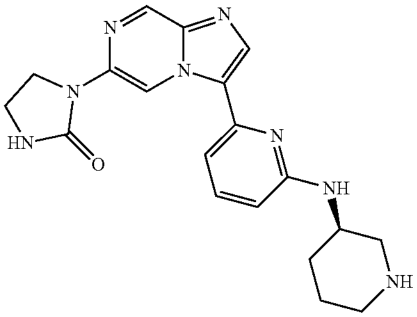 [SMILES: O=C1NCCN1c1cn2c(-c3cccc(N[C@@H]4CCCNC4)n3)cnc2cn1]

Step A. (R)-tert-butyl 3-((6-(6-chloroimidazo[1,2-a]pyrazin-3-yl)pyridin-2-yl)amino)piperidine-1-carboxylate

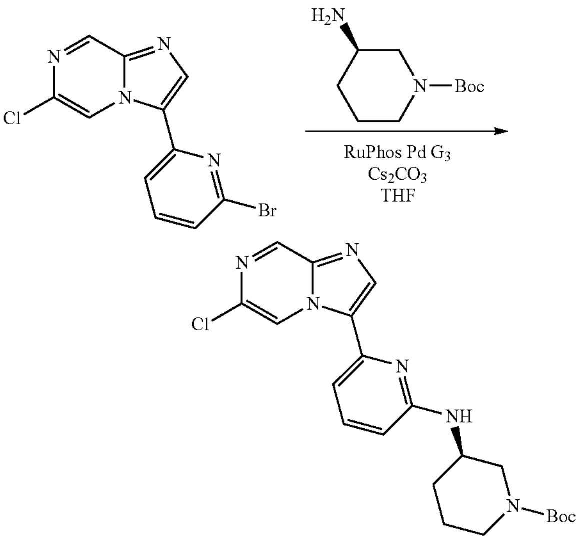

A mixture of 3-(6-bromopyridin-2-yl)-6-chloroimidazo[1,2-a]pyrazine (0.500 g, 1.62 mmol), (R)-tert-butyl 3-aminopiperidine-1-carboxylate (0.324 g, 1.62 mmol), cesium carbonate (1.58 g, 4.85 mmol), and (2-dicyclohexylphosphino-2',6'-diisopropoxy-1,1'-biphenyl)[2-(2'-amino-1,1'-biphenyl)]palladium(II)methanesulfonate (0.135 g, 0.162 mmol) in tetrahydrofuran (10 mL) was purged with nitrogen, and was then heated at 80° C. for 2 hours under nitrogen atmosphere. The reaction was then cooled to room temperature, filtered, concentrated under reduced pressure. The resulting crude product was purified by flash chromatography on silica gel (0-40% ethyl acetate in petroleum ether) to provide the title compound: LCMS m/z 429.3 $[M+H]^+$.

Step B. (R)-tert-butyl 3-((6-(6-(2-oxoimidazolidin-1-yl)imidazo[1,2-a]pyrazin-3-yl)pyridin-2-yl)amino)piperidine-1-carboxylate

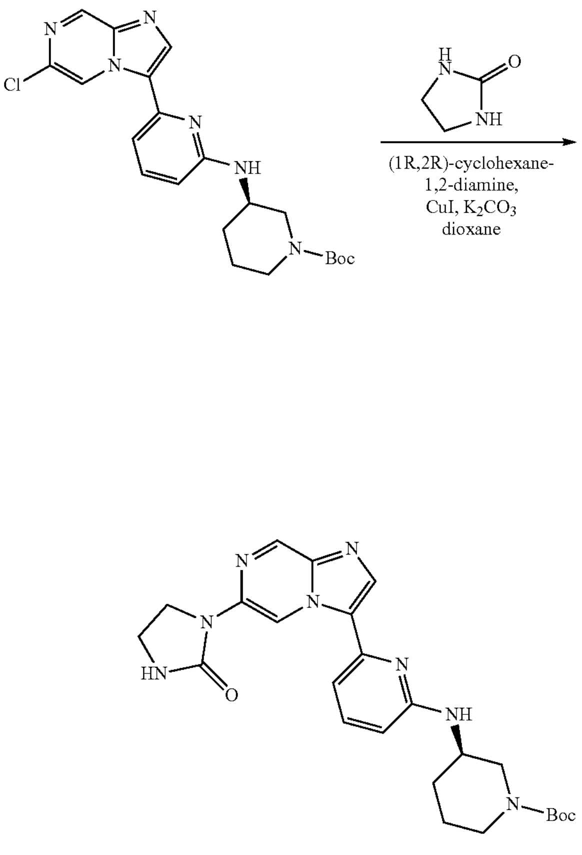

A mixture of (R)-tert-butyl 3-((6-(6-chloroimidazo[1,2-a]pyrazin-3-yl)pyridin-2-yl)amino)piperidine-1-carboxylate (0.060 g, 0.140 mmol), imidazolidin-2-one (0.024 g, 0.280 mmol), copper iodide (0.013 g, 0.070 mmol), (1R,2R)-cyclohexane-1,2-diamine (0.008 g, 0.070 mmol), and potassium carbonate (0.058 g, 0.420 mmol) in dioxane (7 mL) was purged with nitrogen, and was then heated at 120° C. for 16 hours under nitrogen atmosphere. The reaction was then cooled to room temperature, filtered, and concentrated under reduced pressure. The resulting crude product was triturated with ethyl acetate (3x10 mL) to provide the title compound: LCMS m/z 479.4 $[M+H]^+$.

Step C. (R)-1-(3-(6-(piperidin-3-ylamino)pyridin-2-yl)imidazo[1,2-a]pyrazin-6-yl)imidazolidin-2-one

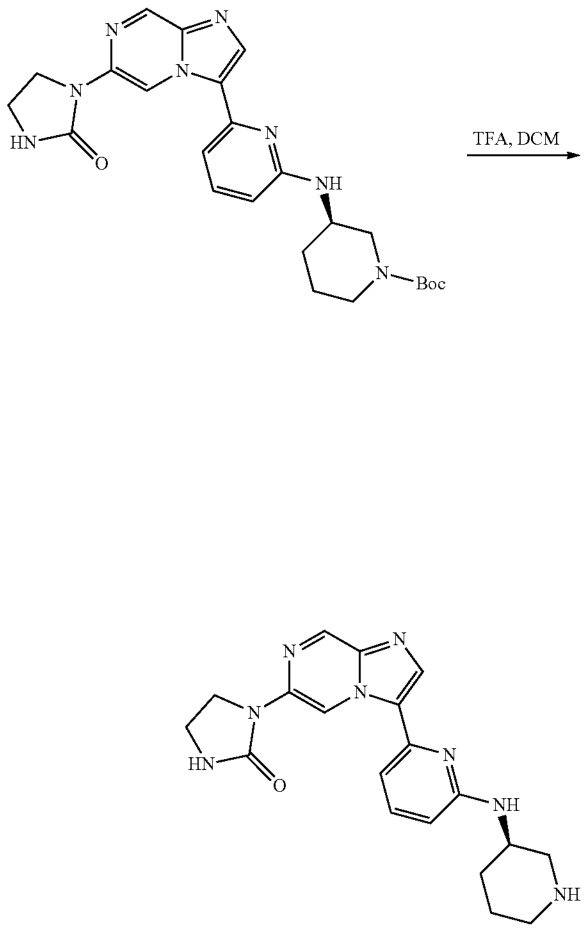

To a solution of (R)-tert-butyl 3-((6-(6-(2-oxoimidazolidin-1-yl)imidazo[1,2-a]pyrazin-3-yl)pyridin-2-yl)amino)piperidine-1-carboxylate (0.040 g, 0.084 mmol) in dichloromethane (1 mL) was added trifluoroacetic acid (0.50 mL). The resulting reaction was stirred at room temperature for 1 hour, and was then filtered and concentrated under reduced pressure. The resulting crude product was purified by HPLC (Phenomenex Luna $C_{18}$ column, 3 micron, 80x30 mm; 1-20% acetonitrile in water containing 0.04% hydrochloric acid) to provide the title compound: LCMS m/z 379.0 $[M+H]^+$; $^1H$ NMR (400 MHz, $CD_3OD$), δ 10.73-10.78 (m, 1H), 9.25-9.31 (m, 1H), 8.81-8.86 (m, 1H), 7.56-7.64 (m, 1H), 7.31 (d, 1H), 6.60-6.65 (m, 1H), 4.91-4.97 (m, 1H), 4.23-4.39 (m, 2H), 3.61-3.76 (m, 3H), 3.46-3.54 (m, 1H), 2.91-2.99 (m, 1H), 2.70-2.81 (m, 1H), 1.95-2.16 (m, 3H), 1.57-1.72 (m, 1H).

The compounds in Table 17 were all prepared using the synthetic procedures described in Example 20.

TABLE 17

Additional compounds prepared according to Example 20.

| Compound # | Structure | IUPAC Name | LCMS |
|---|---|---|---|
| 117 | 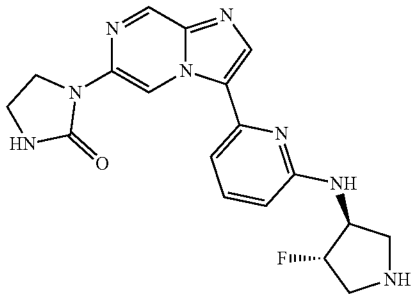 [SMILES: O=C1NCCN1c1cn2c(-c3cccc(N[C@H]4CNC[C@@H]4F)n3)cnc2cn1] | 1-(3-(6-(((3S,4S)-4-fluoropyrrolidin-3-yl)amino)pyridin-2-yl)imidazo[1,2-a]pyrazin-6-yl)imidazolidin-2-one | 383.1 |
| 118 | 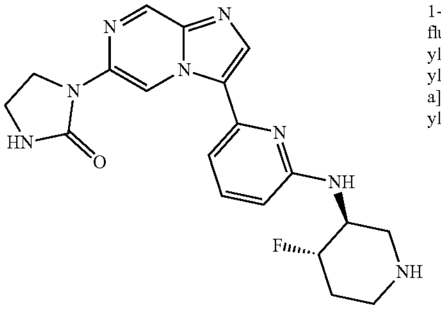 | 1-(3-(6-(((3S,4S)-4-fluoropiperidin-3-yl)amino)pyridin-2-yl)imidazo[1,2-a]pyrazin-6-yl)imidazolidin-2-one | 397.1 |

Example 21

Exemplary Synthetic Procedure #21 (Compounds 119-121)

Compound 119, 1-(3-(6-(((3S,4S)-4-fluoropiperidin-3-yl)amino)pyridin-2-yl)imidazo[1,2-a]pyrazin-6-yl)pyrrolidin-2-one

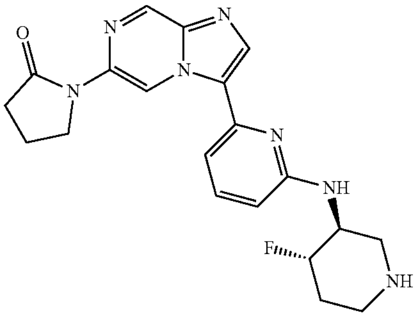 [SMILES: O=C1CCCN1c1cn2c(-c3cccc(N[C@H]4CNCC[C@@H]4F)n3)cnc2cn1]

Step A. (3S,4S)-tert-butyl 3-((6-(6-chloroimidazo[1,2-a]pyrazin-3-yl)pyridin-2-yl)amino)-4-fluoropiperidine-1-carboxylate

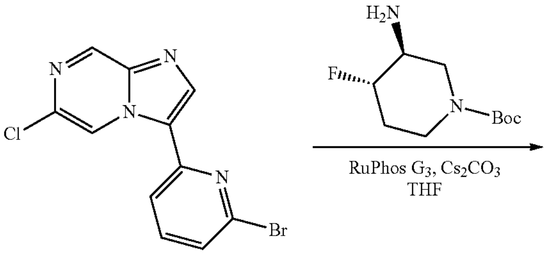

-continued

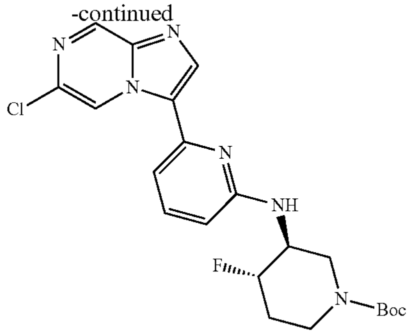

A mixture of 3-(6-bromo-2-pyridyl)-6-chloro-imidazo[1,2-a]pyrazine (0.150 g, 0.485 mmol), tert-butyl (3S,4S)-3-amino-4-fluoro-piperidine-1-carboxylate (0.106 g, 0.485 mmol), (2-dicyclohexylphosphino-2',6'-diisopropoxy-1,1'-biphenyl)[2-(2'-amino-1,1'-biphenyl)]palladium(II)methanesulfonate (0.041 g, 0.049 mmol), and cesium carbonate (0.474 g, 1.45 mmol) in tetrahydrofuran (5 mL) was purged with nitrogen, and was then heated at 80° C. for 2 hours under nitrogen atmosphere. The reaction was then cooled to room temperature, filtered, concentrated under reduced pressure. The resulting crude product was purified by flash chromatography on silica gel (0-40% ethyl acetate in petroleum ether) to provide the title compound: LCMS m/z 447.2 $[M+H]^+$.

Step B. (3S,4S)-tert-butyl 4-fluoro-3-((6-(6-(2-oxopyrrolidin-1-yl)imidazo[1,2-a]pyrazin-3-yl)pyridin-2-yl)amino)piperidine-1-carboxylate

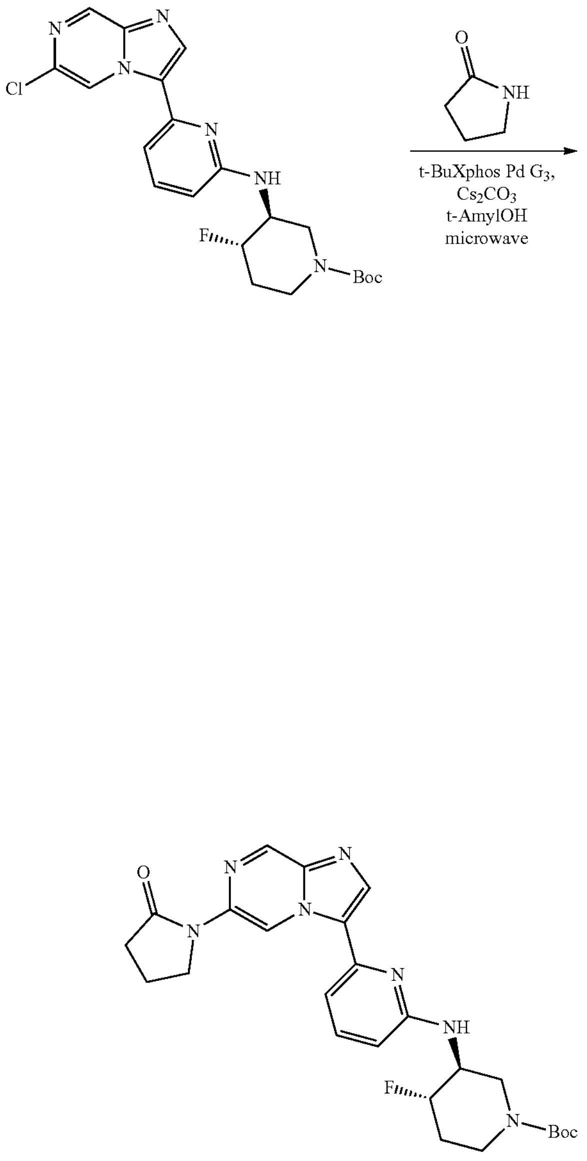

A mixture of (3S,4S)-tert-butyl 3-((6-(6-chloroimidazo[1,2-a]pyrazin-3-yl)pyridin-2-yl)amino)-4-fluoropiperidine-1-carboxylate (0.050 g, 0.112 mmol), pyrrolidin-2-one (0.019 g, 0.224 mmol), cesium carbonate (0.073 g, 0.224 mmol), and [2-(2-aminophenyl)phenyl]-methylsulfonyloxypalladiumditert-butyl-[2-(2,4,6-triisopropylphenyl)phenyl]phosphane (0.009 g, 0.011 mmol) in 2-methylbutan-2-ol (2 mL) was purged with nitrogen, and was then heated at 100° C. for 16 hours under nitrogen atmosphere. The reaction was then cooled to room temperature, concentrated under reduced pressure, diluted with water (5 mL), and extracted with ethyl acetate (3×10 mL). The organic extracts were combined, washed with saturated aqueous sodium chloride solution (5 mL), dried over sodium sulfate, filtered, and concentrated under reduced pressure to provide the title compound: LCMS m/z 496.3 $[M+H]^+$.

Step C. 1-(3-(6-(((3S,4S)-4-fluoropiperidin-3-yl)amino)pyridin-2-yl)imidazo[1,2-a]pyrazin-6-yl)pyrrolidin-2-one

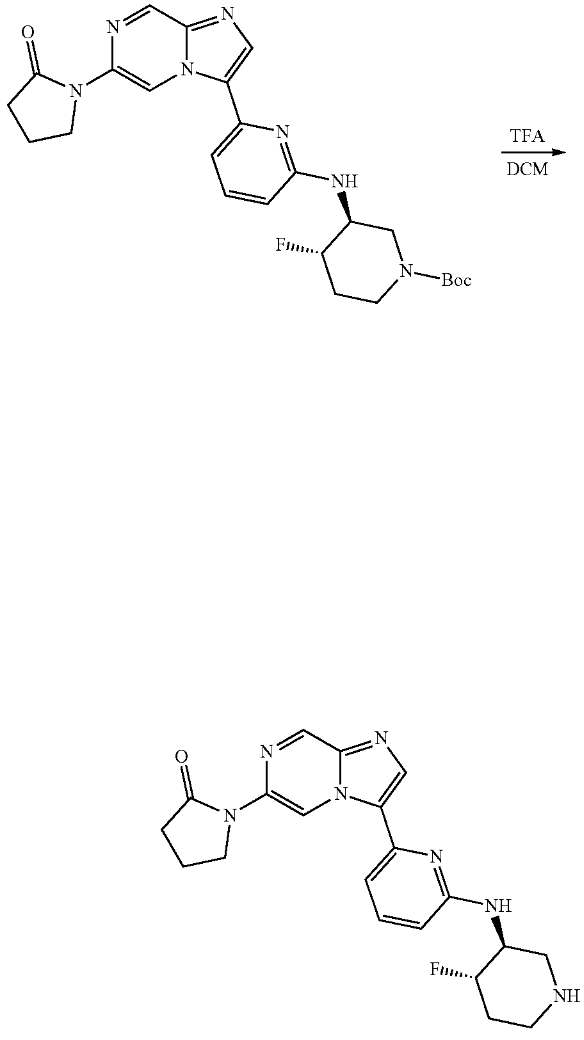

To a solution of (3S,4S)-tert-butyl 4-fluoro-3-((6-(6-(2-oxopyrrolidin-1-yl)imidazo[1,2-a]pyrazin-3-yl)pyridin-2-yl)amino)piperidine-1-carboxylate (0.050 g, 0.101 mmol) in dichloromethane (3 mL) was added trifluoroacetic acid (0.50 mL). The resulting reaction was stirred at room temperature for 1 hour, and was then concentrated under reduced pressure. The resulting crude product was purified by HPLC (Phenomenex Luna $C_{18}$ column, 5 micron, 150×30 mm; 1-35% acetonitrile in water containing 0.04% trifluoroacetic acid) to provide the title compound: LCMS m/z 396.1 $[M+H]^+$; $^1$HNMR (400 MHz, $CD_3OD$) δ 10.59 (s, 1H), 8.94 (s, 1H), 8.40-8.34 (m, 1H), 7.55 (t, J=7.9 Hz, 1H), 7.26 (d, J=7.3 Hz, 1H), 6.55 (d, J=8.3 Hz, 1H), 5.15-5.04 (m, 1H), 4.86-4.76 (m, 1H), 4.68 (dt, J=4.8, 10.0 Hz, 1H), 4.34-4.17 (m, 2H), 3.84-3.72 (m, 1H), 3.69-3.52 (m, 1H), 3.28-3.10 (m, 1H), 2.96-2.75 (m, 3H), 2.53-2.36 (m, 1H), 2.32-2.09 (m, 3H).

The compounds in Table 18 were all prepared using the chemistry described in Example 21.

TABLE 18

| Compound # | Structure | IUPAC Name | LCMS |
| --- | --- | --- | --- |
| Additional compounds prepared according to Example 21. | | | |
| 120 | 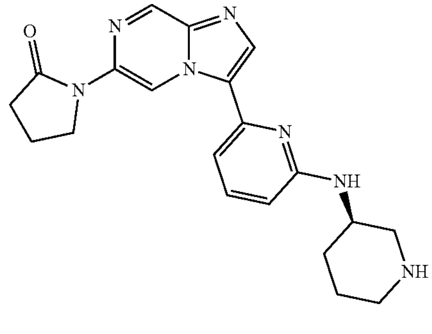 [SMILES: O=C1CCCN1c1cn2c(-c3cccc(N[C@@H]4CCCNC4)n3)cnc2cn1] | 1-[3-[6-[[(3R)-3-piperidyl]amino]-2-pyridyl]imidazo[1,2-a]pyrazin-6-yl]pyrrolidin-2-one | 378.1 |
| 121 | 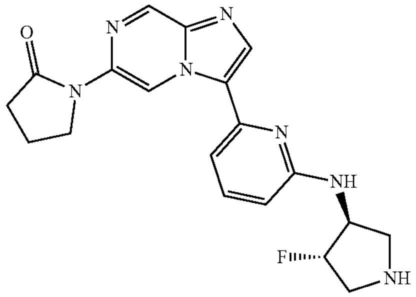 [SMILES: O=C1CCCN1c1cn2c(-c3cccc(N[C@H]4CNC[C@@H]4F)n3)cnc2cn1] | 1-(3-(6-(((3S,4S)-4-fluoropyrrolidin-3-yl)amino)pyridin-2-yl)imidazo[1,2-a]pyrazin-6-yl)pyrrolidin-2-one | 381.1 |

Example 22

Exemplary Synthetic Procedure #22 (Compounds 122-127)

Compound 122, 6-(6-(tert-butyl)imidazo[1,2-a]pyrazin-3-yl)-N-((3S,4S)-4-fluoropyrrolidin-3-yl)pyridin-2-amine

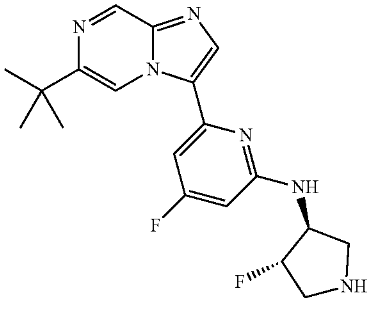 [SMILES: CC(C)(C)c1cn2c(-c3cc(F)cc(N[C@H]4CNC[C@@H]4F)n3)cnc2cn1]

Step A. 1-(3,3-dimethyl-2-oxobutyl)-1H-imidazole-2-carbaldehyde

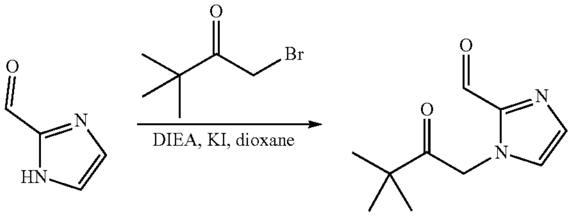

To a solution of 1H-imidazole-2-carbaldehyde (5.00 g, 52.0 mmol) in dioxane (100 mL) were added 1-bromo-3,3-dimethylbutan-2-one (10.3 g, 57.2 mmol, 7.71 mL), diisopropylethyl amine (10.09 g, 78.05 mmol, 13.60 mL), and potassium iodide (2.59 g, 15.6 mmol). The resulting reaction mixture was heated at 80° C. for 5 hours, and was then cooled to room temperature, diluted with water (100 mL), and extracted with ethyl acetate (3×100 mL). The organic extracts were combined, washed with saturated aqueous sodium chloride solution (100 mL), dried over anhydrous sodium sulfate, filtered, and concentrated under reduced pressure to provide the title compound: LCMS m/z 195.2 $[M+H]^+$.

Step B. 6-(tert-butyl)imidazo[1,2-a]pyrazine

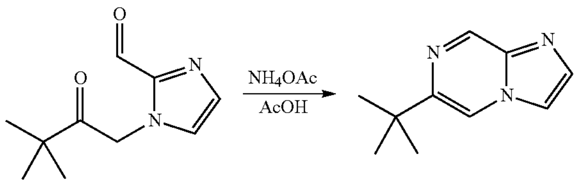

To a solution of 1-(3,3-dimethyl-2-oxobutyl)-1H-imidazole-2-carbaldehyde (10.70 g, 55.09 mmol) in acetic acid (110 mL) was added ammonium acetate (42.46 g, 550.9 mmol). The resulting reaction mixture was heated at 115° C. for 2 hours, and was then cooled to room temperature, diluted with water (100 mL), and extracted with ethyl acetate (3×100 mL). The organic extracts were combined, washed with saturated aqueous sodium chloride solution (100 mL), dried over anhydrous sodium sulfate, filtered, and concentrated under reduced pressure. The resulting crude product was purified by flash chromatography on silica gel (0-70% ethyl acetate in petroleum ether) to provide the title compound: LCMS m/z 176.2 $[M+H]^+$.

Step C. 3-(6-bromo-4-fluoropyridin-2-yl)-6-(tert-butyl)imidazo[1,2-a]pyrazine

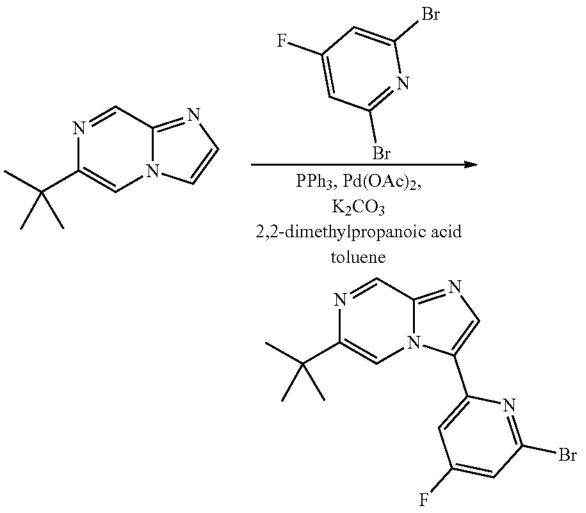

A mixture of 6-(tert-butyl)imidazo[1,2-a]pyrazine (0.200 g, 1.14 mmol), 2,6-dibromo-4-fluoropyridine (0.873 g, 3.42 mmol), triphenylphosphine (0.045 g, 0.171 mmol), palladium(II)acetate (0.026 g, 0.114 mmol), 2,2-dimethylpropanoic acid (0.035 g, 0.342 mmol, 0.039 mL), and potassium carbonate (0.473 g, 3.42 mmol) in toluene (10 mL) was purged with nitrogen, and was then heated at 100° C. for 16 hours under nitrogen atmosphere. The reaction was then cooled to room temperature, filtered, and concentrated under reduced pressure. The resulting crude product was purified by flash chromatography on silica gel (0-60% ethyl acetate in petroleum ether) to provide the title compound: LCMS m/z 351.1$[M+H]^+$.

Step D. (3S,4S)-tert-butyl 3-((6-(6-(tert-butyl)imidazo[1,2-a]pyrazin-3-yl)-4-fluoropyridin-2-yl)amino)-4-fluoropyrrolidine-1-carboxylate

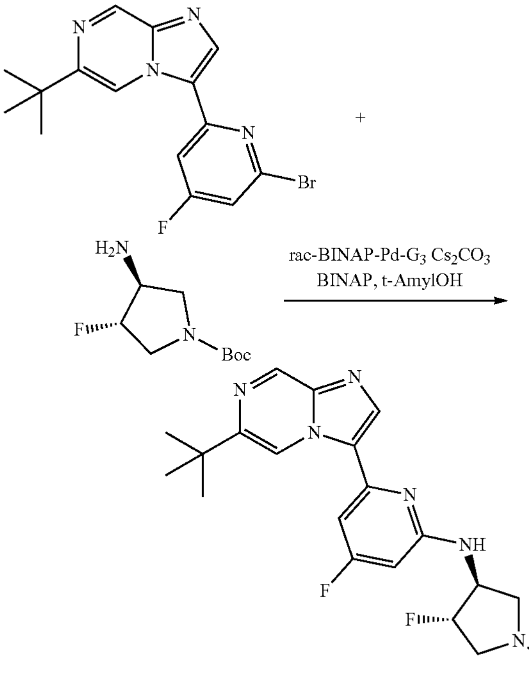

A mixture of 3-(6-bromo-4-fluoropyridin-2-yl)-6-(tert-butyl)imidazo[1,2-a]pyrazine (0.044 g, 0.125 mmol), (3S,4S)-tert-butyl 3-amino-4-fluoropyrrolidine-1-carboxylate (0.038 g, 0.187 mmol), cesium carbonate (0.081 g, 0.249 mmol), methanesulfonato[2,2-bis(diphenylphosphino)-1,1-binaphthyl](2-amino-1,1-biphenyl-2-yl)palladium(II) (0.012 g, 0.012 mmol), and [1-(2-diphenylphosphanyl-1-naphthyl)-2-naphthyl]-diphenyl-phosphane (0.008 g, 0.012 mmol) in 2-methylbutan-2-ol (0.50 mL) was purged with nitrogen, and was then heated at 100° C. for 16 hours under nitrogen atmosphere. The reaction was then cooled to room temperature, filtered, and concentrated under reduced pressure to provide the title compound: LCMS m/z 473.3 $[M+H]^+$.

Step E. 6-(6-(tert-butyl)imidazo[1,2-a]pyrazin-3-yl)-4-fluoro-N-((3S,4S)-4-fluoropyrrolidin-3-yl)pyridin-2-amine

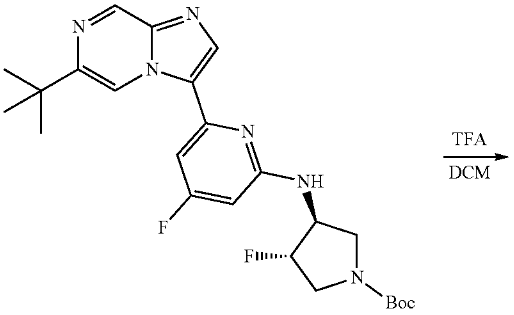

-continued

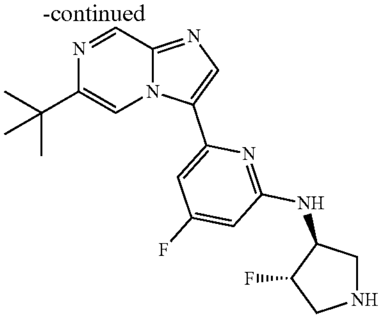

To a solution of (3S,4S)-tert-butyl 3-((6-(6-(tert-butyl)imidazo[1,2-a]pyrazin-3-yl)-4-fluoropyridin-2-yl)amino)-4- fluoropyrrolidine-1-carboxylate (0.090 g, 0.190 mmol) in dichloromethane (3 mL) was added trifluoroacetic acid (0.50 mL). The resulting reaction was stirred at room temperature for 2 hours, and was then concentrated under reduced pressure. The resulting crude product was purified by HPLC (Phenomenex Luna $C_{18}$ column, 5 micron, 80x30 mm; 10-40% acetonitrile in water containing 0.04% trifluoroacetate acid) to provide the title compound: LCMS m/z 373.1 $[M+H]^+$; $^1H$ NMIR (400 MHz, $CD_3OD$) δ 9.49 (d, J=0.9 Hz, 1H), 9.11 (d, J=1.1 Hz, 1H), 8.36 (s, 1H), 7.24-7.14 (m, 1H), 6.43-6.33 (m, 1H), 5.57-5.38 (m, 1H), 5.07-4.96 (m, 1H), 3.93-3.56 (m, 4H), 1.57-1.40 (m, 9H).

The compounds in Table 19 were all prepared using the synthetic procedures described in Example 22.

TABLE 19

Additional compounds prepared according to Example 22.

| Compound # | Structure | IUPAC Name | LCMS |
|---|---|---|---|
| 123 | 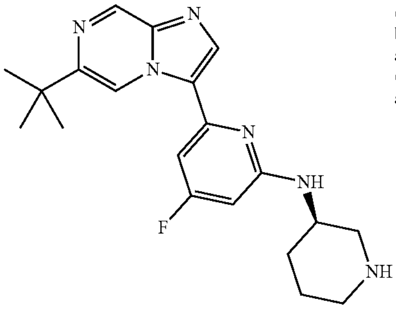 | (R)-6-(6-(tert-butyl)imidazo[1,2-a]pyrazin-3-yl)-4-fluoro-N-(piperidin-3-yl)pyridin-2-amine | 369.1 |
| 124 | 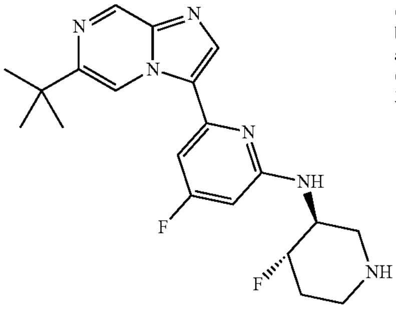 | 6-(6-(tert-butyl)imidazo[1,2-a]pyrazin-3-yl)-4-fluoro-N-((3S,4S)-4-fluoropiperidin-3-yl)pyridin-2-amine | 387.1 |
| 125 | 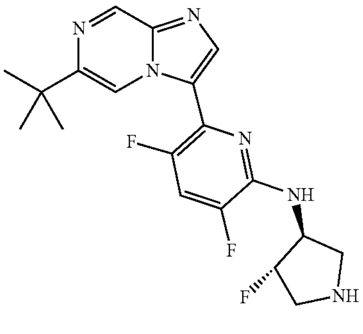 [SMILES: CC(C)(C)c1cn2c(-c3nc(N[C@H]4CNC[C@@H]4F)c(F)cc3F)cnc2cn1] | 6-(6-(tert-butyl)imidazo[1,2-a]pyrazin-3-yl)-N-((3S,4S)-4-fluoropyrrolidin-3-yl)pyridin-2-amine | 391.1 |

TABLE 19-continued

| Additional compounds prepared according to Example 22. | | | |
|---|---|---|---|
| Compound # | Structure | IUPAC Name | LCMS |
| 126 | 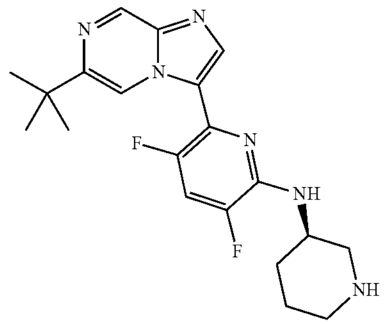 [SMILES: CC(C)(C)c1cn2c(-c3nc(N[C@@H]4CCCNC4)c(F)cc3F)cnc2cn1] | (R)-6-(6-(tert-butyl)imidazo[1,2-a]pyrazin-3-yl)-3,5-difluoro-N-(piperidin-3-yl)pyridin-2-amine | 387.1 |
| 127 | 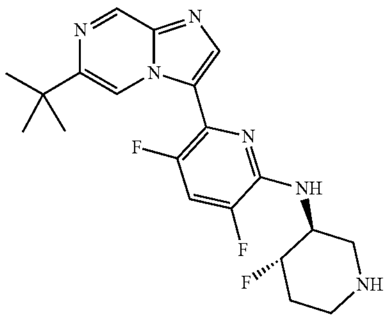 [SMILES: CC(C)(C)c1cn2c(-c3nc(N[C@H]4CNCC[C@@H]4F)c(F)cc3F)cnc2cn1] | 6-(6-(tert-butyl)imidazo[1,2-a]pyrazin-3-yl)-3,5-difluoro-N-((3S,4S)-4-fluoropiperidin-3-yl)pyridin-2-amine | 405.1 |

Example 23

Exemplary Synthetic Procedure #23 (Compounds 128-130)

Compound 128, 6-(6-(tert-butyl)imidazo[1,2-a]pyrazin-3-yl)-N-((3S,4S)-4-fluoropyrrolidin-3-yl)pyridin-2-amine

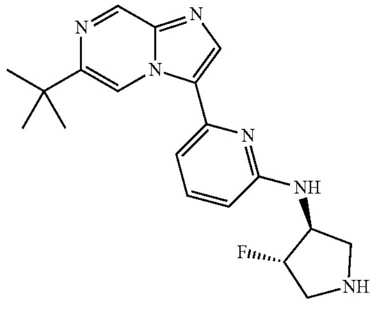 [SMILES: CC(C)(C)c1cn2c(-c3cccc(N[C@H]4CNC[C@@H]4F)n3)cnc2cn1]

Step A. 3-(6-bromopyridin-2-yl)-6-(tert-butyl)imidazo[1,2-a]pyrazine

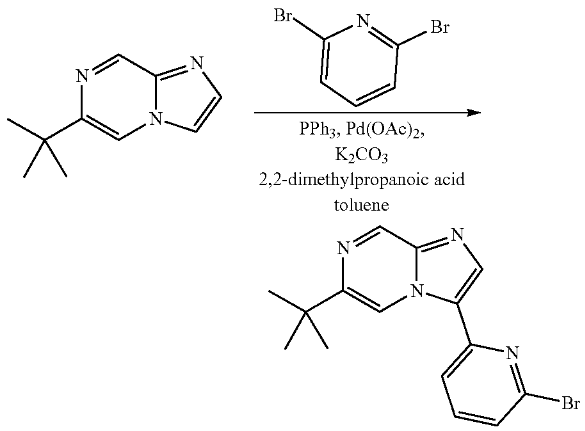

A mixture of 6-(tert-butyl)imidazo[1,2-a]pyrazine (1.00 g, 5.71 mmol), 2,6-dibromopyridine (4.06 g, 17.1 mmol), triphenylphosphine (0.225 g, 0.856 mmol), palladium acetate (0.128 g, 0.571 mmol), potassium carbonate (2.37 g, 17.1 mmol), and 2,2-dimethylpropanoic acid (0.175 g, 1.71 mmol, 0.197 mL) in toluene (40 mL) was purged with nitrogen, and was then heated at 100° C. for 18 hours under nitrogen atmosphere. The reaction was then cooled to room temperature, diluted with water (60 mL), and extracted with ethyl acetate (3x40 mL). The organic extracts were combined, washed with saturated aqueous sodium chloride solution (60 mL), dried over anhydrous sodium sulfate, filtered, and concentrated under reduced pressure. The resulting crude product was purified by flash chromatography on silica gel (0-70% ethyl acetate in petroleum ether) to provide the title compound: LCMS m/z 333.1 $[M+H]^+$.

Step B. (3S,4S)-tert-butyl 3-((6-(6-(tert-butyl)imidazo[1,2-a]pyrazin-3-yl)pyridin-2-yl)amino)-4-fluoropyrrolidine-1-carboxylate

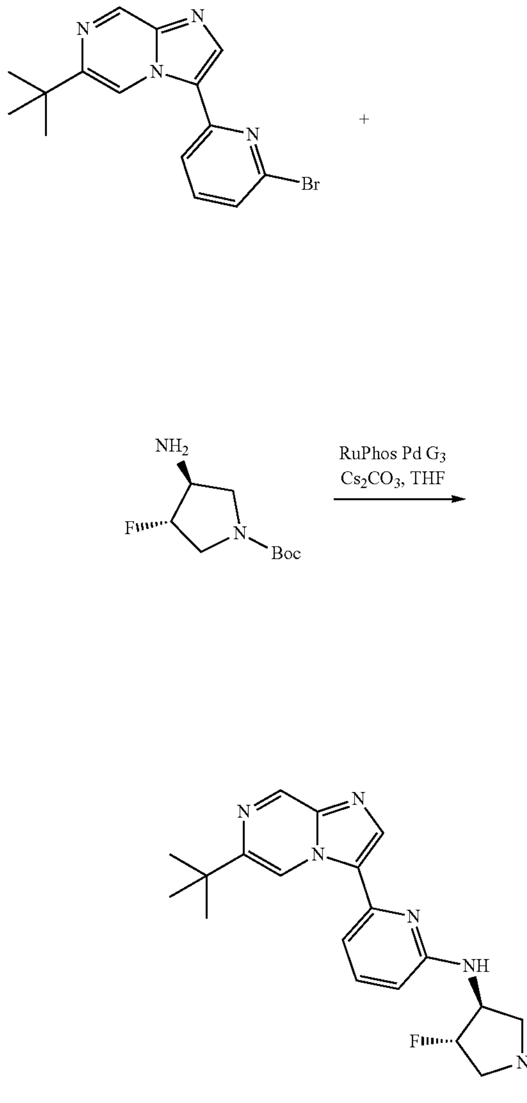

A mixture of 3-(6-bromopyridin-2-yl)-6-(tert-butyl)imidazo[1,2-a]pyrazine (0.050 g, 0.151 mmol), (3S,4S)-4-fluoro-1-methylpyrrolidin-3-amine (0.031 g, 0.151 mmol), (2-dicyclohexylphosphino-2',6'-diisopropoxy-1,1'-biphenyl)[2-(2'-amino-1,1'-biphenyl)]palladium(II)methanesulfonate (0.013 g, 0.015 mmol), and cesium carbonate (0.123 g, 0.377 mmol) in tetrahydrofuran (2 mL) was purged with nitrogen, and was then heated at 80° C. for 2 hours under nitrogen atmosphere. The reaction was then cooled to room temperature, filtered, and concentrated under reduced pressure to provide the title compound: LCMS m/z 455.3 $[M+H]^+$.

Step C. 6-(6-(tert-butyl)imidazo[1,2-a]pyrazin-3-yl)-N-((3S,4S)-4-fluoropyrrolidin-3-yl)pyridin-2-amine

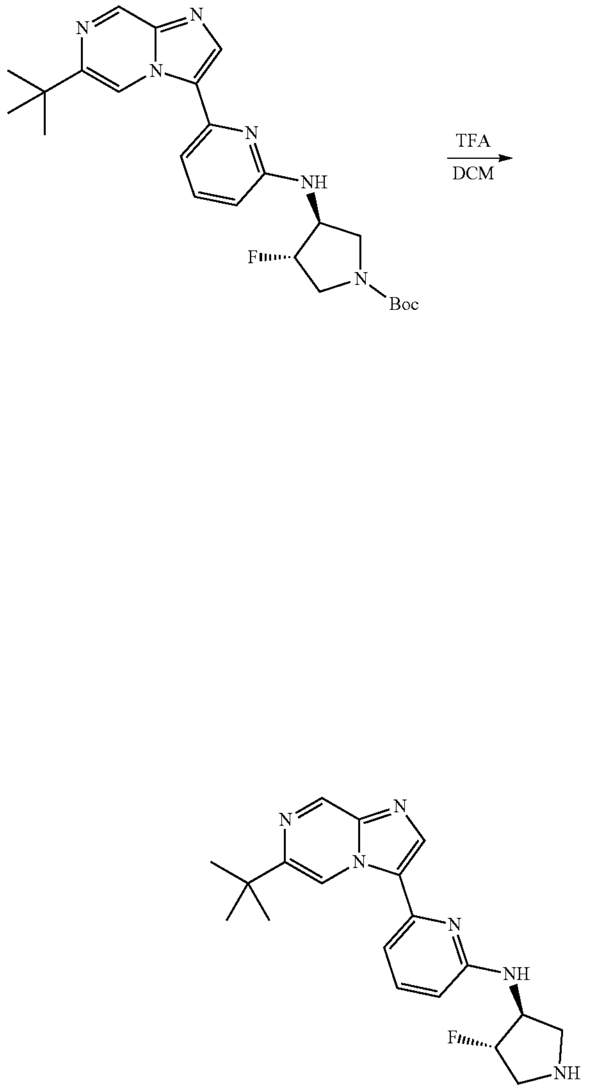

To a solution of (3S,4S)-tert-butyl 3-((6-(6-(tert-butyl)imidazo[1,2-a]pyrazin-3-yl)pyridin-2-yl)amino)-4-fluoropyrrolidine-1-carboxylate (0.072 g, 0.158 mmol) in dichloromethane (3 mL) was added trifluoroacetic acid (0.50 mL). The resulting reaction was stirred at room temperature for 2 hours, and was then concentrated under reduced pressure. The resulting crude product was purified by HPLC (Phenomenex Luna $C_{18}$ column, 5 micron, 100×40 mm; 5-40% acetonitrile in water containing 0.1% trifluoroacetate acid) to provide the title compound: LCMS m/z 355.1 $[M+H]^+$; $^1H$ NMR (400 MHz, $CD_3OD$) δ 9.49 (d, J=1.2 Hz, 1H), 9.10 (d, J=1.2 Hz, 1H), 8.31 (s, 1H), 7.66 (t, J=7.9 Hz, 1H), 7.33-7.28 (m, 1H), 6.65 (d, J=8.3 Hz, 1H), 5.55-5.39 (m, 1H), 4.98-4.91 (m, 1H), 3.83 (dd, J=5.9, 12.7 Hz, 1H), 3.76-3.56 (m, 3H), 1.46 (s, 9H).

The compounds in Table 20 were all prepared using the synthetic procedures described in Example 23.

TABLE 20

Additional compounds prepared according to Example 23.

| Compound # | Structure | IUPAC Name | LCMS |
|---|---|---|---|
| 129 | 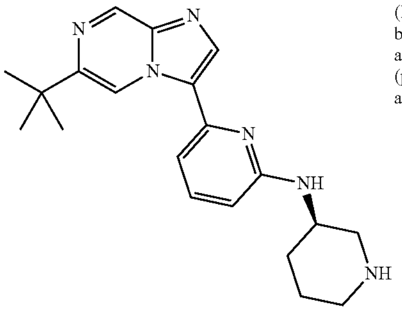 | (R)-6-(6-(tert-butyl)imidazo[1,2-a]pyrazin-3-yl)-N-(piperidin-3-yl)pyridin-2-amine | 351.1 |
| 130 | 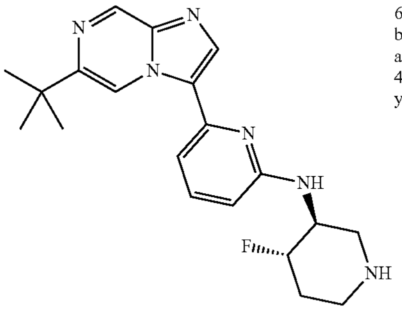 | 6-(6-(tert-butyl)imidazo[1,2-a]pyrazin-3-yl)-N-((3S,4S)-4-fluoropiperidin-3-yl)pyridin-2-amine | 369.1 |

Example 24

Exemplary Synthetic Procedure #24 (Compounds 131-132)

Compound 131, (R)-6-(6-isopropoxyimidazo[1,2-a]pyrazin-3-yl)-N-(piperidin-3-yl)pyridin-2-amine

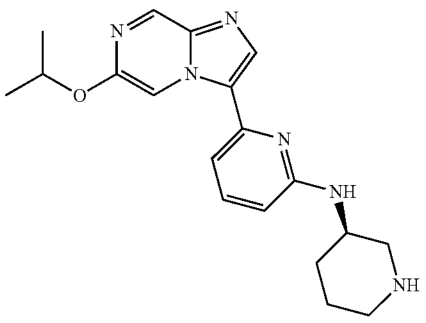 [SMILES: CC(C)Oc1cn2c(-c3cccc(N[C@@H]4CCCNC4)n3)cnc2cn1]

Step A. 6-isopropoxyimidazo[1,2-a]pyrazine

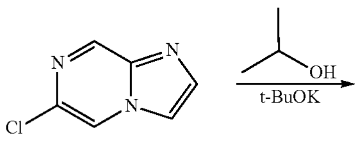

-continued

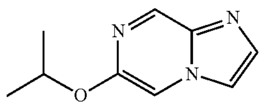

To a solution of 6-chloroimidazo[1,2-a]pyrazine (1.00 g, 6.51 mmol) in propan-2-ol (40 mL) was added potassium 2-methylpropan-2-olate (2.19 g, 19.5 mmol). The resulting reaction mixture was heated at 60° C. for 5 hours. The reaction was then cooled to room temperature, filtered, and concentrated under reduced pressure to give a crude product that was purified by HPLC (Phenomenex Luna $C_{18}$ column, 5 micron, 150×30 mm; 10-40% acetonitrile in water containing 0.04% sodium bicarbonate) to provide the title compound: LCMS m/z 178.2 $[M+H]^+$; $^1H$ NMR (400 MHz, $CD_3OD$) δ 8.77 (s, 1H), 8.08 (d, J=1.2 Hz, 1H), 7.99 (s, 1H), 7.79 (s, 1H), 5.03-5.14 (m, 1H), 1.38 (d, J=6.1 Hz, 6H).

Step B. 3-(6-bromopyridin-2-yl)-6-isopropoxyimidazo[1,2-a]pyrazine

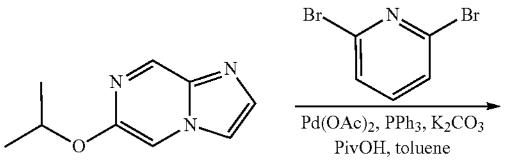

-continued

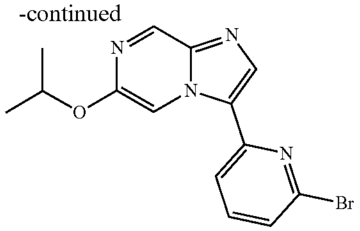

A mixture of 6-isopropoxyimidazo[1,2-a]pyrazine (0.200 g, 1.13 mmol), 2,6-dibromopyridine (0.802 g, 3.39 mmol), palladium(II)acetate (0.025 g, 0.113 mmol), triphenylphosphine (0.044 g, 0.169 mmol), 2,2-dimethylpropanoic acid (0.035 g, 0.339 mmol), and potassium carbonate (0.468 g, 3.39 mmol) in toluene (5 mL) was purged with nitrogen, and was then heated at 100° C. for 16 hours under nitrogen atmosphere. The reaction was then cooled to room temperature and concentrated under reduced pressure. The resulting crude product was purified by flash chromatography on silica gel (0-100% ethyl acetate in petroleum ether) to provide the title compound: LCMS m/z 333.1 [M+H]$^+$.

Step C. (R)-tert-butyl 3-((6-(6-isopropoxyimidazo[1,2-a]pyrazin-3-yl)pyridin-2-yl)amino)piperidine-1-carboxylate

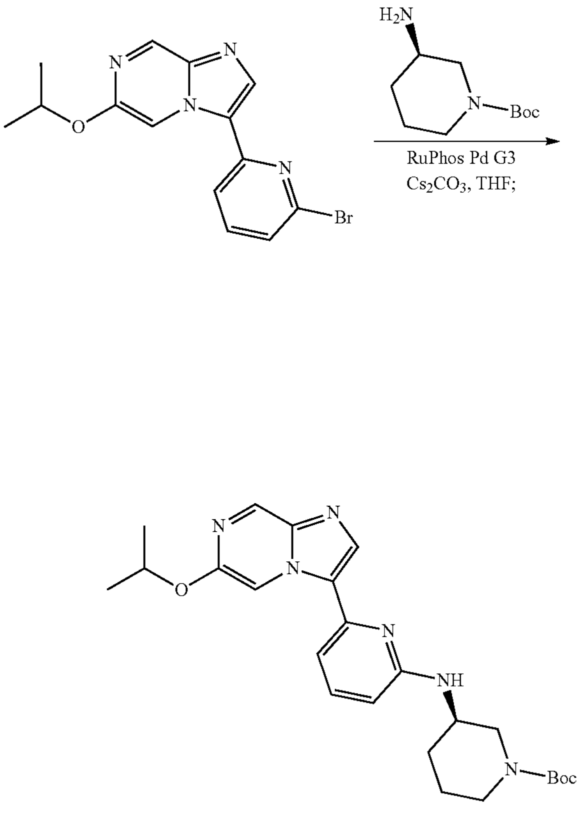

A mixture of 3-(6-bromo-2-pyridyl)-6-isopropoxy-imidazo[1,2-a]pyrazine (0.050 g, 0.150 mmol), tert-butyl (3R)-3-aminopiperidine-1-carboxylate (0.030 g, 0.150 mmol), (2-dicyclohexylphosphino-2',6'-diisopropoxy-1,1'-biphenyl)[2-(2'-amino-1,1'-biphenyl)]palladium(II)methanesulfonate (0.013 g, 0.015 mmol), and cesium carbonate (0.122 g, 0.375 mmol) in tetrahydrofuran (10 mL) was purged with nitrogen, and was then heated at 80° C. for 5 hours under nitrogen atmosphere. The reaction was then cooled to room temperature, filtered, and concentrated under reduced pressure to provide the title compound: LCMS m/z 453.3 [M+H]$^+$.

Step D. (R)-6-(6-isopropoxyimidazo[1,2-a]pyrazin-3-yl)-N-(piperidin-3-yl)pyridin-2-amine

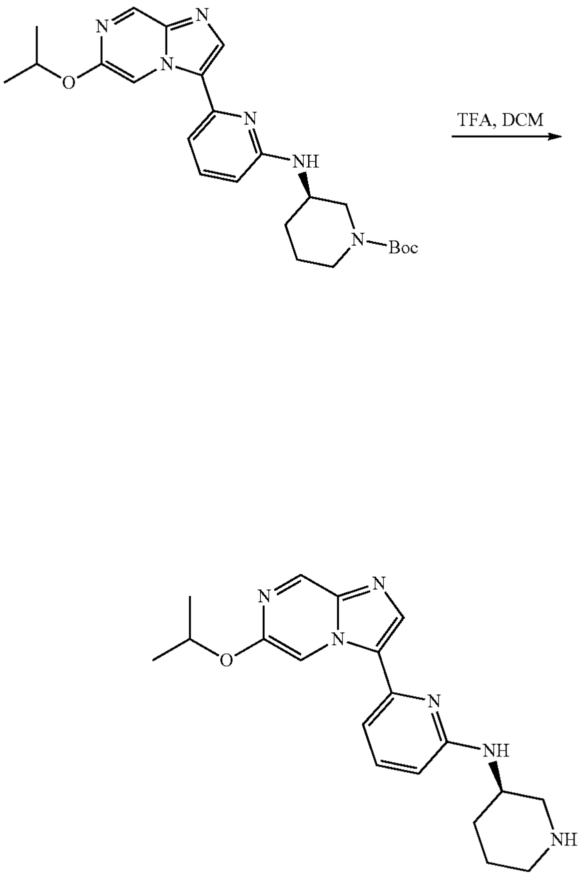

To a solution of tert-butyl (3R)-3-[[6-(6-isopropoxyimidazo[1,2-a]pyrazin-3-yl)-2-pyridyl]amino]piperidine-1-carboxylate (0.170 g, 0.376 mmol) in dichloromethane (3 mL) was added trifluoroacetic acid (0.50 mL). The resulting reaction was stirred at room temperature for 1 hour, and was then concentrated under reduced pressure. The resulting crude product was purified by HPLC (Phenomenex Luna $C_{18}$ column, 5 micron, 150×30 mm; 1-40% acetonitrile in water containing 0.04% trifluoroacetic acid) to provide the title compound: LCMS m/z 353.2 [M+H]$^+$; $^1$H NMR (400 MHz, $CD_3OD$) δ 9.31 (s, 1H), 8.90 (s, 1H), 8.34-8.42 (m, 1H), 7.55-7.64 (m, 1H), 7.23 (d, J=7.4 Hz, 1H), 6.59 (d, J=8.3 Hz, 1H), 5.24-5.33 (m, 1H), 4.23-4.38 (m, 1H), 3.43-3.55 (m, 1H), 3.34-3.42 (m, 1H), 3.06-3.25 (m, 2H), 2.29-2.41 (m, 1H), 2.09-2.22 (m, 1H), 1.96-2.08 (m, 1H), 1.69-1.82 (m, 1H), 1.41 (dd, J=10.4, 6.1 Hz, 6H).

The compounds in Table 21 were all prepared using the synthetic procedures described in Example 24.

TABLE 21

| Additional compounds prepared according to Example 24. | | | |
|---|---|---|---|
| Compound # | Structure | IUPAC Name | LCMS |
| 132 | 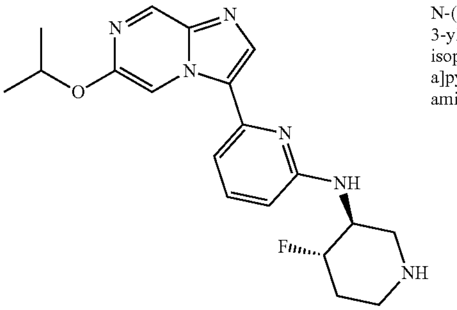 | N-((3S,4S)-4-fluoropiperidin-3-yl)-6-(6-isopropoxyimidazo[1,2-a]pyrazin-3-yl)pyridin-2-amine | 371.2 |

Example 25

Biological Data for Exemplary Compounds

Kinase inhibitory data were obtained for various exemplary compounds prepared according to Examples 1-24 using the RBC HotSpot Kinase Assay Protocol (Anastassiadis T, et al. Comprehensive assay of kinase catalytic activity reveals features of kinase inhibitor selectivity. Nat Biotechnol. 2011 Oct. 30; 29(11):1039-45), as described below. This assay uses the isolated kinase enzyme. This assay is very useful for determining competition of the inhibitor for ATP and/or substrates and for measuring the kinetics of enzyme inhibition. It also allows for measuring the relative affinity of binding to the isolated enzyme protein, and hence determines selectivity. Unlike kinase binding assays that measure competition for ATP, the HotSpot Kinase Assay is a functional assay that measures catalytic activity; as such it measures relative functional potency regardless of the mechanism of enzyme inhibition. This assay uses the form of the various enzymes that are easiest to express, which may not necessarily be the form of the enzyme that exist in the cell. (Sometimes the carboxy terminus has been truncated to aid in expression, or, if it is a receptor kinase, the enzyme itself is isolated from the other parts of the receptor that are involved in regulating kinase activity.)

The reagent used was as follows: Base Reaction buffer; 20 mM Hepes (pH 7.5), 10 mM MgCl2, 1 mM EGTA, 0.01% Brij35, 0.02 mg/ml BSA, 0.1 mM Na3VO4, 2 mM DTT, 1% DMSO. Required cofactors were added individually to each kinase reaction.

The reaction procedure was as follows:

1) Substrates were prepared in freshly prepared Reaction Buffer.
2) Any required cofactors were delivered to the substrate solution above.
3) Kinase was delivered into the substrate solution and gently mixed.
4) Compounds were delivered in 100% DMSO into the kinase reaction mixture by Acoustic technology (Echo550; nanoliter range), followed by incubation for 20 min at room temp.
5) $^{33}$P-ATP was delivered into the reaction mixture to initiate the reaction.
6) The mixture was incubated for 2 hours at room temperature.
7) Kinase activity was detected by P81 filter-binding method.

TABLE 22

| Biological data obtained in accordance with the protocol described in Example 25. | | | |
|---|---|---|---|
| Compound # | IRAK1 IC50 (nM) | IRAK4 IC50 (nM) | FLT3 IC50 (nM) |
| 1 | 63 | 0.5 | 0.6 |
| 2 | 67 | 0.7 | <0.5 |
| 3 | 88 | 0.9 | 0.7 |
| 4 | 451 | 2 | 0.9 |
| 5 | 114 | <0.5 | <0.5 |
| 6 | 926 | 86 | 0.6 |
| 7 | 3280 | 1020 | 1 |
| 8 | 138 | 2 | <0.5 |
| 9 | 126 | 7 | <0.5 |
| 10 | 155 | 2 | <0.5 |
| 11 | 301 | 3 | <0.5 |
| 12 | 165 | 3 | <0.5 |
| 13 | 77 | 5 | <0.5 |
| 15 | 736 | 1020 | 3 |
| 16 | 60 | 1 | <0.5 |
| 17 | 288 | 5 | <0.5 |
| 18 | 82 | 1 | <0.5 |
| 19 | 32 | <0.5 | <0.5 |
| 20 | 150 | 2 | <0.5 |
| 22 | 474 | 669 | 1 |
| 23 | 185 | 7 | <0.5 |
| 24 | 236 | 2 | <0.5 |
| 25 | 144 | 1 | <0.5 |
| 26 | 103 | 0.7 | <0.5 |
| 27 | 116 | 0.9 | 0.8 |
| 28 | 220 | 0.7 | <0.5 |
| 29 | 273 | 1 | 0.6 |
| 30 | 58 | <0.5 | <0.5 |
| 31 | 23 | <0.5 | <0.5 |
| 32 | 385 | 3 | <0.5 |
| 33 | 61 | <0.5 | 0.6 |
| 34 | 47 | 2 | 4 |
| 35 | 45 | 0.8 | 1 |
| 36 | 190 | 1 | <0.5 |
| 37 | 273 | 11 | <0.5 |
| 38 | 92 | 0.8 | <0.5 |
| 39 | 301 | 8 | <0.5 |
| 40 | 101 | 2 | <0.5 |
| 41 | 142 | 110 | <0.5 |
| 42 | 413 | 339 | 0.6 |
| 43 | 895 | 12 | <0.5 |
| 44 | 4280 | 37 | <0.5 |
| 45 | 1990 | 12 | <0.5 |
| 46 | 3640 | 8 | <0.5 |
| 47 | 154 | 7 | <0.5 |
| 48 | 60 | 3 | 0.6 |

TABLE 22-continued

Biological data obtained in accordance with the protocol described in Example 25.

| Compound # | IRAK1 IC50 (nM) | IRAK4 IC50 (nM) | FLT3 IC50 (nM) |
|---|---|---|---|
| 49 | 196 | 1 | <0.5 |
| 50 | 113 | 0.6 | 0.6 |
| 51 | 80 | 1 | <0.5 |
| 52 | 202 | 1 | <0.5 |
| 53 | 1250 | 12 | 0.6 |
| 54 | 2290 | 5 | <0.5 |
| 55 | 304 | <0.5 | <0.5 |
| 56 | 840 | 4 | 0.7 |
| 57 | 165 | 2 | <0.5 |
| 58 | 117 | 1 | 0.7 |
| 59 | 696 | <0.5 | <0.5 |
| 60 | 833 | 2 | <0.5 |
| 61 | 3540 | 46 | 2 |
| 62 | 7010 | 86 | <0.5 |
| 63 | 3430 | 238 | <0.5 |
| 66 | 6020 | 4 | 1 |
| 67 | 8190 | 4 | 0.7 |
| 68 | 727 | 4 | <0.5 |
| 69 | 2030 | 15 | <0.5 |
| 70 | 696 | 20 | <0.5 |
| 71 | 966 | 2 | <0.5 |
| 72 | 4190 | 14 | <0.5 |
| 73 | 622 | 2 | <0.5 |
| 74 | 4780 | 14 | <0.5 |
| 75 | 504 | 4 | <0.5 |
| 76 | 159 | 1 | <0.5 |
| 77 | 237 | 3 | 0.9 |
| 78 | 66 | <0.5 | <0.5 |
| 80 | 64 | 3 | 0.6 |
| 81 | 31 | <0.5 | <0.5 |
| 82 | 16 | <0.5 | <0.5 |
| 83 | 329 | 28 | <0.5 |
| 84 | 114 | 2 | 0.6 |
| 85 | 106 | 54 | 0.6 |
| 86 | 144 | 65 | 0.9 |
| 87 | 46 | 5 | 0.7 |
| 88 | 69 | 15 | 1 |
| 89 | 9 | <0.5 | <0.5 |
| 90 | 16 | 7 | 2 |
| 91 | 40 | 2 | 3 |
| 92 | 11 | 2 | 2 |
| 93 | 8 | <0.5 | 1 |
| 94 | 8 | 0.8 | 1 |
| 95 | 43 | 1 | <0.5 |
| 96 | 49 | 2 | 0.9 |
| 97 | 53 | 6 | 0.6 |
| 101 | 175 | 24 | 0.9 |
| 102 | 281 | 6 | 2 |
| 103 | 265 | 13 | 0.9 |
| 104 | 9 | 1 | <0.5 |
| 105 | 22 | 1 | <0.5 |
| 106 | 21 | 3 | <0.5 |
| 107 | 130 | 38 | 1 |
| 108 | 109 | 13 | 0.9 |
| 109 | 52 | 4 | 0.7 |
| 110 | 4240 | 98 | 3 |
| 111 | 2130 | 136 | 0.5 |
| 112 | 1860 | 140 | <0.5 |
| 113 | 9940 | 1330 | 0.7 |
| 114 | >10000 | 132 | 1 |
| 115 | 9400 | 150 | <0.5 |
| 116 | 125 | 14 | 1 |
| 117 | 75 | 2 | 0.8 |
| 118 | 22 | 4 | 1 |
| 119 | 110 | 10 | <0.5 |
| 120 | 234 | 15 | <0.5 |
| 121 | 207 | 5 | <0.5 |
| 122 | 475 | 31 | <0.5 |
| 123 | 296 | 38 | 0.6 |
| 124 | 143 | 17 | <0.5 |
| 125 | 51 | 0.7 | <0.5 |
| 126 | 80 | 2 | <0.5 |
| 127 | 60 | 2 | <0.5 |
| 128 | 108 | 0.6 | <0.5 |
| 129 | 97 | 1 | <0.5 |
| 130 | 49 | 3 | <0.5 |
| 131 | 438 | 10 | <0.5 |
| 132 | 144 | 2 | <0.5 |

Example 26

Biological Data for Exemplary Compounds

Kinase binding data were obtained for various exemplary compounds prepared according to Examples 1-24 using the DiscoverX KINOMVIEscan® active site-directed competition binding site-directed assay protocol described below. Unlike other kinase competitive binding site assays, KINOIVIEscan® assays do not require ATP. As a result, the data report thermodynamic interaction affinities ($K_d$ values), rather than $IC_{50}$ values that are dependent on ATP concentrations. The assay uses a DNA-tagged version of the protein kinase, and an immobilized ligand bound to a solid support. Compounds that directly or indirectly prevent kinase binding to the immobilized ligand reduce the amount of kinase captured on the solid support, which is detected using an ultra-sensitive qPCR method. Affinity constants reported from the assay have been reported to be independent of the immobilized ligand used that is coupled to the solid support (See supplemental information in Fabian, M. A. et. al., (2005) Nat. Biotechnol. 23, 329-336; Wodicka, L. M. et. al., (2010) Chem. Biol. 17, 1241-1249.)

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions were performed in polypropylene 384-well plates. Each was a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM nonbiotinylated affinity ligand) and incubated at room temperature with shaking for 30 minutes. The kinase concentration in the eluates was measured by qPCR.

Binding constants (Kds) were calculated with a standard dose-response curve using the Hill equation. The Hill Slope was set to −1. Curves were fitted using a non-linear least square fit with the Levenberg-Marquardt algorithm.

TABLE 23

Biological data obtained in accordance with the protocol described in Example 26.

| Compound # | FLT3 $K_d$ (nM) | FLT3 D835H $K_d$ (nM) | FLT3 D835V $K_d$ (nM) | FLT3 D835Y $K_d$ (nM) | FLT3 ITD $K_d$ (nM) | FLT3 ITD, D835V $K_d$ (nM) |
|---|---|---|---|---|---|---|
| 1 | 0.049 | 0.066 | 0.015 | 0.049 | 0.087 | 0.003 |
| 3 | 0.056 | 0.059 | 0.023 | 0.053 | 0.14 | 0.004 |
| 5 | 0.027 | 0.063 | 0.013 | 0.036 | 0.11 | 0.005 |
| 10 | 0.38 | 0.082 | 0.083 | 0.044 | 1.4 | 0.011 |
| 16 | 0.42 | 0.2 | 0.066 | 0.053 | 0.14 | 0.006 |
| 25 | 0.13 | 0.18 | 0.036 | 0.071 | 0.34 | 0.009 |
| 30 | 1.5 | 1.2 | 0.36 | 0.47 | 2.9 | 0.14 |
| 31 | 0.55 | 0.43 | 0.17 | 0.18 | 1.5 | 0.044 |
| 38 | 0.61 | 0.24 | 0.12 | 0.035 | 2.3 | 0.026 |
| 50 | 0.062 | 0.032 | 0.015 | 0.044 | 0.091 | 0.003 |
| 52 | 0.035 | 0.078 | 0.011 | 0.064 | 0.13 | 0.003 |

TABLE 24

Biological data obtained in accordance with the protocol described in Example 26.

| Compound # | FLT3 ITD, F691L $K_d$ (nM) | FLT3 K663Q $K_d$ (nM) | FLT3 N841I $K_d$ (nM) | FLT3 R834Q $K_d$ (nM) | FLT3 Autoinh. $K_d$ (nM) |
|---|---|---|---|---|---|
| 1 | 0.11 | 0.24 | 0.12 | 0.17 | 1 |
| 3 | 0.071 | 0.22 | 0.12 | 0.14 | 1.4 |
| 5 | 0.023 | 0.18 | 0.091 | 0.13 | 0.88 |
| 10 | 0.3 | 0.45 | 0.29 | 0.81 | 4.2 |
| 16 | 0.32 | 1.4 | 0.65 | 1.3 | 3 |
| 25 | 0.074 | 0.59 | 0.27 | 0.47 | 3.6 |
| 30 | 1.8 | 0.83 | 3.5 | 4.3 | 22 |
| 31 | 0.49 | 2.4 | 2.1 | 2.2 | 10 |
| 38 | 0.75 | 2.3 | 0.52 | 1.2 | 7.6 |
| 50 | 0.1 | 0.39 | 0.25 | 0.2 | 1.9 |
| 52 | 0.062 | 0.82 | 0.24 | 0.19 | 1.8 |

Example 27

Biological Data for Exemplary Compounds

Kinase cellular potency data were obtained for various exemplary compounds prepared according to Examples 1-24, using the Reaction Biology NanoBRET assay protocol described below. The NanoBRET assay measures kinase engagement in real time in the context of the intact cell. Unlike the previously described biochemical kinase assay methodologies in Examples 26-27, the NanoBRET assay measures the binding and activity characteristics under equilibrium conditions using full-length kinases in the presence of cellular concentrations of ATP in live, uncompromised cells. As such, the assay provides a more relevant assessment of kinase potency and selectivity that would be expected to be observed in the native cellular environment, where potency is often considerably lower than that observed in the isolated biochemical assays (Vasta, J. D. et al., (2018) Cell Chem. Biol. 25, 206-214). The assay uses a Kinase-NanoLuc® fusion vector expressing a kinase protein to which a luciferase tag has been added, a cell-permeant fluorescent NanoBRET™ tracer, a NanoLuc® substrate, and an extracellular NanoLuc® inhibitor. Upon expression of the luciferase-tagged kinase, cells will produce a strong BRET signal only in the presence of the NanoBRET™ tracer. The extracellular NanoLuc® inhibitor ensures that the BRET signal observed emanates only from live cells. Because the BRET signal has tight distance constraints, addition of the test compound will decrease the BRET signal if the compound competes with the NanoBRET™ tracer for binding to the kinase domain. Under the appropriate tracer conditions established by the manufacturer, quantitative intracellular affinity and relative potency can then be determined using Mass Action model equations.

HEK-293 cells were purchased from ATCC. FuGENEHD Transfection Reagent, Kinase-NanoLucfusion plasmids, Transfection Carrier DNA, NanoBRETTracers and dilution buffer, NanoBRETNano-Glo Substrate, Extracellular NanoLucInhibitor were obtained from Promega.

Assays were conducted following Promega assay protocol with some modifications. HEK-293 Cells were transiently transfected with Kinase-NanoLucFusion Vector DNA by FuGENEHD Transfection Reagent. Testing compounds were delivered into 384 well assay plate by Echo 550 (Labcytelnc, Sunnyvale, CA). Transfected cells were harvested and mixed with NanoBRETTracer Reagent and dispensed into 384 well plates and incubated at 37° C. in 5% $CO_2$ cell culture incubator for 1 hour. The NanoBRETNano-Glo Substrate plus Extracellular NanoLucInhibitor Solution were added into the wells of the assay plate and incubated for 2-3 minutes at room temperature. The donor emission wavelength (460 nm) and acceptor emission wavelength (600 nm) were measured in the EnVisionplate reader. The BRET Ratios were calculated. BRET Ratio=[(Acceptor sample÷Donor sample)−(Acceptor no-tracer control÷Donor no-tracer control)]. The $IC_{50}$ values of compounds were calculated with Prism GraphPad program.

NanoBRET™ Target Engagement Assay Protocol

1. Transient Transfection of HEK-293 Cells NanoLuc® Fusion Vector DNA

1). Cultivate HEK-293 cells (70-80% confluence) appropriately prior to assay. Trypsinize and collect HEK-293 cells.

2). Prepare lipid: DNA complexes as follows:

a. Prepare a 10 g/ml solution of DNA in Opti-MEM without serum that consists of the following ratios of carrier DNA and DNA encoding NanoLuc® fusion. 9.0 g/mL of Transfection Carrier DNA, 1.0 g/mL of Nano- Luc fusion vector DNA and 1 mL of Opti-MEM without phenol red. Mix thoroughly.

b. Add 30 1 of FuGENE HD Transfection Reagent into each milliliter of DNA mixture to form lipid: DNA complex.

c. Mix by inversion 10 times.

d. Incubate at ambient temperature for 20 minutes to allow complexes to form.

3). In a sterile, conical tube, mix 1 part of lipid: DNA complex with 20 parts of HEK-293 cells in suspension. Mix gently by inversion 5 times.

4). Dispense cells+lipid: DNA complex into a sterile tissue culture dish and incubate for 22-24 hours.

2. Addition of Test Compounds (dry plate shooting)

Each test compound is delivered from the compound source plate to the wells of 384-well white NBS plate by Echo 550.

3. Preparation of Cells with NanoBRET™ Tracer Reagent

1). Remove medium from dish with transfected HEK-293 cells via aspiration, trypsinize and allow cells to dissociate from the dish.

2). Neutralize trypsin using medium containing serum and centrifuge at 200×g for 5 minutes to pellet the cells. Adjust the cell density to 2×105 cells/mL in Opti-MEM without phenol red.

3). Prepare Complete 20× NanoBRET™ Tracer Reagent with Tracer Dilution Buffer.

4). Dispense one part of Complete 20× NanoBRET™ Tracer Reagent to 20 parts of cells in the tube. Mix gently by inversion 10 times.

5). Dispense cell suspension into white, 384-well NBS plates. Incubate the plate at 37° C., 5% $CO_2$ for 1 hour.

Note: Prepare a separate set of samples without tracer for background correction steps.

4. NanoBRET™ Assay

1). Remove plate from incubator and equilibrate to room temperature for 15 minutes.

2). Prepare 3× Complete Substrate plus Inhibitor Solution in Assay Medium (Opti-MEMR I Reduced Serum Medium, no phenol red) just before measuring BRET.

3). Add 3× Complete Substrate plus Inhibitor Solution to each well of the 384-well plate. Incubate for 2-3 minutes at room temperature.

4). Measure donor emission wavelength (460 nm) and acceptor emission wavelength (600 nm) using the Envision 2104 plate reader.

5. Determination of BRET Ratio

To generate raw BRET ratio values, divide the acceptor emission value (600 nm) by the donor emission value (460 nm) for each sample. To correct for background, subtract the BRET ratio in the absence of tracer (average of no-tracer control samples) from the BRET ratio of each sample.

*NanoBRET™* ratio equation:

$$BRET\text{ Ratio} = (\text{Acceptor sample} \div \text{Doner sample})$$

*NanoBRET™* ratio equation, including optional background correction:

$$BRET\text{ Ratio} = [(\text{Acceptor sample} \div \text{Doner sample}) - (\text{Acceptor no-tracer control} \div \text{Donor no-tracer control})]$$

Normalized *Bret* Response equation (%):

-continued $$(BRET\text{ Ratio of Compound Treated Sample}/BRET\text{ Ratio of }DMSO\text{ Control Sample}) * 100\%$$

6. Determination of $IC_{50}$ Values $IC_{50}$ curves are plotted and $IC_{50}$ values are calculated using the GraphPad Prism program based on a sigmoidal dose-response equation.

TABLE 25

Biological data obtained in accordance with the protocol described in Example 27.

| Compound # | NanoBRET FLT3 $IC_{50}$ (nM) | NanoBRET IRAK4 $IC_{50}$ (nM) |
|---|---|---|
| 1 | 6 | <0.5 |
| 3 | 3 | <0.5 |
| 5 | <0.5 | <0.5 |
| 16 | 21 | <0.5 |
| 25 | 6 | <0.5 |
| 31 | 136 | <0.5 |
| 33 | 1500 | <0.5 |
| 34 | 177 | <0.5 |
| 35 | 216 | <0.5 |
| 38 | 12 | <0.5 |
| 43 | 73 | 84 |
| 50 | 10 | 1 |
| 51 | 4 | 0.6 |
| 58 | 52 | <0.5 |
| 77 | 277 | <0.5 |
| 78 | 40 | <0.5 |
| 80 | 94 | <0.5 |
| 81 | 15 | <0.5 |
| 82 | 40 | <0.5 |
| 97 | 0.9 | 0.9 |
| 107 | 0.9 | 10 |
| 108 | 31 | 1 |
| 119 | 16 | 2 |
| 121 | 21 | 2 |
| 125 | 937 | <0.5 |
| 126 | 8 | <0.5 |
| 127 | 16 | 0.4 |
| 129 | 12 | <0.5 |
| 130 | 11 | <0.5 |

Example 28

Biological Data for Exemplary Compounds

Cellular potency data were obtained for various exemplary compounds prepared according to Examples 1-24 using the NF-kB assay protocol described below. Activation of NF-kB gene transcription is a downstream signal in the IRAK signaling pathway (Balka, K. R. and DeNardo, D., J. Leukoc. Biol. (2019) 105, 339-351. Because THP-1 cells do not contain activated FLT3 receptors, measurement of the ability of a FLT3/IRAK1/IRAK4 inhibitor compound to inhibit the NF-kB production reflects the ability to inhibit signaling downstream of blocking signaling through the IRAK1/4 complex and is not a composite measurement of activity that includes FLT3 kinase inhibition.

THP-1-Blue NF-xB cells (InvivoGen) carrying a stable integrated NF-κB-inducible secreted embryonic alkaline phosphatase (SEAP) reporter construct were plated at a concentration of $1\times10^5$ cells per well. The cells were stimulated with Pam3CSK4 (1 ng/mL) or hIL1B (1 ng/mL). After 10-20 minutes, the cells were then treated with vehicle (DMSO) or serial dilutions of the test compounds (10 doses tested for each test compound, with a 1:10 dilution series starting at 1 μM or 3 μM) with a final volume of 200 μL for 24 hours at 37° C. After 24 hours, the cells were centrifuged and 20 μL supernatant was incubated with 180 μL QUANTI-Blue reagent at 37° C. for 30-60 minutes. The levels of NF-κB-induced was measured in a microplate reader at 620 nm.

TABLE 26

Biological data obtained in accordance with the protocol described in Example 28.

| Compound # | NF-κB Pam3SCK4 $IC_{50}$ (nM) | NF-κB IL1B $IC_{50}$ (nM) |
|---|---|---|
| 1 | 6 | 9 |
| 16 | 11 | 5 |
| 25 | 12 | 47 |
| 30 | 28 | 40 |
| 31 | 37 | 44 |
| 35 | 23 | 88 |
| 36 | 17 | 40 |
| 50 | 9 | 11 |
| 51 | 20 | 57 |
| 59 | 24 | 144 |
| 60 | 34 | 356 |
| 80 | 44 | 124 |
| 81 | 24 | 72 |
| 82 | 12 | 30 |
| 96 | 20 | 263 |
| 97 | 83 | 164 |
| 107 | 37 | 357 |
| 118 | 101 | 406 |
| 119 | 56 | 1290 |
| 121 | 54 | 76 |
| 129 | 11 | 70 |

Example 29

Biological Data for Exemplary Compounds

Cellular potency data were obtained for various exemplary compounds prepared according to Examples 1-24, using the MOLM14 D835Y and MOLM14 F691L cell viability assay protocols described below. Both cell lines have activated FLT3 receptors, each of which carry additional resistance mutations in the kinase domain (D835Y and F691L, respectively). Leukemias from patients harboring these kinase domain resistance mutations are resistant to FLT3 inhibitors that do not inhibit the mutant kinase. Because the activated FLT3 receptor drives a mitogenic response, and because there can be a discrepancy between activity in the biochemical kinase assay and in the context of a whole cell (Vasta, J. D. et al., (2018) Cell Chem. Biol. 25, 206-214), demonstration of antiproliferative activity in these cell lines with compounds known to inhibit the D835Y or F691L kinases in biochemical assays provides a more relevant cellular context for demonstration of activity.

MOLM14 D835Y and MOLM14 F691L cells were grown in RPMI-1640 media supplemented with 20% fetal bovine serum (FBS). For viability/cytotoxicity assessments, cells were seeded into 1536-well white polystyrene tissue culture-treated Greiner plates using a Multidrop Combi dispenser (ThermoFisher), in final volume 5 μL of growth media per well, at a density of 1000 cells per well. After cell addition, 23 nL of test compound were transferred into individual wells (22 doses tested for each test compound, with a 1:2 dilution series starting at 10 μM) via a 1536 pin-tool. Bortezomib (final concentration 2.3 μM) was used as a positive control for cell cytotoxicity. Plates were incubated for 48 hours at standard incubator conditions covered by a stainless steel gasketed lid to prevent evaporation. 48 hours post compound addition, 3 μL of Cell Titer Glo (Promega) were added to each well and plates were incubated at room temperature for 15 minutes with the stainless-steel lid in place. Luminescence readings were taken using a Viewlux imager (PerkinElmer) with a 2 second exposure time per plate.

TABLE 27

Biological data obtained in accordance with the protocol described in Example 29.

| Compound # | MOLM14 D835Y $IC_{50}$ (nM) | MOLM14 F691L $IC_{50}$ (nM) |
|---|---|---|
| 1 | 18 | 169 |
| 2 | 7 | 34 |
| 3 | 6 | N.D. |
| 5 | 2 | 34 |
| 8 | 44 | 376 |
| 9 | 18 | 106 |
| 10 | 14 | 168 |
| 11 | 15 | N.D. |
| 12 | 7 | 72 |
| 13 | 21 | 159 |
| 16 | 21 | 226 |
| 17 | 10 | 88 |
| 18 | 14 | N.D. |
| 19 | 2 | 19 |
| 25 | 9 | 74 |
| 28 | 94 | 502 |
| 29 | 42 | N.D. |
| 30 | 75 | 381 |
| 31 | 63 | 249 |
| 33 | 168 | 2662 |
| 34 | 106 | 1334 |
| 35 | 94 | 841 |
| 38 | 23 | N.D. |
| 40 | 23 | 152 |
| 43 | 8 | 79 |
| 48 | 9 | 38 |
| 49 | 9 | N.D. |
| 50 | 24 | 192 |
| 51 | 9 | 53 |
| 52 | 11 | 106 |
| 58 | 30 | N.D. |
| 68 | 47 | 473 |
| 75 | 15 | 158 |
| 76 | 19 | 199 |
| 77 | 106 | 376 |
| 78 | 47 | 299 |
| 79 | 84 | 237 |
| 80 | 68 | 196 |
| 81 | 30 | 211 |
| 82 | 34 | 157 |
| 83 | 344 | 486 |
| 84 | 183 | 410 |
| 85 | 154 | 290 |
| 86 | 205 | 365 |
| 87 | 116 | 309 |
| 88 | 97 | 217 |
| 89 | 41 | 649 |
| 90 | 96 | 817 |
| 91 | 195 | 1536 |
| 92 | 87 | 969 |
| 93 | 73 | 969 |
| 94 | 77 | 864 |
| 95 | 21 | 193 |
| 96 | 7 | 39 |
| 97 | 5 | 26 |
| 101 | 217 | 1536 |
| 102 | 386 | 4330 |
| 103 | 193 | 1369 |
| 104 | 11 | 86 |
| 105 | 55 | 686 |
| 106 | 17 | 122 |
| 107 | 21 | 97 |
| 108 | 26 | 183 |
| 109 | 137 | 1934 |

TABLE 27-continued

Biological data obtained in accordance with the protocol described in Example 29.

| Compound # | MOLM14 D835Y $IC_{50}$ (nM) | MOLM14 F691L $IC_{50}$ (nM) |
|---|---|---|
| 110 | 154 | 1453 |
| 111 | 86 | 344 |
| 112 | 49 | 183 |
| 113 | 172 | 579 |
| 114 | 460 | 4859 |
| 115 | 92 | 273 |
| 116 | 39 | 193 |
| 117 | 41 | 273 |
| 118 | 9 | 37 |
| 119 | 19 | 54 |
| 120 | 24 | 86 |
| 121 | 23 | 173 |
| 122 | 334 | 770 |
| 123 | 86 | 244 |
| 124 | 130 | 290 |
| 125 | 163 | 2052 |
| 126 | 21 | 205 |
| 127 | 44 | 410 |
| 128 | 58 | 326 |
| 129 | 33 | 163 |
| 130 | 26 | 130 |
| 131 | 27 | 168 |
| 132 | 19 | 119 |

N.D. = experiment not performed

Example 30

Combination Drug Screening for Exemplary Compounds

Combination drug therapy has the potential to produce enhanced effects with lower side effects not obtained using either agent alone, or beyond the additive effect of the different concentrations of the two different agents. To determine whether enhanced effects are observed in different drug combinations in the setting of FLT3 resistance, combination drug screening was performed as previously described (Mathews-Griner, L. A. et al., Proc. Nat. Acad. Sci., 2014, 111:2439-2454; Lin, G. L. et al., Sci. Trans. Med., 2019, 11:eaaw0064). Briefly, 10 nL of compounds were acoustically dispensed into 1536-well white polystyrene tissue culture-treated plates with an Echo 550 acoustic liquid handler (Labcyte). MOLM14 (D835Y) Cells were then added to compound-containing plates at a density of 500-cells/well in 5 μL of medium. A 10-point custom concentration range was used for all listed drugs. Plates were incubated for 48 hours at standard incubator conditions covered by a stainless steel gasketed lid to prevent evaporation. 48 h post compound addition, 3 μL of Cell Titer Glo (Promega) were added to each well and plates were incubated at room temperature for 15 minutes with the stainless-steel lid in place. Luminescence readings were taken using a Viewlux imager (PerkinElmer) with a 2 second exposure time per plate. The results can be seen in Table 28.

TABLE 28

Sum excess HSA scores for a combination therapy of Compounds 25, 31, 35, 50, 51, 80, 82, 97, 118, and 119 with Venetoclax obtained in MOLM14 (D835Y) cells in a 10 × 10 dataset.

| Compound # | Sum Excess HSA | Interaction with Venetoclax |
|---|---|---|
| Compound 25 | −834.55736 | Synergistic |
| Compound 119 | −762.00142 | |
| Compound 51 | −644.49994 | |
| Compound 50 | −551.98317 | |
| Compound 118 | −550.87189 | |
| Compound 80 | −261.70306 | |
| Compound 97 | −171.65888 | |
| Compound 82 | −155.80548 | |
| Compound 31 | −150.3956 | |
| Compound 35 | 386.44744 | Antagonistic |

The sum excess HSA scores for Compounds 25, 31, 35, 50, 51, 80, 82, 97, 118, and 119 in Table 28 are used herein to quantitate drug interactions for enhanced pharmacological effects in the MOLM14 (D835Y) cell line. This is a FLT3-ITD cell line that harbors a FLT3 resistance mutation in the tyrosine kinase domain at position 835 (D835Y). More information on excess HSA scores can be found in Vlot, Anna H. C. et al., Drug Discovery Today, 2019, 24(12):2286-2298. While there are other methods of quantitating drug interactions, excess HSA method is preferred because it does not require making assumptions about similarities in the mechanism of action of the drugs involved or the shape of the dose-response curves being compared and does not place arbitrary requirements on the computational algorithm that the two drugs produce similar efficacy in the given system. However, different methodologies may yield different numerical scores, and different definitions of what constitutes a deviation from mere additivity vs true drug synergy. Table 28 summarizes the combination results of Compounds 25, 31, 35, 50, 51, 80, 82, 97, 118, and 119 with Venetoclax. A large negative sum excess HSA score indicates profound synergism with Venetoclax, whereas a positive excess HSA score indicates antagonism with Venetoclax in certain drug combinations.

The degree to which combination therapy has to potential to produce enhanced effects with lower side effects not obtained using either agent alone, or beyond the additive effect of the different concentrations of the two different agents depends on the nature of the drugs used in the combination, and the specific doses/concentrations at which they are ultimately used in the therapeutic regimen. A negative excess sum HSA score illustrates that the drug combination is better than either drug alone (at the concentrations being studied), and the sum excess HSA score is a measurement of the overall deviation from additivity that is observed across the entire matrix of concentrations studied. Hence, the drug combinations that are noteworthy as having more profound synergistic effects are those with greater negative excess sum HSA scores. However, the utility in certain drug combinations vs others should not be distinguished based on cutoffs between excess sum HSA scores, because the score itself is only a relative indicator that is completely dependent on experimental design and is not an absolute number. Furthermore, the concept of what constitutes clinically meaningful drug synergy is something that is still being debated, not only between pharmacologists and physicians, but amongst pharmacologists themselves. The data in Table 28 illustrate that the nature of the combined effect is dependent on the characteristics of each individual compound, as not every compound produced a synergistic interaction in combination with Venetoclax.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure.

The various methods and techniques described above provide a number of ways to carry out the disclosure. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature, or step, can be employed in various combinations by one of ordinary skill in this art to perform methods in accordance with the principles described herein. Among the various elements, features, and steps some will be specifically included, and others specifically excluded in diverse embodiments.

Although the application has been disclosed in the context of certain embodiments and examples, it will be understood by those skilled in the art that the embodiments of the disclosure extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements. No language in the specification should be construed as indicating any non-claimed element essential to the practice of the application.

In certain instances, sequences disclosed herein are included in publicly available databases, such as GENBANK© and SWISSPROT. Unless otherwise indicated or apparent the references to such publicly available databases are references to the most recent version of the database as of the filing date of thisapplicationn.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter. As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the disclosure. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A compound of Formula (I):

(I)

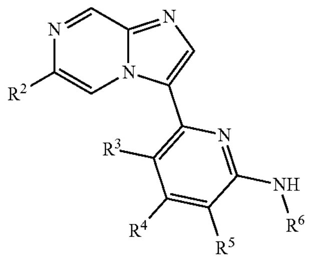

or a salt, ester, solvate, optical isomer, geometric isomer, salt of an isomer, prodrug, or derivative thereof, wherein:

$R^2$, $R^3$, $R^4$, and $R^5$ are each independently selected from H, halogen, hydroxy, oxo (=O), —CN, amino, amido, —O-aryl, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ heteroalkyl, $C_1$-$C_7$ alkoxy, cycloalkyl, spiro-fused cycloalkyl, heterocyclyl, aryl, heteroaryl, or fused ring heteroaryl, wherein amino, amido, —O-aryl, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more of halogen, hydroxy, oxo, methanoyl (—COH), carboxy (—$CO_2H$), nitro (—$NO_2$), —$NH_2$, —$NHCH_3$, —$N(CH_3)_2$, cyano (—CN), ethynyl (—CCH), propynyl, sulfo (—$SO_3H$), heterocyclyl, aryl, heteroaryl, pyrrolyl, piperidyl, piperazinyl, morpholinyl, —CO-morpholin-4-yl, —$CONH_2$, —$CONHCH_3$, —$CON(CH_3)_2$, $C_1$-$C_7$ alkyl, $C_1$-$C_7$ perfluorinated alkyl, $C_1$-$C_7$ alkoxy, $C_1$-$C_7$ haloalkoxy, or $C_1$-$C_7$ alkyl which is substituted with cycloalkyl, wherein two adjacent optional substituents can bond or fuse to form a ring;

$R^6$ is selected from (Ia)

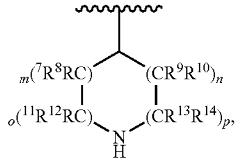

or (Ib)

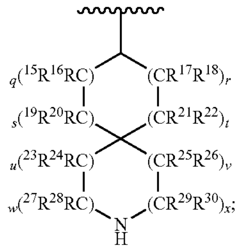

$R^7$, $R^8$, $R^9$, $R^{10}$, $R^{11}$, $R^{12}$, $R^{13}$, and $R^{14}$ are each independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{29}$, and $R^{30}$ are each independently selected from H, halogen, hydroxy, oxo, —CN, methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl, wherein methanoyl (—COH), carboxy (—$CO_2H$), $C_1$-$C_7$ alkyl, $C_2$-$C_7$ alkenyl, $C_2$-$C_7$ alkynyl, $C_1$-$C_7$ alkoxy, cycloalkyl, spiro-fused cycloalkyl, heterocyclyl, aryl, heteroaryl, or fused ring heteroaryl is optionally substituted with one or more halogen and/or $C_1$-$C_6$ alkyl; and m, n, o, p, q, r, s, t, u, v, w, and x are each independently selected from 0, 1, 2, 3, 4, or 5; where q+r+s+t is at least 1, and where u+v+w+x is at least 1.

2. The compound of claim 1, wherein the compound of Formula (I) is a compound of Formula (IIf):

Formula (IIf)

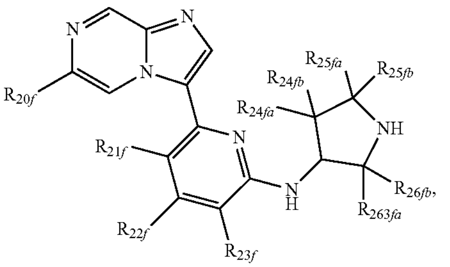

or a salt, ester, solvate, optical isomer, geometric isomer, or salt of an isomer thereof;

wherein:

$R_{20f}$ is selected from H, halogen, $C_1$-$C_6$ alkyl, $C_1$-$C_6$ alkoxy, $C_3$-$C_6$ cycloalkyl, —O—$(CH_2)_a$—($C_3$-$C_6$ cycloalkyl), heteroaryl, and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocyclyl and heteroaryl are optionally substituted with one or more substituents selected from halogen, $C_1$-$C_6$ alkyl, $C_1$-$C_6$ alkoxy, —OH, and —O wherein two adjacent optional substituents can bond or fuse to form a ring;

$R_{21f}$, $R_{22f}$, and $R_{23f}$ are each independently selected from H and halogen;

$R_{24fa}$, $R_{24fb}$, $R_{25fa}$, $R_{25fb}$, $R_{26fa}$, and $R_{26fb}$ are each independently selected from H, halogen, —OH, $C_1$-$C_6$ alkyl, and $C_1$-$C_6$ alkoxy, wherein $C_1$-$C_6$ alkyl and $C_1$-$C_6$ alkoxy are each optionally substituted with one or more halogen atoms; and a is selected from 0, 1, 2, 3, 4, 5, and 6.

3. The compound of claim 2, wherein at least one of (i)-(ix) applies:

(i) $R_{20f}$ is selected from t-butyl, unsubstituted $C_3$ cycloalkyl, pyrrolidinyl, —$OCH_3$, —$OCH_2CH_3$,

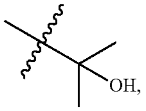 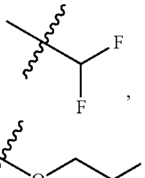 , 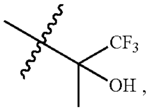

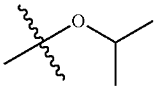 , 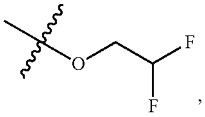 , 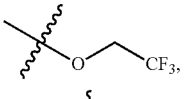

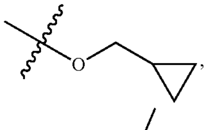 , 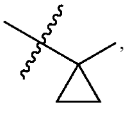 , 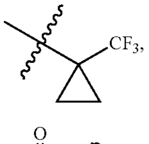

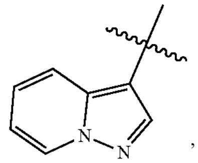 , 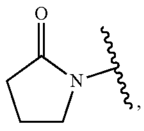 , 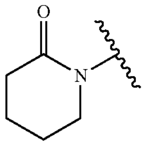 ,

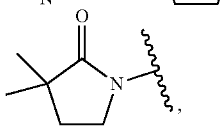 , 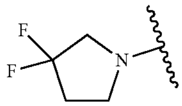 ,

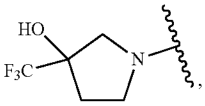 , 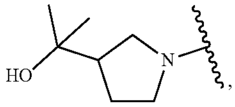 ,

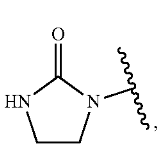 , 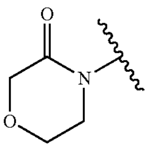 , and

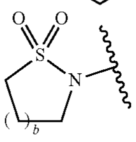

wherein b is 1 or 2;

(ii) $R_{20f}$ is

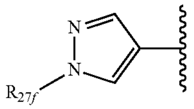

wherein $R_{27f}$ is selected from —$CH_3$,

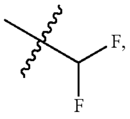 and 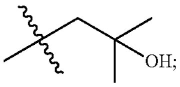

(iii) $R_{20f}$ is

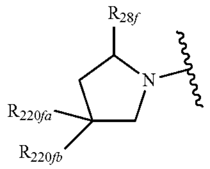

wherein $R_{28f}$ is =O and $R_{220fa}$ and $R_{220fb}$ are each —$CH_3$ or $R_{220fa}$ and $R_{220fb}$ bond or fuse to form oxetanyl;

(iv) $R_{21f}$, $R_{22f}$, and $R_{23f}$ are each H;

(v) $R_{21f}$ and $R_{23f}$ are each F and $R_{22f}$ is H;

(vi) $R_{21f}$ and $R_{23f}$ are each H and $R_{22f}$ is F;

(vii) $R_{24fa}$, $R_{24fb}$, $R_{25fa}$, $R_{25fb}$, $R_{26fa}$, and $R_{26fb}$ are each H;

(viii) $R_{25fa}$, $R_{25fb}$, $R_{26fa}$, and $R_{26fb}$ are each H and $R_{24fa}$ and/or $R_{24fb}$ are selected from F, —$CH_3$, and —$CF_3$; or (ix) $R_{20f}$ is H.

4. The compound of claim 2, wherein the compound is selected from:

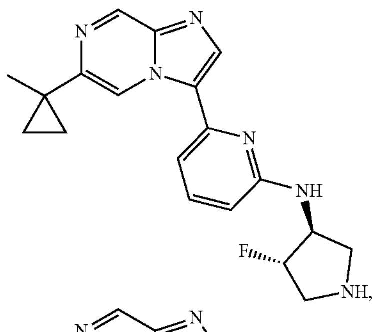

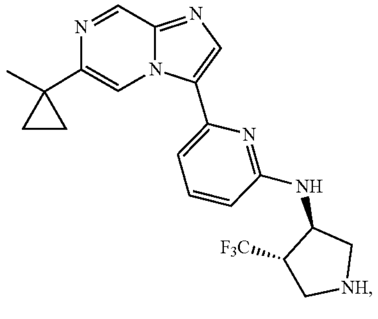

-continued
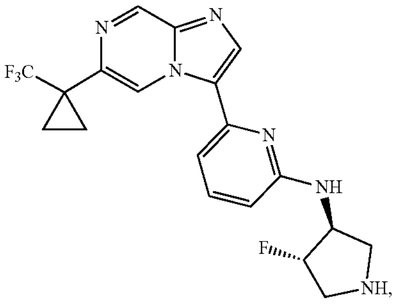
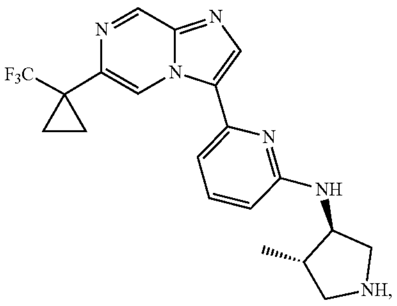
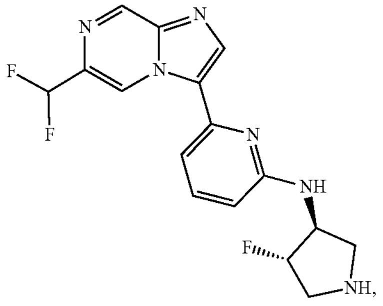
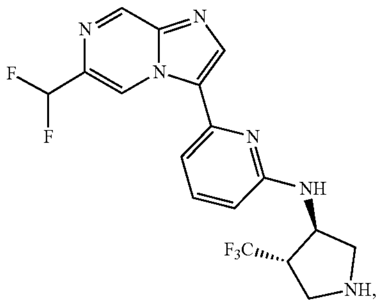
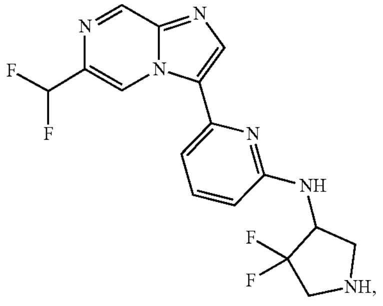
-continued
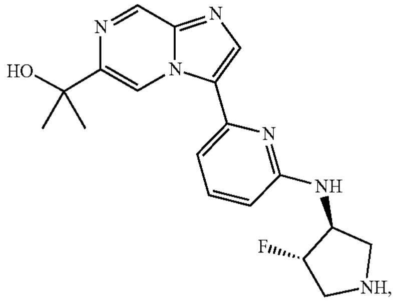
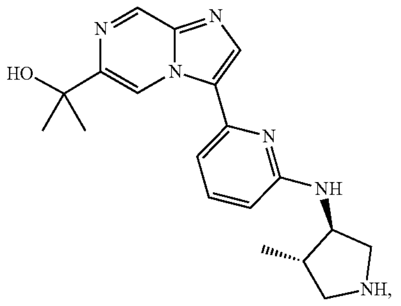
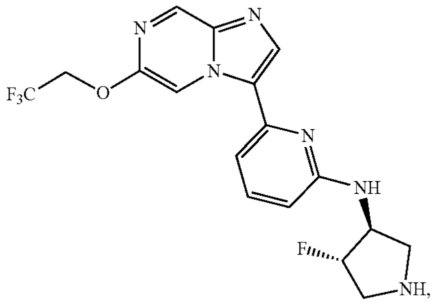
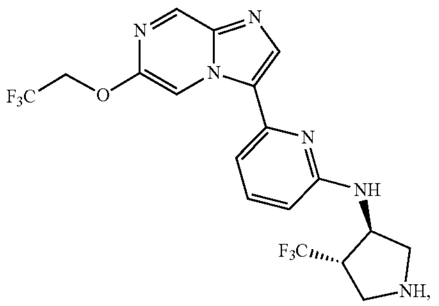
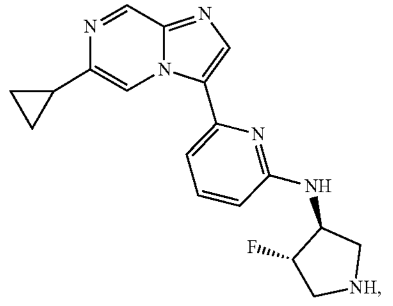

-continued
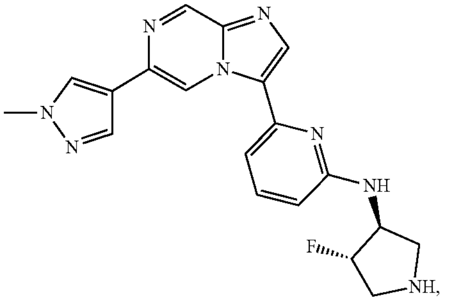
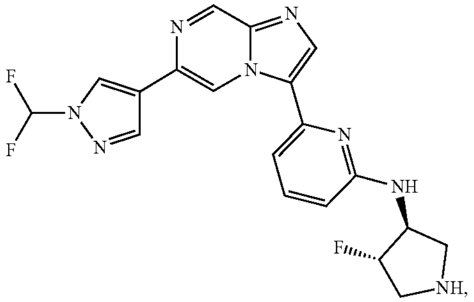
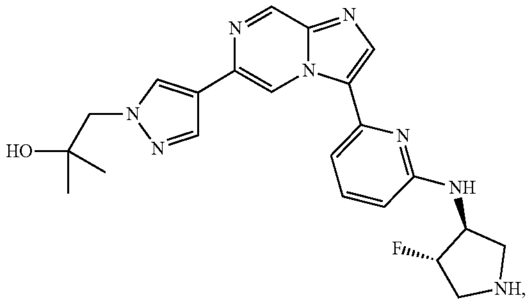
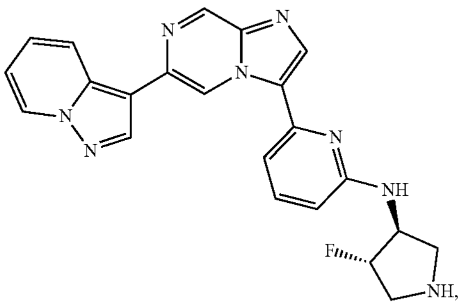
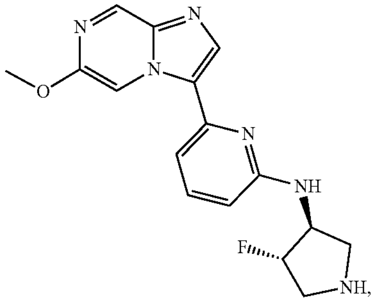
-continued
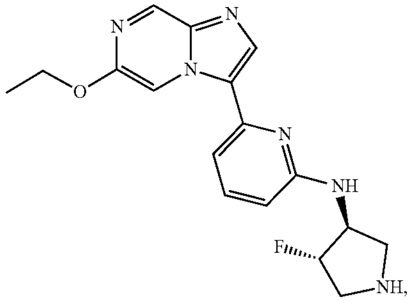
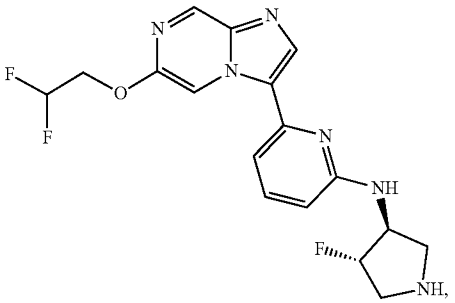
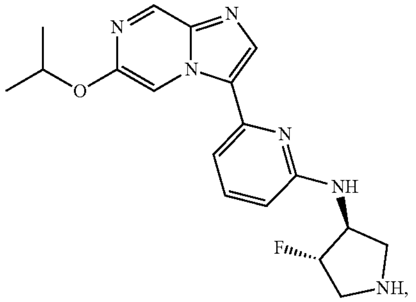
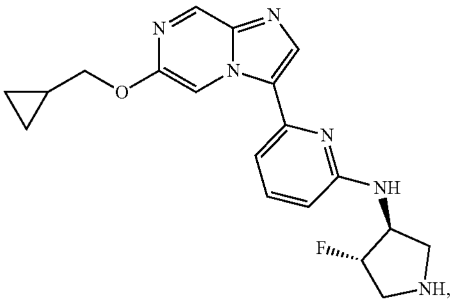
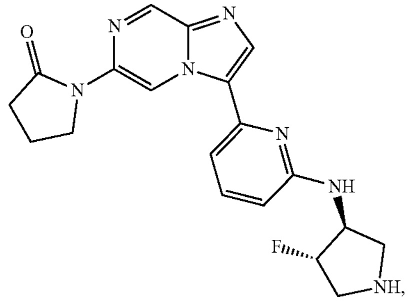

-continued
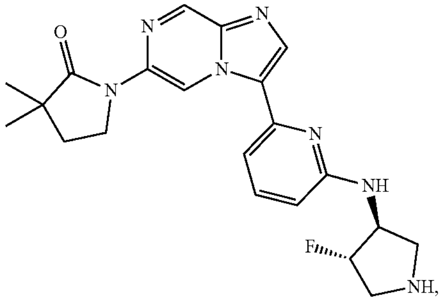
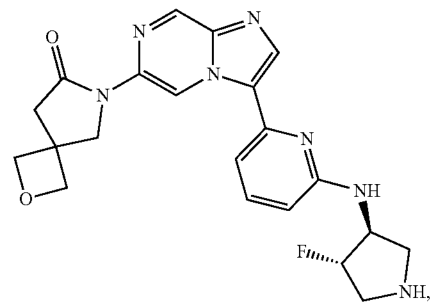
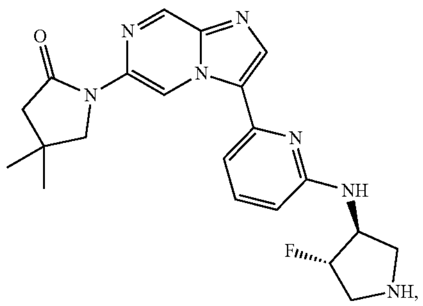
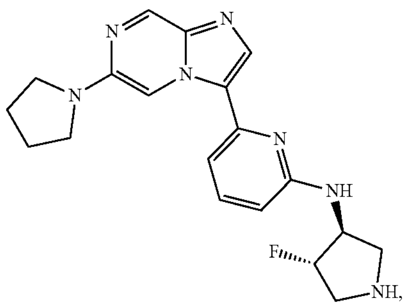
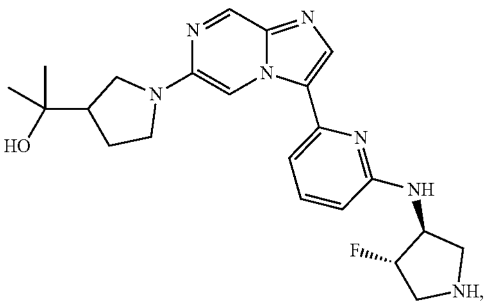
-continued
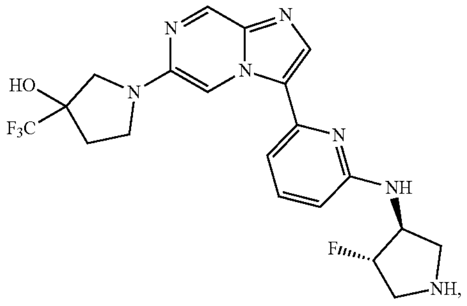
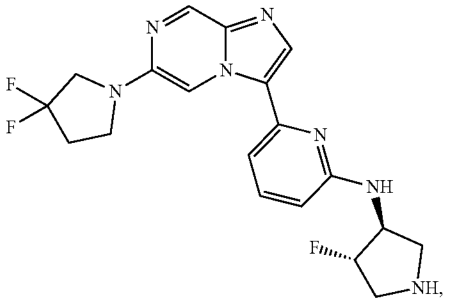
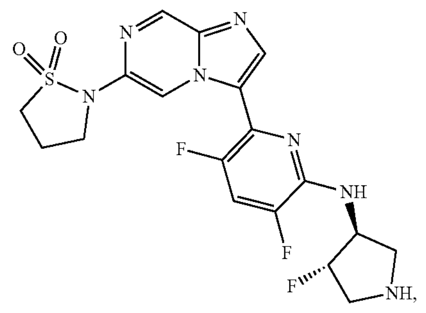
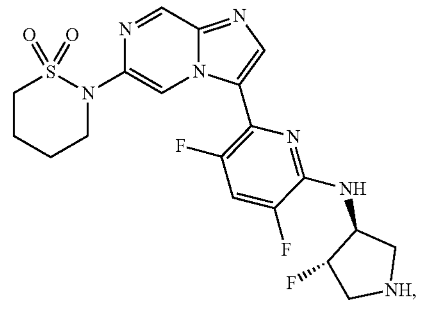
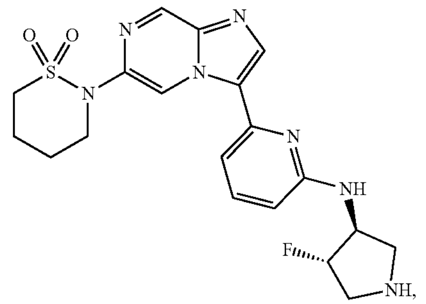

-continued
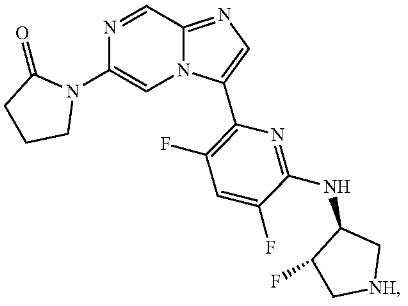
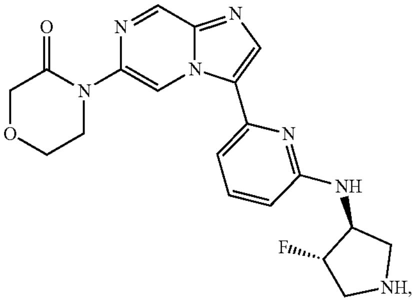
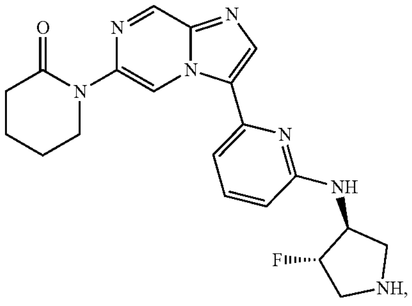
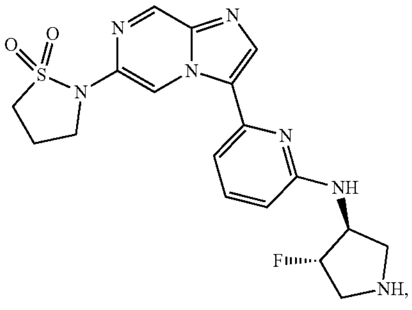
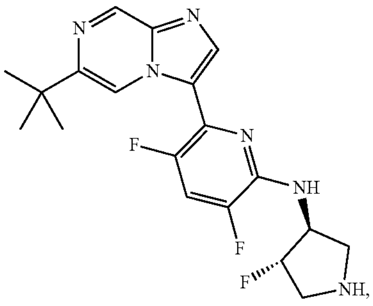
-continued
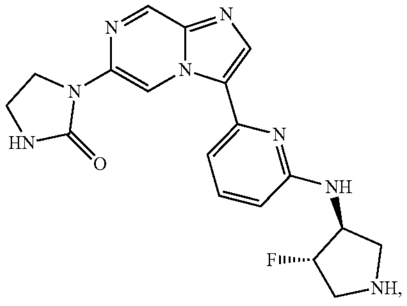
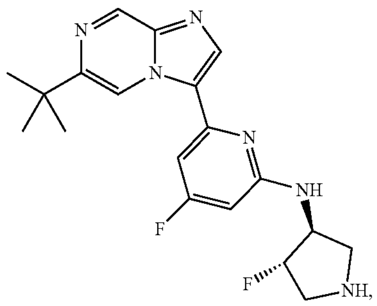
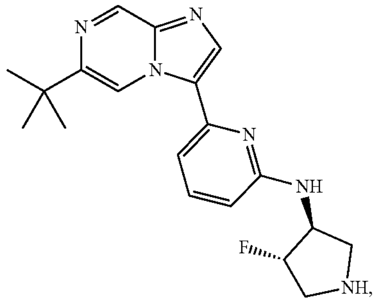
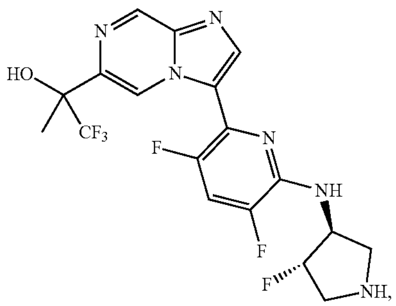
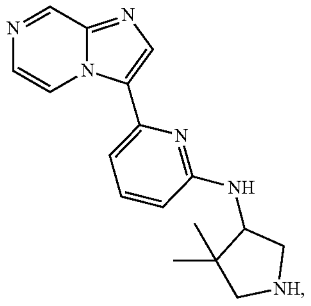

-continued
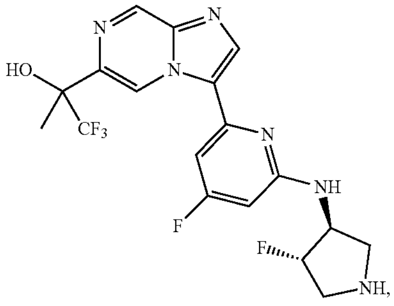
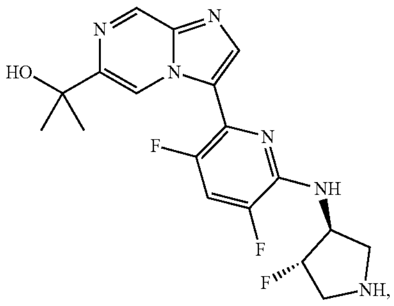
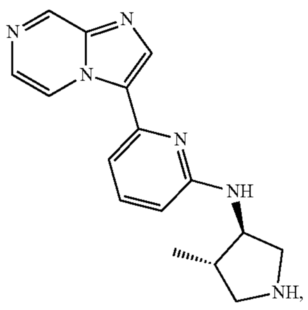
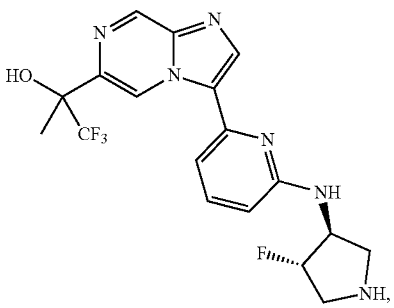
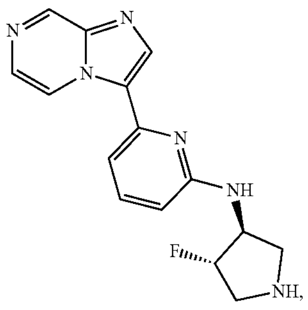
-continued
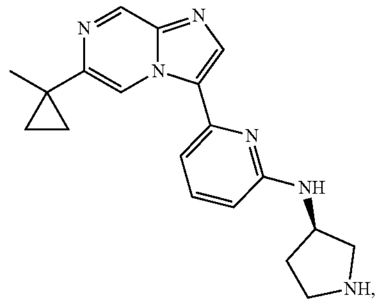
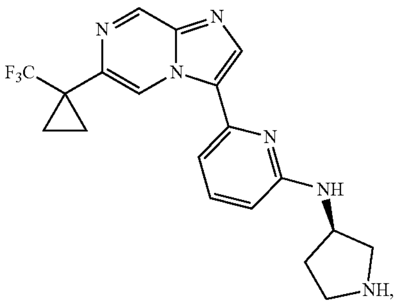
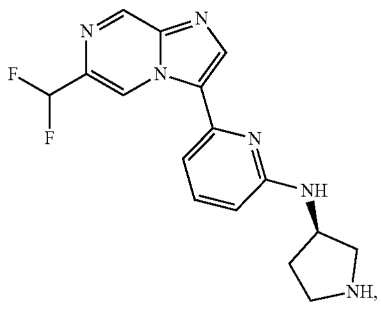
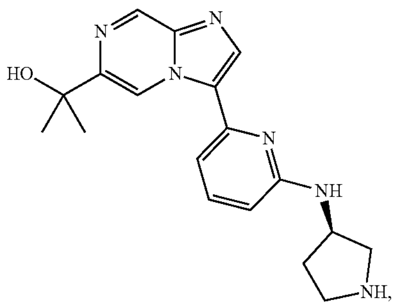
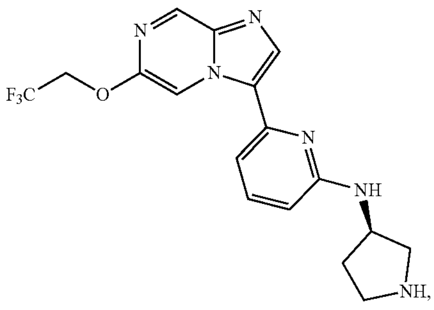
and -continued

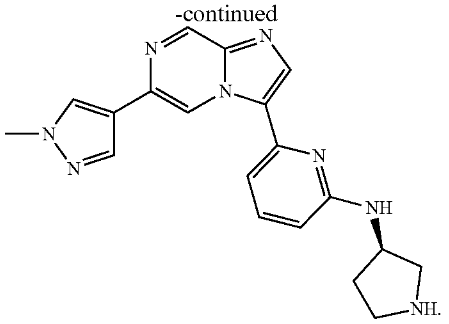

5. The compound of claim 1, wherein the compound of Formula (I) is a compound of Formula (IIg):

Formula (IIg)

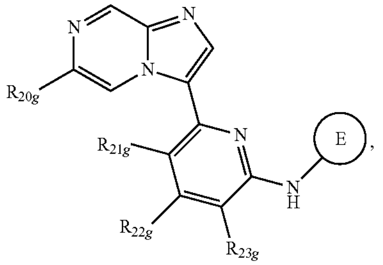

or a salt, ester, solvate, optical isomer, geometric isomer, or salt of an isomer thereof;

wherein:

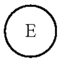

is selected from

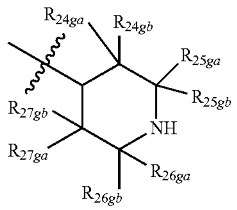

and

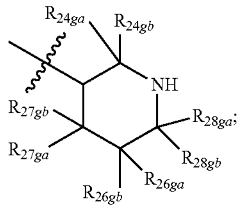

$R_{20g}$ is selected from H, $C_1$-$C_6$ alkyl, $C_1$-$C_6$ alkoxy, $C_3$-$C_6$ cycloalkyl, heteroaryl, and $C_3$-$C_9$ heterocyclyl, wherein $C_1$-$C_6$ alkyl and $C_1$-$C_6$ alkoxy are each optionally substituted with one or more substituents selected from —OH and halogen, wherein $C_3$-$C_6$ cycloalkyl is optionally substituted with one or more substituents selected from $C_1$-$C_6$ alkyl and halogen, and wherein $C_3$-$C_9$ heterocyclyl and heteroaryl are optionally substituted with one or more substituents selected from halogen, $C_1$-$C_6$ alkyl, $C_3$-$C_6$-cycloalkyl, —OH, and =O;

$R_{21g}$, $R_{22g}$, and $R_{23g}$ are each independently selected from H and halogen; and $R_{24ga}$, $R_{24gb}$, $R_{25ga}$, $R_{25gb}$, $R_{26ga}$, $R_{26gb}$, $R_{27ga}$, $R_{27gb}$, $R_{28ga}$, and $R_{28gb}$ are each independently selected from H, halogen, —OH, and $C_1$-$C_6$ alkyl.

6. The compound of claim 5, wherein at least one of (i)-(xii) applies:

(i) $R_{20g}$ is selected from t-butyl, unsubstituted $C_3$ cycloalkyl,

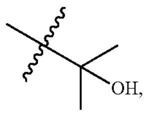

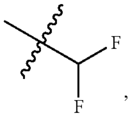,

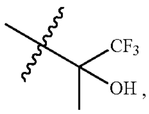

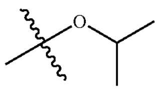,

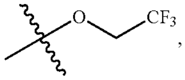,

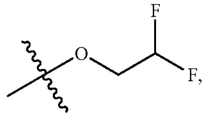

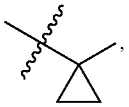,

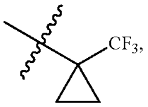

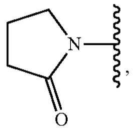

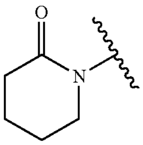,

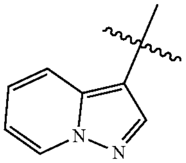,

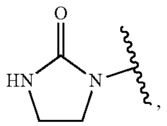

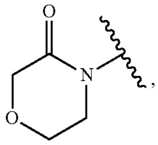, and

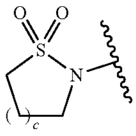

wherein c is 1 or 2;

(ii) $R_{20g}$ is

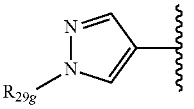

wherein $R_{29g}$ is selected from unsubstituted $C_3$ cycloalkyl, —$CH_3$,

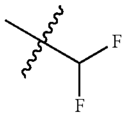

, and

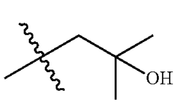

;

(iii) $R_{21g}$, $R_{22g}$, and $R_{23g}$ are each H;

(iv) $R_{21g}$ and $R_{23g}$ are each F and $R_{22g}$ is H;

(v) $R_{21g}$ and $R_{23g}$ are each H and $R_{22g}$ is F;

(vi)

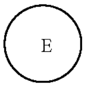

is

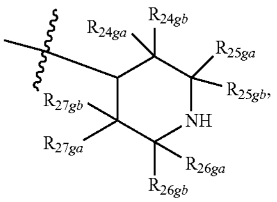

each of $R_{24ga}$, $R_{24gb}$, $R_{25ga}$, $R_{25gb}$, $R_{26ga}$, $R_{26gb}$, $R_{27ga}$, and $R_{27gb}$ is H;

(vii)

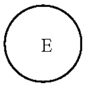 is 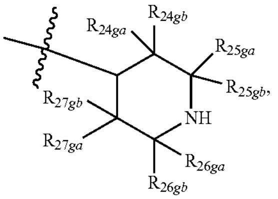

each of $R_{24ga}$, $R_{25ga}$, $R_{25gb}$, $R_{26ga}$, $R_{26gb}$, $R_{27ga}$, and $R_{27gb}$ is H and $R_{24gb}$ is F;

(viii)

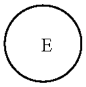 is 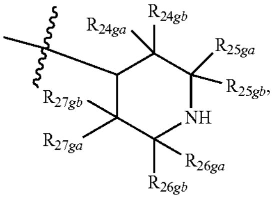

each of $R_{24ga}$, $R_{25ga}$, $R_{25gb}$, $R_{26ga}$, $R_{26gb}$, $R_{27ga}$, and $R_{27gb}$ is H and $R_{25gb}$ is —$CH_3$;

(ix)

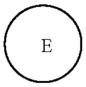 is 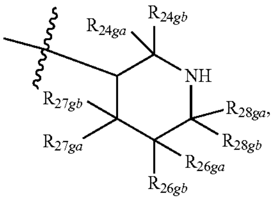

each of $R_{24ga}$, $R_{24gb}$, $R_{26ga}$, $R_{26gb}$, $R_{27ga}$, $R_{27gb}$, $R_{28ga}$, and $R_{28gb}$ is H;

(x)

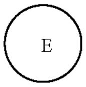 is 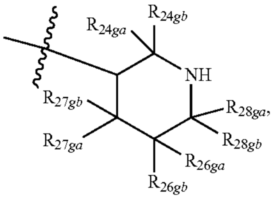

each of $R_{24ga}$, $R_{24gb}$, $R_{26ga}$, $R_{26gb}$, $R_{28ga}$, and $R_{28gb}$ is H and $R_{27ga}$ and/or $R_{27gb}$ is F or —$CH_3$;

(xi)

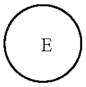 is 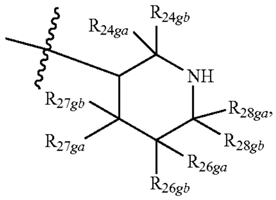

each of $R_{24ga}$, $R_{24gb}$, $R_{27ga}$, $R_{27gb}$, $R_{26ga}$, $R_{28ga}$, and $R_{28gb}$ is H and $R_{26gb}$ is F or —$CH_3$; or (xii) $R_{20g}$ is H.

7. The compound of claim 5, wherein the compound is selected from:

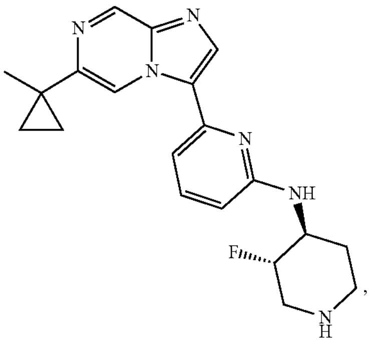
,

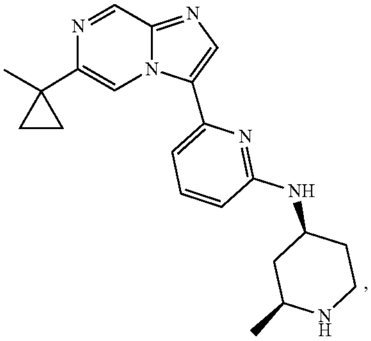
,

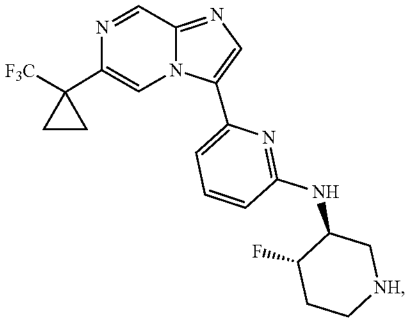
,

-continued
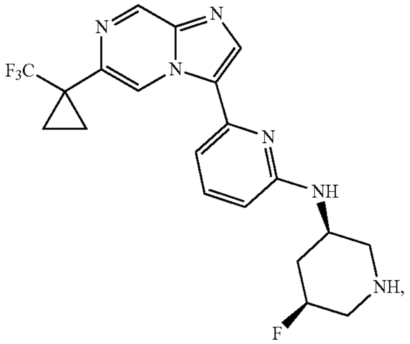
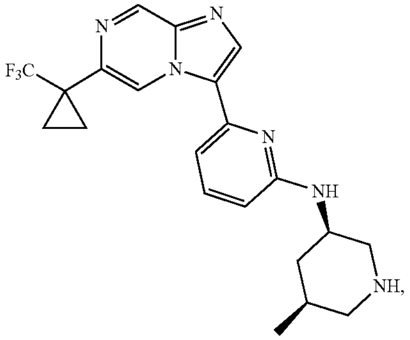
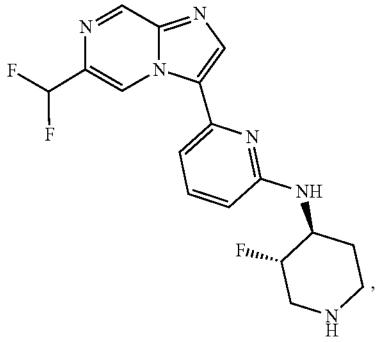
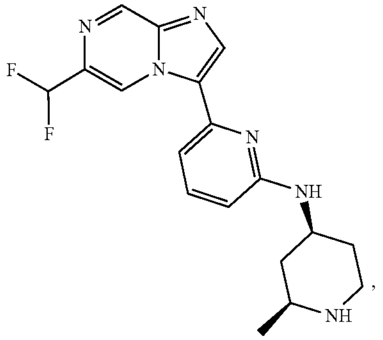
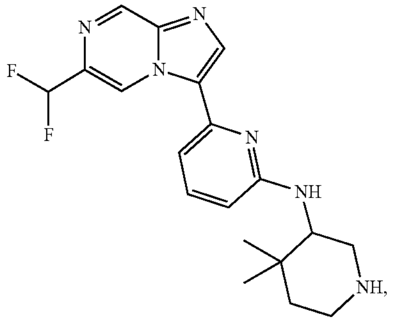
-continued
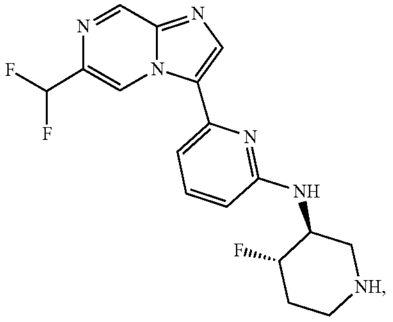
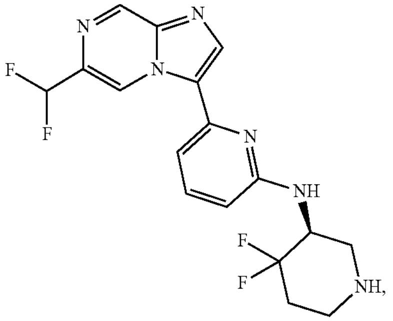
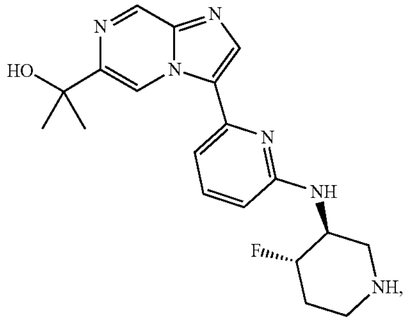
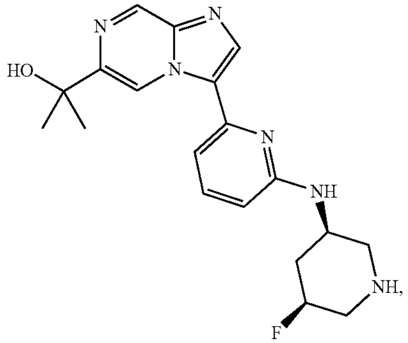
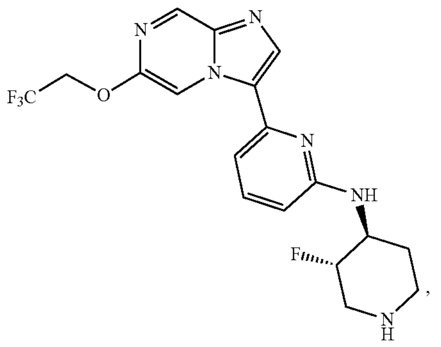

-continued
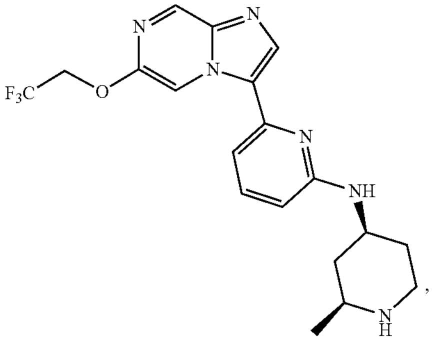
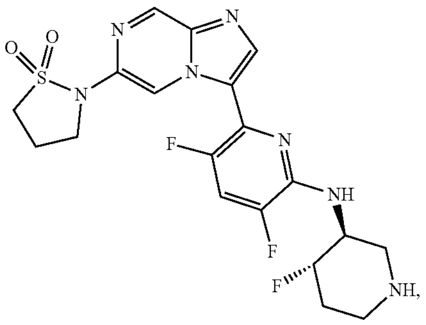
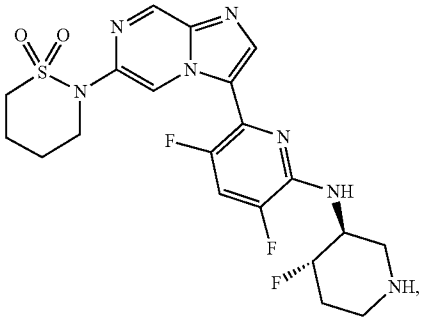
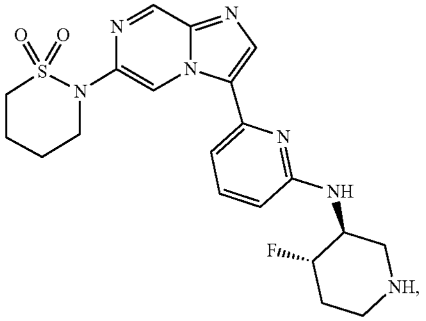
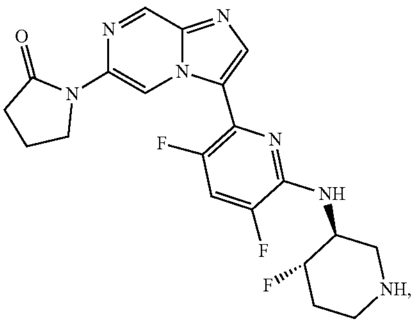
-continued
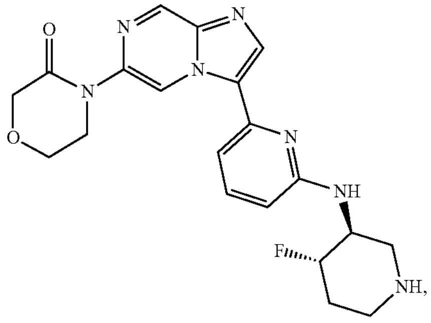
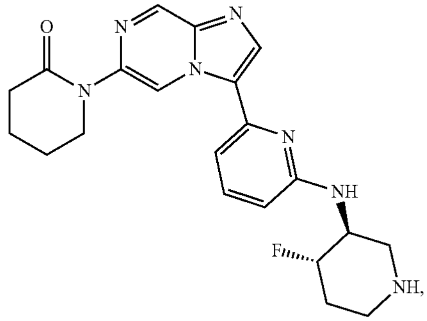
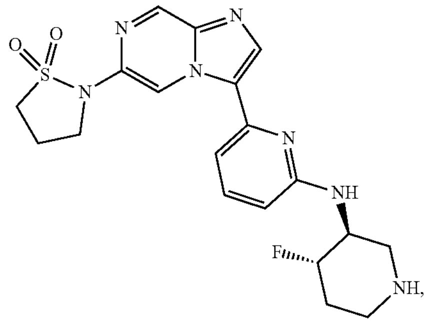
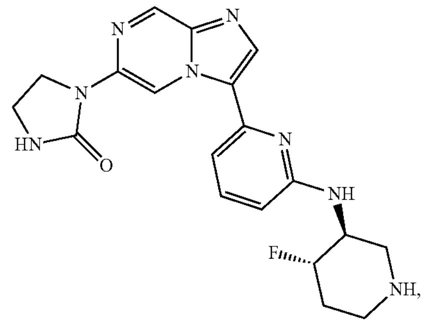
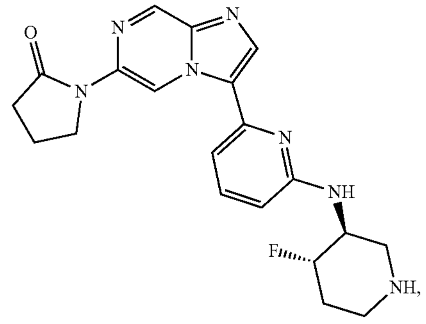

-continued
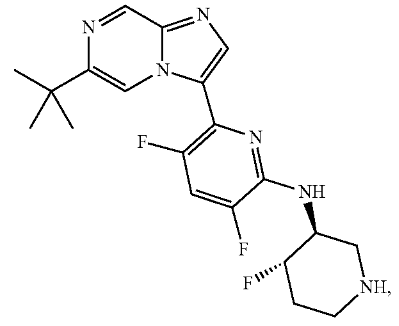
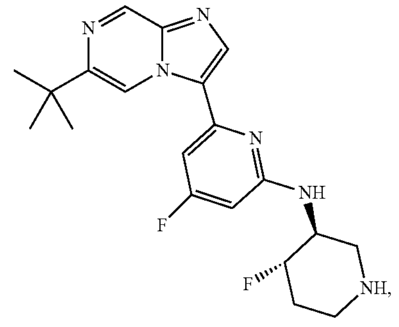
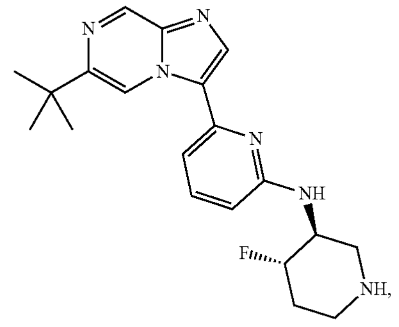
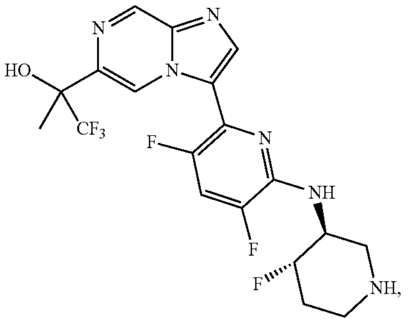
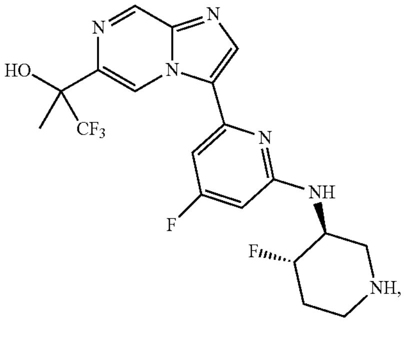
-continued
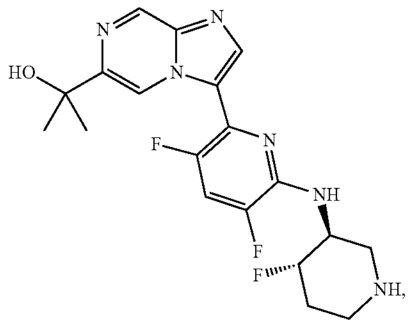
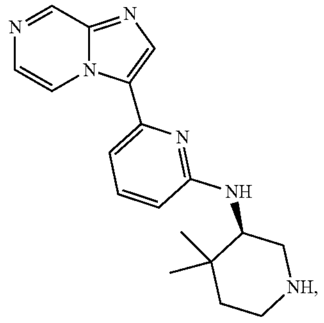
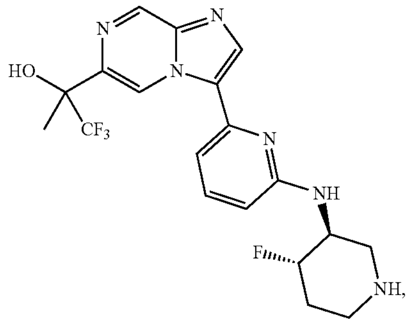
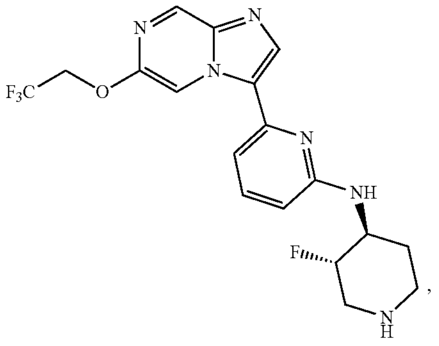
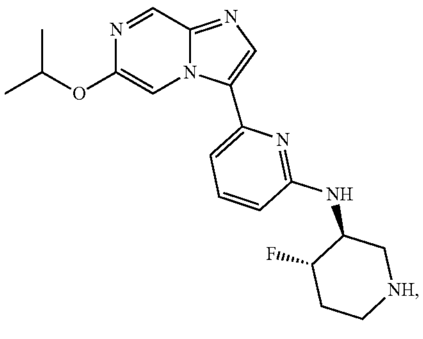

-continued
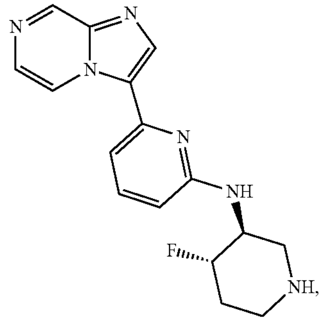
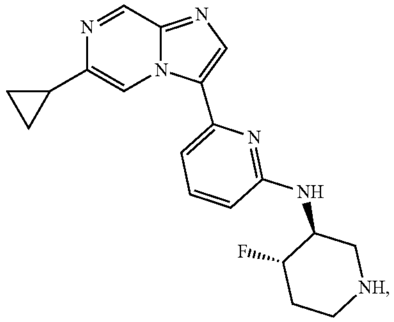
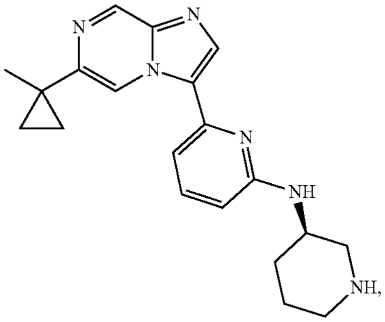
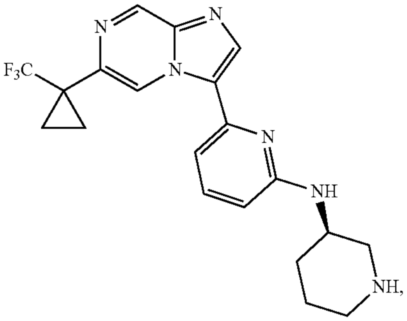
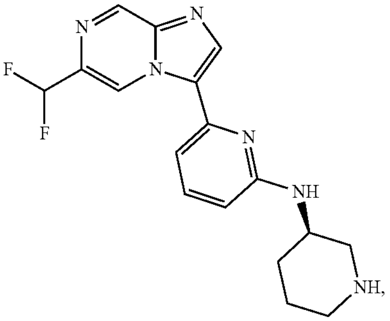
-continued
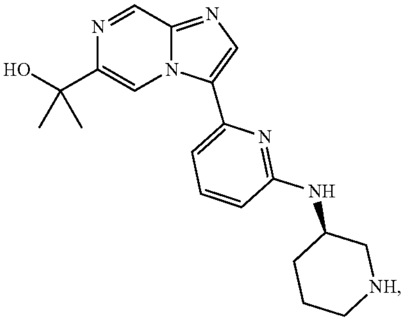
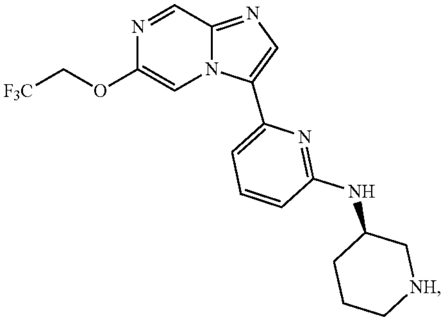
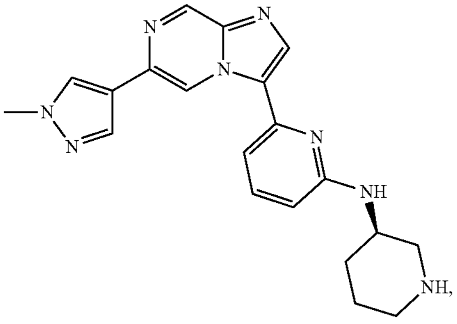
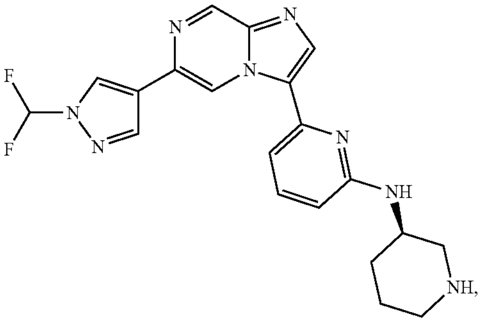
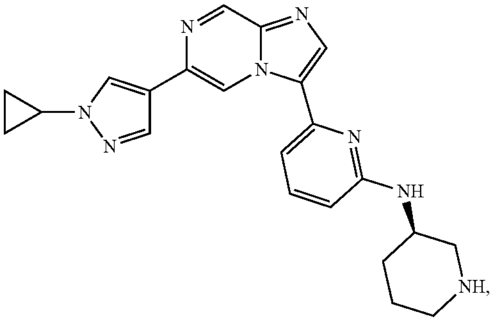

-continued
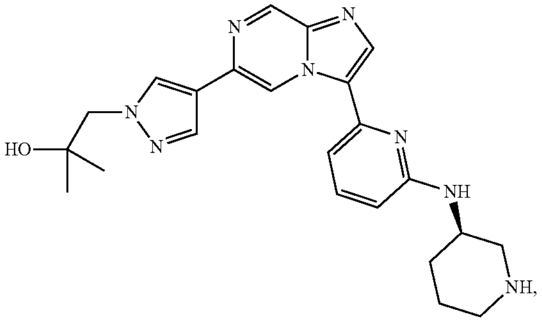
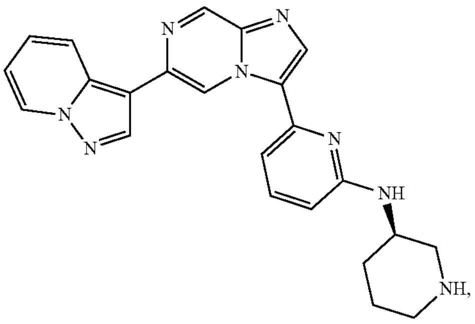
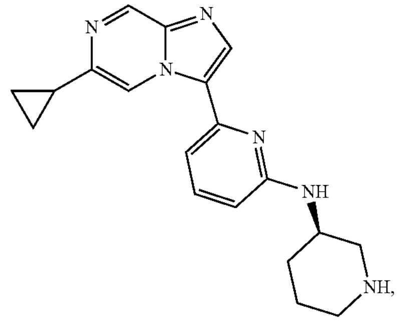
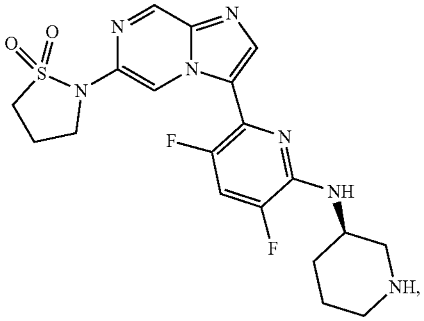
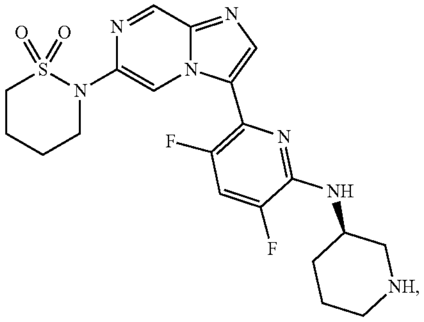
-continued
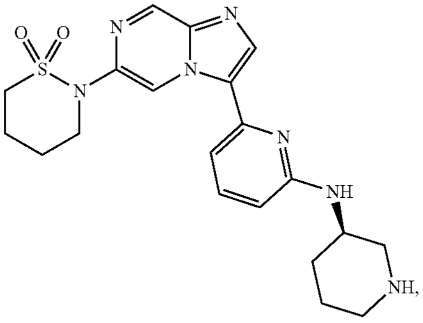
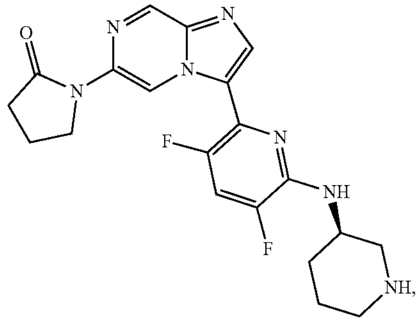
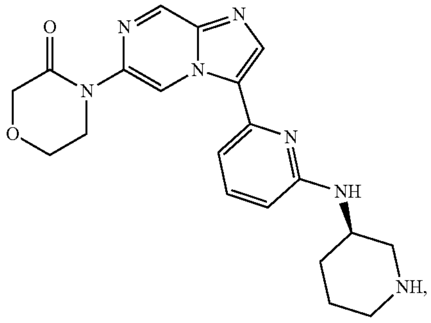
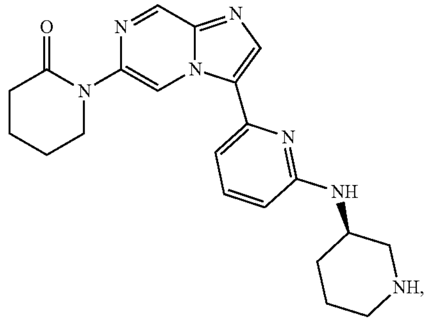
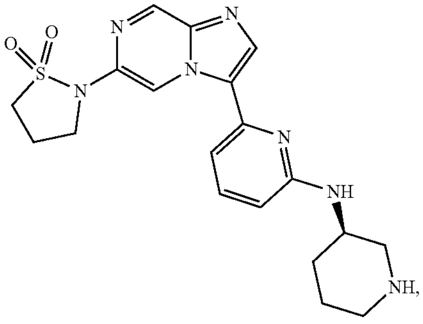

-continued
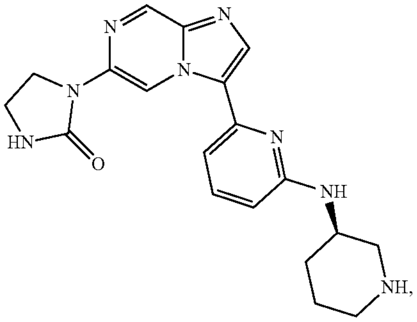
,
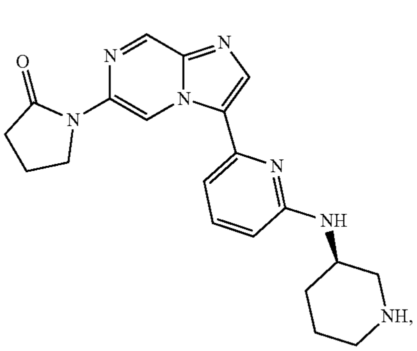
,
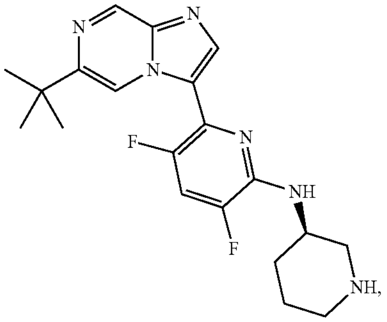
,
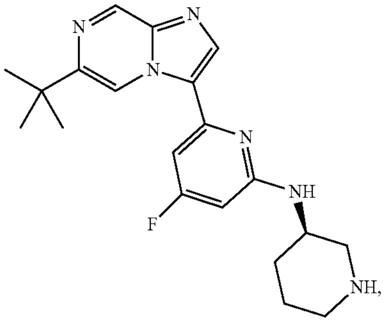
,
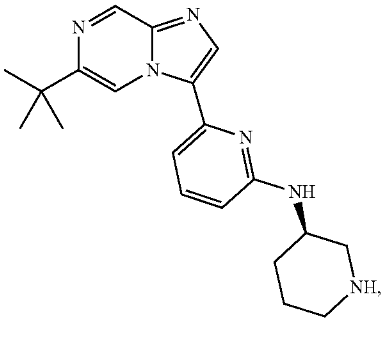
,
-continued
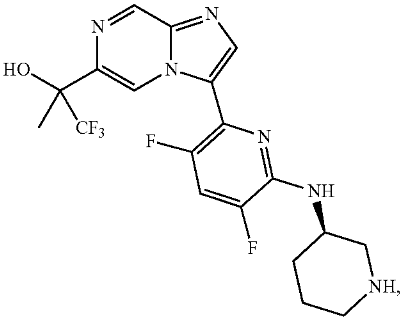
,
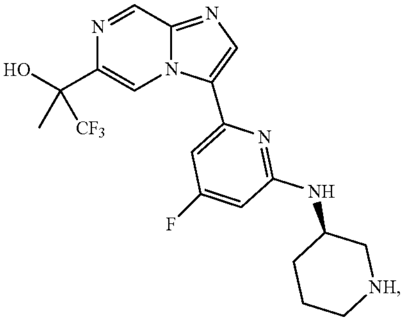
,
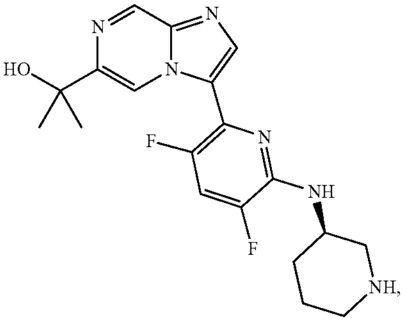
,
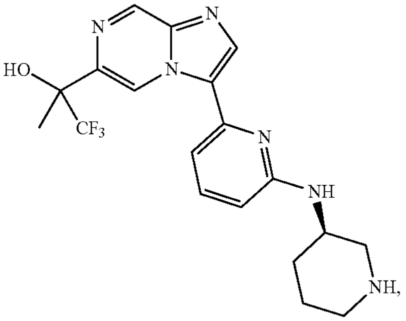
,
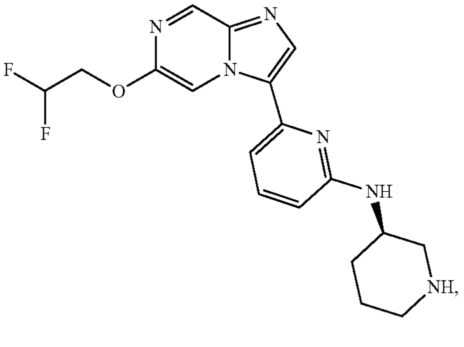
, -continued

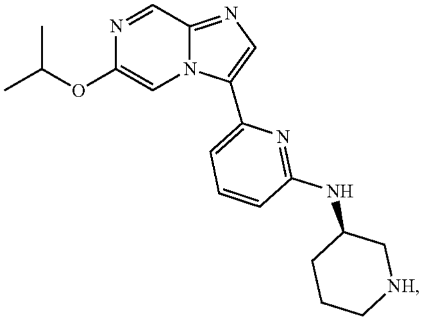

and

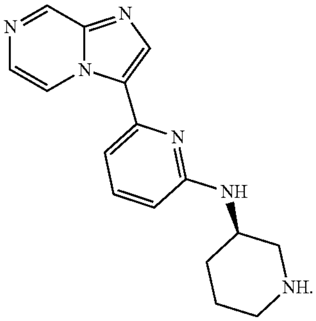

8. The compound of claim 1, wherein the compound of Formula (I) is a compound of Formula (IIh):

Formula (IIh)

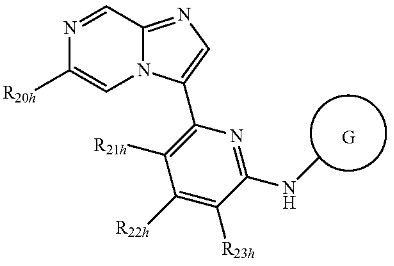

, or a salt, ester, solvate, optical isomer, geometric isomer, or salt of an isomer thereof;

wherein:

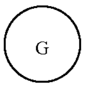

is selected from

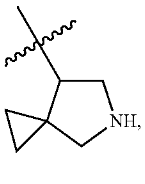

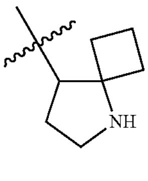

, and

-continued

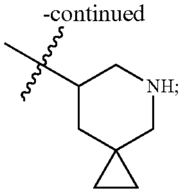

$R_{20h}$ is selected from H, $C_1$-$C_6$ alkyl, $C_1$-$C_6$ alkoxy, and $C_3$-$C_6$ cycloalkyl, wherein $C_1$-$C_6$ alkyl and $C_1$-$C_6$ alkoxy are each optionally substituted with one or more substituents selected from halogen and —OH, and wherein $C_3$-$C_6$ cycloalkyl is optionally substituted with one or more substituents selected from $C_1$-$C_6$ alkyl and halogen; and $R_{21h}$, $R_{22h}$, and $R_{23h}$ are each independently selected from H and halogen.

9. The compound of claim 8, wherein at least one of (i)-(vi) applies:

(i) $R_{20h}$ is selected from

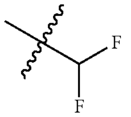

,

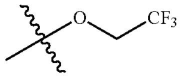

,

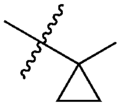

, and

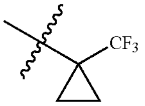

;

(ii) $R_{21h}$, $R_{22h}$, and $R_{23h}$ are each H;

(iii) $R_{21h}$ and $R_{23h}$ are each F and $R_{22h}$ is H;

(iv) $R_{21h}$ and $R_{23h}$ are each H and $R_{22h}$ is F;

(v)

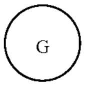

is

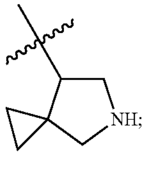

or (vi) $R_{20h}$ is H.

10. The compound of claim 8, wherein the compound is selected from:

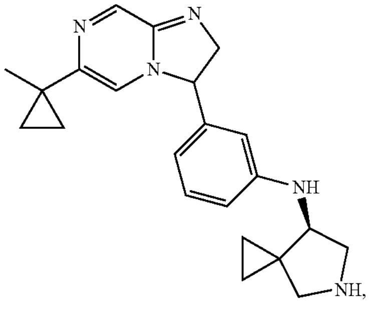

-continued

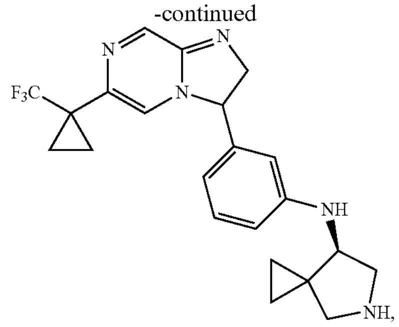

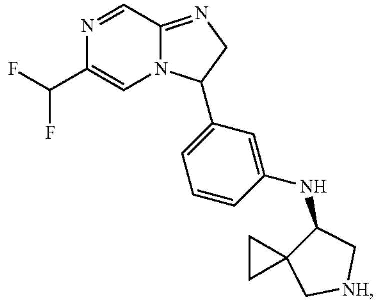

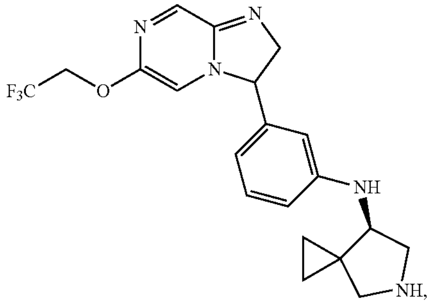

and

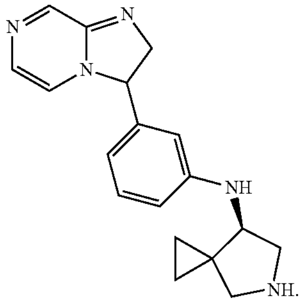

11. The compound of claim 1, wherein the compound is an inhibitor of at least one of IRAK1, IRAK4, and FLT3.

12. A composition comprising a compound of claim 1, wherein the composition further comprises a formulary ingredient, an adjuvant, or a carrier.

13. A method of treating a disease or disorder in a subject, the method comprising administering to the subject a therapeutically effective amount of a compound of claim 11.

14. The method of claim 13, wherein the disease or disorder comprises a hematopoietic cancer.

15. The method of claim 13, wherein the disease or disorder comprises at least one cancer selected from myelodysplastic syndrome (MDS), acute myeloid leukemia (AML), lymphoma, leukemia, chronic lymphocytic leukemia (CLL), chronic myeloid leukemia (CML), acute lymphoblastic leukemia (ALL), bone marrow cancer, non-Hodgkin lymphoma, Waldenstrom's macroglobulinemia, B cell lymphoma, diffuse large B-cell lymphoma (DLBCL), DLBCL with MYD88 mutation, follicular lymphoma, marginal zone lymphoma, glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, rhabdomyosarcoma, meningioma, gastric cancer, Glioma, oral cancer, nasopharyngeal carcinoma, rectal cancer, stomach cancer, and uterine cancer.

16. The method of claim 13, wherein the disease or disorder comprises one or more inflammatory diseases or autoimmune disease selected from chronic inflammation, sepsis, rheumatoid arthritis, hidradenitis suppurativa, systemic lupus erythematosus, inflammatory bowel disease, multiple sclerosis, psoriasis, Sjögren's syndrome, Ankylosing spondylitis, systemic sclerosis, Type 1 diabetes mellitus, or combinations thereof.

17. The method of claim 13, further comprising administering to the subject one or more additional therapies selected from: a chemotherapy agent, a BCL2 inhibitor, an immune modulator, a BTK inhibitor, a DNA methyltransferase inhibitor/hypomethylating agent, an anthracycline, a histone deacetylase (HDAC) inhibitor, a purine nucleoside analogue (antimetabolite), an isocitrate dehydrogenase 1 or 2 (IDH1 and/or IDH2) inhibitor, an antibody-drug conjugate, an mAbs/immunotherapy, a Plk inhibitor, a MEK inhibitor, a CDK inhibitor, a CDK9 inhibitor, a CDK8 inhibitor, a retinoic acid receptor agonist, a TP53 activator, a CELMOD, a smoothened receptor antagonist, an ERK inhibitor including an ERK2/MAPK1 or ERK1/MAPK3 inhibitor, a PI3K inhibitor, an mTOR inhibitor, a steroid or glucocorticoid receptor modulator, an EZH2 inhibitor, a hedgehog (Hh) inhibitor, a Topoisomerase I inhibitor, a Topoisomerase II inhibitor, an aminopeptidase/Leukotriene A4 hydrolase inhibitor, a FLT3/Axl/ALK inhibitor, a FLT3/KIT/PDGFR, PKC, and/or KDR inhibitor, a Syk inhibitor, an E-selectin inhibitor, an NEDD8-activator, an MDM2 inhibitor, a PLK1 inhibitor, an Aura A inhibitor, an aurora kinase inhibitor, an EGFR inhibitor, an AuroraB/C/VEGFR1/2/3/FLT3/CSF-1R/Kit/PDGFRA/B inhibitor, an AKT 1, 2, and/or 3 inhibitor, a ABL1/2/SRC/EPHA2/LCK/YES1/KIT/PDGFRB/FYN inhibitor, a farnesyltransferase inhibitor, a BRAF/MAP2K1/MAP2K2 inhibitor, a Menin-KMT2A/MLL inhibitor, and a multikinase inhibitor.

18. The method of claim 13, wherein the disease or disorder is:

BCL2 inhibitor resistant acute myeloid leukemia (AML),
venetoclax resistant AML,
FLT3 inhibitor resistant AML,
BCL2 inhibitor resistant refractory AML,
venetoclax resistant refractory AML,
FLT3 inhibitor resistant refractory AML,
BCL2 inhibitor resistant relapsed AML,
venetoclax resistant relapsed AML, or
FLT3 inhibitor resistant relapsed AML.

19. The method of claim 17, wherein the compound of claim 1 and the one or more additional therapies are administered together in one administration or composition.

20. The method of claim 17, wherein the compound of claim 1 and the one or more additional therapies are administered separately in more than one administration or more than one composition.

* * * * *